(12) United States Patent
Honda et al.

(10) Patent No.: US 12,036,249 B2
(45) Date of Patent: Jul. 16, 2024

(54) ANTI-BACTERIAL COMPOSITION AGAINST TH1 CELL-INDUCING BACTERIA

(71) Applicant: KEIO UNIVERSITY, Tokyo (JP)

(72) Inventors: Kenya Honda, Tokyo (JP); Koji Atarashi, Tokyo (JP); Seiko Narushima, Tokyo (JP); Wataru Suda, Tokyo (JP); Masahira Hattori, Tokyo (JP); Munehiro Furuichi, Tokyo (JP); Takaaki Kawaguchi, Tokyo (JP); Keiko Mitobe, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 0 days.

(21) Appl. No.: 18/057,335

(22) Filed: Nov. 21, 2022

(65) Prior Publication Data

US 2023/0190827 A1 Jun. 22, 2023

Related U.S. Application Data

(62) Division of application No. 16/631,496, filed as application No. PCT/JP2018/026922 on Jul. 18, 2018, now Pat. No. 11,633,433.

(60) Provisional application No. 62/533,844, filed on Jul. 18, 2017.

(51) Int. Cl.
*A61K 35/74* (2015.01)
*C12Q 1/02* (2006.01)

(52) U.S. Cl.
CPC .............. *A61K 35/74* (2013.01); *C12Q 1/02* (2013.01)

(58) Field of Classification Search
CPC ...................................................... A61K 35/74
See application file for complete search history.

(56) References Cited

U.S. PATENT DOCUMENTS

| 7,253,333 | B2 | 8/2007 | Tanaka et al. |
| 2003/0103938 | A1 | 6/2003 | Jinquan et al. |
| 2003/0108873 | A1 | 6/2003 | Dahlberg |
| 2006/0094649 | A1 | 5/2006 | Keogh |
| 2013/0336944 | A1 | 12/2013 | Chambaud et al. |
| 2016/0271188 | A1 | 9/2016 | Berry et al. |
| 2020/0405669 | A1 | 12/2020 | Scanlan et al. |
| 2020/0405775 | A1 | 12/2020 | Caballero et al. |

FOREIGN PATENT DOCUMENTS

| JP | 2011-200211 A | 10/2011 |
| JP | 2014-501100 A | 1/2014 |
| WO | 2018/084172 A1 | 5/2018 |
| WO | 2019/118515 A2 | 6/2019 |

OTHER PUBLICATIONS

C. Gourgue-Jeannot et al., "Dietary fructooligosaccharides alter the cultivable faecal population of rats but do not stimulate the growth of intestinal bifidobacteria", Can. J. Microbiol, 2006, pp. 924-933, vol. 52.
Shigeo Koyasu, Advanced medical technologies such as treatment achieved by exploring symbiotic strategy of pathogenic microorganism with host immune system, development of control method, intractable immune disorder, and infectious disease, Research representative selected in 2002, Apr. 16, 2009.
Yanfei Chen et al., "Dysbiosis of small intestinal microbiota in liver cirrhosis and its association with etiology", Scientific Reports 6:34055, 2016.
Dirk Gevers et al., "The treatment-naive microbiome in new-onset Crohn's disease", Cell Host Microbe, Mar. 12, 2014, pp. 382-392, vol. 15(3).
Catherine A. Lozupone at al., "Alterations in the Gut Microbiota Associated with HIV-1 Infection", Cell Host & Microbe, Sep. 11, 2013, pp. 329-339, vol. 14.
Ivan Vujkovic-Cvijin et al., "Dysbiosis of the Gut Microbiota is Associated with HIV Disease Progression and Tryptophan Catabolism", Science Translational Medicine, Jul. 10, 2013, vol. 5, Issue 193 193ra91.
Nan Qin et al., "Alterations of the human gut microbiome in liver cirrhosis", Nature, Sep. 4, 2014, pp. 59-64, vol. 513.
Cynthia L. Sears et al., "Microbes, Microbiota and Colon Cancer", Cell Host Microbe, Mar. 12, 2014, pp. 317-328, vol. 15(3).
International Search Report for PCT/JP2018/026922 dated Oct. 16, 2018 [PCT/ISA/210].
Communication, dated Jan. 30, 2020, issued by the International Bureau in International Application No. PCT/JP2018/026922.
Hill et al., "Intestinal Bacteria and the Regulation of Immune Cell Homeostasis", Annu. Rev. Immunol., 2010, vol. 28, pp. 623-667 (54 pages total).
"Uncultured bacterium clone SJTU_B_13_46 16S ribosomal RNA gene, partial sequence" & Li et al., "Symbiotic gut microbes modulate human metabolic phenotypes", Proceedings of the National Academy of Sciences, vol. 105, No. 6, Feb. 28, 2007, Database EMBL [Online], 1 page total.
Heimesaat et al., "Gram-Negative Bacteria Aggravate Murine Small Intestinal Th1-Type Immunopathology following Oral Infection with *Toxoplasma gondii*", The Journal of Immunology, 2006, vol. 177, pp. 8785-8795 (12 pages total).
Partial Supplementary European Search Report, dated May 21, 2021, issued by the European Patent Office in European Patent Application No. 18834915.3.
Database EMBL [Online], "Bacterium NLAE-z1-H424 16S ribosomal RNA gene, partial sequence", Jul. 3, 2012, Database accession No. JX006636 (1 page total).

(Continued)

*Primary Examiner* — Albert M Navarro
(74) *Attorney, Agent, or Firm* — Sughrue Mion, PLLC

(57) ABSTRACT

With the aim of proving an antibacterial composition against oral bacteria and the like capable of inducing Th1 cell proliferation or activation in an intestinal tract, the present inventors have found out that bacteria that suppress colonization and the like of the oral bacteria and the like in the intestinal tract are present in an intestinal microbiota. Moreover, the present inventors have succeeded in isolating intestinal bacteria that suppress intestinal colonization and the like of oral bacteria and the like.

1 Claim, 20 Drawing Sheets

Specification includes a Sequence Listing.

(56) References Cited

OTHER PUBLICATIONS

Database Geneseq [Online], "*Escherichia coli* 16S ribosomal RNA (majority) gene, SEQ ID 9.", Aug. 13, 2015, Database accession No. BCB42203 (1 page total).
Extended European Search Report issued Oct. 5, 2021 in European Application No. 18834915.3.
Ergin et al (J. Clin. Immunol. vol. 31, pp. 998-1009) (Year: 2011).

Fig. 13

| Kegg | Uniprot | Gene category | Annotation |
|---|---|---|---|
| K00971 | | Fructose and mannose metabolism | Mannose-1-phosphate guanylyltransferase 1 |
| K11189 | | | Multiphosphoryl transfer protein |
| K02770 | | | PTS system fructose-specific EIIABC component |
| K15778 | | | Phosphomannomutase/phosphoglucomutase |
| K13058 | | | Mannosylfructose-phosphate synthase |
| K00068 | | | 3-oxoacyl-[acyl-carrier-protein] reductase FabG |
| K12995 | | | rhamnosyltransferase |
| K00094 | | Galactose metabolism | Galactitol-1-phosphate 5-dehydrogenase |
| K02775 | | | Galactitol permease IIC component |
| K02774 | | | Galactitol-specific phosphotransferase enzyme IIB component |
| K16371 | | | D-tagatose-1,6-bisphosphate aldolase subunit GatZ |
| K00882 | | | Tagatose-6-phosphate kinase |
| K08302 | | | D-tagatose-1,6-bisphosphate aldolase subunit GatY |
| K02775 | | | Galactitol permease IIC component |
| K00256 | | Carbohydrate metabolism | GDP-mannose-dependent alpha-(1-2)-phosphatidylinositol mannosyltransferase |
| K00880 | | | L-xylulose/3-keto-L-gulonate kinase |
| K00874 | | | 2-dehydro-3-deoxygluconokinase |
| K00703 | | | Capsular glucan synthase |
| | A0A192AGT5 | | 3-octaprenyl-4-hydroxybenzoate carboxy-lyase partner protein |
| K18800 | | | 2-octaprenylphenol hydroxylase |
| K03182 | | | Phenolic acid decarboxylase subunit C |
| K01572 | | | Oxaloacetate decarboxylase beta chain |
| K01682 | | | Aconitate hydratase 2 |
| | A0A086RUJ0 | | Putative aldolase LsrF |
| K08625 | | | Putative acetyltransferase |
| | P0A1C7 | | Propanediol utilization protein PduA |
| | A0A0H4WDF2 | | Putative glycosyltransferase EpsF |

Fig. 15

| KEGG | Uniprot | Gene category | Annotation |
|---|---|---|---|
| K02016 | | | Hemin-binding periplasmic protein HmuT precursor |
| K09691 | | | Teichoic acids export ATP-binding protein TagH |
| K09692 | | | Teichoic acid translocation permease protein TagG |
| K12340 | | | Outer membrane protein TolC precursor |
| K03297 | | | Multidrug transporter EmrE |
| K06189 | | | Magnesium and cobalt efflux protein CorC |
| K07797 | | | Inner membrane protein YiaH |
| K07085 | | Membrane transportation | Aspartate/alanine antiporter |
| K02014 | | | Ferric enterobactin receptor precursor |
| K20973 | A0A0C7KHL0 | | Signal transduction histidine-protein kinase BasA |
| K15583 | | | Hemolysin transporter protein ShlB precursor |
| K01551 | | | Oligopeptide transport ATP-binding protein OppD |
| K04749 | | | Arsenical pump-driving ATPase |
| K07150 | | | Putative anti-sigma factor antagonist |
| K16087 | | | Putative membrane protein YdfK |
| | | | Putative hemoglobin and hemoglobin-haptoglobin-binding protein 2 precursor |

Fig. 19

| KEGG | Uniprot | Gene category | Annotation |
|---|---|---|---|
| K06218 | | | mRNA interferase RelE |
| K07462 | | | Single-stranded-DNA-specific exonuclease RecJ |
| K04763 | A0A8C7KGA2 | | Tyrosine recombinase XerD_6 |
| K02468 | | | Tyrosine recombinase XerD |
| K18836 | | | Glucitol operon repressor |
| | | Gene regulator | Formate hydrogenlyase transcriptional activator |
| P07774 | A0A0C7KER5 | | HTH-type transcriptional regulator TdiR |
| K07774 | | | HTH-type transcriptional regulator CatM |
| K09892 | | | Transcriptional regulatory protein tctD |
| K13244 | | | HTH-type transcriptional repressor AseR |
| K04757 | | | Cyclic di-GMP phosphodiesterase YahA |
| | | | Serine-protein kinase RsbW |

ANTI-BACTERIAL COMPOSITION AGAINST TH1 CELL-INDUCING BACTERIA

CROSS REFERENCE TO RELATED APPLICATIONS

This application is a divisional of U.S. patent application Ser. No. 16/631,496, filed Jan. 16, 2020, which is a National Stage Entry of PCT/JP2018/026922, filed Jul. 18, 2018, which claims priority from U.S. Provisional Application No. 62/533,844 filed Jul. 18, 2017, the contents of all of which are incorporated herein by reference in their entirety.

The instant application contains a Sequence Listing which has been filed electronically in xml format and is hereby incorporated by reference in its entirety. Said xml copy, created on Nov. 18, 2022, is named SEQ_LIST.xml and is 421 KB in size.

INCORPORATION BY REFERENCE OF SEQUENCE LISTING

The instant application contains a Sequence Listing which has been filed electronically in xml format and is hereby incorporated by reference in its entirety. Said xml copy, created on Dec. 10, 2022, is named Q282093_Sequence_Listing_As_Filed.xml and is 427 KB in size.

TECHNICAL FIELD

The present invention has been made as a result of the research based on the entrusted program in the unit-type research area "Innovation for Ideal Medical Treatment Based on the Understanding of Maintenance, Change and Breakdown Mechanisms of Homeostasis among Interacting Organ Systems" (the title of the research and development: "Discovering therapies for Intractable Diseases through the Identification and Characterization of the Gut Microbiota") in Advanced Research and Development Programs for Medical Innovation by Japan Agency for Medical Research and Development (AMED) in 2015.

The present invention relates to an antibacterial composition against a bacterium capable of inducing Th1 cell proliferation or activation in an intestinal tract (hereinafter also referred to as "Th1 cell-inducible bacterium"). In addition, the present invention relates to a pharmaceutical composition or method for treating, alleviating, or preventing a disease attributable to Th1 cells. Furthermore, the present invention relates to an intestinal bacterium having antibacterial activity against Th1 cell-inducible bacteria. In addition, the present invention relates to a composition for testing for a disease attributable to Th1 cells, the composition comprising a substance for specifically detecting the intestinal bacterium. Furthermore, the present invention relates to use of the intestinal bacterium for producing a pharmaceutical composition for treating, alleviating, or preventing a disease attributable to Th1 cells.

BACKGROUND ART

Diverse indigenous bacteria are present on mucosae of the digestive tract, oral cavity, and so forth, forming a flora as a whole. Indigenous floras play quite major roles in the host physiology and health maintenance. An indigenous floral imbalance is called dysbiosis, which has been gradually revealed to be a cause for various diseases. It is highly likely that a further progress in the elucidation of mucosal indigenous floras leads to novel disease controls and treatment developments against various diseases. Nevertheless, due to the complexity, the detailed mechanism has not been sufficiently revealed yet.

A human generates and swallows approximately 1.5 L of saliva every day. Normally, bacteria contained in saliva (oral bacteria) merely pass through the intestinal tract and do not colonize. However, oral bacteria may colonize in the intestinal tract under certain situations. There have been reports that the intestinal colonization of oral bacteria was observed from the early stage of the disease developments particularly in Crohn's disease, liver cirrhosis, and colorectal cancer. Moreover, it has been known that such colonized oral bacteria influence the disease status (NPLs 1 to 6).

CITATION LIST

Patent Literature

[PTL 1] International Publication No. WO2018/084172

Non Patent Literature

[NPL 1] Y. Chen et al., Scientific reports 6, 34055 (2016)
[NPL 2] D. Gevers et al., Cell host & microbe 15, 382-392 (2014)
[NPL 3] C. A. Lozupone et al., Cell host & microbe 14, 329-339 (2013)
[NPL 4] I. Vujkovic-Cvijin et al., Science translational medicine 5, 193ra191 (2013)
[NPL 5] N. Qin et al., Nature 513, 59-64 (2014)
[NPL 6] C. L. Sears, W. S. Garrett, Cell host & microbe 15, 317-328 (2014)

SUMMARY OF INVENTION

Technical Problem

An object of the present invention is to provide a composition and so on for treating, alleviating, or preventing a disease such as Crohn's disease, which targets oral bacteria that induce Crohn's disease and the like by colonizing in the intestinal tract.

Solution to Problem

The present inventors conducted earnest studies to achieve the above-described object. As a result, the present inventors previously caused oral bacteria of patients with Crohn's disease and others to colonize in the intestinal tract and to induce Th1 cells, and thereby succeeded in isolation-culturing and identifying bacteria involved in the developments of the diseases (PTL 1).

More specifically, the present inventors found out that when salivas derived from some Crohn's disease patients were orally administered to germ-free mice, interferon-gamma (IFN-γ) producing CD4 positive T cells (Th1 cells) markedly increased in the colons as a result.

Then, the present inventors succeeded in isolation-culturing a Kp2H7 strain considered as belonging to *Klebsiella pneumoniae* from the intestine of the mice in which such an increase in Th1 cells had been observed. Moreover, the present inventors also clarified that the bacteria derived from the saliva of Crohn's disease patients are involved in the development of enteritis by colonizing in the intestinal tract and inducing the proliferation or activation of Th1 cells.

In addition, it was also found out that orally administering saliva of some ulcerative colitis patient to germ-free mice markedly induces Th1 cells in the colons as in the case of the above-described Crohn's disease patients. Moreover, as a result of identifying a bacterium that induces Th1 cells, it was also clarified that the Ka11E12 strain, which is a strain different from the Kp2H7 strain and belongs to *Klebsiella aeromobilis* closely related to *K. pneumoniae*, is involved in the induction of Th1 cells in the colons.

This time, the present inventors have found out that when the Kp2H7 strain or Ka11E12 strain is orally administered to SPF (specific-pathogen-free) mice, intestinal colonization of either of these bacterial strains is not observed unlike in the case of the germ-free mice. Moreover, it has also been clarified that administration of an antibiotic to SPF mice may allow these bacterial strains to colonize in the intestinal tracts of the mice.

Then, the present inventors assumed from these results that intestinal bacteria that inhibit intestinal colonization of Th1 cell-inducible bacteria (such as the Kp2H7 strain and the Ka11E12 strain) are present in the intestinal tract, and the administration of an antibiotic eliminates the intestinal bacteria from the intestinal tract, thereby enabling the intestinal colonization of the bacteria.

Based on the above, among human intestinal bacteria, the present inventors tried to identify bacteria that suppress the intestinal colonization of Th1 cell-inducible bacteria. As a result, the present inventors isolation-cultured 68, 37, and 42 intestinal bacterial strains from fecal samples derived from three healthy individuals (#K, #F, and #I), respectively, and succeeded in determining the sequence of 16S rDNA of each strain.

Furthermore, the present inventors have found out that administration of these bacterial strains suppresses the intestinal colonization of Th1 cell-inducible bacteria. This finding has led to the completion of the present invention.

In summary, the present invention provides the following.

[1] An antibacterial composition against a bacterium capable of inducing Th1 cell proliferation or activation in an intestinal tract, comprising an intestinal bacterium as an active ingredient.

[2] The antibacterial composition according to [1], wherein the intestinal bacterium is at least one bacterium having a DNA composed of a base sequence specified at any of SEQ ID NOs: 1 to 147 or a base sequence having at least 90% identity with the base sequence.

[3] The antibacterial composition according to [1], wherein the intestinal bacterium is at least one bacterium having a DNA composed of a base sequence specified at any of SEQ ID NOs: 1 to 68 or a base sequence having at least 90% identity with the base sequence.

[4] The antibacterial composition according to [1], wherein the intestinal bacterium is at least one bacterium having a DNA composed of a base sequence specified at any of SEQ ID NOs: 69 to 105 or a base sequence having at least 90% identity with the base sequence.

[5] The antibacterial composition according to [1], wherein the intestinal bacterium is at least one bacterium having a DNA composed of a base sequence specified at any of SEQ ID NOs: 106 to 147 or a base sequence having at least 90% identity with the base sequence.

[6] The antibacterial composition according to any one of [1] to [5], which is a pharmaceutical composition.

[7] The antibacterial composition according to any one of [1] to [5], which is a pharmaceutical composition for treating, alleviating, or preventing a disease attributable to Th1 cells.

[8] A bacterium having an antibacterial activity against a bacterium capable of inducing Th1 cell proliferation or activation in an intestinal tract.

[9] At least one bacterium having a DNA composed of a base sequence specified at any of SEQ ID NOs: 1 to 147 or a base sequence having at least 90% identity with the base sequence.

[10] At least one bacterium having a DNA composed of a base sequence specified at any of SEQ ID NOs: 1 to 68 or a base sequence having at least 90% identity with the base sequence.

[11] At least one bacterium having a DNA composed of a base sequence specified at any of SEQ ID NOs: 69 to 105 or a base sequence having at least 90% identity with the base sequence.

[12] At least one bacterium having a DNA composed of a base sequence specified at any of SEQ ID NOs: 106 to 147 or a base sequence having at least 90% identity with the base sequence.

[13] The bacterium according to any one of [9] to [12], which is a bacterium having an antibacterial activity against a bacterium capable of inducing Th1 cell proliferation or activation in an intestinal tract.

[14] A composition for testing for a disease attributable to Th1 cells, the composition comprising an antibody that specifically recognizes the bacterium according to any one of [8] to [13].

[15] A composition for testing for a disease attributable to Th1 cells, the composition comprising a polynucleotide for detecting a nucleotide sequence specific to the bacterium according to any one of [8] to [13].

[16] A method comprising providing a subject with the bacterium according to any one of [8] to [13], to thereby treat, alleviate, or prevent a disease attributable to Th1 cells in the subject.

[17] Use of the bacterium according to any one of [8] to [13] for producing a pharmaceutical composition for treating, alleviating, or preventing a disease attributable to Th1 cells.

Note that, as explained in Examples to be described later, the base sequences specified in SEQ ID NOs: 1 to 68 are the 16 rDNA base sequences of the 68 bacterial strains isolated from the feces derived from healthy individual #K, the base sequence specified at any of SEQ ID NOs: 69 to 105 is the 16 rDNA base sequence of the corresponding one of the 37 bacterial strains isolated from the feces derived from healthy individual #F, and the base sequence specified at any of SEQ ID NOs: 106 to 147 is the 16 rDNA base sequence of the corresponding one of the 42 bacterial strains isolated from the feces derived from healthy individual #I.

Advantageous Effects of Invention

According to the present invention, suppression of the colonization and the like of Th1 cell-inducible bacteria in the intestinal tract makes it possible to suppress Th1 cell proliferation or activation, suppress intestinal immunity, and moreover treat, alleviate, or prevent a disease attributable to Th1 cells. In addition, the present invention makes it possible to test for a disease attributable to Th1 cells.

BRIEF DESCRIPTION OF DRAWINGS

In FIG. 1, "Amp" indicates an SPF mouse administered with ampicillin, and "Tyl" indicates an SPF mouse administered with tylosin. Note that the line completely overlapping the horizontal axis of the graph indicates a mouse (control) unfed with an antibiotic, and the two broken lines overlapping the horizontal axis of the graph after the 7th day following administration of the Kp2H7 strain indicate an SPF mouse administered with metronidazole and an SPF mouse administered with spectinomycin.

In FIG. 2, "VCM" indicates an SPF mouse administered with vancomycin, and "Tyl" indicates an SPF mouse administered with tylosin. Note that the line overlapping the horizontal axis of the graph indicates a mouse (control) unfed with an antibiotic, and the broken line overlapping the horizontal axis of the graph after the 7th day following administration of the Ka11E12 strain indicates an SPF mouse administered with metronidazole.

In FIG. 3, "ABPC" indicates an ampicillin administration period, and "MNZ" indicates a metronidazole administration period.

In FIG. 4, "FMT" indicates the administration date of the fecal samples, and "ABPC" indicates the ampicillin administration period.

In FIG. 5, "FMT" indicates the administration date of the fecal samples.

In FIG. 6, "FMT" indicates the administration date of the fecal samples.

In FIG. 7, "FMT" indicates the administration date of the fecal samples.

In FIG. 9, "K_47mix" indicates a germ-free mouse administered with a cocktail composed of 47 types of bacterial strains isolated from the feces of the healthy individual #K, "F_37mix" indicates a germ-free mouse administered with a cocktail composed of 37 types of bacterial strains isolated from the feces of the healthy individual #F, "I_42mix" indicates a germ-free mouse administered with a cocktail composed of 42 types of bacterial strains isolated from the feces of the healthy individual #I, and "fece I" indicates a germ-free mouse administered with a fecal sample derived from the healthy individual #I. In addition, "FMT" indicates the administration date of the bacterial cocktail or fecal sample. The notation in FIG. 9 is also the same in FIG. 10.

In FIG. 11, "K_68mix" indicates a germ-free mouse administered with a cocktail composed of 68 types of bacterial strains isolated from the feces of the healthy individual #K. The notation in FIG. 11 is also the same in FIG. 12.

FIG. 13 shows annotations of and information (KEGG or UniProt) on genes related to carbohydrate metabolism, among the genes related to the induction of the colonic Th1 cells.

FIG. 15 shows annotations of and information (KEGG or UniProt) on genes related to membrane transport, among the genes related to the induction of the colonic Th1 cells.

FIG. 19 shows annotations of and information (KEGG or UniProt) on genes related to gene regulation, among the genes related to the induction of the colonic Th1 cells.

DESCRIPTION OF EMBODIMENTS

Figure 1:
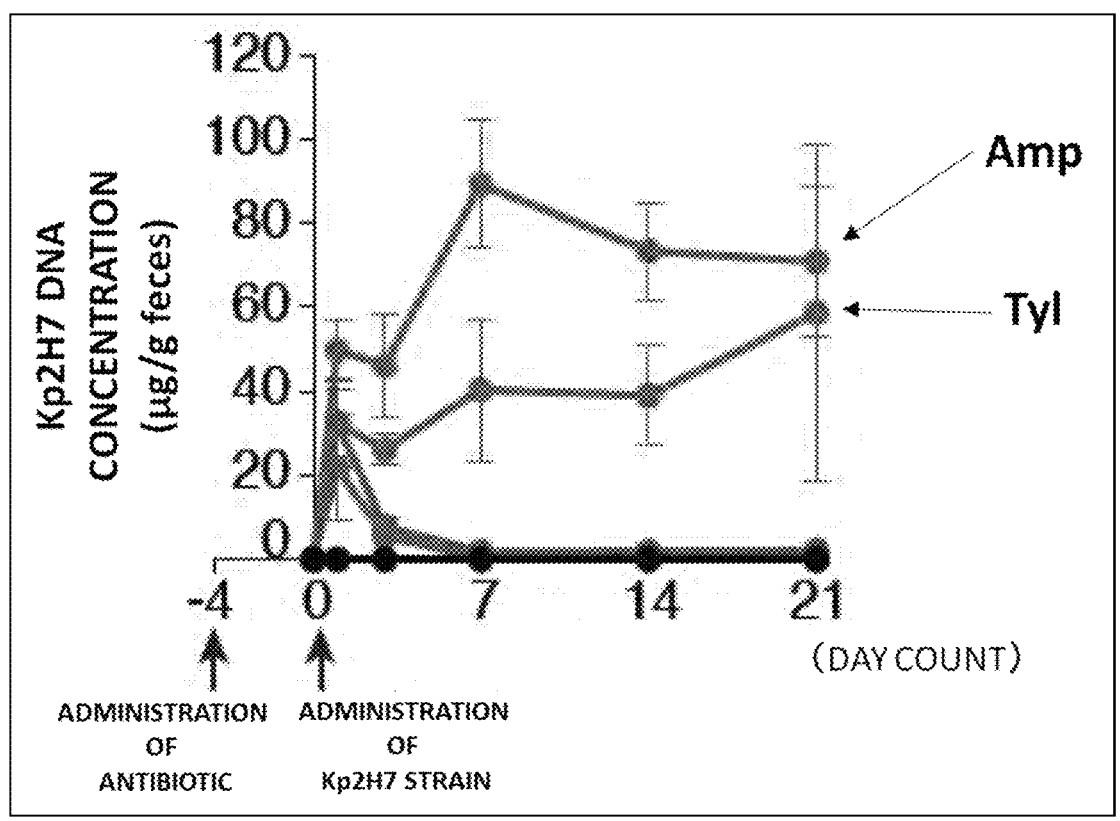
FIG. 1 is a graph illustrating the results of qPCR analysis of the change over time of the intestinal colonization level of a Kp2H7 strain in SPF mice administered with various antibiotics and then fed with the strain.

As explained in Examples to be described later, it has been clarified by the present inventors that intestinal bacteria suppress intestinal colonization and the like of bacteria capable of inducing Th1 cell proliferation or activation in an intestinal tract.

Therefore, the present invention provides an antibacterial composition against a bacterium capable of inducing Th1 cell proliferation or activation in an intestinal tract (Th1 cell-inducible bacterium), comprising an intestinal bacterium as an active ingredient.

First, description is provided for a bacterium capable of inducing Th1 cell proliferation or activation in an intestinal tract, which is the target of antibacterial activity of the composition.

(Bacteria that Induce Th1 Cells in Intestinal Tract)

In the present invention, the "bacterium capable of inducing Th1 cell proliferation or activation in an intestinal tract" is a bacterium normally present in the human oral cavity and capable of inducing Th1 cell proliferation or activation upon intestinal colonization, and is a bacterium belonging to preferably *Klebsiella*, more preferably *Klebsiella pneumoniae* or *Klebsiella aeromobilis*, and being capable of inducing Th1 cell proliferation or activation in an intestine. The "bacterium capable of inducing Th1 cell proliferation or activation in an intestinal tract" is preferably a bacterium easily colonizing in an intestinal environment where the diversity changes by antibacterial drug administration in comparison with a healthy state, and is also a bacterium easily colonizing in an intestinal environment where the diversity changes by colitis or the like in comparison with a healthy state.

Specific examples of the "bacterium capable of inducing Th1 cell proliferation or activation in an intestinal tract" include Kp2H7 strain, Ka11E12 strain, 34E1 strain, BAA-1705 strain, 700603 strain, and 40B3 strain belonging to *Klebsiella*, which have been revealed by the present inventors to cause significant induction of Th1 cells upon colonization in the intestinal tract, as described in PTL 1.

Note that the Kp2H7 strain, the Ka11E12 strain, the 34E1 strain, and the 40B3 strain are bacteria normally present in the human oral cavity (oral bacteria). Meanwhile, the BAA-1705 strain and the 700603 strain are also bacteria normally present in the human oral cavity, but the bacteria are detected in human urine (bacteria in urine).

In addition, the induction levels and genome sequences of colon Th1 cells were compared between these strains. As a result, as shown in FIGS. 13-22 to be described later, the present inventors have found 64 genes whose functions are already known that are related to induction of induction of Th1 cell proliferation or activation.

Thus, the "bacterium capable of inducing Th1 cell proliferation or activation in an intestinal tract" of the present invention preferably comprises genes encoding at least five proteins selected from the following protein group encoded by each of the 64 genes; more preferably, comprises genes encoding at least 10 proteins selected from the following protein group; further preferably comprises genes encoding at least 20 proteins selected from the following protein group; furthermore preferably, comprises genes encoding at least 30 proteins selected from the following protein group; and still furthermore preferably, comprises genes encoding at least 50 proteins selected from the following protein group.

Group of proteins:
Mannose-1-phosphate guanylyltransferase 1,
Multiphosphoryl transfer protein,
PTS system fructose-specific EIIABC component,
Phosphomannomutase/phosphoglucomutase,
Mannosylfructose-phosphate synthase,
3-oxoacyl-[acyl-carrier-protein] reductase FabG,
rhamnosyl/mannosyltransferase,
Galactitol-1-phosphate 5-dehydrogenase,
Galactitol permease IIC component,
Galactitol-specific phosphotransferase enzyme IIB component,
D-tagatose-1,6-bisphosphate aldolase subunit GatZ,
Tagatose-6-phosphate kinase,
D-tagatose-1,6-bisphosphate aldolase subunit GatY,
Galactitol permease IIC component,
GDP-mannose-dependent alpha-(1-2)-phosphatidylinositol mannosyltransferase,
L-xylulose/3-keto-L-gulonate kinase,
2-dehydro-3-deoxygluconokinase,
Capsular glucan synthase,
3-octaprenyl-4-hydroxybenzoate carboxy-lyase partner protein,
2-octaprenylphenol hydroxylase,
Phenolic acid decarboxylase subunit C,
Oxaloacetate decarboxylase beta chain,
Aconitate hydratase 2,
Putative aldolase LsrF,
Putative acetyltransferase,
Propanediol utilization protein PduA,
Putative glycosyltransferase EpsF,
Hemin-binding periplasmic protein HmuT precursor,
Teichoic acids export ATP-binding protein TagH,
Teichoic acid translocation permease protein TagG,
Outer membrane protein TolC precursor,
Multidrug transporter EmrE,
Magnesium and cobalt efflux protein CorC,
Inner membrane protein YibH,
Aspartate/alanine antiporter,
Ferric enterobactin receptor precursor,
Signal transduction histidine-protein kinase BarA,
Hemolysin transporter protein ShlB precursor,
Oligopeptide transport ATP-binding protein OppD,
Arsenical pump-driving ATPase,
Putative anti-sigma factor antagonist,
Putative membrane protein YdfK,
Putative hemoglobin and hemoglobin-haptoglobin-binding protein 2 precursor,
(2R)-3-sulfolactate dehydrogenase (NADP(+)),
Peptidase E,
Oligopeptidase A,
Phosphinothricin N-acetyltransferase,
Putative 2-hydroxyacid dehydrogenase YoaD,
mRNA interferase RelE,
Single-stranded-DNA-specific exonuclease RecJ,
Tyrosine recombinase XerD_6,
Tyrosine recombinase XerD,
Glucitol operon repressor,
Formate hydrogenlyase transcriptional activator,
HTH-type transcriptional regulator TdfR,
HTH-type transcriptional regulator CatM,
Transcriptional regulatory protein tctD,
HTH-type transcriptional repressor AseR,
Cyclic di-GMP phosphodiesterase YahA,
Serine-protein kinase RsbW,
Filamentous hemagglutinin,
Dihydropteroate synthase,
Delta-aminolevulinic acid dehydratase, and
Aerobic respiration control protein ArcA.

Note that, in FIGS. 13-22, 2242, 2552, KP-1, 700721, 13882, 40B3, 34E1, 1705, 11E12, 700603, and 2H7 indicate the 2242 strain, the BAA-2552 strain, the KP-1 strain, the 700721 strain, the 13882 strain, the 40B3 strain, the 34E1 strain, the BAA-1705 strain, the Ka11E12 strain, the 700603 strain, and the Kp2H7 strain to be described later, respectively. In addition, weak, medium, and strong indicate the degree of action that induces the Th1 cell proliferation or activation in the intestinal tract of each strain.

FIG. 13 shows annotations of and information (KEGG or UniProt) on genes related to carbohydrate metabolism, among the genes related to the induction of the colonic Th1 cells.

Figure 14:
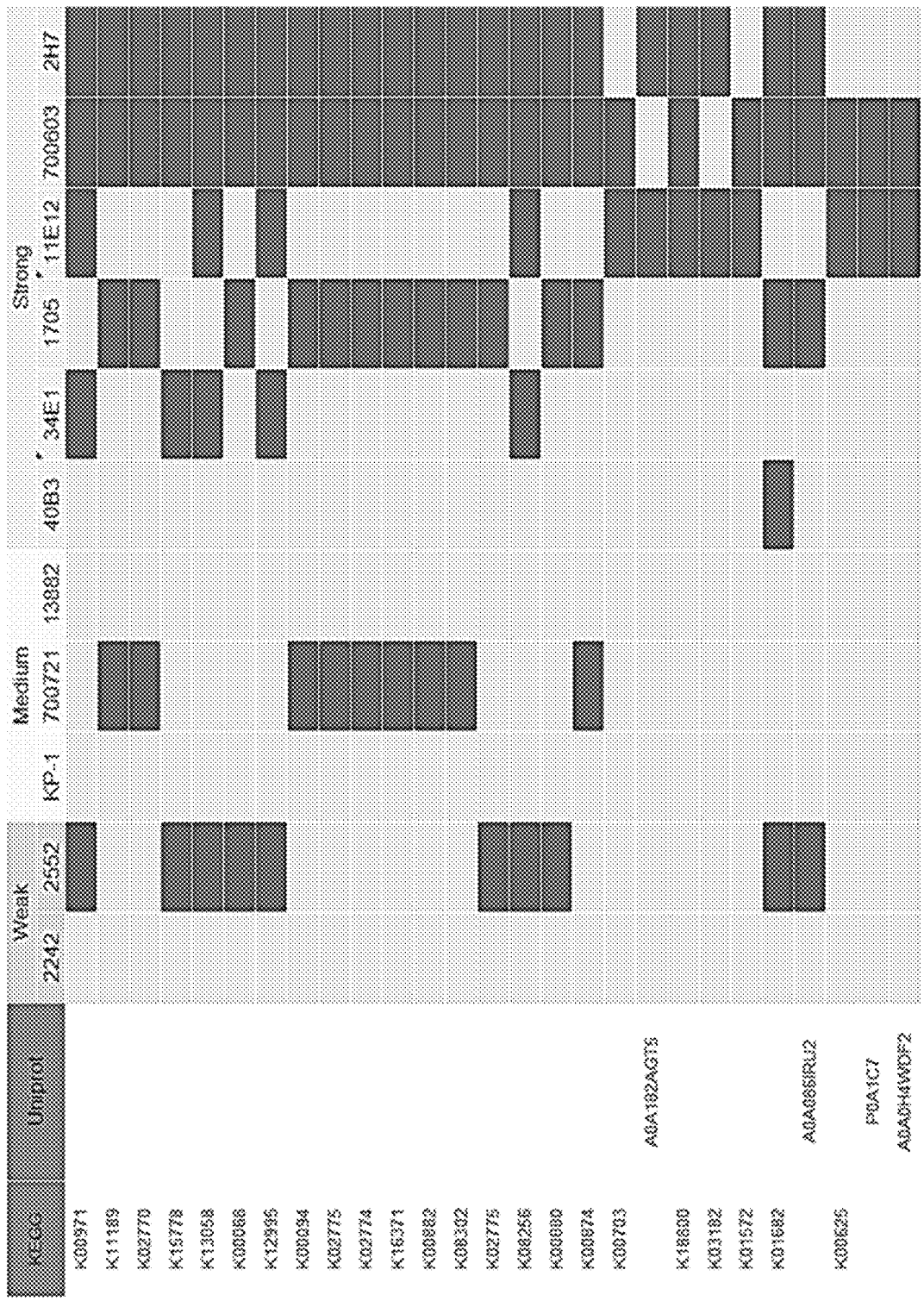
FIG. 14 shows the levels of colonic Th1 cells induced by the bacterial strains belonging to *Klebsiella*, and the levels of the genes related to the carbohydrate metabolism the bacterial strains comprise.

FIG. 14 shows the levels of colonic Th1 cells induced by the bacterial strains belonging to *Klebsiella*, and the levels of the genes related to the carbohydrate metabolism the bacterial strains comprise.

FIG. 15 shows annotations of and information (KEGG or UniProt) on genes related to membrane transport, among the genes related to the induction of the colonic Th1 cells.

Figure 16:
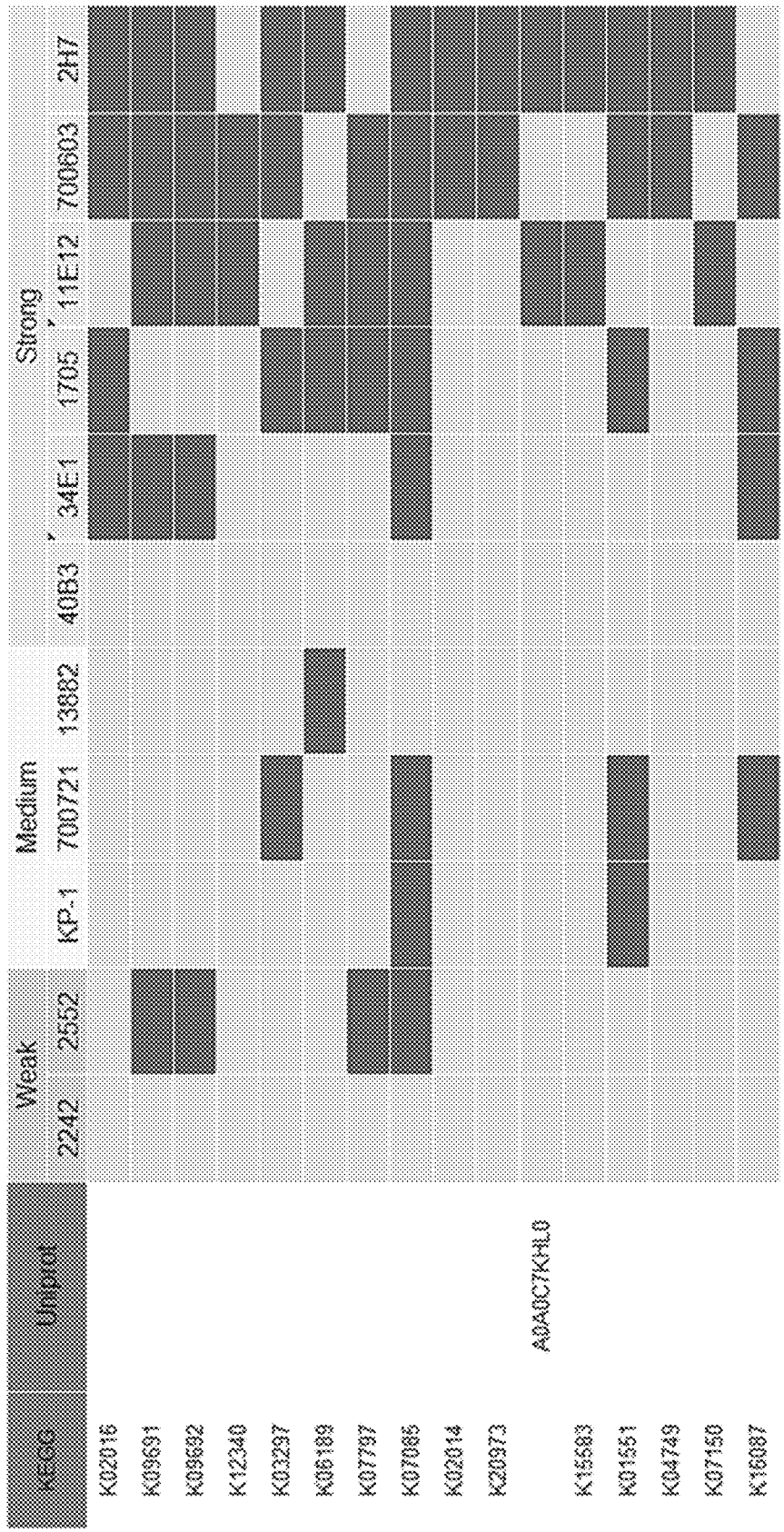
FIG. 16 shows the levels of colonic Th1 cells induced by the bacterial strains belonging to *Klebsiella*, and the levels of the genes related to the membrane transport the bacterial strains comprise.

FIG. 16 shows the levels of colonic Th1 cells induced by the bacterial strains belonging to *Klebsiella*, and the levels of the genes related to the membrane transport the bacterial strains comprise.

Figures 17, 18:
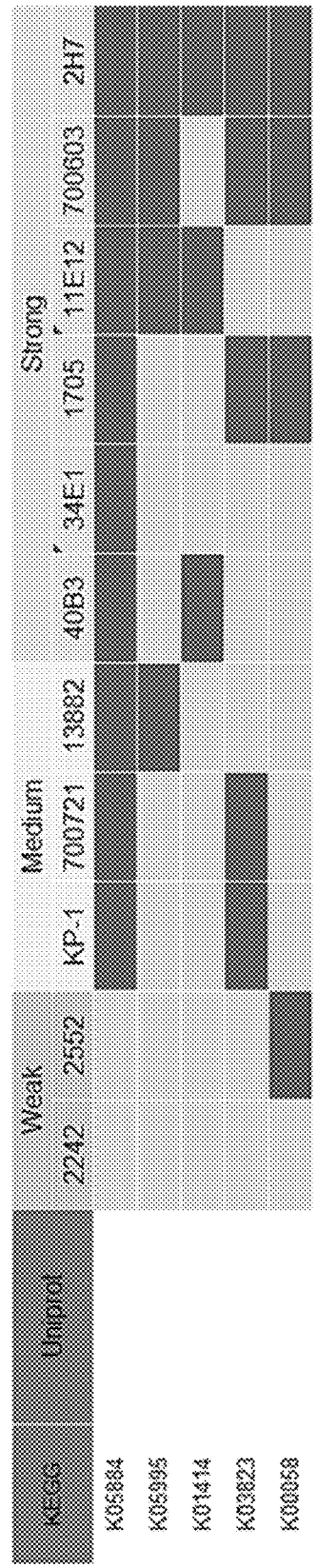
FIG. 17 shows annotations of and information (KEGG or UniProt) on genes related to amino acid metabolism, among the genes related to the induction of the colonic Th1 cells.
FIG. 18 shows the levels of colonic Th1 cells induced by the bacterial strains belonging to *Klebsiella*, and the levels of the genes related to the amino acid metabolism the bacterial strains comprise.

FIG. 17 shows annotations of and information (KEGG or UniProt) on genes related to amino acid metabolism, among the genes related to the induction of the colonic Th1 cells.

FIG. 18 shows the levels of colonic Th1 cells induced by the bacterial strains belonging to *Klebsiella*, and the levels of the genes related to the amino acid metabolism the bacterial strains comprise.

FIG. 19 shows annotations of and information (KEGG or UniProt) on genes related to gene regulation, among the genes related to the induction of the colonic Th1 cells.

Figure 20:
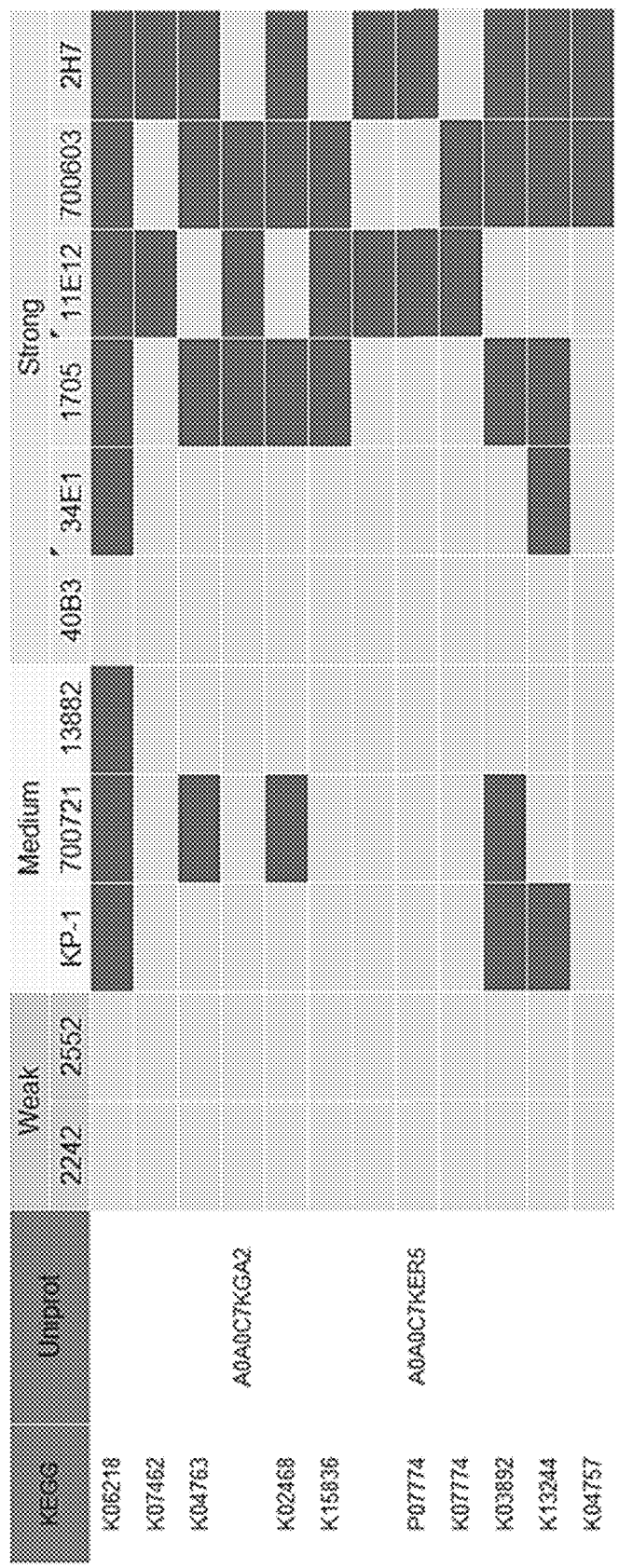
FIG. 20 shows the levels of colonic Th1 cells induced by the bacterial strains belonging to *Klebsiella*, and the levels of the genes related to the gene regulation the bacterial strains comprise.

FIG. 20 shows the levels of colonic Th1 cells induced by the bacterial strains belonging to *Klebsiella*, and the levels of the genes related to the gene regulation the bacterial strains comprise.

Figures 21, 22:
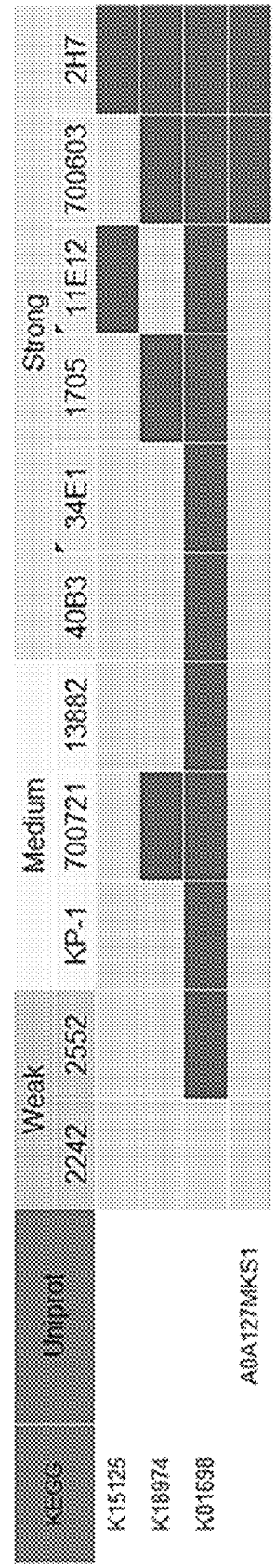
FIG. 21 shows annotations of and information (KEGG or UniProt) on other genes than those in FIGS. 13-20, among the genes related to the induction of the colonic Th1 cells.
FIG. 22 shows the levels of colonic Th1 cells induced by the bacterial strains belonging to *Klebsiella*, and the levels of the other genes the bacterial strains comprise.

FIG. 21 shows annotations of and information (KEGG or UniProt) on other genes than those in FIGS. 13-20, among the genes related to the induction of the colonic Th1 cells.

FIG. 22 shows the levels of colonic Th1 cells induced by the bacterial strains belonging to *Klebsiella*, and the levels of the other genes the bacterial strains comprise.

Meanwhile, although these proteins are specified by particular amino acid sequences (amino acid sequences specified under KEGG or UniProt ID) in FIGS. 13-22, the proteins according to the present invention include not only the proteins specified by these typical amino acid sequences, but also functionally active derivatives thereof, functionally active fragments thereof, homologs thereof, and mutants encoded by nucleic acids capable of hybridizing to nucleic acids encoding the proteins under high stringency conditions or low stringency conditions. In addition, such derivatives, fragments, homologs, or mutants include proteins having a homology of at least 60% (preferably 70%, more preferably 80%, further preferably 90%, furthermore preferably 95%, particularly preferably 99%) with the particular amino acid sequences.

Note that the homology or identity of sequences (amino acid sequences or nucleotide (base) sequences) can be determined using a program (Altschul et al. J. Mol. Biol., 215:403-410, 1990) for BLAST (Basic Local Alignment Search). The program is based on the algorithm BLAST by Karlin and Altschul (Proc. Natl. Acad. Sci. USA, 87:2264-2268, 1990, Proc. Natl. Acad. Sci. USA, 90:5873-5877, 1993). When analyzing homology or identity between sequences by BLAST, determination is possible using, for example, BLAST from the National Center for Biotechnology Information (NCBI) (for example, using default, i.e., initially set parameters).

As shown in FIGS. 13 and 14, the proteins according to the present invention include proteins involved in a metabolism of mannose, fructose, or galactose. Thus, the "bacterium capable of inducing Th1 cell proliferation or activation in an intestinal tract" preferably expresses a gene involved in a metabolism of mannose, fructose, or galactose.

Further, the "bacterium capable of inducing Th1 cell proliferation or activation in an intestinal tract" is preferably a bacterium which belongs to *Klebsiella*, forms no capsule, and induces Th1 cell proliferation or activation in an intestinal tract; more preferably, a bacterium which belongs to *Klebsiella pneumoniae*, forms no capsule, produces outer membrane vesicles (OMV) or OMV-like structures, and induces Th1 cell proliferation or activation in an intestinal tract.

Furthermore, the "bacterium capable of inducing Th1 cell proliferation or activation in an intestinal tract" is preferably a bacterium which belongs to *Klebsiella* and has a flagellum, or preferably a bacterium which belongs to *Klebsiella* and has a stimulatory action on TLR5.

As described above, examples of the "bacterium capable of inducing Th1 cell proliferation or activation in an intestinal tract" of the present invention typically include the Kp2H7 strain, the Ka11E12 strain, the 34E1 strain, the BAA-1705 strain, the 700603 strain, and the 40B3 strain belonging to *Klebsiella*. Of these, the Kp2H7 strain or the Ka11E12 strain is more preferable, and the Kp2H7 strain is particularly preferable. Note that, regarding details of these bacteria, see Table 1.

| Bacterial Name | Supplier | Information from Supplier | Registry number |
| --- | --- | --- | --- |
| KCTC2242 | KOTO | http://kctc.kribb.re.kr/English/_SearchView.aspx?sn = 2242 | NCBI Taxonomy ID: 1049565 |
| BAA-2552 | ATCC | https://www.atcc.org/Products/All/BAA-2552.aspx | NCBI Taxonomy ID: 507522 |
| KP-1 | — | — | NCBI Taxonomy ID: 1365186 |
| 700721 | ATCC | https://www.atcc.org/Products/All/700721.aspx | NCBI Taxonomy ID: 272620 |
| 13882 | JCM | https://www.atcc.org/Products/All/13882.aspx | NCBI Taxonomy ID: 1913574 |
| 40B3 | — | — | SAMD00083913 |
| 34E1 | — | — | SAMD00083911 |
| BAA-1705 | ATCC | https://www.atcc.org/Products/All/BAA-1705.aspx | NCBI Taxonomy ID: 1276652 |
| Ka11E12 | — | — | SAMD00083912 |
| 700603 | ATCC | https://www.atcc.org/Products/All/700603.aspx | NCBI Taxonomy ID: 1276653 |
| Kp2H7 | — | — | SAMD00083910 |

The bacteria belonging to *Klebsiella*, the bacteria belonging to *Klebsiella aeromobilis*, the bacteria belonging to *Klebsiella pneumoniae*, the Kp2H7 strain, the Ka11E12 strain, the 34E1 strain, the BAA-1705 strain, the 700603 strain, and the 40B3 strain can be identified, for example, by determining the nucleotide sequence encoding 16S rRNA (such as the base sequence of 16S rDNA). In addition, these bacteria can also be identified based on a nucleotide sequence specific thereto, and so forth. Note that the nucleotide sequence specific to the Kp2H7 strain or the Ka11E12 strain is not particularly limited. Nevertheless, preferable examples of the nucleotide sequence include nucleotide sequences which the Kp2H7 strain or the Ka11E12 strain has, but which are not found in a BAA-2552 strain and a 700721 strain belonging to the same *Klebsiella* as those strains (more preferably, nucleotide sequences not found in the BAA-2552 strain, a KCTC2242 strain, the KP-1 strain, the 700721 strain, and a 13882 strain).

Note that the 700721 strain, 13882 strain, KP-1 strain, BAA-2552 strain, and KCTC2242 strain are *K. pneumoniae* strains, and have a weak or medium action of inducing the Th1 cell proliferation or activation in the intestinal tract (see FIGS. 13-22 and Table 1 and PTL 1 for these bacteria).

Moreover, the examples of the "bacterium capable of inducing Th1 cell proliferation or activation in an intestinal tract" of the present invention include bacteria comprising a DNA containing a nucleotide sequence having an identity of 90% or more (91% or more, 92% or more, 93% or more, 94% or more, 95% or more, 96% or more, 97% or more, 98% or more, 99% or more) with the nucleotide sequence encoding 16S rRNA of the Kp2H7 strain, the Ka11E12 strain, the 34E1 strain, the BAA-1705 strain, the 700603 strain, or the 40B3 strain. The examples further includes bacteria comprising a DNA containing a nucleotide sequence having a homology or an identity of 70% or more (preferably 80% or more, more preferably 85% or more, further preferably 90% or more, furthermore preferably 95% or more (96% or more, 97% or more, 98% or more, 99% or more) with the nucleotide sequence specific to the Kp2H7 strain, the Ka11E12 strain, the 34E1 strain, the BAA-1705 strain, the 700603 strain, or the 40B3 strain.

In the present invention, the term "Th1 cell" means a subtype of CD4 positive helper T cells (Th cells), and the cell enhances cell-mediated immunity. Moreover, the "activity of Th1 cells" and related terms mean to include: production of Th1 cytokines (such as IFN-γ) by the cells; activation of cells such as macrophages and cytotoxic T cells (CTL) with the cytokines; and enhancement of cell-mediated immunity through the activation. Further, "inducing Th1 cell proliferation or activation" and similar phrases mean to include differentiation induction from naive T cells to Th1 cells, leading to Th1 cell proliferation or activation.

The action of inducing Th1 cell proliferation or activation in an intestine can be evaluated by quantitatively detecting a marker (for example, CD4 and IFN-γ) specific to Th1 cells. Such quantitative detection can be conducted by known methods, for example, detection methods using an antibody (immunological methods) such as flow cytometry, imaging cytometry, ELISA methods, radioimmunoassay, immunohistochemical staining, immunoprecipitation, immunoblotting, and antibody array analyses.

Whether certain bacterium or the like has an action of inducing Th1 cell proliferation or activation in an intestine or not can be determined as follows. For example, if the percentage of IFN-γ$^+$ cells detected in an intestine by flow cytometry is 10% or more among CD4$^+$TCRβ$^+$T cells, it can be determined that the bacterium or the like has an action of inducing Th1 cell proliferation or activation in an intestine (It is preferable to determine that the bacterium or the like has an action of inducing Th1 cell proliferation or activation in an intestine if the percentage is 25% or more. It is more preferably to determine that the bacterium, substance, or the like has an action of inducing Th1 cell proliferation or activation in an intestine if the percentage is 30% or more).

Next, description is provided for intestinal bacteria contained as an active ingredient of the antibacterial composition of the present invention.

(Intestinal Bacterium)

In the present invention, the intestinal bacteria contained as an active ingredient of the antibacterial composition have an antibacterial activity against bacteria capable of inducing Th1 cell proliferation or activation in an intestinal tract.

In the present invention, the "antibacterial activity" means an activity that suppresses bacterial activity, and more specifically an activity that suppresses bacterial growth or colonization or kills bacteria.

The "Intestinal bacteria" means bacteria present in the intestinal tract of an animal. In addition, examples of animals in which such bacteria are present include humans and non-human animals (such as mice, rats, monkeys, pigs, cattle, horses, sheep, goats, chickens, ducks, ostriches, domesticated ducks, dogs, cats, rabbits, and hamsters). Among these animals, humans are preferable.

In the present invention, "intestinal bacteria" may be one strain of bacteria or a mixture of bacterial strains composed of two or more strains. In addition, in the case of two or more bacterial strains, it is desirable that at least one of the bacterial strains has antibacterial activity against Th1 cell-inducible bacteria. In addition, in that case, even in the case of a bacterial strain not having the above-described antibacterial activity, the two or more bacterial strains may include a bacterial strain having an action of enhancing the antibacterial activity of a bacterial strain, a bacterial strain having an action of maintaining the growth of a bacterial strain having the antibacterial activity, or a bacterial strain having an action of suppressing the inhibitory activity of a bacteria that inhibit the antibacterial activity.

In the present invention, examples of "intestinal bacteria" include at least one bacterium having a DNA composed of a base sequence specified at any of SEQ ID NOs: 1 to 147 or a base sequence having at least 70% identity with the base sequence, at least one bacterium having a DNA composed of a base sequence specified at any of SEQ ID NOs: 1 to 68 or a base sequence having at least 70% identity with the base sequence, at least one bacterium having a DNA composed of a base sequence specified at any of SEQ ID NOs: 69 to 105 or a base sequence having at least 70% identity with the base sequence, or at least one bacterium having a DNA composed of a base sequence specified at any of SEQ ID NOs: 106 to 147 or a base sequence having at least 70% identity with the base sequence.

Note that, regarding "at least 70% identity" in the intestinal bacterium of the present invention, the identity with each base sequence is preferably 80% or more, more preferably 85% or more, further preferably 90% or more (for example, 91% or more, 92% or more, 93% or more, 94% or more), more preferably 95% or more (for example, 96% or more, 97% or more, 98% or more), and particularly preferably 99% or more.

In the present invention, the "intestinal bacterium" having a DNA composed of a base sequence specified at any of SEQ ID NOs: 1 to 147 or a base sequence having at least 70% identity with the base sequence is preferably at least 15 bacteria in the intestinal bacterium group, more preferably at least 30 bacteria in the intestinal bacterium group, further preferably at least 75 bacteria in the intestinal bacterium group, more preferably at least 120 bacteria in the intestinal bacterium group, further preferably at least 135 bacteria in the intestinal bacterium group, more preferably at least 140 bacteria in the intestinal bacterium group, further preferably 147 intestinal bacteria each of which has a DNA composed of a base sequence specified at any of SEQ ID NOs: 1 to 147 or a base sequence having at least 70% identity with the base sequence, and particularly preferably 147 bacteria each of which has a DNA composed of a base sequence specified at any of SEQ ID NOs: 1 to 147.

In the present invention, the "intestinal bacterium" having a DNA composed of a base sequence specified at any of SEQ ID NOs: 1 to 68 or a base sequence having at least 90% identity with the base sequence is preferably at least 7 bacteria in the intestinal bacterium group, more preferably at least 15 bacteria in the intestinal bacterium group, further preferably at least 35 bacteria in the intestinal bacterium group, more preferably at least 60 bacteria in the intestinal bacterium group, further preferably at least 65 bacteria in the intestinal bacterium group, more preferably 68 intestinal bacteria each of which has a DNA composed of a base sequence specified at any of SEQ ID NOs: 1 to 68 or a base sequence having at least 70% identity with the base sequence, and particularly preferably 68 bacteria each of which has a DNA composed of a base sequence specified at any of SEQ ID NOs: 1 to 68. In addition, the "intestinal bacterium" having a DNA composed of a base sequence specified at any of SEQ ID NOs: 1 to 68 or a base sequence having at least 70% identity with the base sequence is desirably resistant to ampicillin. In addition, as shown in the Examples to be described later, 46 bacteria each having a DNA composed of a base sequence specified at any of SEQ ID NOs: 1 to 46 or a base sequence having at least 70% identity with the base sequence are also used suitably in the present invention.

In the present invention, the "intestinal bacterium" having a DNA composed of a base sequence specified at any of SEQ ID NOs: 69 to 105 or a base sequence having at least 70% identity with the base sequence is preferably at least 4 bacteria in the intestinal bacterium group, more preferably at least 8 bacteria in the intestinal bacterium group, further preferably at least 19 bacteria in the intestinal bacterium group, more preferably at least 30 bacteria in the intestinal bacterium group, further preferably at least 33 bacteria in the intestinal bacterium group, more preferably at least 35 bacteria in the intestinal bacterium group, further preferably 37 intestinal bacteria each of which has a DNA composed of a base sequence specified at any of SEQ ID NOs: 69 to 105 or a base sequence having at least 70% identity with the base sequence, and particularly preferably 37 bacteria each of which has a DNA composed of a base sequence specified at any of SEQ ID NOs: 69 to 105. In addition, the "intestinal bacterium" having a DNA composed of a base sequence specified at any of SEQ ID NOs: 69 to 105 or a base sequence having at least 70% identity with the base sequence is desirably susceptible to ampicillin.

In the present invention, the "intestinal bacterium" having a DNA composed of a base sequence specified at any of SEQ ID NOs: 106 to 147 or a base sequence having at least 70% identity with the base sequence is preferably at least 4 bacteria in the intestinal bacterium group, more preferably at least 9 bacteria in the intestinal bacterium group, further preferably at least 22 bacteria in the intestinal bacterium group, more preferably at least 34 bacteria in the intestinal bacterium group, further preferably at least 39 bacteria in the intestinal bacterium group, more preferably at least 41 bacteria in the intestinal bacterium group, further preferably 42 intestinal bacteria each of which has a DNA composed of a base sequence specified at any of SEQ ID NOs: 106 to 147 or a base sequence having at least 70% identity with the base sequence, and particularly preferably 42 bacteria each of which has a DNA composed of a base sequence specified at any of SEQ ID NOs: 106 to 147. In addition, the "intestinal bacterium" having a DNA composed of a base sequence specified at any of SEQ ID NOs: 106 to 147 or a base sequence having at least 70% identity with the base sequence is desirably susceptible to ampicillin.

In addition, as shown in Examples to be described later, an aspect of the "intestinal bacterium" in the present invention is an intestinal bacterium which is resistant to at least one compound selected from the group consisting of spectinomycin, and/or susceptible to at least one compound selected from the group consisting of ampicillin, tylosin, and chloroform. In addition, another aspect is an intestinal bacterium which is resistant to metronidazole and/or susceptible to at least one compound selected from the group consisting of vancomycin and tylosin.

<Antibacterial Composition and Pharmaceutical Composition>

The composition of the present invention only needs to contain the above-described intestinal bacteria, and the bacteria may be living cells or dead cells. Alternatively, the composition can be used in combination. As a result of the combinational use, when the composition is provided or absorbed (when the composition is used in combination), the above-described intestinal bacteria may exist separately in two or more compositions.

The composition of the present invention may be in the form of a pharmaceutical composition, a food or drink (including an animal feed), or a reagent used for a research purpose (for example, in vitro or in vivo experiment).

The composition of the present invention suppresses the immunity and the Th1 cell induction in an intestine by the bacterium capable of inducing Th1 cell proliferation or activation in an intestinal tract. Accordingly, the composition of the present invention is suitably used as a pharmaceutical composition, food, or drink for treating, preventing, or alleviating the disease attributable to Th1 cells.

The composition of the present invention can be formulated by known formulation methods. The composition can be used for administration orally, parenterally (for example, intestinally, intramuscularly, intravenously, intratracheally, intranasally, transdermally, intradermally, subcutaneously, intraocularly, intravaginally, intraperitoneally, rectally or by inhalation), or through multiple routes consisting of a combination of these, in the form of, for example, a capsule, a tablet, a pill, a liquid, a powder, a granule, a fine granule, a film coating agent, a pellet, a troche, a sublingual tablet, a masticatory, a buccal, a paste, a syrup, a suspension, an elixir, an emulsion, an endermic liniment, an ointment, a plaster, a poultice, a percutaneous absorption preparation, a lotion, an inhalation, an aerosol, an injection, a suppository, or the like.

When formulated, these can be combined as appropriate with a pharmacologically acceptable carrier or a carrier acceptable as a food or drink, concretely, sterile water, a saline, a buffer solution, a medium, a vegetable oil, a solvent, a base, an emulsifier, a suspension, a surfactant, a stabilizer, a flavor, an aromatic substance, an excipient, a vehicle, an antiseptic, a binder, a diluent, an isotonic agent, a soothing agent, a filler, a disintegrant, a buffer, a coating agent, a lubricant, a colorant, a sweetener, a viscous agent, a corrigent, a solubilizer, or other additives.

Meanwhile, in these formulations, from the viewpoints such as more efficiently suppressing the immunity and the Th1 cell proliferation or activation in an intestine, particularly in formulating a pharmaceutical preparation for oral administration, the composition of the present invention may be combined with a composition which enables an efficient delivery to an intestine. Such a composition enabling the delivery to an intestine is not particularly limited, and known compositions can be employed as appropriate. Examples thereof include pH sensitive compositions, compositions for suppressing the release into the intestinal tract (such as cellulose-based polymers, acrylic acid polymers and copolymers, vinyl acid polymers and copolymers), bioadhesive compositions which specifically adhere to mucosas of the intestinal tract (for example, a polymer described in the specification of U.S. Pat. No. 6,368,586), protease inhibitor-containing compositions, and compositions specifically degraded by enzymes in the intestine).

In addition, in the case where the antibacterial composition of the present invention is used as a pharmaceutical composition, the composition may further comprise a known substance (for example, an anti-inflammatory agent, an immunosuppressant) used for treating, preventing, or alleviating a disease attributable to Th1 cells, or may be used in combination with such a substance.

In the case where the composition of the present invention is used as a food or drink, the food or drink may be, for example, a health food, a functional food, a food for specified health use, a food with nutrient function claims, a function-labeled food, a nutritional supplementary food, a medical food for the ill, or an animal feed. Concrete examples of the food or drink include liquid foods such as fermented drinks, oil-containing products, soups, dairy drinks, refreshing drinks, tea drinks, alcoholic drinks, energy drinks, and jelly drinks, carbohydrate-containing foods, livestock-processed foods, processed seafoods; vegetable-processed foods, semi-solid foods, fermented foods, confectionaries, retort pouch foods, microwave foods, and the like. The examples further include health foods or drinks prepared in the form of powder, granule, tablet, capsule, liquid, paste, or jelly. Note that, in the present invention, the food or drink can be produced by production techniques known in this technical field. To the food or drink, an active ingredient (for example, a nutrient or the like) for alleviating or preventing a disease attributable to Th1 disease may be added. Moreover, in combination with another ingredient or another functional food which exhibit a function other than the alleviation or the like, a multi-functional food or drink can be prepared.

A product (drug, food, drink, reagent) of the composition of the present invention or a manual thereof may be provided with an indication stating that the product is used for suppressing Th1 cell proliferation or activation, or treating, alleviating, or preventing a disease attributable to Th1 cells. Meanwhile, in the case of the food or drink, the product of the composition or the like of the present invention may be provided with an indication of the health function as a health functional food (a food for specified health use, a food with nutrient function claims, a function-labeled food) to be distinguished from general foods by the appearance, target persons, and so forth. Herein, "a product or a manual provided with an indication" means that the indication is attached to the main body, container, package, or the like of the product, or that the indication is provided in the manual, package insert, advertisement, other printed materials, or the like disclosing information on the product. Further, the composition of the present invention may be in the form of a kit.

In addition, as described above, a pharmaceutical composition can be produced by a known formulation technique using the intestinal bacterium and the like of the present invention. Therefore, the present invention also provides use of the intestinal bacterium and the like of the present invention for producing a pharmaceutical composition for treating, alleviating, or preventing a disease attributable to Th1 cells.

<Bacteria Having Antibacterial Activity Against Bacteria that Induce Th1 Cells in Intestinal Tract>

Regarding the present invention, as shown in FIG. 1, intestinal colonization of the Kp2H7 strain was not observed when the Kp2H7 strain was orally administered to SPF mice. However, it has been clarified that administration of ampicillin or tylosin to SPF mice allows the Kp2H7 strain to colonize in the mouse intestine. On the other hand, is has also been found by the present inventors that administration of metronidazole or spectinomycin to SPF mice does not cause intestinal colonization of the Kp2H7 strain.

Figure 2:
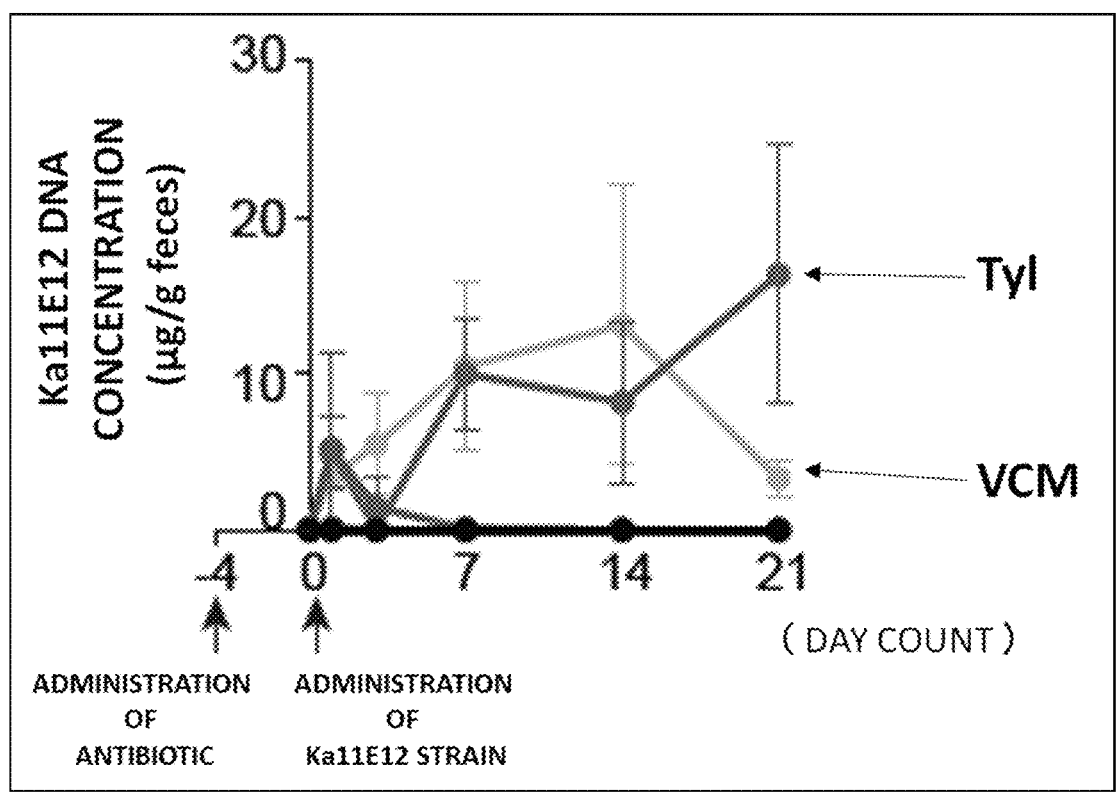
FIG. 2 is a graph illustrating the results of qPCR analysis of the change over time of the intestinal colonization level of a Ka11E12 strain in SPF mice administered with various antibiotics and then fed with the strain.
Figure 3:
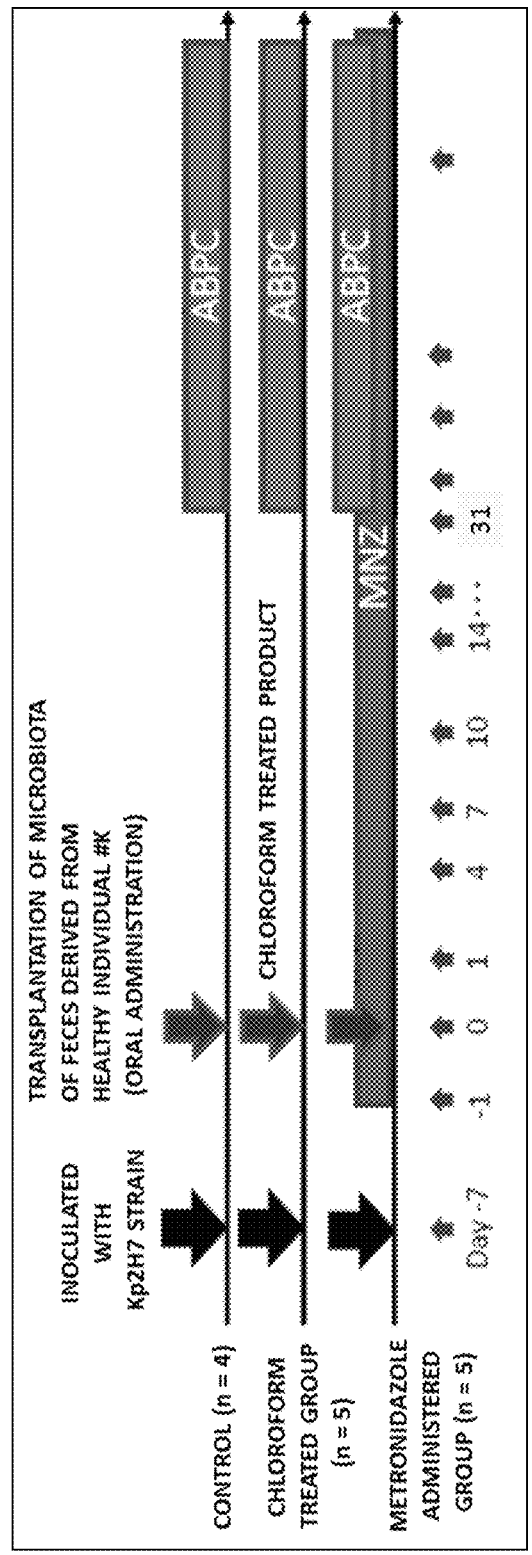
FIG. 3 is a diagram illustrating an overview of an experiment of administering fecal samples derived from a healthy individual (#K) to germ-free mice inoculated with the Kp2H7 strain.

In addition, germ-free mice were orally administered with the Kp2H7 strain, and were further provided with human (healthy individual) fecal samples. As a result, as shown in FIGS. 2 and 3, intestinal colonization of the Kp2H7 strain was not observed as in the above-described SPF mice. However, it has been revealed that the Kp2H7 strain is allowed to colonize in the mouse intestine when provided with a sample obtained by treating human feces with chloroform having a final concentration of 3%. On the other hand, it has also been found by the present inventors that administration of metronidazole to germ-free mice does not cause intestinal colonization of the Kp2H7 strain as in the above-described SPF mice. That is, the present inventors have also revealed for the first time that, in intestinal bacteria, there are bacteria that suppress colonization and the like of bacteria that induce Th1 cells in the intestinal tract.

Therefore, the present invention provides a bacterium having antibacterial activity against bacteria that induce Th1 cell proliferation or activation in the intestinal tract. Such a bacterium only needs to have the antibacterial activity, and examples thereof include the intestinal bacteria described above.

In addition, whether bacteria have the above-described antibacterial activity can be evaluated using the method or screening method described in Examples to be described later.

<Methods for Treating Disease Attributable to Th1 Cells, and the Like>

The present invention also provides a method for suppressing the proliferation or activation of Th1 cells in a subject, a method for suppressing immunity in the subject, or a method for treating, alleviating, or preventing a disease attributable to Th1 cells in the subject, the method comprising providing the subject with the above-described antibacterial composition or pharmaceutical composition, or the above-described intestinal bacterium or the above-mentioned bacterium having antibacterial activity, the bacteria serving as active ingredients of the compositions (hereinafter also collectively referred to as "the pharmaceutical and other compositions of the present invention or the active ingredients thereof").

In the present invention, the term "disease attributable to Th1 cells" means a disease induced by the Th1 cell proliferation or activation. Examples of the disease include inflammatory bowel diseases (chronic inflammatory bowel diseases such as Crohn's disease, ulcerative colitis, and inflammatory bowel diseases, and the like), diabetes mellitus type 1, autoimmune diseases such as rheumatoid arthritis, experimental autoimmune encephalomyelitis (EAE), multiple sclerosis, and systemic lupus erythematosus, and chronic inflammatory diseases. In addition, the "immunity" to be suppressed in the present invention includes not only mucosal immunity (such as intestinal immunity) but also general immunity. Moreover, the "immunity" includes not only cell-mediated immunity but also humoral immunity.

The pharmaceutical and other compositions of the present invention or the active ingredients thereof can be used for animals including human as the subject. The animals other than human are not particularly limited, and various domestic animals, poultry, pet animals, experimental animals, and the like can be the subject.

Moreover, the subject to be provided with the intestinal bacterium and the like of the present invention includes animals comprising the Th1 cell-inducible bacterium, regardless of the development of the disease attributable to Th1 cells. In addition, from the viewpoint of the prevention, animals which do not comprise or may comprise the bacterium may be provided with the pharmaceutical and other compositions of the present invention or the active ingredients thereof.

The method for providing the pharmaceutical and other compositions of the present invention or the active ingredients thereof is not particularly limited. They may be orally administered, or may be parenterally administered (for example, administered into an intestine). In the case of oral administration, from the viewpoint of further enhancing the effects of the pharmaceutical and other compositions of the present invention or the active ingredients thereof, the subject to be provided with the pharmaceutical and other compositions of the present invention or the active ingredients thereof is preferably provided with a proton-pump inhibitor (PPI) or the like in advance to reduce the production of gastric acid.

Moreover, when the pharmaceutical and other compositions of the present invention or the active ingredients thereof are provided, the amount provided can be selected as appropriate by those skilled in the art, depending on the age, body weight, disease symptom, and health state of the subject, the type of the composition (such as drug, food, drink), the providing method, and so forth.

<Composition for Testing for Disease Attributable to Th1 Cells>

As described above, the present invention has revealed the presence of intestinal bacteria that can suppress the colonization and the like of the Th1 cell-inducible bacteria in the intestinal tract. Hence, a disease attributable to Th1 cells can be tested by detecting the presence of the intestinal bacterium.

Thus, the present invention provides the following compositions for testing for a disease attributable to Th1 cells.

A composition for testing for a disease attributable to Th1 cells, the composition comprising an antibody capable of specifically recognizing the intestinal bacterium and the like of the present invention.

A composition for testing for a disease attributable to Th1 cells, the composition comprising a polynucleotide for detecting a nucleotide sequence specific to the intestinal bacterium and the like of the present invention.

In the present invention, the "antibody capable of specifically recognizing the intestinal bacterium and the like of the present invention" may be a polyclonal antibody, a monoclonal antibody, or a functional fragment of an antibody (for example, Fab, Fab', F(ab')2, a variable region fragment (Fv), a disulfide-stabilized Fv, a single-chain Fv (scFv), sc(Fv)2, a diabody, a polyspecific antibody, or polymers thereof), as long as it is possible to specifically recognize the bacterium. If the antibody of the present invention is a polyclonal antibody, the polyclonal antibody can be obtained as follows. Concretely, a host animal is immunized with an antigen (such as a polypeptide, a polynucleotide, a carbohydrate, or a lipid derived from the intestinal bacterium and the like of the present invention). Then, an antiserum from the animal is purified by conventional means (for example, salting-out, centrifugation, dialysis, column chromatography, or the like). Thus, the polyclonal antibody can be obtained. Meanwhile, a monoclonal antibody can be prepared by a hybridoma method or a recombinant DNA method.

Moreover, as the antibody used in the test of the present invention, an antibody bound to a labeling substance can be used. Detecting the labeling substance enables direct measurement of the amount of the antibody bound to the intestinal bacterium and the like of the present invention or a substance derived from the bacterium. The labeling substance is not particularly limited, as long as the labeling substance can bind to the antibody and can be detected by a chemical or optical method. Examples of the labeling substance include fluorescent dyes (such as GFP), enzymes (such as HRP), and radioactive substances.

The testing composition of the present invention may comprise other ingredients acceptable as a composition than the antibody ingredient. Examples of such other ingredients includes carriers, excipients, disintegrants, buffers, emulsifiers, suspensions, stabilizers, preservatives, antiseptics, physiological salts, labeling substances, and secondary antibodies. Further, besides the testing composition, a substrate necessary for detection of the labeling substance, a positive control or a negative control, a buffer solution used to dilute or wash a sample, a tube or a plate used for the reaction between the sample and the antibody of the present invention, or the like can be combined, so that a kit for testing for a disease attributable to Th1 cells can also be provided. Meanwhile, in a case where the antibody preparation is an unlabeled antibody, a labeled substance (for example, secondary antibody, Protein G, Protein A, or the like) capable of binding to the antibody can be combined. Additionally, the kit for testing for a disease attributable to Th1 cells may comprise an instruction for the kit.

Further, the testing composition of the present invention can also be combined with a device for detecting the antibody of the present invention. Examples of the device include flow cytometers and microplate readers.

In the present invention, the "polynucleotide for detecting a nucleotide sequence specific to the intestinal bacterium and the like of the present invention" is not particularly limited, as long as the sequence specific to the bacterium is detected. Examples of the polynucleotide include any polynucleotides according to the following (a) and (b) each of which has a chain length of at least 15 nucleotides:

(a) a polynucleotide that is a pair of primers designed to flank the specific nucleotide sequence; and (b) a polynucleotide that is a primer or a probe capable of hybridizing to a nucleotide sequence containing the specific nucleotide sequence.

The polynucleotide of the present invention has a base sequence complementary to a nucleotide sequence of the intestinal bacterium and the like of the present invention. Herein, being "complementary" does not always have to be completely complementary, as long as the hybridization is possible. These polynucleotides have a homology of normally 80% or more, preferably 90% or more, more preferably 95% or more, and particularly preferably 100%, with the nucleotide sequence.

The "chain length" of the polynucleotide of the present invention is normally 15 to 100 nucleotides, preferably 17 to 30 nucleotides, and more preferably 20 to 25 nucleotides, in the case where the polynucleotide is used as the primer. Meanwhile, in the case where the polynucleotide is used as the probe, the chain length is normally 15 to 1000 nucleotides, and preferably 20 to 100 nucleotides.

The polynucleotide of the present invention may be a DNA or an RNA, or may have part or all of the nucleotide substituted with an artificial nucleic acid such as LNA (registered trademark, locked nucleic acid), ENA (registered trademark, 2'-0,4'-C-Ethylene-bridged nucleic acids), GNA (glycerol nucleic acid), TNA (threose nucleic acid), or PNA (peptide nucleic acid).

Note that the polynucleotide of the present invention can be chemically synthesized by using a commercially-available automated nucleotide synthesizer or the like. Moreover, as the polynucleotide used in the test of the present invention, a polynucleotide bound to a labeling substance can be used. The labeling substance is not particularly limited, as long as the labeling substance can bind to the polynucleotide and can be detected by a chemical or optical method. Examples of the labeling substance include fluorescent dyes (such as DEAC, FITC, R6G, TexRed, Cy5), dyes (chromogens) such as DAB other than the fluorescent dyes, enzymes, and radioactive substances.

The testing composition of the present invention may comprise other pharmacologically acceptable ingredients than the above-described polynucleotide. Examples of such other ingredients include buffers, emulsifiers, suspensions, stabilizers, antiseptics, physiological salts, and the like.

Further, besides the testing composition, a preparation such as a substrate necessary for detection of the labeling substance added to the polynucleotide, a positive control or a negative control, or a buffer solution used to dilute or wash a sample can be combined, and a tube or a plate used for the reaction between the sample and the polynucleotide of the present invention, or the like can be combined, so that a kit for testing for a disease attributable to Th1 cells can also be provided. Furthermore, the kit for testing for a disease attributable to Th1 cells may comprise an instruction for the kit.

Further, the testing composition of the present invention can also be combined with a device for detecting the nucleotide sequence specific to the intestinal bacterium and the like of the present invention. Examples of the device include thermal cyclers, sequencers, and microarrays.

Moreover, the present invention also provides a method for testing for a disease attributable to Th1 cells by using the above-described antibody, polynucleotide, or testing composition. To be more specific, the present invention provides a method for testing for a disease attributable to Th1 cells, the method comprising the steps of:

bringing the antibody, polynucleotide, or testing composition into contact with a sample isolated from a subject; and detecting the presence or absence of the intestinal bacterium and the like of the present invention in an intestine, as a result of the contact.

The subject is not particularly limited, and includes animals, such as human, which may have a disease attributable to Th1 cells. Moreover, the sample isolated from such a subject is not particularly limited, either, and a fecal sample of the subject, a culture thereof, a polypeptide, a polynucleotide, a carbohydrate, or a lipid extracted therefrom, or the like is suitably used in the method of the present invention.

Examples of the method for detecting the presence or absence of the intestinal bacterium and the like of the present invention by bringing the antibody of the present invention or the testing composition comprising the antibody into contact with the sample include detection methods using an antibody (immunological methods) such as ELISA methods, immunoblotting, antibody array analyses, immunohistochemical staining, flow cytometry, imaging cytometry, radioimmunoassay, and immunoprecipitation.

Meanwhile, as the method for detecting the presence or absence of the intestinal bacterium and the like of the present invention by bringing the polynucleotide of the present invention or the testing composition comprising the polynucleotide into contact with the sample, it is possible to employ, for example, PCR (RT-PCR, real-time PCR, quantitative PCR), DNA microarray analysis, northern blotting, 16s rRNA sequencing, a new generation sequencing method (sequencing-by-synthesis, for example, sequencing using SOLEXA genome analyzer or HISEQ (registered trademark) 2000 manufactured by Illumina, Inc.), pyrosequencing (for example, sequencing using a sequencer GSLX or FLX manufactured by Roche Diagnostics K. K. (454) (what is called 454 sequencing)), sequencing by ligation (for example, sequencing using SOLID (registered trademark) or 5500xl manufactured by Life Technologies Corporation), bead array method, in situ hybridization, dot blot, RNase protection assay, mass spectrometry, genomic PCR, or Southern blotting.

In the present invention, "testing" a disease attributable to Th1 cells includes testing not only whether the disease has developed or not, but also the risk of the development. If the presence of the intestinal bacterium and the like of the present invention in an intestine is detected by the above-described method, it can be determined that a disease attributable to Th1 cells has not developed or that the risk of the development is low.

A disease attributable to Th1 cells in a subject is normally diagnosed by a doctor (including one instructed by the doctor). The data obtained by the method of the present invention are useful in the diagnosis by a doctor. Thus, the method of the present invention can also be described as a method for collecting and presenting data useful in a diagnosis by a doctor.

Additionally, the present invention can also provide a companion diagnostic method utilizing the above-described test method and a drug used in the companion diagnostic method. Accordingly, the present invention also provides the following.

A method for determining effectiveness of pharmaceutical and other compositions of the present invention or active ingredients thereof in treating, alleviating, or preventing a disease attributable to Th1 cells, the method comprising the steps of:

bringing the antibody, polynucleotide, or testing composition into contact with a sample isolated from a subject;

detecting the presence or absence of the intestinal bacterium and the like, as a result of the contact; and determining that the effectiveness of the pharmaceutical and other compositions of the present invention or the active ingredients thereof in treating, alleviating, or preventing the disease is high for the subject, if the presence of the bacterium is not detected in the previous step.

A method for treating, alleviating, or preventing a disease attributable to Th1 cells, the method comprising providing pharmaceutical and other compositions of the present invention or active ingredients thereof to a patient for whom the effectiveness of the pharmaceutical and other compositions or the active ingredients thereof has been determined to be high according to the above-described determination method.

A composition for treating, alleviating, or preventing a disease attributable to Th1 cells, the composition comprising, as an active ingredient, an intestinal bacterium and the like of the present invention, wherein the composition is provided to a subject for whom/which the effectiveness has been determined to be high according to the above-described determination method.

<Method for Screening Intestinal Bacterium Having Antibacterial Activity Against Bacterium Capable of Inducing Th1 Cell Proliferation or Activation in Intestinal Tract>

As described above, the present inventors have also revealed for the first time that, in intestinal bacteria, there are bacteria that suppress colonization and the like of bacteria that induce Th1 cells in the intestinal tract. Therefore, the present invention provides a method for screening an intestinal bacterium having antibacterial activity against a bacterium capable of inducing Th1 cell proliferation or activation in an intestinal tract, the method comprising the following steps;

providing a non-human germ-free animal with a bacterium capable of inducing Th1 cell proliferation or activation in an intestinal tract and a test intestinal bacterium;

detecting the bacterium capable of inducing Th1 cell proliferation or activation in an intestinal tract of the non-human germ-free animal; and determining that the test intestinal bacterium is an intestinal bacterium having antibacterial activity against a bacterium capable of inducing Th1 cell proliferation or activation in an intestinal tract, if the number of bacteria detected in the previous step is reduced compared to a case where the test intestinal bacteria are not provided.

The "bacterium capable of inducing Th1 cell proliferation or activation in an intestinal tract" is as described above. The "non-human germ-free animal" means an animal born and grown under a germ-free condition, excluding human. Examples of the animals other than human include mice, rats, monkeys, pigs, cattle, horses, sheep, goats, chickens, ducks, ostriches, domesticated ducks, dogs, cats, rabbits, hamsters, and the like, but are not limited thereto. Additionally, among these animals, mice are suitably used.

The test intestinal bacteria to be provided to the non-human germ-free animal may be bacteria present in the intestines of animals. Examples of the animal include humans and non-human animals (such as mice, rats, monkeys, pigs, cattle, horses, sheep, goats, chickens, ducks, ostriches, domesticated ducks, dogs, cats, rabbits, and hamsters). In addition, the intestinal bacteria to be provided to the non-human germ-free animal may be isolated intestinal bacteria, and includes a sample containing intestinal bacteria (for example, a fecal sample of the animal or a culture thereof).

In addition, the method for "providing" a non-human animal with the test intestinal bacterium and the Th1 cell-inducible bacterium is not particularly limited. Normally, the bacteria are orally administered, but may be parenterally administered (for example, administered into an intestine). Additionally, the test intestinal bacterium and the Th1 cell-inducible bacterium may be provided simultaneously, the test intestinal bacterium may be provided to the non-human animal and then the Th1 cell-inducible bacterium may be provided to the animal, or the Th1 cell-inducible bacterium may be provided to the non-human animal and then the test intestinal bacterium may be provided to the animal.

The Th1 cell-inducible bacteria in the intestinal tract can be "detected" by detecting a nucleotide sequence specific to the Th1 cell-inducible bacteria. Examples of the detection method include PCR (RT-PCR, real-time PCR, quantitative PCR), DNA microarray analysis, northern blotting, 16s rRNA sequencing, a new generation sequencing method (sequencing-by-synthesis, for example, sequencing using Solexa genome analyzer or Hiseq (registered trademark) 2000 manufactured by Illumina, Inc.), pyrosequencing (for example, sequencing using a sequencer GSLX or FLX manufactured by Roche Diagnostics K. K. (454) (what is called 454 sequencing)), sequencing by ligation (for example, sequencing using SoliD (registered trademark) or 5500xl manufactured by Life Technologies Corporation), bead array method, in situ hybridization, dot blot, RNase protection assay, mass spectrometry, genomic PCR, or Southern blotting.

In addition, the Th1 cell-inducible bacteria in the intestinal tract can be "detected" by detecting, for example, an amino acid sequence specific to the Th1 cell-inducible bacteria. Examples of the detection method include detection methods using an antibody (immunological methods) such as ELISA methods, immunoblotting, antibody array analyses, immunohistochemical staining, flow cytometry, imaging cytometry, radioimmunoassay, and immunoprecipitation.

Moreover, the timing of the detection is not particularly limited, and can be adjusted as appropriate by those skilled in the art, depending on the type of the animal used, and so forth.

Note that if the intestinal bacterium having antibacterial activity against the bacterium capable of inducing Th1 cell proliferation or activation in an intestinal tract cannot be obtained by performing the screening method of the present invention one time, the obtained bacterium-containing sample in the intestine is provided as the next test intestinal bacterium to another non-human germ-free animal, and the above-described screening is performed multiple times, so that the intestinal bacterium having antibacterial activity can be isolated.

EXAMPLES

Hereinafter, the present invention will be described more specifically based on Examples. However, the present invention is not limited to the following Examples.

Example 1

<Colonization of Th1 Cell-Inducible Bacterium in Antibiotic-Treated Mice>

Prior to gavage of Th1 cell-inducible bacteria, the following antibiotics were administered to SPF mice (wild type C57BL/6) through the drinking water for 4 days. Moreover, mice without these antibiotics administered were also prepared. Antibiotics: ampicillin (200 mg/L), tylosin (500 mg/L), metronidazole (500 mg/L), spectinomycin (200 mg/L), vancomycin (200 mg/L).

The Kp2H7 strain or the Ka11E12 strain, which is a Th1 cell-inducible bacterium, was cultured to log phase in LB broth, and 1 to $2 \times 10^8$ CFUs were used to inoculate the mice.

Feces were collected 1, 3, 7, 14, and 21 days after the gavage of Th1 cell-inducible bacteria, and DNAs were extracted therefrom. Then, these DNAs were used as templates to perform qPCR using the following primers specific to each bacterial strain, thereby evaluating the intestinal colonization level of each bacterial strain.

*Klebsiella* (ompK36-3_F: 5'-GCGACCAGACCTACAT GCGT-3' [SEQ ID NO: 148], ompK36-3_R: 5'-AGT CGAAAGAGCCCGCGTC-3' [SEQ ID NO: 149]), Kp-2H7 (sca4_298_F: 5'-AGCACTAGCGGCTGTGGTAT-3' [SEQ ID NO: 150], sca4_298_R: 5'-ACTTACTCGGGCCCTT-GATT-3' [SEQ ID NO: 151]), Ka-11E12 (group_4037_F: 5'-CTTCGCCTTCATCAGCTTCA-3' [SEQ ID NO: 152], group_4037_R: 5'-TCATCATTAACGCGGGTCAG-3' [SEQ ID NO: 153])

FIG. 1 and FIG. 2 show the obtained results.

As described in PTL 1, the present inventors have revealed that, when administered to germ-free mice, the Kp2H7 strain colonizes in their intestinal tract and induces Th1 cells. In addition, the present inventors have confirmed that the bacterial strain is a bacterial strain which is resistant to ampicillin, tylosin, metronidazole, or spectinomycin.

However, when the Kp2H7 strain was administered to SPF mice, colonization of the bacterial strain in the intestinal tract was not observed unlike the case of administration to germ-free mice, as shown in FIG. 1.

Interestingly, in the SPF mice administered with metronidazole or spectinomycin, the Kp2H7 strain was resistant to these antibiotics, but no intestinal colonization of the bacterial strain was observed. On the other hand, intestinal colonization of the Kp2H7 strain was observed in the SPF mice administered with ampicillin or tylosin (see "Amp" and "Tyl" in FIG. 1).

Additionally, as described in PTL 1, the present inventors have revealed that, when administered to germ-free mice, the Ka11E12 strain also colonizes in their intestinal tract and induces Th1 cells. Moreover, the present inventors have confirmed that the bacterial strain is a bacterial strain which is resistant to vancomycin, tylosin, or metronidazole.

However, as in the case of the Kp2H7 strain, when the Ka11E12 strain was administered to SPF mice, colonization of the bacterial strain in the intestinal tract was not observed unlike the case of administration to germ-free mice, as shown in FIG. 2.

On the other hand, colonization of the Ka11E12 strain in the intestinal tract was observed in the SPF mice administered with vancomycin or tylosin (see "VCM" and "Tyl" in FIG. 2).

The above results suggest that antibiotic exposure suppressed the resistance to intestinal colonization of oral-derived Th1 cell-inducible bacteria caused by specific bacteria in the intestinal microbiota (such as bacteria resistant to ampicillin and tylosin but susceptible to metronidazole and spectinomycin, and bacteria resistant to metronidazole but susceptible to vancomycin and tylosin), thereby enhancing the intestinal colonization.

Example 2

<Administration of Human Fecal Sample to Germ-Free Mice Inoculated with Th1 Cell-Inducible Bacteria 1>

As shown in FIG. 3, germ-free mice were inoculated with the Kp2H7 strain in the same manner as in Example 1. Then, one week after the inoculation, a human fecal sample collected from a healthy individual (#K) was orally administered. In addition, during the period of 31 to 94 days after the oral administration, ampicillin was continuously administered in the same manner as in Example 1 (hereinafter, the mice thus treated is also referred to as the "controls").

In addition, germ-free mice were treated in the same manner as for the control except for orally administering the sample treated with chloroform at a final concentration of 3% instead of the human fecal sample (hereinafter, the mice thus treated are also referred to as the "chloroform treated group").

Moreover, germ-free mice were treated in the same manner as for the control except that metronidazole was continuously administered in the same manner as in Example 1 from one day before oral administration of human fecal sample (hereinafter, the mice thus treated are also referred to as the "metronidazole administered group").

Figure 4:
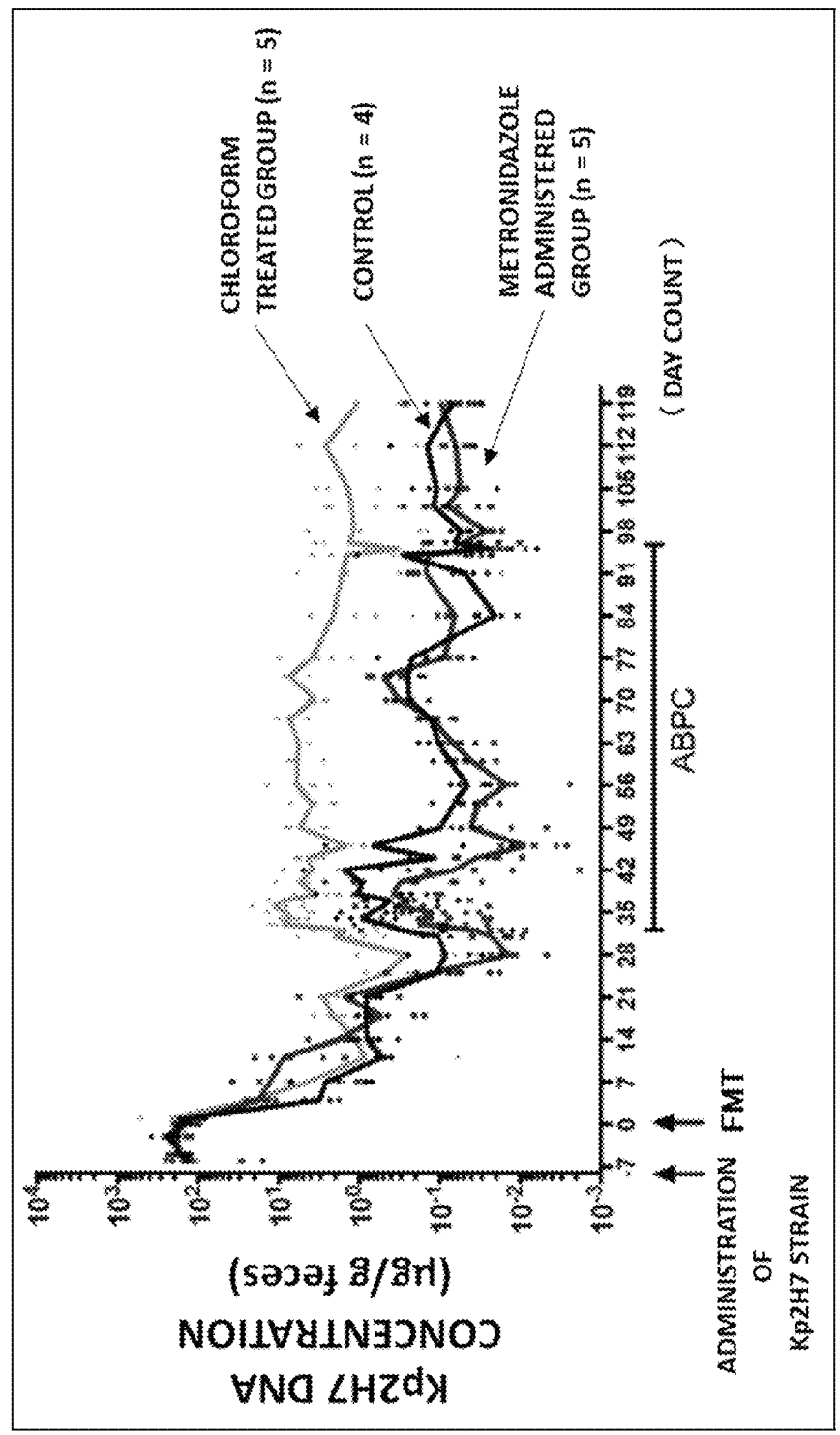
FIG. 4 is a graph illustrating the results of qPCR analysis of the change over time of the intestinal colonization level of a Kp2H7 strain in germ-free mice inoculated with the Kp2H7 strain and then fed with fecal samples derived from a healthy individual (#K).

Then, feces of the SPF mice thus treated were collected, and the intestinal colonization level of the Kp2H7 strain was evaluated by qPCR in the same manner as Example 1. FIG. 4 shows the obtained results.

As is apparent from the results shown in FIG. 4, the germ-free mice were orally administered with the Kp2H7 strain and further provided with human (healthy human) fecal samples, and as a result, intestinal colonization of the Kp2H7 strain was not observed as in the SPF mice. However, it was revealed that the Kp2H7 strain can colonize in the mouse intestine when provided with a sample obtained by treating human feces with chloroform. Meanwhile, as in the SPF mice, administration of metronidazole to germ-free mice did not cause intestinal colonization of the Kp2H7 strain.

Example 3

<Administration of Human Fecal Sample to Germ-Free Mice Inoculated with Th1 Cell-Inducible Bacteria 2>

Preparation of Fecal Sample

Feces (#K fecal sample, #F fecal sample, and #I fecal sample) provided from healthy volunteers (#K, F, and I) were diluted 5 times by weight with a glycerol PBS solution (final concentration of glycerol: 20% by volume) and filtered through a 100 μm-diameter filter, and the resultant was stored at −80° C. as a stock solution. Note that the healthy volunteer #K in the present example and the healthy individual #K in Example 2 are the same person.

Preparation of Kp2H7 Single-Bacterium-Colonized Mice

C57BL/6N Jcl gnotobiotic mice (manufactured by CLEA Japan, Inc., 4 to 8 weeks of age) were bred in a breeding vinyl isolator (sterile isolator) (manufactured by ICM Inc.; ICM-1B) for 1 week or more under free drinking and feeding conditions to acclimatize to the environment.

The Kp2H7 strain was cultured in a Schaedler blood medium, an LB medium, or an agar plate thereof in an anaerobic environment at 37° C. and 10% $CO_2$. A suspension at 200 μL of any of the above media containing $1\times10^{10}$ CFU equivalent Kp2H7 was orally administered into the stomach of mice of 8 to 11 weeks of age. Thereafter, the mice were bred in a sterile isolator for 1 week to prepare Kp2H7 single-bacterium-colonized mice.

Colonization of Bacteria by Fecal Transplantation

The stock solution of each fecal sample prepared as described above was melted at room temperature and diluted to 10 times volume with PBS. The diluted solution at 200 μL was orally administered into the stomach of Kp2H7 single-bacterium-colonized mice. Moreover, for one month, the mice were bred in a sterile isolator under free drinking and feeding conditions, and the bacteria in the transplanted feces were colonized in the mice.

Elimination of Colonized Bacteria by Administration of Antibiotic Ampicillin

After the culture for 1 month, the free drinking water was changed to a 200 mg/L aqueous solution of ampicillin, and the mice were further bred for 1 month to eliminate ampicillin non-resistant bacteria.

Measurement of Intestinal Kp2H7 Colonization Level

The qPCR measurement of CFU and intestinal bacterium genome was used to obtain the abundance ratio of Kp2H7 strains colonized in the intestine of the Kp2H7 single-bacterium-colonized mice orally administered with healthy individual fecal samples and further administered with ampicillin.

For CFU, only the Kp2H7 strain was selectively cultured by adding mouse feces suspended in PBS to a DHL medium to which ampicillin and spectinomycin were added to a final concentration of 30 μg/mL. Then, the absorbance (OD600) was calculated as an index.

In the qPCR measurement method, bacterial genomic DNA extracted from mouse feces was amplified and quantified with a Kp2H7 genome-specific primer and a universal bacterial primer, and the abundance ratio of the Kp2H7 strain in the bacteria in the mouse fecal sample was calculated.

The bacterial genome was extracted by the following steps.

To 10 mg of mouse feces, 5 times weight of PBS solution containing EDTA and glycerol (final concentration of EDTA: 10 mM, final concentration of glycerol: 20% by volume) was added, and the mixture was subjected to vigorous shaking and crushing suspension.

To 100 μL of the sample solution filtered through a 100 μm-diameter filter, 800 μL of 10 mM Tris/10 mM EDTA buffer solution obtained by dissolving 15 mg of lysozyme (manufactured by Sigma-Aldrich, Lysozyme from chicken egg white; L4919) and 5 μL of RNase (manufactured by Thermo Fisher Scientific, PureLink RNase A (20 mg/mL); 12091-021) (PH 8.0, hereinafter also referred to as "TE10") was added and shaken at 37° C. for 1 hour. Subsequently, 2,000 U of ACHROMOPEPTIDASE (registered trademark) (Wako; 015-09951) was added, and the mixture was shaken at 37° C. for 30 minutes for bacterium-lysis.

A 20% SDS TE10 solution at 50 μL and a TE10 solution at 50 μL obtained by dissolving proteinase K (Roche, Proteinase K, recombinant, PCR Grade; 03115852001) to a final concentration of 20 mg/ml were added and shaken at 55° C. for 60 minutes.

DNA was extracted by a liquid-liquid extraction method using Phenol/Chloroform/Isoamyl alcohol (25:24:1) (Wako; 311-90151), and bacterial genomic DNA was obtained by ethanol precipitation.

The qPCR measurement was performed by the following steps.

LIGHTCYCLER (registered trademark) 480 II (Roche; 05015243001) and THUNDERBIRD (registered trademark) SYBR (registered trademark) qPCR Mix (TOYOBO; QPS-201X5) were used to perform amplification and quantification with a Kp2H7 genome-specific primer and a universal bacterial primer, and the calculated DNA concentration ratio was defined as the abundance ratio of Kp2H7.

The sequence of each primer is as follows.

```
Kp2H7 primer:
Forward
                            [SEQ ID NO: 150]
(5'-AGCACTAGCGGCTGTGGTAT-3'), Reverse
                            [SEQ ID NO: 151]
(5'-ACTTACTCGGGCCCTTGATT-3')

universal bacterial primer:
Forward
                            [SEQ ID NO: 154]
(5'-GGTGAATACGTTCCCGG-3'), Reverse
                            [SEQ ID NO: 155]
(5'-TACGGCTACCTTGTTACGACTT-3')
```

FIGS. 5 to 8 show the obtained results (qPCR measurement results of intestinal bacterium genome).

As described above, the mice that had been intragastrically administered with $10 \times 10^{10}$ CFUs of Kp2H7 strains and then bred for 1 week for sufficient colonization of only the single bacterial species Kp2H7 were transplanted with the feces of healthy volunteers #F, I, and K. As a result, along with the progress of free breeding for 1 month after the treatment, the mice transplanted with any feces showed a marked elimination of the Kp2H7 strain, as shown in FIGS. 5 to 8. This suggests that all of #F, I, and K include bacterial strains having an activity of eliminating the Kp2H7 strain.

As shown by the present inventors in PTL 1, the Kp2H7 strain is a multidrug-resistant bacterium which is resistant to at least ampicillin, tylosin, spectinomycin, and metronidazole (nitroimidazole).

Figure 5:
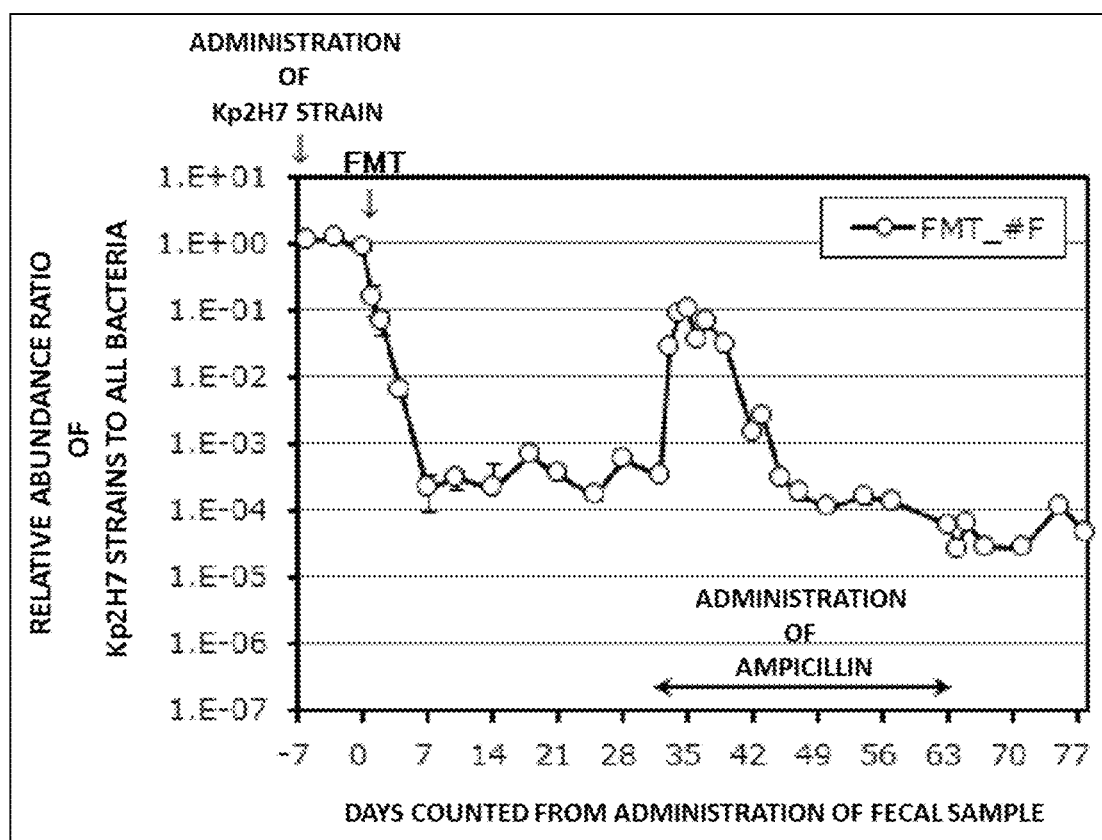
FIG. 5 is a graph illustrating the results of qPCR analysis of the change over time of the intestinal colonization level of a Kp2H7 strain in germ-free mice inoculated with the Kp2H7 strain and then fed with fecal samples derived from a healthy individual (#F).
Figure 6:
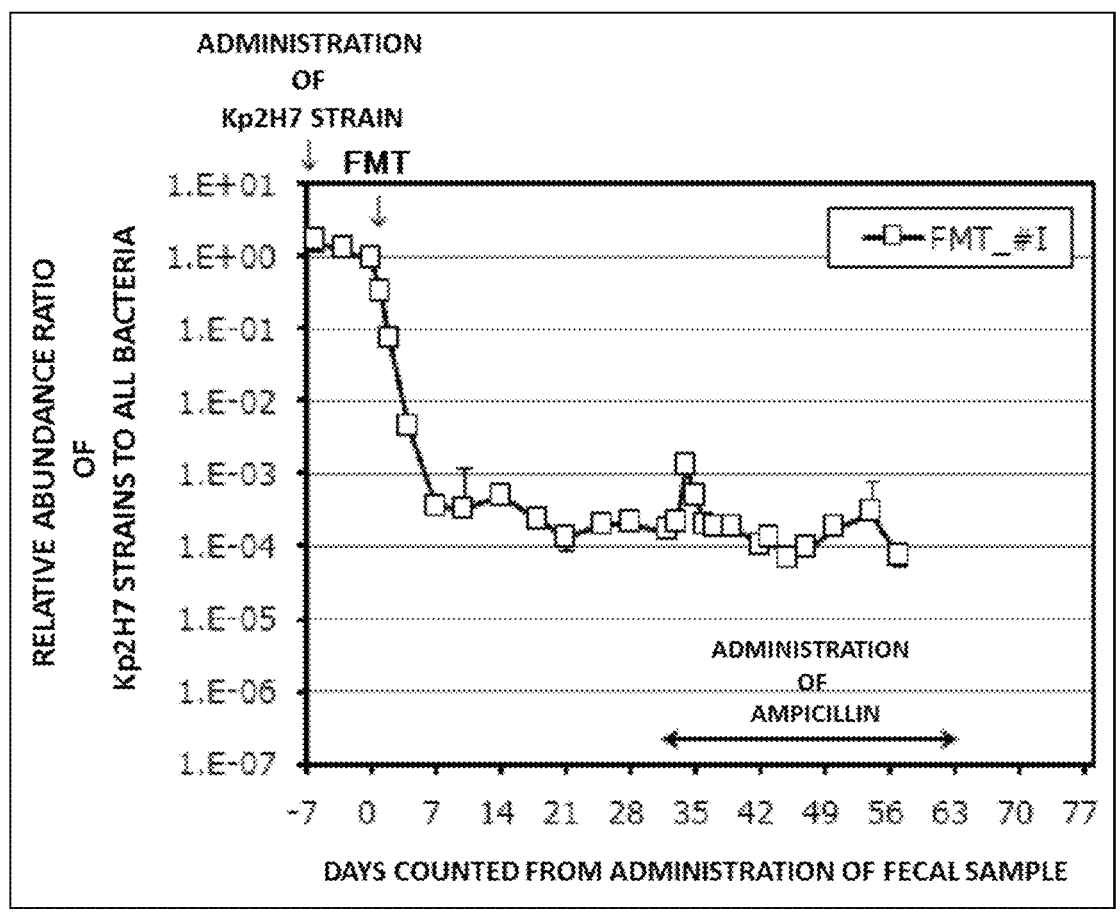
FIG. 6 is a graph illustrating the results of qPCR analysis of the change over time of the intestinal colonization level of a Kp2H7 strain in germ-free mice inoculated with the Kp2H7 strain and then fed with fecal samples derived from a healthy individual (#I).
Figure 7:
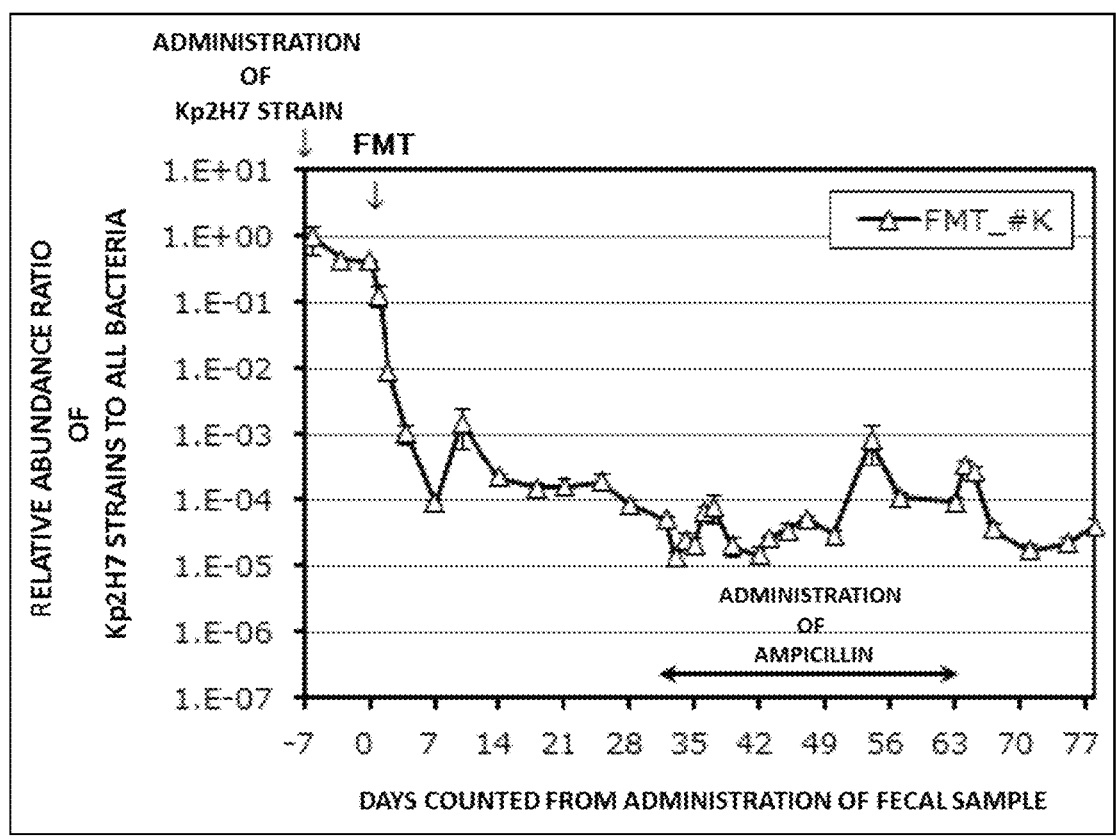
FIG. 7 is a graph illustrating the results of qPCR analysis of the change over time of the intestinal colonization level of a Kp2H7 strain in germ-free mice inoculated with the Kp2H7 strain and then fed with fecal samples derived from the healthy individual (#K).
Figure 8:
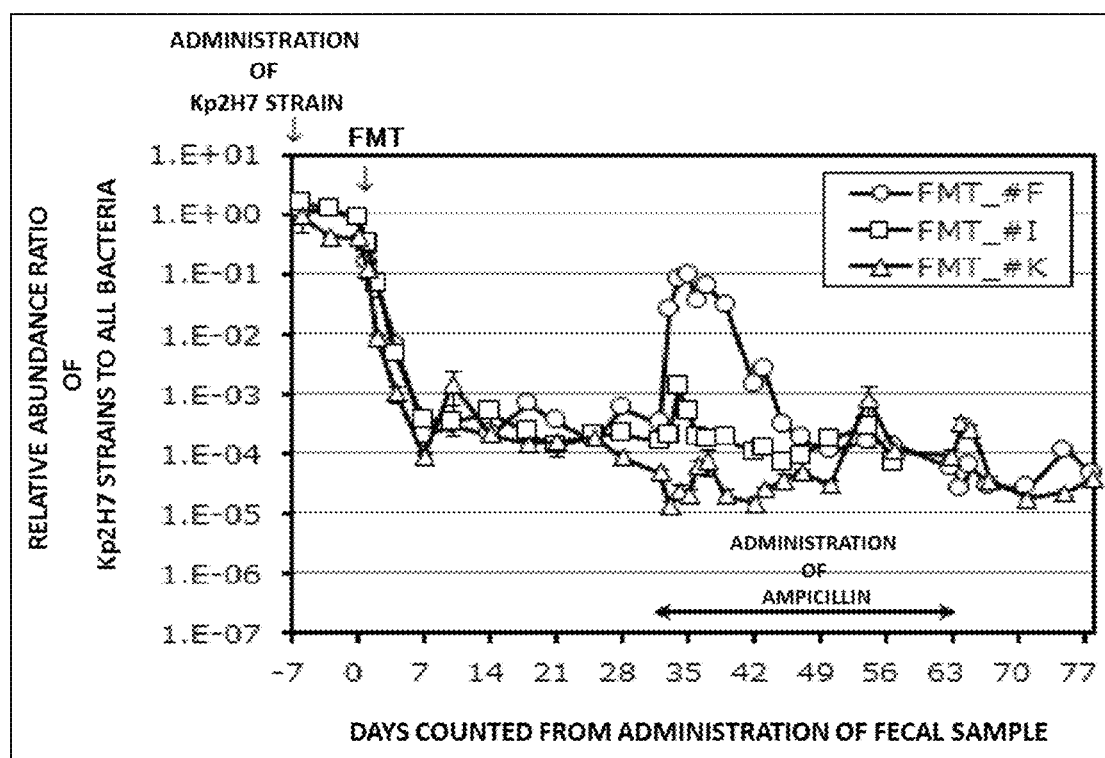
FIG. 8 is a diagram obtained by superimposing the graphs illustrated in FIGS. 5 to 7.

From one month after fecal transplantation, the mice were bred for another month while being administered with the antibiotic ampicillin. Then, as shown in FIG. 5, steep growth of the Kp2H7 strain was observed in the mice transplanted with #F feces. On the other hand, as shown in FIGS. 6 and 7, no significant change was observed in the mice transplanted with #I and K feces. This suggests that the main bacteria contained in the #F feces and involved in the elimination of colonization of the Kp2H7 strain are strains non-resistant (susceptible) to ampicillin. In addition, it is also suggested that the bacteria contained in #I and K feces and involved in the elimination of colonization of the Kp2H7 strain include at least one or more ampicillin withstandable (resistant) strains.

Example 4

Isolation 1 of Bacteria from Healthy Volunteer Feces

The frozen fecal samples derived from #I and #F prepared in Example 3 were thawed at room temperature, diluted with PBS, and cultured on an agar plate of Schaedler blood medium (manufactured by Wako; 517-45805), Luria Bertani (LB) medium (manufactured by Nacalai Tesque Inc.; 20068-75), DHL medium (manufactured by NIHON PHARMACEUTICAL CO., LTD.; 05040), or MacConkey medium (manufactured by Merck; 1.46461.0010) in an anaerobic environment at 37° C. and 10% $CO_2$, and the formed colonies were isolated.

Among the isolated bacteria, 42 types of bacteria derived from #I and 37 types of bacteria derived from #F were subjected to 16S rDNA analysis by the Sanger method to analyze the gene sequences and estimate the bacterial species. The sequencer was 3130 DNA Analyzer manufactured by Thermo Fisher Scientific, and a primer set of the following sequence was used.

```
27 Forward-mod
                                 [SEQ ID NO: 156]
(5'-AGRGTTTGATYMTGGCTCAG-3')

1492 Reverse
                                 [SEQ ID NO: 157]
(5'-GGYTACCTTGTTACGACTT-3').
```

Example 5

Isolation 2 of Bacteria from Healthy Volunteer Feces

Kp2H7 single-bacterium-colonized mice that had been intragastrically administered with a Kp2H7 strain single bacterium and bred for 1 week for colonization of the bacterium were intragastrically administered with fecal samples derived from the healthy volunteer #K by the method according to Example 3. In addition, a fecal sample treated with chloroform by the following procedure was similarly administered intragastrically.

Chloroform treatment: A stock solution of K-derived fecal sample prepared in Example 3 was melted at room temperature. Chloroform was added to the melt to a final concentration of 3%, and the mixture was stirred with shaking at 37° C. for 1 hour, and then the chloroform was removed through nitrogen gas.

The feces-transplanted mice prepared as described above were allowed to drink either water or the following antibiotic aqueous solution freely for 2 months, and then feces were was collected.

ampicillin, spectinomycin, tylosin, and metronidazole: 200 mg/L streptomycin: 50 mg/L.

After fecal collection, isolation-culture was performed by the method according to Example 4. As a result, 47 strains were isolated. In addition, different Kp2H7 single-bacterium-colonized mice were intragastrically administered with fecal samples derived from #K, and feces were collected and isolation-cultured by the above method. As a result, 68 strains were isolated.

Additionally, the gene sequence analysis of these isolated bacteria and estimation of bacterial species were carried out by the method according to Example 4.

Tables 2 to 5 below show the results obtained in Examples 4 and 5.

TABLE 2

| No. | Species | SEQ ID NO: |
|---|---|---|
| K01 | Ruminococcus sp. ID8 | 1 |
| K02 | Bacteroides sp. S-17 | 2 |
| K03 | Blautia coccoides | 3 |
| K04 | Blautia producta | 4 |
| K05 | Bilophila wadsworthia | 5 |
| K06 | Alistipes onderdonkii | 6 |
| K07 | [Clostridium] clostridioforme | 7 |
| K08 | [Clostridium] innocuum | 8 |
| K09 | Bacteroides fragills | 9 |
| K10 | Eggerthella lenta | 10 |
| K11 | cf. Clostridium, sp. MLG055 | 11 |
| K12 | Erysipelatoclostridium ramosum | 12 |
| K13 | Enterococcus faecalis | 13 |
| K14 | Bacteroides intestinalis | 14 |

TABLE 2-continued

| No. | Species | SEQ ID NO: |
|---|---|---|
| K15 | [Clostridium] symbiosum | 15 |
| K16 | [Clostridium] hylemonae | 16 |
| K17 | Hungatella hathewayi | 17 |
| K18 | Bacteroides sp. D8 | 18 |
| K19 | [Clostridium] clostridioforme | 19 |
| K20 | Flavonifractor plautii | 20 |
| K21 | Bacteroides sp. Smarlab 3302996 | 21 |
| K22 | Bacteroides thetaiotaomicron | 22 |
| K23 | Parabacteroides merdae | 23 |
| K24 | Bacteroides vulgatus | 24 |
| K25 | [Clostridium] aldenense | 25 |
| K26 | Bacteroides uniformis | 26 |
| K27 | Gordonibacter pamelaeae | 27 |
| K28 | Clostridium sp. 14505 | 28 |
| K29 | Anaerostipes caccae | 29 |
| K30 | [Ruminococcus] gnavus | 30 |
| K31 | [Ruminococcus] gnavus | 31 |
| K32 | Alistipes shahii | 32 |
| K33 | Bacteroides sp. DJF B097 | 33 |
| K34 | Blautia sp. SerS | 34 |

TABLE 3

| No. | Species | SEQ ID NO: |
|---|---|---|
| K35 | Butyricicoccus putlicaecorum | 35 |
| K36 | [Clostridium] bolteae | 30 |
| K37 | Anaerotruncus sp. NML 070203 | 37 |
| K38 | Holdemania massiliensis | 38 |
| K39 | Escherichia coli | 39 |
| K40 | Agathobaculum desmoians | 40 |
| K41 | [Eubacterium] rectale | 41 |
| K42 | Lactonifactor longoviformis | 42 |
| K43 | Oscillibacter ruminantium | 43 |
| K44 | Pseudoflavonifractor capiltosus | 44 |
| K45 | Streptococcus pasteurianus | 45 |
| K46 | Sutterella wadsworthensis | 40 |
| K47 | Bifidobacterium adolescentis | 47 |
| K48 | [Clostridium] clostridioforme | 48 |
| K49 | Fusicatenibacter saccharivorans | 49 |
| K50 | Hungatella hathewayi | 50 |
| K51 | Clostridium sp. TM-40 | 51 |
| K52 | Ruminococcus sp. DJF_VR70k1 | 52 |
| K53 | Ruminococcus sp. 5_1_39BFAA | 53 |
| K54 | Phascolarctobacterium faecium | 54 |
| K55 | Odoribacter spfanchnicus | 55 |
| K56 | Faecalibacterium prausnitzii | 50 |
| K57 | Clostridium sp. 019 | 57 |
| K58 | Eubacterium sp. WAL 17303 | 58 |
| K59 | Alistipes finegoldii | 59 |
| K60 | Subdoligranulum sp. 4_3_54A2FAA | 60 |
| K61 | Christensenella minuta | 61 |
| K62 | Clostridium scindens | 62 |
| K63 | Enterococcus faecalis | 63 |
| K64 | Blautia coccoides | 64 |
| K65 | Alistipes ihumiii | 65 |
| K66 | Intestinimonas butyriciproducens | 66 |
| K67 | Bacteroides uniformis | 67 |
| K68 | Akkermansia muciniphila | 68 |

TABLE 4

| No. | Species | SEQ ID NO: |
|---|---|---|
| F01 | Bifidobacterium longum | 69 |
| F02 | Bacteroides xylanisolvens | 70 |
| F03 | Bacteroides fraqilis | 71 |

TABLE 4-continued

| No. | Species | SEQ ID NO: |
|---|---|---|
| F04 | Bacteroides uniformis | 72 |
| F05 | Bacteroides thetaiotaomicron | 73 |
| F06 | Bacteroides uniformis | 74 |
| F07 | Bacteroides sp. Smarlab 3302996 | 75 |
| F08 | Bacteroides fragilis | 76 |
| F09 | Parabacteroides goldsteinii | 77 |
| F10 | [Ruminocoecus] gnavus | 78 |
| F11 | Blautia wexlerae | 79 |
| F12 | Blautia sp. canine oral taxon 143 | 80 |
| F13 | Clostridium sp. M62/1 | 81 |
| F14 | Tyzzerella nexilis | 82 |
| F15 | [Ruminocoecus] gnavus | 83 |
| F16 | Anaerostipes hadrus | 84 |
| F17 | Blautia sp. YHC-4 | 85 |
| F18 | [Clostridium] bolteae | 86 |
| F19 | Blautia sp. YHC-4 | 87 |
| F20 | [Clostridium] innocuum | 88 |
| F21 | Blautia sp. Ser8 | 89 |
| F22 | [Clostridium] asparagiforme | 90 |
| F23 | [Clostridium] glycyrrhizinilyticum | 91 |
| F24 | [Clostridium] clostridioforme | 92 |
| F25 | [Clostridium] glycyrrhizinilyticum | 93 |
| F26 | Flavonifractor plautii | 94 |
| F27 | Blautia wexlerae | 95 |
| F28 | Intestinibacter bartlettii | 96 |
| F29 | [Ruminococcus] gnavus | 97 |
| F30 | Clostridium sp. TM-40 | 98 |
| F31 | [Clostridium] indolis | 99 |
| F32 | Blautia producta | 100 |
| F33 | Erysipelatoclostridium ramosum | 101 |
| F34 | Veillonella sp. 6_1_27 | 102 |
| F35 | Fusobacterium ulcerans | 103 |
| F36 | Fusobacterium ulcerans | 104 |
| F37 | Escherichia coli | 105 |

TABLE 5

| No. | Species | SEQ ID NO: |
|---|---|---|
| I01 | Bifidobacterium adolescentis | 106 |
| I02 | Bifidobacterium pseudocatenuiafum | 107 |
| I03 | Bifidobacterium bifidum | 108 |
| I04 | Bifidobacterium longum | 109 |
| I05 | Collinsella aerofaciens | 110 |
| I06 | Collinsella aerofaciens | 111 |
| I07 | Bifidobacterium longum | 112 |
| I08 | Bacteroides stercoris | 113 |
| I09 | Bacteroides massiliensis | 114 |
| I10 | Bacteroides vulgatus | 115 |
| I11 | Bacteroides dorei | 116 |
| I12 | Parabacteroides merdae | 117 |
| I13 | Parabacteroides distasonis | 118 |
| I14 | Alistipes putredinis | 119 |
| I15 | Bacteroides uniformis | 120 |
| I16 | Bacteroides ovatus | 121 |
| I17 | Alistipes shahii | 122 |
| I18 | Odoribacter splanchnicus | 123 |
| I19 | Faecalibacterium prausnitzii | 124 |
| I20 | Faecalibacterium prausnitzii | 125 |
| I21 | Blairtia luti | 126 |
| I22 | Faecalicatena orotica | 127 |
| I23 | Ruminococcus albus | 128 |
| I24 | Faecalibacterium prausnitzii | 129 |
| I25 | Dorea longicatena | 130 |
| I26 | Dorea formicigenerans | 131 |
| I27 | Anaerostipes hadrus | 132 |
| I28 | Intestinibacter bartlettii | 133 |
| I29 | Flavonifractor plautii | 134 |
| I30 | Pseudoflavonifractor capillosus | 135 |
| I31 | [Clostridium] spiroforme | 136 |
| I32 | Megasphaera elsdenii | 137 |

TABLE 5-continued

| No. | Species | SEQ ID NO: |
|---|---|---|
| I33 | Dialister suednatiphilus | 138 |
| I34 | Acidaminococcus intestini | 139 |
| I35 | Allisonella histaminiformans | 140 |
| I36 | Megasphaera massiliensis | 141 |
| I37 | Sutterella wadsworthensis | 142 |
| I38 | Clostridium baratii | 143 |
| I39 | Anaeromassilibacillus senegalensis | 144 |
| I40 | Flintibacter butyricus | 145 |
| I41 | Flavonifractor plautii | 146 |
| I42 | Phocea massiliensis | 147 |

Note that the 47 strains isolated from the fecal sample derived from #K were duplicated with the 68 strains (K1 to K46 described in Tables 2 and 3) except for one strain.

Example 6

Colonization of Bacteria by Isolated Bacteria Culture Solution

The strains isolated in Examples 4 and 5 were cultured for 1 to 3 days in a Schaedler blood medium, LB medium, DHL medium, or MacConkey medium in an anaerobic environment of 37° C. and 10% $CO_2$. The bacterial solution that reached the stationary phase was mixed in equal volumes, and 200 μL thereof was orally administered into the stomach of the Kp2H7 single-bacterium-colonized mice prepared in Example 3. The mice were bred for another 1 month in a sterile isolator under free water and feed conditions to colonize the bacteria. Then, after elimination of the colonized bacteria by administration of the antibiotic ampicillin by the method described in Example 3, the intestinal Kp2H7 colonization level was measured. FIGS. 9 to 12 show the obtained results.

Figure 9:
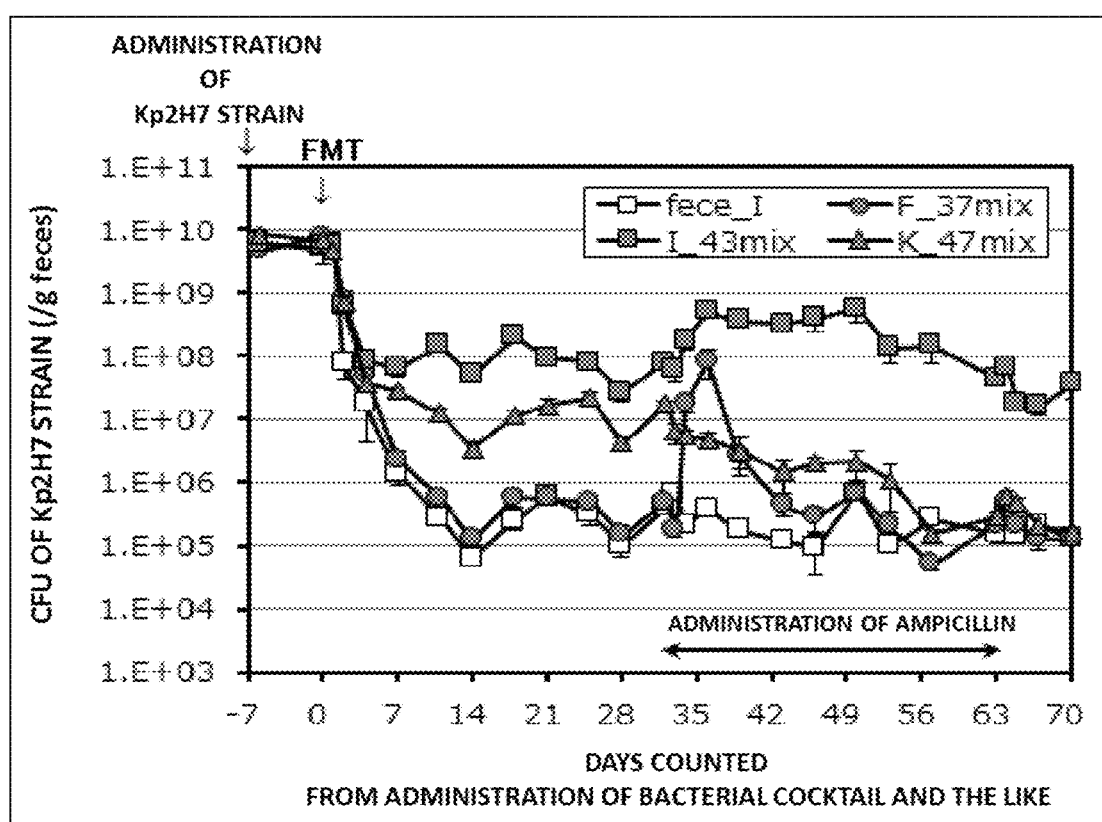
FIG. 9 is a graph illustrating in CFU the change over time of the intestinal colonization level of the Kp2H7 strain in germ-free mice inoculated with the Kp2H7 strain and then fed with a bacterial cocktail derived from the feces of a healthy individual.
Figure 10:
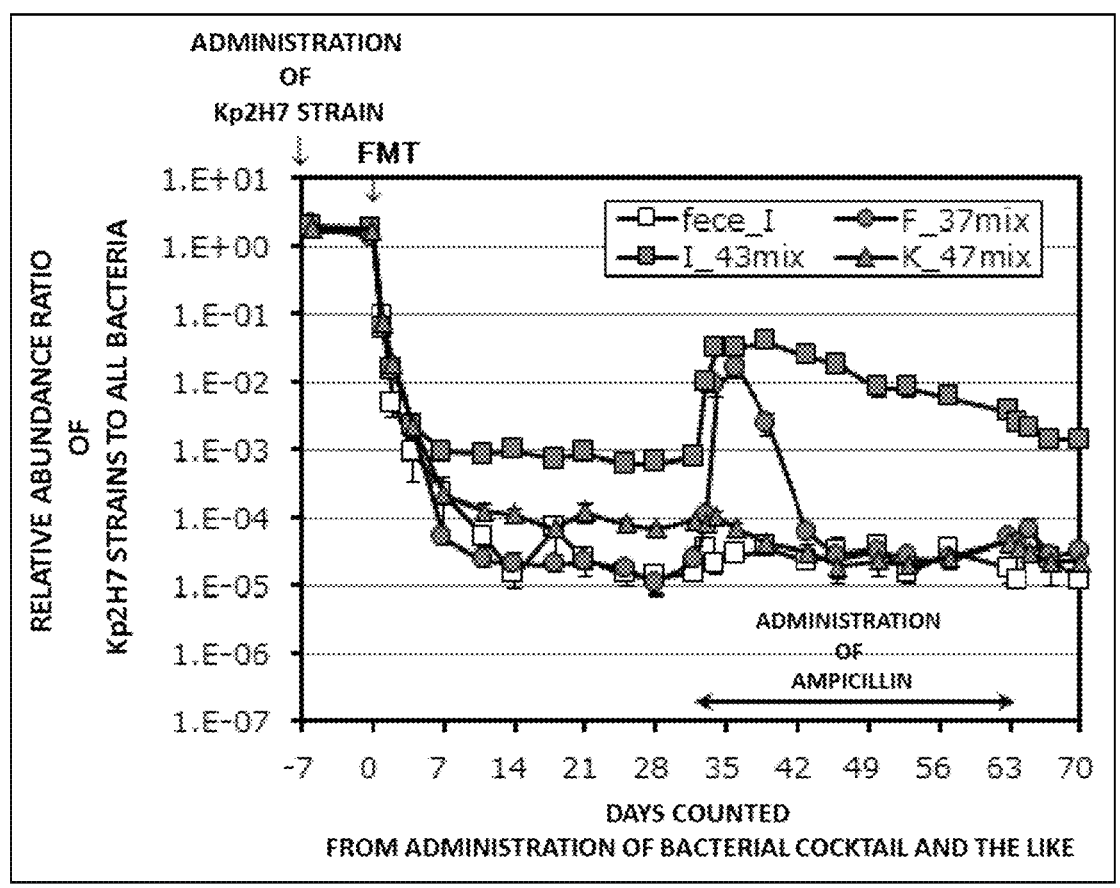
FIG. 10 is a graph illustrating the results of qPCR analysis of the change over time of the intestinal colonization level of the Kp2H7 strain in germ-free mice inoculated with the Kp2H7 strain and then fed with a bacterial cocktail derived from the feces of a healthy individual.

As described above, the mice that had been intragastrically administered with $10 \times 10^{10}$ CFUs of Kp2H7 strains and then bred for 1 week for sufficient colonization of only the single bacterial species Kp2H7 were intragastrically administered with the bacterial cocktails isolated from healthy volunteers #F, I, and K. As a result, along with the progress of free breeding for 1 month after the treatment, the mice administered with any bacterial cocktails showed a significant elimination of the Kp2H7 strain, as shown in FIGS. 9 and 10. This suggests that all of F_37mix, I_42mix, and K_47mix include bacterial strains having an activity of eliminating the Kp2H7 strain.

From one month after bacterial cocktail administration, the mice were bred for another month while being administered with the antibiotic ampicillin. Then, as shown in FIGS. 9 and 10, growth of Kp2H7 was observed in the mice administered with F_37mix and I_42mix. On the other hand, no significant change was observed in the mice transplanted with K_47mix. This suggests that the main bacteria contained in F_37mix and I_42mix and capable of eliminating colonization of the Kp2H7 strain are strains non-resistant (susceptible) to ampicillin. Meanwhile, it is also suggested that the bacteria contained in K_47mix and capable of eliminating colonization of the Kp2H7 strain include at least one or more ampicillin withstandable (resistant) strains.

In addition, when the case of administration of isolated bacteria (Example 6) is compared with the case of fecal transplantation before bacterium isolation (Example 3), the following is suggested.

The 37 bacteria isolated from #F feces and the 47 bacteria isolated from #K feces had an activity to eliminate the Kp2H7 strain, which was equal to or higher than that against the feces before isolation. In particular, the activity of F_37mix to eliminate Kp2H7 exceeded that of the Kp2H7 strain by the transplantation of #F feces before isolation. That is, it is considered that F_37mix is enriched with bacteria that inhibit the colonization of the Kp2H7 strain, or excludes bacteria that do not participate in the colonization of the Kp2H7 strain or support the colonization. Therefore, F_37mix is a bacterial cocktail effective in eliminating the Kp2H7 strain.

The 42 bacteria isolated from #I feces had a sufficient activity to eliminate Kp2H7, but did not reach the Kp2H7 elimination activity by the transplantation of #I feces before isolation. In addition, susceptibility to ampicillin, which was not observed in the case of transplantation of #I feces before isolation, was observed. That is, it is considered that I_42mix does not contain ampicillin-resistant bacteria capable of eliminating the colonization of Kp2H7, which are contained in #I feces before isolation. Therefore, I_42mix is a bacterial cocktail effective in eliminating the Kp2H7 strain.

Figure 11:
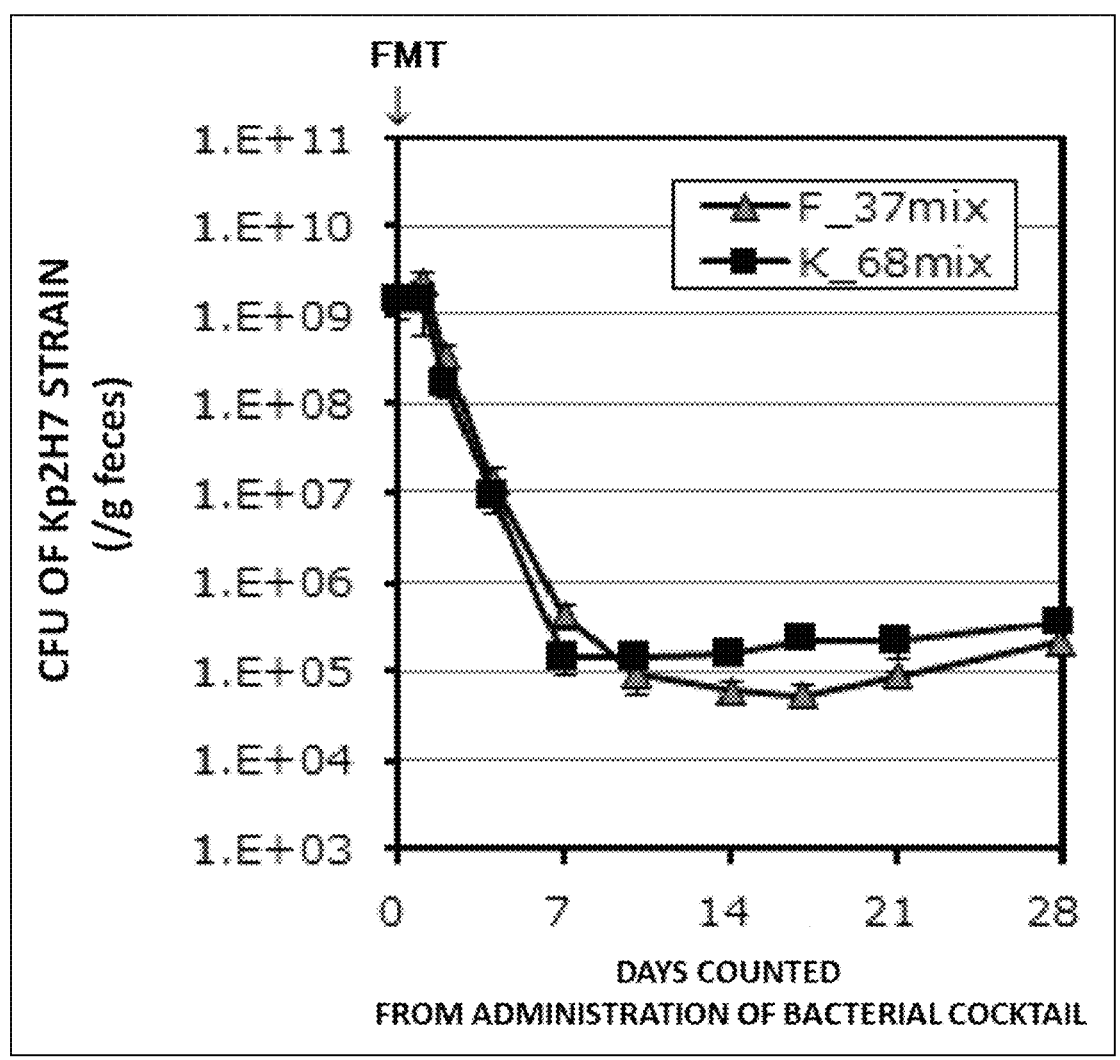
FIG. 11 is a graph illustrating in CFU the change over time of the intestinal colonization level of the Kp2H7 strain in germ-free mice inoculated with the Kp2H7 strain and fed 7 days after with a bacterial cocktail derived from the feces of a healthy individual.
Figure 12:
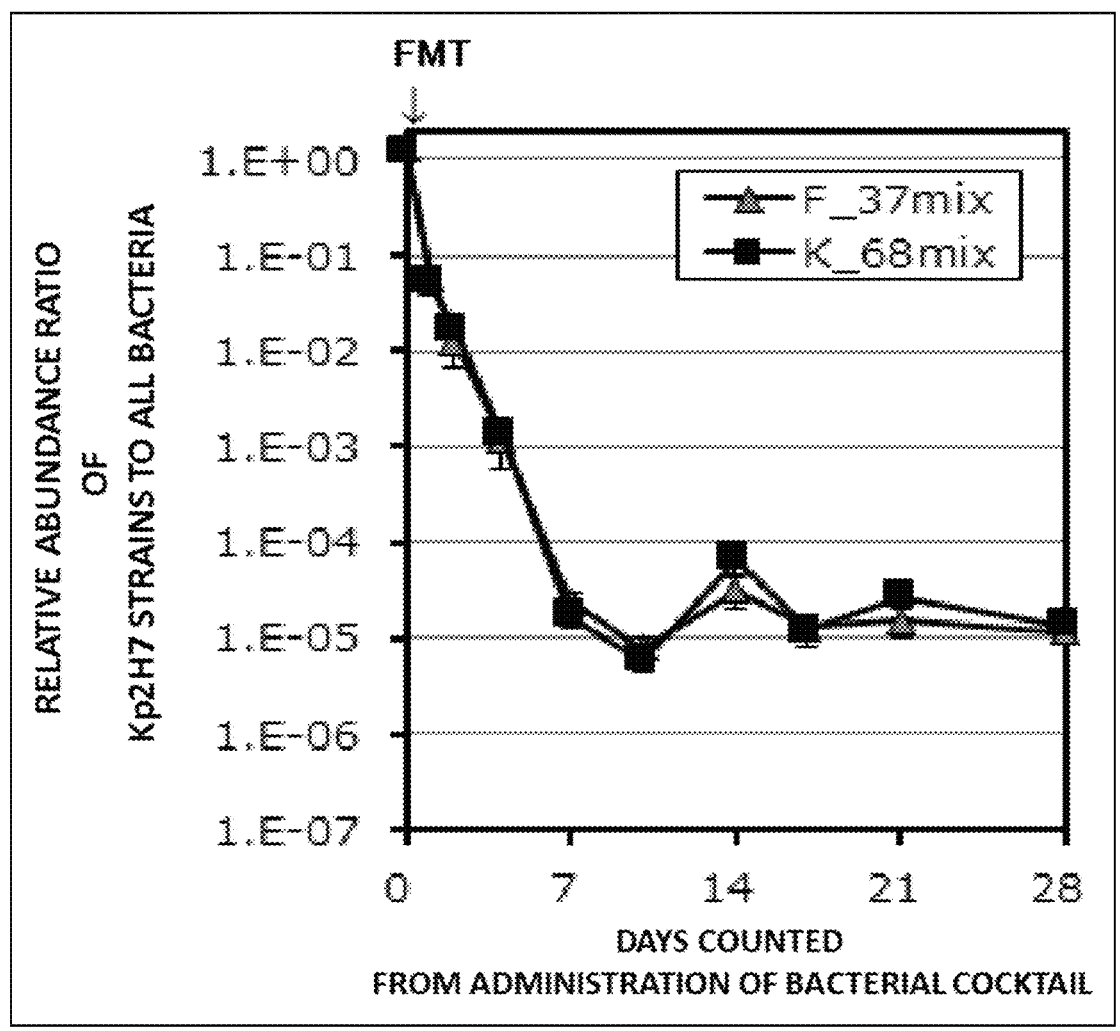
FIG. 12 is a graph illustrating the results of qPCR analysis of the change over time of the intestinal colonization level of the Kp2H7 strain in germ-free mice inoculated with the Kp2H7 strain and fed 7 days after with a bacterial cocktail derived from the feces of a healthy individual.

In addition, the mice that had been intragastrically administered with $10 \times 10^{10}$ CFUs of Kp2H7 and then bred for 1 week for sufficient colonization of only the single bacterial species Kp2H7 were intragastrically administered with K_68mix. As a result, along with the progress of free breeding for 1 month after the treatment, the elimination of Kp2H7 was observed, as shown in FIGS. 11 and 12. In addition, in K_68mix, a significant level of Kp2H7 elimination equivalent to that in the case of F_37mix was observed.

In particular, the activity of K_68mix to eliminate the Kp2H7 strain exceeded that of the Kp2H7 strain by the transplantation of #K feces before isolation. That is, it is considered that K_68mix is enriched with bacteria that inhibit the colonization of the Kp2H7 strain, or excludes bacteria that do not participate in the colonization of the Kp2H7 strain or support the colonization. Therefore, K_68mix is a bacterial cocktail effective in eliminating the Kp2H7 strain.

INDUSTRIAL APPLICABILITY

As described above, according to the present invention, suppression of the colonization and the like of Th1 cell-inducible bacteria in the intestinal tract makes it possible to suppress Th1 cell proliferation or activation, suppress intestinal immunity, and moreover treat, alleviate, or prevent a disease attributable to Th1 cells. In addition, the present invention makes it possible to test for a disease attributable to Th1 cells.

Therefore, the present invention is extremely useful in the pharmaceutical development, treatment, alleviation, prevention, and diagnosis relating to inflammatory bowel disease, autoimmune disease, chronic inflammatory disease, and the like attributable to Th1 cells.

[Sequence Listing Free Text]
SEQ ID NOs: 148 to 157
<223> Artificially synthesized primer sequence

The invention claimed is:

1. A method for treating, or alleviating, a disease attributable to Th1 cells in a subject, said method comprising administering to said subject:
   (1) a bacterium having a DNA composed of a base sequence specified at SEQ ID NO: 69 or a base sequence having at least 90% identity with the base sequence,
   (2) a bacterium having a DNA composed of a base sequence specified at SEQ ID NO: 70 or a base sequence having at least 90% identity with the base sequence,
   (3) a bacterium having a DNA composed of a base sequence specified at SEQ ID NO: 71 or a base sequence having at least 90% identity with the base sequence, (4) a bacterium having a DNA composed of a base sequence specified at SEQ ID NO: 72 or a base sequence having at least 90% identity with the base sequence,
(5) a bacterium having a DNA composed of a base sequence specified at SEQ ID NO: 73 or a base sequence having at least 90% identity with the base sequence,
(6) a bacterium having a DNA composed of a base sequence specified at SEQ ID NO: 74 or a base sequence having at least 90% identity with the base sequence,
(7) a bacterium having a DNA composed of a base sequence specified at SEQ ID NO: 75 or a base sequence having at least 90% identity with the base sequence,
(8) a bacterium having a DNA composed of a base sequence specified at SEQ ID NO: 76 or a base sequence having at least 90% identity with the base sequence,
(9) a bacterium having a DNA composed of a base sequence specified at SEQ ID NO: 77 or a base sequence having at least 90% identity with the base sequence,
(10) a bacterium having a DNA composed of a base sequence specified at SEQ ID NO: 78 or a base sequence having at least 90% identity with the base sequence,
(11) a bacterium having a DNA composed of a base sequence specified at SEQ ID NO: 79 or a base sequence having at least 90% identity with the base sequence,
(12) a bacterium having a DNA composed of a base sequence specified at SEQ ID NO: 80 or a base sequence having at least 90% identity with the base sequence,
(13) a bacterium having a DNA composed of a base sequence specified at SEQ ID NO: 81 or a base sequence having at least 90% identity with the base sequence,
(14) a bacterium having a DNA composed of a base sequence specified at SEQ ID NO: 82 or a base sequence having at least 90% identity with the base sequence,
(15) a bacterium having a DNA composed of a base sequence specified at SEQ ID NO: 83 or a base sequence having at least 90% identity with the base sequence,
(16) a bacterium having a DNA composed of a base sequence specified at SEQ ID NO: 84 or a base sequence having at least 90% identity with the base sequence,
(17) a bacterium having a DNA composed of a base sequence specified at SEQ ID NO: 85 or a base sequence having at least 90% identity with the base sequence,
(18) a bacterium having a DNA composed of a base sequence specified at SEQ ID NO: 86 or a base sequence having at least 90% identity with the base sequence,
(19) a bacterium having a DNA composed of a base sequence specified at SEQ ID NO: 87 or a base sequence having at least 90% identity with the base sequence,
(20) a bacterium having a DNA composed of a base sequence specified at SEQ ID NO: 88 or a base sequence having at least 90% identity with the base sequence,
(21) a bacterium having a DNA composed of a base sequence specified at SEQ ID NO: 89 or a base sequence having at least 90% identity with the base sequence,
(22) a bacterium having a DNA composed of a base sequence specified at SEQ ID NO: 90 or a base sequence having at least 90% identity with the base sequence,
(23) a bacterium having a DNA composed of a base sequence specified at SEQ ID NO: 91 or a base sequence having at least 90% identity with the base sequence,
(24) a bacterium having a DNA composed of a base sequence specified at SEQ ID NO: 92 or a base sequence having at least 90% identity with the base sequence,
(25) a bacterium having a DNA composed of a base sequence specified at SEQ ID NO: 93 or a base sequence having at least 90% identity with the base sequence,
(26) a bacterium having a DNA composed of a base sequence specified at SEQ ID NO: 94 or a base sequence having at least 90% identity with the base sequence,
(27) a bacterium having a DNA composed of a base sequence specified at SEQ ID NO: 95 or a base sequence having at least 90% identity with the base sequence,
(28) a bacterium having a DNA composed of a base sequence specified at SEQ ID NO: 96 or a base sequence having at least 90% identity with the base sequence,
(29) a bacterium having a DNA composed of a base sequence specified at SEQ ID NO: 97 or a base sequence having at least 90% identity with the base sequence,
(30) a bacterium having a DNA composed of a base sequence specified at SEQ ID NO: 98 or a base sequence having at least 90% identity with the base sequence,
(31) a bacterium having a DNA composed of a base sequence specified at SEQ ID NO: 99 or a base sequence having at least 90% identity with the base sequence,
(32) a bacterium having a DNA composed of a base sequence specified at SEQ ID NO: 100 or a base sequence having at least 90% identity with the base sequence,
(33) a bacterium having a DNA composed of a base sequence specified at SEQ ID NO: 101 or a base sequence having at least 90% identity with the base sequence,
(34) a bacterium having a DNA composed of a base sequence specified at SEQ ID NO: 102 or a base sequence having at least 90% identity with the base sequence,
(35) a bacterium having a DNA composed of a base sequence specified at SEQ ID NO: 103 or a base sequence having at least 90% identity with the base sequence,

(36) a bacterium having a DNA composed of a base sequence specified at SEQ ID NO: 104 or a base sequence having at least 90% identity with the base sequence, and
(37) a bacterium having a DNA composed of a base sequence specified at SEQ ID NO: 105 or a base sequence having at least 90% identity with the base sequence, wherein the disease attributable to Th1 cells is inflammatory bowel disease, autoimmune disease, or chronic inflammatory disease.

* * * * *

SEQUENCE LISTING

```
Sequence total quantity: 157
SEQ ID NO: 1            moltype = DNA  length = 1391
FEATURE                 Location/Qualifiers
misc_feature            1..1391
                        note = K01
source                  1..1391
                        mol_type = unassigned DNA
                        organism = unidentified
SEQUENCE: 1
gcaagtcgag cgaagcgctg ttttcagaat cttcggagga agaggacagc gactgagcgg   60
cggacgggtg agtaacgcgt gggcaacctg cctcatacag ggggataaca gttagaaatg  120
actgctaata ccgcataagc gcacgggacc gcatggtcta gtgtgaaaaa ctccggtggt  180
atgagatgga cccgcgtctg attaggtagt tggtggggta aaggcctacc aagccgacga  240
tcagtagccg acctgagagg gtgaccggcc acattgggac tgagacacgg cccaaactcc  300
tacgggaggc agcagtgggg aatattgcac aatggggggaa accctgatgc agcgacgccg  360
cgtgaaggaa gaagtatttc ggtatgtaaa cttctatcag cagggaagaa aatgacggta  420
cctgagtaag aagcaccggc taaatacgtg ccagcagccg cggtaatacg tatgtgcaa   480
gcgttatccg gatttactgg gtgtaaaggg agcgtagacg gataggcaag tctgagtga   540
aaacccaggg ctcaaccctg ggactgcttt ggaaactgca gatctggagt gccggagagg   600
taagcggaat tcctagtgta gcggtgaaat gcgtagatat taggaggaac accagtggcg   660
aaggcggctt actggacggt gactgacgtt gaggctcgaa agcgtgggga gcaaacagga   720
ttagataccc tggtagtcca cgccgtaaac gatgactact aggtgtcggt gtgcaaagca   780
catcggtgcc gcagcaaacg caataagtag tccacctggg gagtacgttc gcaagaatga   840
aactcaaagg aattgacggg gacccgcaca agcggtggag catgtggttt aattcgaagc   900
aacgcgaaga accttacctg gtcttgacat ccggatgacg ggcgagtaat gtcgccgtcc   960
cttcgggggca tccgagacag gtggtgcatg gttgtcgtca gctcgtgtcg tgagatgttg  1020
ggttaagtcc cgcaacgagc gcaacccta tcttcagtag ccagcatata aggtgggcac  1080
tctggagaga ctgccaggga gaacctggag gaaggtgggg atgacgtcaa atcatcatgc  1140
ccccttatggc cagggctaca cacgtgctac aatggcgtaa acaaagggaa gcgagagggt  1200
gacctgaagc gaatcccaaa aataacgtct cagttcggat tgtagtctgc aactcgacta  1260
catgaagctg gaatcgctag taatcgcgga tcagcatgcc gcggtgaata cgttcccggg  1320
tcttgtacac accgcccgtc acaccatggg agtcagtaac gcccgaagcc agtgacccaa  1380
ccttgaggag g                                                      1391

SEQ ID NO: 2            moltype = DNA  length = 1383
FEATURE                 Location/Qualifiers
misc_feature            1..1383
```

```
                    note = K02
source              1..1383
                    mol_type = unassigned DNA
                    organism = unidentified
SEQUENCE: 2
tcgagggca  gcattttagt  ttgcttgcaa  actgaagatg  cgaccggcg   cacgggtgag   60
taacacgtat  ccaacctgcc  gataactccg  gaatagcctt  tcgaaagaaa  gattaatacc  120
ggatagcata  cgaatatcgc  atgatatttt  tattaaagaa  tttcggttat  cgatggggat  180
gcgttccatt  agtttgttgg  cggggtaacg  gcccaccaag  actacgatgg  atagggttc   240
tgagaggaag  gtcccccaca  ttggaactga  gacacggtcc  aaactcctac  ggggggcagc  300
agtgaggaat  attggtcaat  gggcgagagc  ctgaaccagc  caagtagcgt  gaaggatgaa  360
ggctctatgg  gtcgtaaact  tcttttatat  gggaataaag  ttttccacgt  gtggaatttt  420
gtatgtacca  tatgaataag  gatcggctaa  ctccgtgcca  gcagccgcgg  taatacgag   480
gatccgagcg  ttatccggat  ttattgggtt  taaagggagc  gtaggtggat  tgttaagtca  540
gttgtgaaag  tttgcggctc  aaccgtaaaa  ttgcagttga  aactggcagt  cttgagtaca  600
gtagaggtgg  gcggaattcg  tggtgtagcg  gtgaatgct   tagatatcac  gaagaactcc  660
gattgcgaag  gcagctcact  agactgttac  tgacactgat  gctcgaaagt  gtgggtatca  720
aacaggatta  gataccctgg  tagtccacac  agtaaacgat  gaatactcgc  tgtttgcgat  780
atacagtaag  cggccaagcg  aaagcattaa  gtattccacc  tggggagtac  gccggcaacg  840
gtgaaactca  aaggaattga  cgggggcccc  cacaagcgga  ggaacatgtg  gtttaattcg  900
atgatacgcg  aggaaccta   cccgggctta  aattgcaaca  gaatatattg  gaaacagtat  960
agccgtaagg  ctgttgtgaa  ggtgctgcat  ggttgtcgtc  agctcgtgcc  gtgaggtgtc  1020
ggcttaagtg  ccataacgag  cgcaaccctt  atctttagtt  actaacaggt  tatgctgagg  1080
actctagaga  gactgccgtc  gtaagatgtg  aggaaggtgg  ggatgacgtc  aaatcagcac  1140
ggcccttacg  tccggggcta  cacacgtgtt  acaatggggg  gtacagaagg  cggctacctg  1200
gtgacaggat  gctaatccca  aaaacctctc  tcagttcgga  tcgaagtcgc  caacccgact  1260
tcgtgaagct  ggattcgcta  gtaatcgcgc  atcagccatg  gcgcggtgaa  tacgttcccg  1320
ggccttgtac  acaccgcccg  tcaagccatg  aaagccgggg  tacctgaag   tacgtaaccg  1380
caa                                                                    1383

SEQ ID NO: 3           moltype = DNA   length = 1396
FEATURE                Location/Qualifiers
misc_feature           1..1396
                       note = K03
source                 1..1396
                       mol_type = unassigned DNA
                       organism = unidentified
SEQUENCE: 3
tgcagtcgag  cgaagcgcta  agacaggatt  tcttcggatt  gaagtctttg  tgactgagcg   60
gcggacgggt  gagtaacgcg  tgggtaacct  gcctcataca  gggggataac  agttagaaat  120
gactgctaat  accgcataag  cgcacaggac  cgcatggtct  ggtgtgaaaa  actccggtgg  180
tatgagatgg  acccgcgtct  gattagctag  ttggagggt   aacggccac   caaggcgacg  240
atcagtagcc  ggcctgagag  ggtgaacagc  cacattggga  ctgagacacg  gcccagactc  300
ctacgggagg  cagcagtggg  gaatattgca  caatggggga  aaccctgatg  cagcgacgcc  360
gcgtgaagga  agaagtatct  cggtatgtaa  acttctatca  gcaggaaga   aaatgacggt  420
acctgactaa  gaagccccgg  ctaactacgt  gccagcagcc  gcggtaatac  gtaggggca   480
agcgttatcc  ggatttactg  ggtgtaaagg  gagcgtagac  ggaagagcaa  gtctgatgtg  540
aaaggctggg  gcttaacccc  aggactgcat  tggaaactgt  tgttctagag  tgccggagag  600
gtaagcggaa  ttcctagtgt  agcggtgaaa  tgcgtagata  ttaggaggaa  caccagtggc  660
gaaggcggct  tactggacgg  taactgacgt  tgaggctcga  aagcgtgggg  agcaaacagg  720
attagatacc  ctggtagtcc  acgccgtaaa  cgatgaatac  taggtgtcgg  gtggcaaagc  780
cattcggtgc  cgcagcaaac  gcaataagta  ttccacctgg  ggagtacgtt  cgcaagaatg  840
aaaactcaaag  gaattgacgg  ggacccgcac  aagcggtgga  gcatgtggtt  taattcgaag  900
caacgcgaag  aaccttacca  agtcttgaca  tccctctgac  cgtcccgtaa  cggggggcttc  960
ccttcgggcg  agaggagaca  ggtggtgcat  ggttgtcgtc  agctcgtgtc  gtgagatgtt  1020
gggttaagtc  ccgcaacgag  cgcaacccctt  atccttagta  gccagcacat  gatggtgggc  1080
actctaggga  gactgccggg  gataacccgg  aggaaggcgg  ggacgacgtc  aaatcatcat  1140
gccccttatg  atttgggcta  cacacgtgct  acaatgcgt   aaacaaaggg  aagcgagaca  1200
gcgatgttga  gcgaatccca  aaaataacgt  cccagttcgg  actgcagtct  gcaactcgac  1260
tgcacgaagc  tggaatcgct  agtaatcgcg  gatcagaatg  ccgcggtgaa  tacgttcccg  1320
ggtcttgtac  acaccgcccg  tcacaccatg  ggagtcagta  acgcccgaag  tcagtgacct  1380
aaccgaaagg  aaggag                                                     1396

SEQ ID NO: 4           moltype = DNA   length = 1395
FEATURE                Location/Qualifiers
misc_feature           1..1395
                       note = K04
source                 1..1395
                       mol_type = unassigned DNA
                       organism = unidentified
SEQUENCE: 4
cagtcgagcg  aagcgtctta  gaatgatctc  ttcggattga  gtcttatatg  actgagcggc   60
ggacgggtga  gtaacgcgtg  gtaacctgc   ctcatacagg  gggataacag  ttagaaatga  120
ctgctaatac  cgcataagcg  cacagggctg  catggtcct   tgtgaaaaac  tccggtgta   180
tgagatggac  ccgcgtctga  ttagctagtt  ggaggggtaa  cggccacca   aggcgacgat  240
cagtagccgg  cctgagaggg  tgaacggcca  cattgggact  gagacacggc  ccagactcct  300
acggaggca   gcagtgggga  atattgcaca  atgggggaa   ccctgatgca  gcgacgccgc  360
gtgaaggaag  aagtatctcg  gtatgtaaac  ttctatcagc  aggaagaaa   atgacggtac  420
ctgactaaga  agccccggct  aactacgtgc  cagcagccgc  ggtaatacgt  aggggcaag   480
```

-continued

```
cgttatccgg atttactggg tgtaaaggga gcgtagacgg aagagcaagt ctgatgtgaa    540
aggctgggc  ttaacccag  gactgcattg  gaaactgttt  ttctagagtg  ccggagaggt    600
aagcggaatt cctagtgtag cggtgaaatg cgtagatatt aggaggaaca ccagtggcga    660
aggcggctta ctgacggta  actgacgttg aggctcgaaa gcgtgggag  caaacaggat    720
tagataccct ggtagtccac gccgtaaacg atgaatacta ggtgtcggt  ggcaaagcca    780
ttcggtgccg cagcaaacgc aataagtatt ccacctgggg agtacgttcg caagaatgaa    840
actcaaagga attgacgggg acccgcacaa gcggtggagc atgtggttta attcgaagca    900
acgcgaagaa ccttaccaag tcttgacatc cttctgacgt gcccgtaacg gggcattccc    960
ttcggggcag aggagacagg tggtgcatgg ttgtcgtcag ctcgtgtcgt gagatgttgg   1020
gttaagtccc gcaacgagcg caaccccat  ccttagtagc cagcacatca tggtgggcac   1080
tctagggaga ctgccgggga taaccccgga gaaggcgggg acgacgtcaa atcatcatgc   1140
cccttatgat ttgggctaca cacgtgctac aatggcgtaa acaagggaa gcgagacagc   1200
gatgtttagc aaatcccaaa aataacgtcc cagttcggac tgcagtctgc aactcgactg   1260
cacgaagctg gaatcgctag taatcgcgaa tcagaatgtc gcggtgaata cgttcccggg   1320
tcttgtacac accgcccgtc acaccatggg agtcagtaac gcccgaagtc agtgacccaa   1380
cctcacggag ggagc                                                    1395

SEQ ID NO: 5           moltype = DNA   length = 1411
FEATURE                Location/Qualifiers
misc_feature           1..1411
                       note = K05
source                 1..1411
                       mol_type = unassigned DNA
                       organism = unidentified
SEQUENCE: 5
gcagtcgaac gtgaaagtcc ttcgggacga gtaaagtggc gcacgggtga gtaacgcgtg     60
gataatctac ccttaagatg gggataacgc ctggaaacgg tcgctaatac cgaatacgct    120
cccgatttta tcattggggg gaaagatggc ctctgcttgc aagctatcgc ttaaggatga    180
gtccgcgtcc cattagctag ttggcggggt aacggcccac caaggcgacg atgggtagcc    240
ggtctgagag gatgaccggc cacactgaaa ctggaacacg gtccagactc ctacgggagg    300
cagcagtggg gaatattgcg caatgggcga agcctgacg  cagcgacgcc gcgtgaggga    360
tgaaggttct cggatcgtaa acctctgtca ggggggaaga aacccctcg  tgtgaataat    420
gcgagggctt gacggtaccc ccaaaggaag caccggctaa ctccgtgcca gcagccgcgg    480
taatacggag ggtgcaagcg ttaatcgaa  tcactgggcg taaagcgcac gtaggcggct    540
tggtaagtca ggggtgaaat cccacagccc aactgtgaa  ctgccttga  tactgccagg    600
cttgagtacc ggagagggtg gcggaattcc aggtgtagga gtgaaatccg tagatatctg    660
gaggaacacc ggtggcgaag gcggccacct ggacggtaac tgacgctgag gtgcgaaagc    720
gtgggtagca aacaggatta gataccctgg tagtccacgc tgtaaacgat gggtgctggg    780
tgctgggatg tatgtctcgg tgccgtagct aacgcgataa gcaccccgcc tggggagtac    840
ggtcgcaagg ctgaaactca aagaaattga cggggcccg  cacaagcggt ggagtatgtg    900
gtttaattcg atgcaacgcg aagaaccta  cccaggcttg acatcaggg  aacccttcgg    960
aaatgaaggg gtgcccttcg gggagcccta agacaggtgc tgcatggctg tcgtcagctc   1020
gtgccgtgag gtgttgggtt aagtcccgca acgagcgcaa ccctatctt  cagttgccag   1080
caggtaaggc tgggcactct ggagagaccg ccccggtcaa cggggaggaa ggtgggacg    1140
acgtcaagtc atcatggccc ttacgcctgg ggctacacac gtactacaat ggcgcgcaca   1200
aagggtagca agaccgcgag gtggagccaa tcccaaaaaa cgcgtcccag tccggattgg   1260
agtctgcaac tcgactccat gaagtcggaa tcgctagta  ttcgagatca gcatgctcgg   1320
gtgaatgcgt tcccgggcct tgtacacacc gcccgtcaca ccacgaaagt cggttttacc   1380
cgaagccggt gagctaactc gcaagagaag c                                  1411

SEQ ID NO: 6           moltype = DNA   length = 1383
FEATURE                Location/Qualifiers
misc_feature           1..1383
                       note = K06
source                 1..1383
                       mol_type = unassigned DNA
                       organism = unidentified
SEQUENCE: 6
gaggggcatc gggattgaag cttgcttcaa ttgccggcga ccggcgcacg ggtgcgtaac     60
gcgtatgtaa cctacctata acaggggcat aacactgaga aattggtact aattccccat    120
aatattcgga gaggcatctc tccggggttga aaactccggt ggttatagat ggacatgcgt    180
tgtattagct agttggtgag gtaacggctc accaaggcaa cgatacatag ggggactgag    240
aggttaaccc cccacactgg tactgagaca cggaccagac tcctacggga ggcagcagtg    300
aggaatattg gtcaatggac gcaagtctga accagccatg ccgcgtgcag gaagacgcct    360
ctatgagttg taaactgctt ttgtacgagg gtaaactcac ctacgtgtag gtgactgaaa    420
gtatcgtacg aataaggatc ggctaactcc gtgccagcag ccgcggtaat acggaggatt    480
caagcgttat ccgatttat  tgggtttaaa gggtgcgtag gcggtttgat aagttagagg    540
tgaaatcccg ggcttaact  ccggaactgc ctctaatact gttagactag agagtagttg    600
cggtaggcga aatgtatggt gtagcggtga gcatgtaaga aacaccgatt    660
gcgaaggcag cttaccaaac tatatctgac gttgaggcgc gaaagcgtgg ggagcaaaca    720
ggattagata ccctggtagt ccacgcagta acgatgata  actcgttgtc ggcgatacac    780
agtcggtgac taagcgaaag cgataagtta tccacctggg ggagtacgtt cgcaagaatg    840
aaaactcaaa ggaattgacg ggggcccgca  caagcggagg  acatgtggtt taattcgatg    900
atacgcgagg aaccttaccc gggcttgaaa gttactgaaa caggatttcc    960
cttcggggca ggaaactagg tgctgcatgg ttgtcgtcag ctcgtgccgt gaggtgtcgg   1020
gttaagtccc ataacgagcg caaccccac  cgttagttgc catcaggtca gctgggcac    1080
tctgccggga ctgccggtgt aagccgagag gaaggtgggg atgacgtcaa atcagcacgg   1140
cccttacgtc cggggctaca cacgtgttac aatggtaggt acagagggtc gctacccgt    1200
gagggatgc  caatctcgaa agcctatctc agttcggatt ggaggctgaa accgcctcc    1260
```

```
atgaagttgg attcgctagt aatcgcgcat cagccatggc gcggtgaata cgttcccggg   1320
ccttgtacac accgcccgtc aagccatgga agctgggggt gcctgaagtt cgtgaccgca   1380
agg                                                                 1383

SEQ ID NO: 7           moltype = DNA   length = 1393
FEATURE                Location/Qualifiers
misc_feature           1..1393
                       note = K07
source                 1..1393
                       mol_type = unassigned DNA
                       organism = unidentified
SEQUENCE: 7
cagtcgaacg gagttatgca gaggaagttt tcggatggaa tcggcgtaac ttagtggcgg     60
acgggtgagt aacgcgtggg aaacctgccc tgtaccgggg gataacactt agaaataggt    120
gctaataccg cataagcgca cagcttcaca tgaggcagtg tgaaaaactc cggtggtaca    180
ggatggtccc gcgtctgatt agccagttgg caggtaacgg cctaccaaa gcgacgatca     240
gtagccggc tgagagggtg aacggccaca ttgggactga gacacggccc aaactcctac     300
gggaggcagc agtggggaat attgcacaat gggggaaacc ctgatgcagc gacgccgcgt    360
gagtgaagaa gtatttcggt atgtaaagct ctatcagcag gaagaaaat gacggtacct     420
gactaagaag cccccggctaa ctacgtgcca gcagccgcgg taatacgtag ggggcaagcg   480
ttatccggat ttactgggtg taaagggagc gtagacggca tgacaagcca gatgtgaaaa   540
cccagggctc aaccctggga ctgcatttgg aactgccagg ctggagtgca ggagaggtaa   600
gcggaattcc tagtgtagcg gtgaaatgcg tagatattag gaggaacacc agtggcgaag   660
gcggcttact ggactgtaac tgacgttgag gctcgaaagc gtgggagca acaggatta     720
gataccctgg tagtccacgc ggtaaacgat gattgctagg tgtaggtggg tatggaccca   780
tcggtgccgc agctaacgca ataagcaatc cacctggtga gtacgttcg caagaatgaa   840
actcaaagga attgacgggg acccgcacaa gcggtggagc atgtggttta attcgaagca   900
acgcgaagaa ccttaccaag tcttgacatc ccaatgacgt gtccgtaacg ggcattctc    960
ttcggagcat tggagacagg tggtgcatgg ttgtcgtcag ctcgtgtcgt gagatgttgg   1020
gttaagtccc gcaacgagcg caaccctttat ccttagtagc cagcaggtag agctgggcac 1080
tctagggaga ctgccgggga taacccggag gaaggcgggg atgacgtcaa atcatcatgc   1140
cccttatgat ttgggctaca cacgtgctac aatggcgtaa acaaagggaa gcgagacagt   1200
gatgttgagc aaatcccaga aataacgtct cagttcggat tgtagtctgc aactcgacta   1260
catgaagctg aatcgctag taatcgcgaa tcagcatgtc gcggtgaata cgttcccggg   1320
tcttgtacac accgcccgtc acaccatggg agttggaaat gcccgaagcc tgtgacctaa   1380
ccgcaaggga gga                                                     1393

SEQ ID NO: 8           moltype = DNA   length = 1402
FEATURE                Location/Qualifiers
misc_feature           1..1402
                       note = K08
variation              947..949
                       note = n is a, c, g, or t
variation              953..955
                       note = n is a, c, g, or t
variation              967..970
                       note = n is a, c, g, or t
source                 1..1402
                       mol_type = unassigned DNA
                       organism = unidentified
SEQUENCE: 8
caagtcgaac gaagtttcga ggaagcttgc ttccaaagag acttagtggc gaacgggtga     60
gtaacacgta ggtaacctgc ccatgtgtcc gggataactg ctggaaacgg tagctaaaac    120
cggatagta tacagagcgc atgctcagta tattaaagcg cccatcaagg cgtgaacatg     180
gatgcagtca cggcgcatta gctagttggt gaggtaacgg cccaccaagg cgatgatgcg    240
tagccggcct gagagggtaa acggccacat tgggactgag acacggccca aactcctacg    300
ggaggcagca gtaggggaatt tcgtcaatg ggggaaaccc tgaacgagca atgccgcgtg   360
agtgaagaag gtcttcggat cgtaaagctc tgttgtaagt gaagaacggc tcatagagga    420
aatgctatgg gagtgacggt agcttaccag aaagccactg ctaactacgt gccagcagcc    480
gcggtaatac gtaggtggca agcgttatcc ggaattcattg gcgtaaagg gtgcgtaggt   540
ggcgtactaa gtctgtagta aaaggcaatg gctcaaccat tgtaagctat ggaaactggt    600
atgctggagt gcagaagagg gcgatggaat tccatgtgta gcggtaaaat gcgtagatat    660
atggaggaac accagtggcg aaggcggtcg cctggtctgt aactgacact gaggcacgaa    720
agcgtgggga gcaaatagga ttagatacc tagtagtcca cgccgtaaac gatgagaact    780
aagtgttgga ggaattcagt gctgcagtta acgcaataag ttctccgcct ggggagtatg    840
cacgcaagtg tgaaactcaa aggaattgac ggggccccgc acaagcggtg gagtatgtgg   900
tttaattcga agcaacgcga agaacctttac caggccttga catggannna aannncctag    960
agatagnnnn ataattatgg atcacacagg tggtgcatgg ttgtcgtcag ctcgtgtcgt   1020
gagatgttgg gttaagtccc gcaacgagcg caaccctttcg catgttac cagcatcaag   1080
ttggggactc atgcgagact gccgtgaca aacggagga aggtgggggat gacgtcaaat    1140
catcatgccc cttatggcct gggctacaca cgtactacaa tggcgaccac aaagagcagc   1200
gacacagtga tgtgaagcga atctcataaa ggtcgtctca gttcggattg aagtctgcaa    1260
ctcgacttca tgaagtcgga atcgctagta atcgcagatc agcatgctgc ggtgaatacg   1320
ttctcgggcc ttgtacacac cgcccgtcaa accatggag tcagtaatac cgaagccggt   1380
tggcataacc gtaaggagtg ag                                            1402

SEQ ID NO: 9           moltype = DNA   length = 1386
FEATURE                Location/Qualifiers
misc_feature           1..1386
```

|  | note = K09 |  |
| --- | --- | --- |
| source | 1..1386 |  |
|  | mol_type = unassigned DNA |  |
|  | organism = unidentified |  |

SEQUENCE: 9

```
agtcgagggg catcaggaag aaagcttgct ttctttgctg gcgaccggcg cacgggtgag    60
taacacgtat ccaacctgcc ctttactcgg ggatagcctt tcgaaagaaa gattaatacc   120
cgatggcata atgattccgc atggtttcat tattaaagga ttccggtaaa ggatggggat   180
gcgttccatt aggttgttgg tgaggtaacg gctcaccaag ccttcgatgg ataggggttc   240
tgagaggaag gtcccccaca ttggaactga gacacggtcc aaactcctac gggaggcagc   300
agtgaggaat attggtcaat gggcgctagc ctgaaccagc caagtagcgt gaaggatgaa   360
ggctctatgg gtcgtaaact tcttttatat aagaataaag tgcagtatgt atactgtttt   420
gtatgtatta tatgaataag gatcggctaa ctccgtgcca gcagccgcgg taatacggag   480
gatccgagcg ttatccggat ttattgggtt taaagggagc gtaggtggac tggtaagtca   540
gttgtgaaag tttgcggctc aaccgtaaaa ttgcagttga tactgtcagt cttgagtaca   600
gtagaggtgg gcggaattcg tggtgtagcg gtgaaatgct tagatatcac gaagaactcc   660
gattgcgaag gcagctcact ggactgcaac tgacactgat gctcgaaagt gtgggtatca   720
aacaggatta gataccctgg tagtccacac agtaaacgat gaatactcgc tgtttgcgat   780
atacagtaag cggccaagcg aaagcattaa gtattccacc tggggagtac gccggcaacg   840
gtgaaactca aaggaattga cggggggccc cacaagcgga ggaacatgtg gtttaattcg   900
atgatacgcg aggaaccta cccgggctta aattgcagtg gaatgatgtg aaacatgtc    960
agtgagcaat caccgctgtg aaggtgctgc atggttgtcg tcagctcgtg ccgtgaggtg  1020
tcggcttaag tgccataacg agcgcaaccc ttatcttcag ttactaacag gtcatgctga  1080
ggactctgga gagactgccg tcgtaagatg tgaggaaggt ggggatgacg tcaaatcagc  1140
acggccctta cgtccgggc tacacacgtg ttacaatggg ggtacagaa ggcagctagc   1200
gggtgaccgt atgctaatcc caaaatcctc tctcagttcg gatcgaagtc tgcaacccgc  1260
cttcgtgaag ctggattcgc tagtaatcgc gcatcagcca cggcgcggtc aatacgttcc  1320
cgggccttgt acacaccgcc cgtcaagcca tgggagccgg ggtacctga agtacgtaac  1380
cgcaag                                                            1386
```

| SEQ ID NO: 10 | moltype = DNA   length = 1366 |
| --- | --- |
| FEATURE | Location/Qualifiers |
| misc_feature | 1..1366 |
|  | note = K10 |
| source | 1..1366 |
|  | mol_type = unassigned DNA |
|  | organism = unidentified |

SEQUENCE: 10

```
agtcgaacga tgaaaccgcc ctcgggcgga catgaagtgg cgaacgggtg agtaacacgt    60
gaccaacctg cccttgctc cgggacaacc ttgggaaacc gaggctaata ccggatactc   120
ctcgcccccc tcctgggggg cccgggaaag cccagacggc aagggatggg gtcgcggccc   180
attaggtagt aggcggggta acggcccacc tagcccgcga tgggtagccg ggttgagaga   240
ccgaccggcc acattgggac tgagatacgg cccagactcc tacgggaggc agcagtggga   300
aattttgcgc aatgggggaa acctgacgc agcaacgccg cgtgcgggac gacggccttc   360
gggttgtaaa ccgcttcag cagggaagaa attcgacggt acctgcagaa gaagctccgg   420
ctaactacgt gccagcagcc gcggtaatac gtagggagcg agcgttatcc ggattcattg   480
ggcgtaaaga gcgcgtaggc ggcctctcaa gcgggatctc taatccgagg gctcaacccc   540
cggccggatc ccgaactggg aggctcgagt tcgtagagg caggcggaat tcccggtgta   600
gcggtggaat gcgcagatat cggaagaac accgatggcg aaggcagcct gctgggccgc   660
aactgacgct gaggcgcgaa agctagggga gcaacagga ttagataccc tggtagtcct   720
agccgtaaac gatggatact aggtgtgggg ggctccgtcc tccgtgccgc agccaacgca   780
ttaagtatcc cgcctgggga gtacggccgc aaggctaaaa ctcaaaggaa ttgacggggg   840
cccgcacaag cagcggagca tgtggcttaa ttcgaagcaa cgcgaagaac cttaccaggg   900
cttgacatgg acgtgaagcc ggggaaaccc ggtggccgag aggagcgtcc gcaggtggtg   960
catgctgtc gtcagctcgt gtcgtgagat gttgggttaa gtcccgcaac gagcgcaacc  1020
cctgccccat gttgccagca ttaggttggg gactcatggg gactgccgg cgtcaagccg  1080
gaggaaggtg gggacgacgt caagtcatca tgccctttat gccctgggct gcacacgtgc  1140
tacaatggcc ggtacaacgg gctgcgagac cgcgaggtcg agcgaatccc tcaaagccgg  1200
ccccagttcg gatcggaggc tgcaacccgc ctccgtgaag tcggagttgc tagtaatcgc  1260
ggatcagcat gccgcggtga atacgttccc gggccttgta cacaccgccc gtcacaccac  1320
ccgagtcgtc tgcaccccgaa gccgccggcc gaacccgacc ggggcg               1366
```

| SEQ ID NO: 11 | moltype = DNA   length = 1395 |
| --- | --- |
| FEATURE | Location/Qualifiers |
| misc_feature | 1..1395 |
|  | note = K11 |
| source | 1..1395 |
|  | mol_type = unassigned DNA |
|  | organism = unidentified |

SEQUENCE: 11

```
cagtcgaacg aagtgaagat agcttgctat tggaacttag tggcgaacgg gtgagtaaca    60
cgtagataac ctgcctgtat gaccgggata acagttggaa acgactgcta ataccggata   120
ggcagagagg aggcatctct tctctgttaa agttgggata caacgcaaac agatggatct   180
gcggtcatt agctagttgg tgaggtaacg gcccaccaag gcgatgatgc atagccgcc    240
tgagagggcg aacggccaca ttgggactga gacacggccc aaactcctac gggaggcagc   300
agtagggaat tttcggcaat gggggaaacc ctgaccgagc aatgccgcgt gagtgaagac   360
ggccttcggg ttgtaaagct ctgttgtaag ggaagaacgg catagagagg gaatgctcta   420
tgagtgacgg taccttacca gaaagccacg gctaactacg tgccagcagc cgcggtaata   480
cgtaggtggc aagcgttatc cggaattatt gggcgtaaag ggtgcgtagg cggcgagata   540
```

```
agtctgaggt aaaagcccgt ggctcaacca cggtaagcct tggaaactgt ctggctggag    600
tgcaggagag gacaatggaa ttccatgtgt agcggtaaaa tgcgtagata tatggaggaa    660
caccagtggc gaaggcggtt gtctggcctg taactgacgc tgaagcacga aagcgtgggg    720
agcaaatagg attagatacc ctagtagtcc acgccgtaaa cgatgagaac taagtgttgg    780
ggaaactcag tgctgcagtt aacgcaataa gttctctcgc ctggggagtat gcacgcaagt    840
gtgaaactca aaggaattga cgggggcccg cacaagcggt ggagtatgtg gtttaattcg    900
acgcaacgcg aagaacctta ccaggccttg acatggtatc aaaggcccta gagatagggg    960
gatagttatg atacacacag gtggtgcatg gttgtcgtca gctcgtgtcg tgagatgttg   1020
ggttaagtcc cgcaacgagc gcaacccttg tttctagtta ccaacagtaa gatgggact   1080
ctagagagac tgccggtgac aaaccggagg aaggtgggga tgacgtcaaa tcatcatgcc   1140
ccttatggcc tgggctacac acgtactaca atggcgtcta caaagagcag cgagcaggtg   1200
actgtaagca aatctcataa aggacgtctc agttcggatt gaagtctgca actcgacttc   1260
atgaagtcgg aatcgctagt aatcgcggat cagcatgccg cggtgaatac gttctcgggc   1320
cttgtacaca ccgcccgtca aaccatggga gttgataata cccgaagccg gtggcctaac   1380
catttatgga gggag                                                     1395

SEQ ID NO: 12            moltype = DNA  length = 1383
FEATURE                  Location/Qualifiers
misc_feature             1..1383
                         note = K12
source                   1..1383
                         mol_type = unassigned DNA
                         organism = unidentified
SEQUENCE: 12
cagtcgaacg cgagcacttg tgctcgagtg gcgaacgggt gagtaataca taagtaacct    60
gccctagaca gggggataac tatttggaaac gatagctaag accgcatagg tacggacact   120
gcatggtgac cgtattaaaa gtgcctcaaa gcactggtag aggatggact tatggcgcat   180
tagctggttg gcggggtaac ggcccaccaa ggcgacgatg cgtagccgac ctgagagggt   240
gaccggccac actgggactg agacacggcc cagactccta cgggaggcag cagtagggaa   300
ttttcggcaa tgggggaaac cctgaccgag caacgccgcg tgaaggaaga aggttttcgg   360
attgtaaaact tctgttataa aggaagaacc gcggctacga gaaatggtag ccgagtgacg   420
gtactttatt agaaagccac ggctaactac gtgccagcag ccgcggtaat acgtaggtgg   480
caagcgttat ccggaattat tgggcgtaaa gagggagcga gcggcagcaa gggtctgtgg   540
tgaaagcctg aagcttaact tcagtaagcc atagaaacta ggcagctaga gtgcaggaga   600
ggatcgtgga attccatgtg tagcggtgaa atgcgtagat atatgaggaa acaccagtgg   660
cgaaggcgac gatctggcct gcaactgacg ctcagtcccg aaagcgtggg gagcaaatag   720
gattagatac cctagtagtc cacgccgtaa acgatgagta ctaagtgttg gatgtcaaag   780
ttcagtgctg cagttaacgc aataagtact ccgcctgagt agtacgttcg caagaatgaa   840
actcaaagga attgacgggg gcccgcacaa gcggtggagc atgtggttta attcgaagca   900
acgcgaagaa ccttaccagg tcttgacata ctcataaagg ctccagagat ggagagatag   960
ctatatgaga tacaggtggt gcatggttgt cgtcagctcg tgtcgtgaga tgttgggtta   1020
agtcccgcaa cgagcgcaac cctatcgtt agttaccatc attaagttgg ggactctagc   1080
gagactgcca gtgacaagct ggaggaaggc ggggatgacg tcaaatcatc atgccccta   1140
tgacctgggc tacacacgtg ctacaatgga tggtgcagag ggaagcgaag ccgcgaggtg   1200
aagcaaaacc cataaaacca ttctcagttc ggattgtagt ctgcaactcg actacatgaa   1260
gttggaatcg ctagtaatcg cgaatcagca tgtcgcggtg aatacgttct cgggccttgt   1320
acacaccgcc cgtcacacca cgagagttga taacacccga agccggtggc taaccgcaa   1380
gga                                                                 1383

SEQ ID NO: 13            moltype = DNA  length = 1423
FEATURE                  Location/Qualifiers
misc_feature             1..1423
                         note = K13
variation                4
                         note = n is a, c, g, or t
source                   1..1423
                         mol_type = unassigned DNA
                         organism = unidentified
SEQUENCE: 13
tgcnagtcga acgcttcttt cctcccgagt gcttgcactc aattggaaag aggagtggcg    60
gacgggtgag taacacgtgg gtaacctacc catcagaggg ggataacact tggaaacagg   120
tgctaatacc gcataacagt ttatgccgca tggcataaga gtgaaaggcg ctttcgggtg   180
tcgctgatgg atggacccgc ggtgcattag ctagttggtg aggtaacggc tcaccaaggc   240
cacgatgcat agccgacctg agagggtgat cggccacact gggactgaga cacggcccag   300
actcctacgg gaggcagcag tagggaatct tcggcaatgg acgaaagtct gaccgagcaa   360
cgccgcgtga gtgaagaagg ttttcggatc gtaaaactct gttgttagag aagaacaagg   420
acgttagtaa ctgaacgtcc cctgacggta tctaaccaga agccacggc taactacgtg   480
ccagcagccg cggtaatacg taggtggcaa gcgttgtccg gatttattgg gcgtaaagcg   540
agcgcaggcg gtttcttaag tctgatgtga aagccccgg ctcaaccgga gggtcatt    600
ggaaactggg agacttgagt gcagaagagg agagtggaat tccatgtgta gcggtgaaat   660
gcgtagatat atgaggaaca ccagtgcgc aaggcggctc tctggtctgt aactgacgct   720
gaggctcgaa agcgtgggga gcaaacagga ttagataccc tggtagtcca cgccgtaaac   780
gatgagtgct aagtgttgga ggttcccgc ccttcagtgc tgcagcaaac gcattaagca   840
ctccgcctgg ggagtacgac cgcaaggttg aaactcaaag gaattgacgg gggcccgcac   900
aagcggtgga gcatgtggtt taattcgaag caacgcgaag aaccttacca ggtcttgaca   960
tcctttgacc actctagaga tagagctttc ccttcgggga caaagtgaca ggtggtgcat   1020
ggttgtcgtc agctcgtgtc gtgagatgtt gggttaagtc ccgcaacgag cgcaacccct   1080
attgttagtt gccatcattt agttgggcac tctagcgaga ctgccggtga caaaccggag   1140
gaaggtgggg atgacgtcaa atcatcatgc cccttatgac ctgggctaca cacgtgctac   1200
```

```
aatgggaagt acaacgagtc gctagaccgc gaggtcatgc aaatctctta aagcttctct   1260
cagttcggat tgcaggctgc aactcgcctg catgaagccg gaatcgctag taatcgcgga   1320
tcagcacgcc gcggtgaata cgttcccggg ccttgtacac accgcccgtc acaccacgag   1380
agtttgtaac acccgaagtc ggtgaggtaa ccttttttgga gcc                    1423

SEQ ID NO: 14           moltype = DNA   length = 1381
FEATURE                 Location/Qualifiers
misc_feature            1..1381
                        note = K14
source                  1..1381
                        mol_type = unassigned DNA
                        organism = unidentified
SEQUENCE: 14
aagtcgaggg gcatcatgac ctagcaatag gttgatggcg accggcgcac gggtgagtaa   60
cacgtatcca acctgccgat tattccggga tagcctttcg aaagaaagat taatactgga   120
tagcataacg agaaggcatc ttcttgttat taaagaattt cgataatcga tggggatgcg   180
ttccattagt ttgttggcgg ggtaacggcc caccaagaca tcgatggata gggggttctga  240
gaggaaggtc ccccacattg gaactgagac acggtccaga ctcctacggg aggcagcagt   300
gaggaatatt ggtcaatgga cgagagtctg aaccagccaa gtagcgtgaa ggatgactgc   360
cctatgggtt gtaaacttct tttatatggg aataaagtgc agtatgtata ctgttttgta   420
tgtaccatac gaataaggat cggctaactc cgtgccagca gccgcggtaa tacggaggat   480
ccgagcgtta tccggattta ttgggtttaa agggagcgta ggcggattat taagtcagtt   540
gtgaaagttt gcggctcaac cgtaaaattg cagttgatac tggtagtctt gagtgcagca   600
gaggtaggcg gaattcgtgg tgtagcggtg aaatgcttag atatcacgaa gaactccgat   660
tgcgaaggca gcttactgga ctgtaactga cgctgatgct cgaaagtgtg ggtatcaaac   720
aggattagat accctggtag tccacacagt aaacgatgaa tactcgctgt ttgcgatata   780
cagcaagcgg ccaagcgaaa gcattaagta ttccacctgg ggagtacgcc ggcaacggtg   840
aaactcaaag gaattgacgg gggcccgcac aagcggagga catgtggtt taattcgatg    900
atacgcgagg aaccttaccc gggcttaaat tgcaactgac ggatttggaa acagatcttc   960
cttcgggcag ttgtgaaggt gctgcatggt tgtcgtcagc tcgtgccgtg aggtgtcggc   1020
ttaagtgcca taacgagcgc aacccttatc tttagttact aacaggtcat gctgaggact   1080
ctagagagac tgccgtcgta agatgtgagg aaggtgggga tgacgtcaaa tcagcacggc   1140
ccttacgtcc gggggctacac acgtgttaca atggggggta cagaaggcag ctacacagcg   1200
atgtgatgct aatcccaaaa gcctctctca gttcggattg gagtctgcaa cccgactcca   1260
tgaagctgga ttcgctagta atcgcgcatc agccacggcg cggtgaatac gttcccgggc   1320
cttgtacaca ccgcccgtca agccatgaaa gccggggta cctgaagtac gtaaccgcaa   1380
g                                                                   1381

SEQ ID NO: 15           moltype = DNA   length = 1391
FEATURE                 Location/Qualifiers
misc_feature            1..1391
                        note = K15
source                  1..1391
                        mol_type = unassigned DNA
                        organism = unidentified
SEQUENCE: 15
cagtcgaacg aagcgattta acggaagttt tcggatgcaa gttggattga ctgagtggcg   60
gacgggtgag taacgcgtgg gtaacctgcc ttgtactggg ggacaacagt tagaaatgac   120
tgctaatacc gcataagcgc acagtatcgc atgatacagt gtgaaaaact ccggtggtac   180
aagatggacc cgcgtctgat tagctagttg gtaaggtaac ggcttaccaa ggcgacgatc   240
agtagccgac ctgagagggt gaccggccac atttgggcta agacacggcc caaactccta   300
cgggaggcag cagtgggaa tattgcacaa tgggcgaaag cctgatgcag cgacgccgcg    360
tgagtgaaga agtatttcgg tatgtaaagc tctatcagca gggaagaaaa tgacggtacc   420
tgactaagaa gccccggcta actacgtgcc agcagccgcg gtaatacgta gggggcaagc   480
gttatccgga tttactgggt gtaaagggag cgtagacgta aaagcaagtc tgaagtgaaa   540
gcccgcggct caactgcggg actgctttgg aaactgttta actggagtgt cggagaggta   600
agtggaattc ctagtgtagc ggtgaaatgc gtagatatta ggaggaacac cagtggcgaa   660
ggcgacttac tggacgataa ctgacgttga ggctcgaaag cgtggggagc aaacaggatt   720
agataccctg gtagtccacg ccgtaaacga tgaatactag gtgtgtggga gcaaaagtct   780
tcggtgccgt cgcaaacgca gtaagtattc cacctgggga gtacgttcgc aagaatgaaa   840
ctcaaaggaa ttgacgggga cccgcacaag cggtggagca tgtggtttaa ttcgaagcaa   900
cgcgaagaac cttaccaggt cttgacatcg atccgacggg ggagtaacgt cccctttccct   960
tcggggcgga agacaggt ggtgcatggt tgtcgtcagc tcgtgtcgtg agatgttggg      1020
ttaagtcccg caacgagcgc aacccttatt ctaagtagcc agcggttcgg ccgggaactc    1080
ttggagact gccagggata acctggagga aggtggggat gacgtcaaat catcatgccc    1140
cttatgatct gggctacaca cgtgctacaa tggcgtaaac aaagagaagc aagaccgcga   1200
ggtggagcaa atctcaaaaa taacgtctca gttcggactg caggctgcaa ctcgcctgca   1260
cgaagctgga atcgctagta atcgcgaatc agaatgtcgc ggtgaatacg ttcccgggtc   1320
ttgtacacac cgcccgtcac accatgggag tcagtaacgc ccgaagtcag tgacccaacc   1380
gcaaggaggg a                                                        1391

SEQ ID NO: 16           moltype = DNA   length = 1402
FEATURE                 Location/Qualifiers
misc_feature            1..1402
                        note = K16
source                  1..1402
                        mol_type = unassigned DNA
                        organism = unidentified
SEQUENCE: 16
```

```
agtcgaacga agcaatactg tgtgaagaga ttagcttgct aagatcagaa cttttgtattg    60
actgagtggc ggacgggtga gtaacgcgtg ggcaacctgc cttacacagg gggataacag   120
ctagaaatgg ctgctaatac cgcataagac ctcagtaccg catggtagag gggtaaaaac   180
tccggtggtg taagatgggc ccgcgtctga ttaggtagtt ggtagggtaa cggcctacca   240
agccgacgat cagtagccga cctgagaggg tgaccgacca cattgggact gagacacggc   300
ccaaactcct acgggaggca gcagtgggga atattgcaca atgggggaaa ccctgatgca   360
gcgacgccgc gtgaaggatg aagtatttcg gtatgtaaac ttctatcagc agggaagaag   420
atgacgctac ctgactaaga agccccggct aactacgtgc cagcagccgc ggtaatacgt   480
agggggcaag cgttatccgg atttactggg tgtaaaggga gcgtagacgg catggcaagt   540
ctgaagtgaa agcccggggc tcaacccccgg gactgcttgg gaaactgtca ggctagagtg   600
tcggagaggc aagtggaatt cctagtgtag cggtgaaatg cgtagatatt aggaggaaca   660
ccagtggcga aggcggcttg ctggacgatg actgacgttg aggctcgaaa gcgtgggag    720
caaacaggat tagataccct ggtagtccac gccgtaaacg atgattacta ggtgtcggga   780
agcaaagctt ttcggtgccg cagccaacgc aataagtaat ccacctgggg agtacgttcg   840
caagaatgaa actcaaagga attgacgggg acccgcacaa gcggtggagc atgtggttta   900
attcgaagca acgcgaagaa ccttacctga tcttgacatc ccggtgacaa gtatgtaat    960
gtactctttc ttcggaacac cggtgacagg tggtgcatgg ttgtcgtcag ctcgtgtcgt   1020
gagatgttgg gttaagtccc gcaacgagcg caacccttat ctttagtagc cagcatttga   1080
ggtgggcact ctagagagac tgccagggat aacctggagg aaggtgggga tgacgtcaaa   1140
tcatcatgcc ccttatgacc agggctacac acgtgctaca atggcgtaaa caaagggaag   1200
cgaccctgtg aaggcaagca aatcccaaaa ataacgtctc agttcggatt gtagtctgca   1260
actcgactac atgaagctgg aatcgctagt aatcgcgaat cagaatgtcg cggtgaatac   1320
gttcccgggt cttgtacaca ccgcccgtca caccatggga gtcagtaacg cccgaagccg   1380
gtgacctaac cgaaaggaag ga                                            1402

SEQ ID NO: 17          moltype = DNA  length = 1393
FEATURE                Location/Qualifiers
misc_feature           1..1393
                       note = K17
variation              942..945
                       note = n is a, c, g, or t
source                 1..1393
                       mol_type = unassigned DNA
                       organism = unidentified
variation              953..956
                       note = n is a, c, g, or t
variation              1067..1069
                       note = n is a, c, g, or t
SEQUENCE: 17
gcaagtcgag cgaagcggtt tcgatgaagt tttcggatgg atttgaaatt gacttagcgg    60
cggacgggtg agtaacgcgt gggtaacctg ccttacactg ggggataaca gttagaaatg   120
actgctaata ccgcataagc gcacaggggcc gcatggtctg tgtgaaaaa ctccggtggt   180
gtaagatgag cccgcgtctg attaggtagt tggtggggta aaggcccacc aagccgacga   240
tcagtagccg aactgagagg gtgaccggcc acattgggac tgagacacgg cccaaactcc   300
tacgggaggc agcagtgggg aatattggac aatgggcgaa agcctgatcc agcgacgccg   360
cgtgagtgaa gaagtatttc ggtatgtaaa gctctatcag cagggaagaa aatgacggta   420
cctgactaag aagccccggc taactacgtg ccagcagccg cggtaataag taggggggcaa   480
gcgttatccg gatttactgg gtgtaaaggg agcgtagacg gttaagcaag tctgaagtga   540
aagcccgggg ctcaacccccg gtactgctttt ggaaactgtt tgacttgagt gcaggagagg   600
taagtggaat tcctagtgta gcggtgaaat gcgtagatat taggaggaac accagtggcg   660
aaggcggctt actgggactgt aactgacgtt gaggctcgaa agcgtgggga gcaaacaggg   720
ttagataccc tggtagtcca cgccgtaaac gatgaatact aggtgtcggg ggacaaagtc   780
cttcggtgcc gccgctaacg caataagtat tccacctggg gagtacgttc gcaagaatga   840
aactcaaagg aattgacggg gacccgcaca agcggtggag catgtggttt aattcgaagc   900
aacgcgaaga accttaccaa gtcttgacat cccattgaaa annnnnttaac cgnnnnnccct   960
cttcggagca atggagacag gtggtgcatg gttgtcgtca gctcgtgtcg tgagatgttg   1020
ggttaagtcc cgcaacgagc gcaacccttat ccttagtag ccagcannna atggtgggca   1080
ctctggggag actgccaggg ataacctgga ggaaggtggg gatgacgtca aatcatcatg   1140
cccccttatga tttgggctac acacgtgcta caatgggcgta aacaaaggga agcaaagga   1200
cgatctggag caaaccccaa aaataacgtc tcagttcgga ttgtcaggctg caactcgcct   1260
gcatgaagct ggaatcgcta gtaatcgcga atcagaatgt cgcggtgaat acgttcccgg   1320
gtcttgtaca caccgcccgt cacaccatgg gagttggtaa cgcccgaagt cagtgaccca   1380
accgcaagga ggg                                                      1393

SEQ ID NO: 18          moltype = DNA  length = 1389
FEATURE                Location/Qualifiers
misc_feature           1..1389
                       note = K18
source                 1..1389
                       mol_type = unassigned DNA
                       organism = unidentified
SEQUENCE: 18
gtcgaggggc agcatggtct tagcttgcta aggctgatgg cgaccggcgc acgggtgagt    60
aacacgtatc caacctgccg tctactcttg gccagccttc tgaaaggaag attaatccag   120
gatggcatca tgagttcaca tgtccgcatg attaaaggta ttttccggta gacgatgggg   180
atgcgttcca ttagatagta ggcggggtaa cggcccacct agtcaacgat ggatagggt    240
tctgagagga aggtccccca cattggaact gagacacgt ccaaactcct acgggaggca   300
gcagtgagga atattggtca atgggcgatg gcctgaacca gccaagtagc gtgaaggatg   360
actgccctat gggttgtaaa cttctttat aaaggaataa agtcgggtat gcataccgt    420
```

```
ttgcatgtac tttatgaata aggatcggct aactccgtgc cagcagccgc ggtaatacgg    480
aggatccgag cgttatccgg atttattggg tttaaaggga gcgtagatgg atgtttaagt    540
cagttgtgaa agtttgcggc tcaaccgtaa aattgcagtt gatactggat gtcttgagtg    600
cagttgaggc aggcggaatt cgtggtgtag cggtgaaatg cttagatatc acgaagaact    660
ccgattgcga aggcagcctg ctaagctgca actgacattg aggctcgaaa gtgtgggtat    720
caaacaggat tagatacccct ggtagtccac acggtaaacg atgaatactg ctgtttgcg    780
atatacggca gcggccaag cgaaagcgtt aagtattcca cctggggagt acgccggcaa    840
cggtgaaact caaaggaatt gacggggcc cgcacaagcg gaggaacatg tggtttaatt    900
cgatgatacg cgaggaacct tacccgggct taaattgcac tcgaatgatc cggaaacggt    960
tcagctagca atagcgagtg tgaaggtgct gcatggttgt cgtcagctcg tgccgtgagg   1020
tgtcggctta agtgccataa cgagcgcaac ccttgttgtc agttactaac aggtgatgct   1080
gaggactctg acaagactgc catcgtaaga tgtgaggaag gtgggatga cgtcaaatca   1140
gcacggccct tacgtccggg gctacacacg tgttacaatg gggggtacag agggccgcta   1200
ccacgcgagt ggatgccaat ccctaaaacc cctctcaatt cggactggag tctgcaaccc   1260
gactccacga agctggattc gctagtaatc gcgcatcagc cacggcgcgg tgaatacgtt   1320
cccgggcctt gtacacaccg cccgtcaagc catgggagcc ggggtacct gaagtgcgta   1380
accgcgagg                                                          1389

SEQ ID NO: 19           moltype = DNA   length = 1393
FEATURE                 Location/Qualifiers
misc_feature            1..1393
                        note = K19
variation               1205..1206
                        note = n is a, c, g, or t
source                  1..1393
                        mol_type = unassigned DNA
                        organism = unidentified SEQUENCE: 19
gcagtcgaac gaagcaatta agatgaagtt ttcggatgga atcttgattg actgagtggc     60
ggacgggtga gtaacgcgtg gataacctgc ctcacactgg gggataacag ttagaaatga   120
ctgctaatac cgcataagcg cacagtgccg catggcagtg tgtgaaaaac tccggtggtg   180
tgagatggat ccgcgtctga ttagccagtt ggcggggtaa cggcccacca aagcgacgat   240
cagtagccga cctgagaggg tgaccggcca cattgggact gagacacggc ccaaactcct   300
acgggaggca gcagtgggga atattgcaca atgggcgaaa gcctgatgca gcgacgccgc   360
gtgagtgaag aagtatttcg gtatgtaaag ctctatcagc agggaagaaa atgacggtac   420
ctgactaaga agccccggct aactacgtgc cagcagccgc ggtaatacgt aggggggcaag   480
cgttatccgg atttactggg tgtaaaggga gcgtagacgg cgaagcaagt ctgaagtgaa   540
aacccagggc tcaaccctgg gactgctttg gaaactgttt tgctagagtg tcggagaggt   600
aagtggaatt cctagtgtag cggtgaaatg cgtagatatt aggaggaaca ccagtggcga   660
aggcggctta ctggacgata actgacgttg aggctcgaaa gcgtggggag caaacaggat   720
tagatacccct ggtagtccac gccgtaaacg atgaatgcta ggtgttgggg ggcaaagccc   780
ttcggtgccg ccgcaaacgc agtaagcatt ccacctgggg agtacgttcg caagaatgaa   840
actcaaagga attgacgggg acccgcacaa gcggtggagc atgtggttta attcgaagca   900
acgcgaagaa ccttaccaag tcttgacatc ccctgacggg gccggtaacg cggcctttcc   960
ttcgggacag gggagacagg tggtgcatgg ttgtcgtcag ctcgtgtcgt gagatgttgg   1020
gttaagtccc gcaacgagcg caaccctttat ccttagtagc cagcacgtga aggtgggcac   1080
tctagggaga ctgccaggga taacctggag gaaggtggga atgacgtcaa atcatcatgc   1140
cccttatgat ttgggctaca cacgtgctac aatggcgtaa acaaagggaa gcgagacagt   1200
gatgnngagc aaatcccaaa aataacgtcc cagttcggac tgtagtctgc aacccgacta   1260
cacgaagctg gaatcgctag taatcgcgaa tcagaatgtc gcggtgaata cgttcccggg   1320
tcttgtacac accgcccgtc acaccatggg agtcagcaac gcccgaagtc agtgacccaa   1380
ccgaaaggag gga                                                      1393

SEQ ID NO: 20           moltype = DNA   length = 1394
FEATURE                 Location/Qualifiers
misc_feature            1..1394
                        note = K20
source                  1..1394
                        mol_type = unassigned DNA
                        organism = unidentified SEQUENCE: 20
tgcaagtcga acggggtgct catgacgag gattcgtcca acggattgag ttacctagtg     60
gcggacgggt gagtaacgcg tgaggaacct gccttgagga ggggaataac actccgaaag   120
gagtgctaat accgcatgat gcagttgggt cgcatgcctc tgactgccaa agatttatcg   180
ctctgagatg gcctcgcgtc tgattagcta gtaggcgggg taacggccca cctaggcgac   240
gatcagtagc cggactgaga ggttgaccgg ccacattggg actgagacac ggcccagact   300
cctacgggag gcagcagtgg ggaatattgg caatgggcg caagcctgac ccagcaacgc   360
cgcgtgaagg aagaaggctt cgggttgta aacttctttt gtcggggacg aaacaaatga   420
cggtacccga cgaataagcc acgctaact acgtgccagc agccgcggta atacgtaggg   480
ggcaagcgtt atccggattt actggtgta aagggcgtgt aggcgggatt gcaagtcaga   540
tgtgaaaact ggggggctcaa cctccagcct gcatttgaaa ctgtagttct tgagtgctgg   600
agaggcaatc ggaattccgt gtgtagcgg gaaatgcgta gatatacgga ggaacaccag   660
tggcgaaggc ggattgctgg acagtaactg acgctgaggc gcgaaagcgt ggggagcaaa   720
caggattaga taccctggta gtccacgccg taaacacgatg atactaggtg tgggggtct   780
gacccccctcc gtgccgcagt taacacaata agtatcccac ctgggagta cgatcgcaag   840
gttgaaactc aaaggaattg acgggggccc gcacaagcgg tggagtatgt ggtttaattc   900
gaagcaacgc gaagaacctt accagggctt gacatcccac taacgaagca gagatgcatt   960
aggtgccctt cggggaaagt ggagacaggt ggtgcatggt tgtcgtcagc tcgtgtcgtg  1020
agatgttggg ttaagtcccg caacgagcgc aacccttatt gttagttgct acgcaagagc  1080
```

```
actctagcga gactgccgtt gacaaaacgg aggaaggtgg ggacgacgtc aaatcatcat 1140
gcccctttatg tcctgggcca cacacgtact acaatggtgg ttaacagagg gaggcaatac 1200
cgcgaggtgg agcaaatccc taaaagccat cccagttcgg attgcaggct gaaacccgcc 1260
tgtatgaagt tggaatcgct agtaatcgcg gatcagcatg ccgcggtgaa tacgttcccg 1320
ggccttgtac acaccgcccg tcacaccatg agagtcggga acacccgaag tccgtagcct 1380
aaccgcaagg aggg                                                   1394
```

| SEQ ID NO: 21 | moltype = DNA length = 1385 |
|---|---|
| FEATURE | Location/Qualifiers |
| misc_feature | 1..1385 |
| | note = K21 |
| source | 1..1385 |
| | mol_type = unassigned DNA |
| | organism = unidentified |

SEQUENCE: 21
```
agtcgagggg cagcattta gtttgcttgc aaactaaaga tggcgaccgg cgcacgggtg 60
agtaacacgt atccaacctg ccgataactc ggggatagcc tttcgaaaga aagattaata 120
tccgatggta tattaaaacc gcatggtttt actattaaag aatttcggtt atcgatgggg 180
atgcgttcca ttagtttgtt ggcgggtaa cggcccacca agactacgat ggataggggt 240
tctgagagga aggtccccca cattggaact gagacacggt ccaaactcct acgggaggca 300
gcagtgagga atattggtca atggacgaga gtctgaacca gccaagtagc gtgaaggatg 360
actgccctat gggttgtaaa cttctttat atgggaataa agtattccac ggtgtggaatt 420
ttgtatgtac catatgaata aggatcggct aactccgtgc cagcagccgc ggtaatacgg 480
aggatccgag cgttatccgg atttattggg tttaaaggga gcgtaggtgg attgttaagt 540
cagttgtgaa agtttgcggc tcaaccgtaa aattgcagtt gaaactggca gtcttgagta 600
cagtagaggt gggcggaatt cgtggtgtag cggtgaaatg cttagatatc acgaagaact 660
ccgattgcga aggcagctca ctagactgca actgacactg atgctcgaaa gtgtgggtat 720
caaacaggat tagataccct ggtagtccac acagtaaacg atgaatactc gctgtttgcg 780
atatacagta agcggccaag cgaaagcatt aagtattcca cctggggagt acgccggcaa 840
cggtgaaact caaaggaatt gacggggcc cgcacaagcg gtgtttaatt 900
cgatgatacg cgaggaacct tacccggct taaattgcat ttgaataatc tggaaacagg 960
ttagccgcaa ggcaaatgtg aaggtgctgc atggttgtcg tcagctcgtg ccgtgaggtg 1020
tcggcttaag tgccataacg agcgcaaccc ttatctttag ttactaacag gtcatgctga 1080
ggactctaga gagactgccg tcgtaagatg tgaggaaggt ggggatgacg tcaaatcagc 1140
acggccctta cgtccggggc tacacacgtg ttacaatggg ggtacagaa ggcagctacc 1200
tggcgacagg atgctaatcc caaaaacctc tctcagttcg gatcgaagtc tgcaacccga 1260
cttcgtgaag ctggattcgc tagtaatcgc gcatcagcca tggcgcggtg aatacgttcc 1320
cgggccttgt acacaccgcc cgtcaagcca tgaaagccgg gggtacctga agtacgtaac 1380
cgcaa                                                             1385
```

| SEQ ID NO: 22 | moltype = DNA length = 1385 |
|---|---|
| FEATURE | Location/Qualifiers |
| misc_feature | 1..1385 |
| | note = K22 |
| source | 1..1385 |
| | mol_type = unassigned DNA |
| | organism = unidentified |

SEQUENCE: 22
```
agtcgagggg cagcattca gtttgcttgc aaactggaga tggcgaccgg cgcacgggtg 60
agtaacacgt atccaacctg ccgataactc ggggatagcc tttcgaaaga aagattaata 120
cccgatggta taattagacc gcatggtctt gttattaaag aatttcggtt atcgatgggg 180
atgcgttcca ttaggcagtt ggtgaggtaa cggctcacca aaccttcgat ggataggggt 240
tctgagagga aggtccccca cattggaact gagacacggt ccaaactcct acgggaggca 300
gcagtgagga atattggtca atgggcgcag gcctgaacca gccaagtagc gtgaaggatg 360
actgccctat gggttgtaaa cttctttat atgggaataa agttttccac gtgtggaatt 420
ttgtatgtac catatgaata aggatcggct aactccgtgc cagcagccgc ggtaatacgg 480
aggatccgag cgttatccgg atttattggg tttaaaggga gcgtaggtgg acagttaagt 540
cagttgtgaa agtttgcggc tcaaccgtaa aattgcagtt gatactggct gtcttgagta 600
cagtagaggt gggcggaatt cgtggtgtag cggtgaaatg cttagatatc acgaagaact 660
ccgattgcga aggcagctca ctggactgca actgacactg atgctcgaaa gtgtgggtat 720
caaacaggat tagataccct ggtagtccac acagtaaacg atgaatactc gctgtttgcg 780
atatacagta agcggccaag cgaaagcatt aagtattcca cctggggagt acgccggcaa 840
cggtgaaact caaaggaatt gacggggcc cgcacaagcg gaggaacatg tggtttaatt 900
cgatgatacg cgaggaacct tacccggct taaattgcat ttgaataatc tggaaacagg 960
atagccgtaa ggcaaatgtg aaggtgctgc atggttgtcg tcagctcgtg ccgtgaggtg 1020
tcggcttaag tgccataacg agcgcaaccc ttatctttag ttactaacag gtcatgctga 1080
ggactctaga gagactgccg tcgtaagatg tgaggaaggt ggggatgacg tcaaatcagc 1140
acggccctta cgtccggggc tacacacgtg ttacaatggg ggtacagaa ggcagctacc 1200
tggtgacagg atgctaatcc caaaaacctc tctcagttcg gatcgaagtc tgcaacccga 1260
cttcgtgaag ctggattcgc tagtaatcgc gcatcagcca tggcgcggtg aatacgttcc 1320
cgggccttgt acacaccgcc cgtcaagcca tgaaagccgg gggtacctga agtacgtaac 1380
cgcaa                                                             1385
```

| SEQ ID NO: 23 | moltype = DNA length = 1387 |
|---|---|
| FEATURE | Location/Qualifiers |
| misc_feature | 1..1387 |
| | note = K23 |
| source | 1..1387 |
| | mol_type = unassigned DNA |

-continued

```
                          organism = unidentified
SEQUENCE: 23
agtcgagggg cagcatgatt tgtagcaata cagattgatg cgaccggcg cacgggtgag   60
taacgcgtat gcaacttacc tatcagaggg ggatagcccg gcgaaagtcg gattaatacc  120
ccataaaaca ggggtcccgc atgggaatat ttgttaaaga ttcatcgctg atagataggc  180
atgcgttcca ttaggcagtt ggcggggtaa cggcccacca aaccgacgat ggataggggt  240
tctgagagga aggtccccca cattggtact gagacacgga ccaaactcct acggggagca  300
gcagtgagga atattggtca atggccgaga ggctgaacca gccaagtcgc gtgaaggaag  360
aaggatctat ggtttgtaaa cttctttat agggggaataa agtggaggac gtgtcctttt  420
ttgtatgtac cctatgaata agcatcggct aactccgtgc cagcagccgc ggtaatacgg  480
aggatgcgag cgttatccgg atttattggg tttaaagggt gcgtaggtgg tgatttaagt  540
cagcggtgaa agtttgtggc tcaaccataa aattgccgtt gaaactgggt tacttgagtg  600
tgtttgaggt aggcggaatg cgtggtgtag cggtgaaatg catagatatc acgcagaact  660
ccgattgcga aggcagctta ctaaaccata actgacactg aagcacgaaa gcgtgggat  720
caaacaggat tagataccct ggtagtccac gcagtaaacg atgattacta ggagtttgcg  780
atacaatgta agctctacag cgaaagcgtt aagtaatcca cctgggggagt acgccggcaa  840
cggtgaaact caaaggaatt gacggggccc cgcacagcgg aggaacatgt ggtttaattc  900
gatgatacgc gaggaacctt acccgggttt aacgtagtc tgaccgacggt gaaaccgta   960
tttctagcaa tagcagatta cgaggtgctg catggttgtc gtcagctcgt gccgtgaggt 1020
gtcggcttaa gtgccataac gagcgcaacc cttatcacta gttactaaca ggtgaagctg 1080
aggactctgg tgagactgcc agcgtaagct gtgaggaagg tggggatgac gtcaaatcag 1140
cacggccctt acatccgggg cgacacacgt gttacaatgg cagcagctac             1200
ctggtgacag gatgctaatc tccaaaccat gtctcagttc ggatcggagt ctgcaactcg 1260
actccgtgaa gctggattcg ctagtaatcg cgcatcagcc atggcgcggt gaatacgttc 1320
ccgggccttg tacacaccgc ccgtcaagcc atggagccg ggggtacctg aagtccgtaa  1380
ccgcaag                                                           1387

SEQ ID NO: 24         moltype = DNA   length = 1384
FEATURE               Location/Qualifiers
misc_feature          1..1384
                      note = K24
source                1..1384
                      mol_type = unassigned DNA
                      organism = unidentified
SEQUENCE: 24
gtcgagggc agcatggtct tagcttgcta aggccgatgg cgaccggcgc acgggtgagt   60
aacacgtatc caacctgccg tctactcttg gacagccttc tgaaaggaag attaatacaa  120
gatggcatca tgagtccgca tgttcacatg attaaaggta ttccggtaga cgatgggat   180
gcgttccatt agatagtagg cggggtaacg gcccacctag tcttcgatgg ataggggtc  240
tgagaggaag gtccccaca ttggaactga gacacggtcc aaactcctac ggaggcagc   300
agtgaggaat attggtcaat gggcgagagc ctgaaccagc caagtagcgt gaaggatgac  360
tgccctatgt tgtaaact tcttttataa aggaataaag tgggtatgg atacccgttt    420
gcatgtactt tatgaataag gatcggctaa ctccgtgcca cagccgcgta ataacgccgc  480
gatccgagcg ttatccggat ttattgggtt taaagggggc gtagatggat gtttaagtca  540
gttgtgaaag tttgcggctc aaccgtaaaa ttgcagttga tactggatat cttgagtgca  600
gttgaggcag gcggaattcg tggtgtagcg gtgaaatgct tagatatcac gaagaactcc  660
gattgcgaag gcagcctgct aagctgcaac tgacattgag gctcgaaagt gtgggtatca  720
aacaggatta gatacctgg tagtccacac ggtaaacgat gaatactcgc tgtttgcgat   780
atactgcaag cggccaagcg aaagcgttaa gtattccacc tgggagtac gccggcaacg   840
gtgaaactca aaggaattga cggggcccg cacaagcgga ggaacatgtg gtttaattcg  900
atgatacgcg aggaaccta cccgggctta aattgcagat gaattacgc gaaagccgta  960
agccgcaagg catctgtgaa ggtgctgcat ggttgtcgtc agctcgtgcc gtgaggtgtc 1020
ggcttaagtg ccataacgag cgcaacccct tttgtcagtt actaacaggt tccgctgagg 1080
actctgacaa gactgccatc gtaagatgtg aggaaggtgg ggatgacgtc aaatcagcac 1140
ggcccttacg tccgggcta cacacgtgtt acaatgggta cagagggca gcgctaccac  1200
gcgagtggat gccaatcccc aaaacctctc tcagttcgga ctggagtctg caacccgact 1260
ccacgaagct ggattcgcta gtaatcgcgc atcagccacg gcgcggtgaa tacgttcccg 1320
ggccttgtac acaccgcccg tcaagccatg ggagccgggg gtacctgaag tgcgtaaccg 1380
cgag                                                              1384

SEQ ID NO: 25         moltype = DNA   length = 1396
FEATURE               Location/Qualifiers
misc_feature          1..1396
                      note = K25
source                1..1396
                      mol_type = unassigned DNA
                      organism = unidentified
variation             943..944
                      note = n is a, c, g, or t
variation             1072
                      note = n is a, c, g, or t
variation             1290
                      note = n is a, c, g, or t
SEQUENCE: 25
gcagtcgaac gaagcgatct gggatgaagt tttcggatgg attcctggtt gactgagtgg   60
cggacgggtg agtaacgcgt ggataacctg cctcacactg ggggataaca gttagaaatg  120
gctgctaata ccgcataagc gcacagtacc gcatggtacg gtgtgaaaaa cccaggtggt  180
gtgagatgga tccgcgtctg attagccagt tggcgggta acggcccacc aaagcgacga  240
tcagtagccg acctgagagg gtgaccggcc acattgggac tgagacacgg cccaaactcc  300
```

```
tacgggaggc agcagtgggg aatattgcac aatgggcgaa agcctgatgc agcgacgccg    360
cgtgagtgaa gaagtatctc ggtatgtaaa gctctatcag cagggaagaa aatgacggta    420
cctgactaag aagccccggc taactacgtg ccagcagccg cggtaatacg tagggggcaa    480
gcgttatccg gatttactgg gtgtaaaggg agcgtagacg gcgacgcaag tctggagtga    540
aagcccgggg cccaacccg ggactgcttt ggaaactgtg ctgctggagt gcaggagagg    600
taagtggaat tcctagtgta gcggtgaaat gcgtagatat taggaggaac accagtggcg    660
aaggcggctt actggactgt aactgacgtt gaggctcgaa agcgtgggga gcaaacagga    720
ttagataccc tggtagtcca cgccgtaaac gatgaatgct aggtgtcggg gggcaaagcc    780
cttcggtgcc gccgctaacg caataagcat tccacctggg gagtacgttc gcaagaatga    840
aactcaaagg aattgacggg gacccgcaca agcggtggag catgtggttt aattcgaagc    900
aacgcgaaga accttaccaa gtcttgacat ccccctgacc ggnncgtaac ggtgcccttc    960
cttcgggaca ggggagacag gtggtgcatg gttgtcgtca gctcgtgtcg tgagatgttg   1020
ggttaagtcc cgcaacgagc gcaaccctta tccttagtag ccagcacgtg anggtgggca   1080
ctctagggag actgccaggg ataacctgga ggaaggtgga gatgacgtca aatcatcatg   1140
cccccttatga tttgggctac acacgtgcta caatggcgta aacaaaggga ggcgaccctg   1200
cgaaggcaag caaatcccaa aaataacgtc ccagttcgga ctgtagtctg caacccgact   1260
acacgaagct ggaatcgcta gtaatcgcgn atcagaatgc cgcggtgaat acgttccgg    1320
gtcttgtaca caccgcccgt cacaccatgg gagtcagcaa cgcccgaagt cagtgaccca   1380
accttaacag gaggga                                                    1396
SEQ ID NO: 26           moltype = DNA  length = 1382
FEATURE                 Location/Qualifiers
misc_feature            1..1382
                        note = K26
source                  1..1382
                        mol_type = unassigned DNA
                        organism = unidentified
SEQUENCE: 26
gtcgaggggc atcaggaaga aagcttgctt tctttgctgg cgaccggcgc acgggtgagt     60
aacacgtatc caacctgccg atgactcggg gatagccttt cgaaagaaag attaataccc    120
gatggtatat ctgaaaggca tcttcagct attaaagaat ttcggtcatt gatgggatg     180
cgttccatta ggttgttggc ggggtaacgg cccaccaagc cgtcgatgga tagggttct    240
gagaggaagt tcccccacat tggaactgag acacggtcca aactcctacg ggaggcagca    300
gtgaggaata ttggtcaatg gacgagagtc tgaaccagcc aagtagcgtg aaggatgact    360
gccctatggg ttgtaaactt cttttatacg ggaataagt taggcacgtg tgccttttg    420
tatgtaccgt atgaataagg atcggctaac tccgtgccag cagccgcggt aatacggagg    480
atccgagcgt tatccggatt tattgggttt aagggagcg taggcggatg cttaagtcag    540
ttgtgaaagt ttgcggctca accgtaaaat tgcagttgat actgggtgtc ttgagtacag    600
tagaggcgag cggaattcgt ggtgtagcgg tgaaatgctt agatatcacg aagaactccg    660
attgcgaagg cagcttgctg gactgtaact gacgctgatg ctcgaaagtg tgggtatcaa    720
acaggattag ataccctggt agtccacaca gtaaacgatg aatactcgct gtttgcgata    780
tacagtaagc ggccaagcga aagcgttaag tattccacct ggggagtacg ccggcaacgg    840
tgaaactcaa aggaattgac gggggcccgc acaagcggag gaacatgtgg tttaattcga    900
tgatacgcga ggaaccttac ccgggcttaa attgcaaatg aatgttctgg aaacagatca    960
gccgcaaggc atttgtgaag gtgctgcatg gttgtcgtca gctcgtgccg tgaggtgtcg   1020
gcttaagtgc cataacgagc gcaaccctta tcgatagtta ccatcaggtt atgctgggga   1080
ctctgtcgag actgccgtcg taagatgtga ggaaggtgga gatgacgtca aatcagcagg   1140
gcccttacgt ccggggctac acacgtgtta caatgggggg tacagaaggc agctacacgg   1200
tgacgtgatg ctaatcccta aaacctctct cagttcggat tggagtctgc aacccgactc   1260
catgaagctg gattcgctag taatcgcgca tcagccacgg cgcggtgaat acgttccgg    1320
gccttgtaca caccgcccgt caagccatga aagccggggg tacctgaagt gcgtaacgc    1380
ga                                                                   1382
SEQ ID NO: 27           moltype = DNA  length = 1370
FEATURE                 Location/Qualifiers
misc_feature            1..1370
                        note = K27
variation               916..917
                        note = n is a, c, g, or t
source                  1..1370
                        mol_type = unassigned DNA
                        organism = unidentified
SEQUENCE: 27
tgcaagtcga acggttaagg cgccttcggg cgcgaataga gtggcgaacg ggtgagtaac     60
acgtgaccaa cctgcccccc tccccgggat aacgcgagga aacccgcgct aataccggat    120
actccgcccc tcccgcatgg gagggcggg aaagcccga cggagggga tgggtcgcg     180
gcccattagg tagacggcgg ggcaacggcc caccgtgcct gcgatgggta gccgggttga    240
gagaccgacc ggccacattg ggactgagat acggcccaga ctcctacggg aggcagcagt    300
ggggaatttt gcgcaatggg gggaaccctg acgcagcaac gccgcgtgcg ggacgaaggc    360
cttcggttg taaaccgctt tcagcaggga agaagttgac ggtacctgca gaagaagccc    420
cggctaacta cgtgccagca gccgcggtaa tacgtagggg cgagcgtta ccggattca     480
ttgggcgtaa agcgcgcgta ggcggcccgt caagcggaac ctctaacccg agggctcaac    540
ccccggtcgg gttccgaact gcaggctcg agtttggtag aggaagatgg aattcccggt    600
gtagcggtga aatgcgcaga tatcggggaag aacaccgatg gcgaaggcag tcttctgggta    660
catcaactga cgctgaggcg cgaaagctgg gggagcgaac aggattagat accctgtag    720
tcccagccgt aaacgatggg cgctaggtgt gggggatca tccctccgtg ccgcagccaa    780
cgcattaagc gccccgcctg gggagtacgg ccgcaaggct aaaactcaaa ggaattgacg    840
ggggcccgca caagcagcgg agcatgtggc ttaattcgaa gcaacgcgaa gaaccttacc    900
agggcttgac atgctnntga agccggggaa accggtggc cgagaggagc cagcgcaggt    960
```

```
ggtgcatggc tgtcgtcagc tcgtgtcgtg agatgttggg ttaagtcccg caacgagcgc  1020
aaccctgcc atatgttgcc agcattcagt tggggactca tatgggactg ccggcgtcaa   1080
gccggaggaa ggtggggacg acgtcaagtc atcatgccct ttatgccctg ggctgcacac  1140
gtgctacaat ggccggtaca acgggccgcg acctggcgac aggaagcgaa tccctcaaag  1200
ccggcCCcag ttcggatcgg aggctgcaac ccgcctccgt gaagtcggag ttgctagtaa  1260
tcgcggatca gcatgccgcg gtgaatacgt tcccgggcct tgtacacacc gcccgtcaca  1320
ccacccgagt cgtctgcacc cgaagccgcc ggccgaaccc gcaaggggcg              1370

SEQ ID NO: 28          moltype = DNA   length = 1394
FEATURE                Location/Qualifiers
misc_feature           1..1394
                       note = K28
variation              909..911
                       note = n is a, c, g, or t
source                 1..1394
                       mol_type = unassigned DNA
                       organism = unidentified
SEQUENCE: 28
caagtcgaac gaagcactta cttccaaatc ttcggaagag gaggtatttg actgagtggc  60
ggacgggtga gtaacgcgtg gggaacctgc cccgtaccgg gggataacag tcagaaatga  120
ctgctaatac cgcataagcg cacgaaggcg catgcttttg tgtgaaaaac tccggtggta  180
cgggatggtc ccgcgtctga ttagccagtt ggcggggtaa cggcccacca aagcgacgat  240
cagtagccgg cctgagaggg tggacggcca cattgggact gagacacggc ccagactcct  300
acggGaggca gcagtgggga atattgcaca atgggggaaa ccctgatgca gcgacgccgc  360
gtgagcgaag aagtatttcg gtatgtaaag ctctgtcagc agggaagaaa atgacggtac  420
ctgaccaaga agcaccggct aaatacgtgc cagcagccgc ggtaatacgt atggtgcaag  480
cgttatccgg atttactggg tgtaaaggga gcgtagacgg aggggcaagt ctgaagtgaa  540
agcccggggc caaccccgg gactgctttg gaaactgtcc gtctggagtg ccggagaggt  600
aagcggaatt cccagtgtag cggtgaaatg cgtagatatt gggaggaaca ccagtggcga  660
aggcggctta ctggacggtc actgacgttg aggctcgaaa gcgtggggag caaacaggat  720
tagatacccct ggtagtccac gccgtaaacg atgactacta ggtgtcgggt ggcagagcca  780
ttcggtgccg cagccaacgc agtaagtagt ccacctgggg agtacgttcg caagaatgaa  840
actcaaagga attgacgggg acccgcacaa gcggtggagc atgtggttta attcgaagca  900
acgcgaagnn ncttacctgg ccttgacatc cccctgaccg gcgctaagtg gtgccttttcc  960
ttcgggacag gggagacagg tggtgcatgg ttgtcgtcag ctcgtgtcgt gagatgttgg  1020
gttaagtccc gcaacgagcg caacccttat cttcagtagc cagcattcag gatgggcact  1080
ctggagagac tgccagggac aacctggagg aaggtgggga tgacgtcaaa tcatcatgcc  1140
ccttatggcc agggctacac acgtgctaca atggcgtaaa cagagggaag cgagcccgcg  1200
aggggagca aatcccaaaa ataacgtccc agttcggact gcaggctgca accgcctgc   1260
acgaagctgg aatcgctagt aatcgcgaat cagcatgtcg cggtgaatac gttcccgggt  1320
cttgtacaca ccgcccgtca caccatggga gtcggtaacg cccgaagtca gtgacccaac  1380
ctccggggagg gagc                                                   1394

SEQ ID NO: 29          moltype = DNA   length = 1387
FEATURE                Location/Qualifiers
misc_feature           1..1387
                       note = K29
variation              895..896
                       note = n is a, c, g, or t
variation              910..912
                       note = n is a, c, g, or t
variation              942..946
                       note = n is a, c, g, or t
variation              953..954
                       note = n is a, c, g, or t
source                 1..1387
                       mol_type = unassigned DNA
                       organism = unidentified
SEQUENCE: 29
agtcgaacga agcatttagg attgaagttt tcggatggat ttcctttatg actgagtggc  60
ggacgggtga gtaacgcgtg gggaacctgc cctatacagg gggataacag ctggaaacgg  120
ctgctaatac cgcataagcg cacagaatcg catgattcag tgtgaaaagc cctggcagta  180
taggatggtc ccgcgtctga ttagctggtt ggtgaggtaa cggctcacca aggcgacgat  240
cagtagccgg cttgagagag tgaacggcca cattgggact gagacacggc ccaaactcct  300
acggGaggca gcagtgggga atattgcaca atgggggaaa ccctgatgca gcgacgccgc  360
gtgagtgaag aagtatttcg gtatgtaaag ctctatcagc agggaagaaa acagacggta  420
cctgactaag aagccccggc taactacgtg ccagcagccg cggtaatacg tagggggcaa  480
gcgttatccg gaattactgg gtgtaaaggg tgcgtaggtg gcatggtaag tcagaagtga  540
aagcccgggg cttaaccccg ggactgcttt tgaaactgtc atgctggagt gcaggagagga  600
taagcggaat tcctagtgta gcggtgaaat gcgtagatat taggaggaac accagtggcg  660
aaggcggctt actggactgt cactgacact gatgcacgaa agcgtgggga caaacagga   720
ttagataccc tggtagtcca cgccgtaaac gatgaatact aggtgtcggg gccgtagagg  780
cttcggtgcc gcagcaaacg cagtaagtat tccacctggg gagtacgttc gcaagaatga  840
aactcaaagg aattgacggg gacccgcaca agcggtggtt aattnnaagc aattg        900
aacgcgaagn nncttacctg gtcttgacat cccaatgacc gnnnnntaac cgnntttttc  960
tttcgagaca ttgagacag tggtgcatg gttgtcgtca gctcgtgtcg tgagatgttg  1020
ggttaagtcc cgcaacgagc gcaacccta tctttagtag ccagcattag aggtgggcac  1080
tctagagaga ctgccaggga taacctggag gaaggtgggg aggacgtcaa atcatcatgc  1140
cccttatggc cagggctaca cacgtgctac aatggcgtaa acaaagggaa gcgaagtcgt  1200
```

```
gaggcgaagc aaatcccaga aataacgtct cagttcggat tgtagtctgc aactcgacta   1260
catgaagctg gaatcgctag taatcgtgaa tcagaatgtc acggtgaata cgttcccggg   1320
tcttgtacac accgcccgtc acaccatggg agtcagtaac gcccgaagtc agtgacccaa   1380
ccgcaag                                                             1387

SEQ ID NO: 30           moltype = DNA   length = 1392
FEATURE                 Location/Qualifiers
misc_feature            1..1392
                        note = K30
source                  1..1392
                        mol_type = unassigned DNA
                        organism = unidentified
SEQUENCE: 30
gcaagtcgag cgaagcacct tgacggattt cttcggattg aagccttggt gactgagcgg    60
cggacgggtg agtaacgcgt gggtaacctg cctcatacag ggggataaca gttggaaacg   120
gctgctaata ccgcataagc gcacagtacc gcatggtacg gtgtgaaaaa ctccggtggt   180
atgagatgga cccgcgtctg attaggtagt tggtggggta acggcctacc aagccgacga   240
tcagtagccg acctgagagg gtgaccggcc acattggact gagacacggc ccaaactcc    300
tacgggaggc agcagtgggg aatattgcac aatgggggaa accctgatgc agcgacgccg   360
cgtgagcgat gaagtatttc ggtatgtaaa gctctatcag cagggaagaa atgacggta    420
cctgactaag aagccccggc taactacgtg ccagcagccg cggtaatacg tagggggcaa   480
gcgttatccg gatttactgg gtgtaaaggg agcgtagacg gcatggcaag ccagatgtga   540
aagcccgggg ctcaaccccg ggactgcatt tggaactgtc aggctagagt gtcggagagg   600
aaaagcggaat tcctagtgta gcggtgaaat gcgtagatat taggaggaac accagtggcg   660
aaggcggctt tctggacgat gactgacgtt gaggctcgaa agcgtgggga gcaaacagga   720
ttagataccc tggtagtcca cgccgtaaac gatgaatact aggtgtcggg tggcaaagcc   780
attcggtgcc gcagcaaacg caataagtat tccacctggg gagtacgttc gcaagaatga   840
aactcaaagg aattgacggg gacccgcaca agcggtggag catgtggttt aattcgaagc   900
aacgcgaaga accttacctg gtcttgacat ccctctgacc gctctttaat cggagctttc   960
cttcgggaca gaggagacag gtggtgcatg gttgtcgtca gctcgtgtcg tgagatgttg  1020
ggttaagtcc gcaacgagcg caacccccta tctttagtag ccagcatttt ggatgggcac  1080
tctagagaga ctgccaggga taacctggag gaaggtgggg atgacgtcaa atcatcatgc  1140
cccttatgac cagggctaca cacgtgctac aatggcgtaa acaaaggaa gcgagcccgc   1200
gaggggggagc aaatcccaaa aataacgtct cagttcggat tgtagtctgc aactcgacta  1260
catgaagctg gaatcgctag taatcgcgaa tcagaatgtc gcggtgaata cgttcccggg  1320
tcttgtacac accgcccgtc acaccatggg agtcagtaac gcccgaagtc agtgacccaa  1380
ccgcaaggag gg                                                      1392

SEQ ID NO: 31           moltype = DNA   length = 1394
FEATURE                 Location/Qualifiers
misc_feature            1..1394
                        note = K31
variation               1073..1074
                        note = n is a, c, g, or t
source                  1..1394
                        mol_type = unassigned DNA
                        organism = unidentified
SEQUENCE: 31
cagtcgagcg aagcgctttg tgcggatttc ttcggattga agcaactgtg actgagcggc    60
ggacgggtga gtaacgcgtg ggtaacctgc ctcatacagg gggataacag ttggaaacgg   120
ctgctaatac cgcataagcg cacagtaccg catggtacgt gtgaaaaact ccggtggta    180
tgagatggac ccgcgtctga ttaggtagtt ggtggggtaa cggcctacca aggcgacgat   240
cagtagccga cctgagaggg tgaccggcca cattgggact gagacacggc ccaaactcct   300
acgggaggca gcagtgggga atattgcaca atggggggaaa ccctgatgca gcgacgccgc   360
gtgagcgatg aagtatttcg gtatgtaaag ctctatcagc agggaagaaa atgacggtac   420
ctgactaaga agccccggct aactacgtgc cagcagccgc ggtaatacgt agggggcaag   480
cgttatccgg atttactggg tgtaaaggga gcgtagacgg catggcaagc cagatgtgaa   540
agcccggggc tcaaccccgg gactgcattt ggaactgtca ggctagagtg tcggagagga   600
aagcggaatt cctagtgtag cggtgaaatg cgtagatatt aggaggaaca ccagtggcga   660
aggcggcttt ctggacgatg actgacgttg aggctcgaaa gcgtggggag caaacaggat   720
tagataccct ggtagtccac gccgtaaacg atgaatacta ggtgtcgggt ggcaaagcca   780
ttcggtgccg cagcaaacgc aataagtatt ccacctgggg agtacgttc gcaagaatga    840
aactcaaagg aattgacggg gacccgcaca agcggtggag catgtggttt aattcgaagc   900
aacgcgaaga accttacctg gtcttgacat ccctctgacc gctctttaat cggagcttc    960
tttcgggaca gaggagacag gtggtgcatg gttgtcgtca gctcgtgtcg tgagatgttg  1020
ggttaagtcc gcaacgagcg caacccccta tctttagtag ccagcattta gnngggcac   1080
tctagagaga ctgccaggga taacctggag gaaggtgggg atgacgtcaa atcatcatgc  1140
cccttatgac cagggctaca cacgtgctac aatggcgtaa acaaaggaa gcgagcccgc   1200
gaggggggagc aaatcccaaa aataacgtct cagttcggat tgtagtctgc aactcgacta  1260
catgaagctg gaatcgctag taatcgcgaa tcagaatgtc gcggtgaata cgttcccggg  1320
tcttgtacac accgcccgtc acaccatggg agtcagtaac gcccgaagtc agtgacccaa  1380
ccgcaaggag ggag                                                    1394

SEQ ID NO: 32           moltype = DNA   length = 1383
FEATURE                 Location/Qualifiers
misc_feature            1..1383
                        note = K32
source                  1..1383
                        mol_type = unassigned DNA
```

```
                               organism = unidentified
SEQUENCE: 32
aagtcgaggg gcagcacggt gtagcaatac actggtggcg accggcgcac gggtgcgtaa    60
cgcgtatgca acctacccat aacaggggga taacactgag aaattggtac taataccca   120
taacatcagg accggcatcg gttctggttg aaaactccag tggttatgga tggggcatgcg  180
ttgtattagc tggttggtga ggtaacggct caccaaggca acgatacata gggggactga   240
gaggttaacc ccccacattg gtactgagac acggaccaaa ctcctacggg aggcagcagt   300
gaggaatatt ggtcaatgga cgcaagtctg aaccagccat gccgcgtgca ggaagacggc   360
tctatgagtt gtaaactgct tttgtacgag ggtaaacgct cttacgtgta agagcctgaa   420
agtatcgtac gaataaggat cggctaactc cgtgccagca gccgcggtaa tacggaggat   480
ccaagcgtta tccggattta ttgggtttaa agggtgcgta ggcggtttga taagttagag   540
gtgaaatacc ggtgcttaac accggaactg cctctaatac tgttaaacta gagagtagtt   600
gcggtaggcg aatgtatggt gtagcggtga aatgcttag agatcataca gaacaccgat   660
tgcgaaggca gcttaccaaa ctatatctga cgttgaggca cgaaagcgtg gggagcaaac   720
aggattagat accctggtag tccacgcagt aaacgatgat aactcgctgt cggcgataca   780
cagtcggcgc taagcgaaa gcgataagtt atccacctgg ggagtacgtt cgcaagaatg    840
aaactcaaag gaattgacgg gggcccgcac aagcggagga acatgtggtt taattcgatg   900
atacgcgagg aaccttaccc gggcttgaaa gttactgacg attctggaaa caggattccc   960
cttcggggca ggaaactagg tgctgcatgg ttgtcgtcag ctcgtgccgt gaggtgtcgg  1020
gttaagtccc ataacgagcg caaccccctac cgttagttgc catcaggtca agctgggcac  1080
tctggcggga ctgccggtgt aagccgagag aaggtgggg atgacgtcaa atcagcacgg    1140
cccttacgtc cggggctaca cacgtgttac aatggtaggt acagagggca gctacccagt  1200
gatgggatgc gaatctcgaa agcctatctc agttcggatc ggaggctgaa acccgcctcc  1260
gtgaagttgg attcgctagt aatcgcgcat cagccatggc gcggtgaata cgttcccggg  1320
ccttgtacac accgcccgtc aagccatgga agctgggggt gcctgaagtt cgtgaccgca  1380
agg                                                                1383

SEQ ID NO: 33         moltype = DNA    length = 1378
FEATURE               Location/Qualifiers
misc_feature          1..1378
                      note = K33
source                1..1378
                      mol_type = unassigned DNA
                      organism = unidentified
SEQUENCE: 33
gaggggcagc atcattaaag cttgctttga tggatggcga ccggcgcacg ggtgagtaac    60
acgtatccaa cctgccgaca acactgggat agcctttcga agaaagatt aataccggat    120
ggcatagttt tcccgcatgg gataattatt aaagaatttc ggttgtcgat ggggatgcgt   180
tccattaggc agttggcggg gtaacggccc accaaaccaa cgatggatag gggttctgag   240
aggaaggtcc cccacattgg aactgagaca cggtccaaac tcctacggga ggcagcagtg   300
aggaatattg tcaatggac gagagtctga accagccaag tagcgtgaag gatgactgcc    360
ctatggggttg taaacttctt ttatacggga ataaagttag ccacgtgtgg ctttttgtat  420
gtaccgtatg aataaggatc ggctaactcc gtgccagcag ccgcggtaat acggaggatc   480
cgagcgttat ccggatttat tgggtttaaa gggagcgtag gcgggttgtt aagtcagttg   540
tgaaagtttg cggctcaacc gtaaaattgc agttgatact ggcgaccttg agtgcaacag   600
aggtaggcga aattcgtggt gtagcggtga atgcttaga tatcacgaag aactccgatt    660
gcgaaggcag cttactggat tgtaactgac gctgatgctc gaaagtgtgg gtatcaaaca   720
ggattagata ccctggtagt ccacacagta aacgatgaat actcgctgtt ggcgatatac   780
ggtcagcggc caagcgaaag cattaagtat tccacctggg gagtacgccg caacggtga    840
aactcaaagg aattgacggg ggcccgcaca agcggaggaa catgtggttt aattcgatga   900
tacgcgagga accttacccg ggcttaaatt gcaactgaac gaaccggaaa cggttctttc   960
ttcggacagt tgtgaaggtg ctgcatggtt gtcgtcagct cgtgccgtga ggtgtcggct  1020
taagtgccat aacgagcgca acccttatcg atagttacta gcaggtcatg ctgaggactc  1080
tattgagact gccgtcgtaa gatgtgagga aggtgggat gacgtcaaat cagcacggcc   1140
cttacgtccg gggctacaca cgtgttacaa tggggggtac agaagggcag ctacacggcga  1200
cgtggtgcta atcccgaaag cctctctcag ttcggattgg agtctgcaac ccgactccat  1260
gaagctggat tcgctagtaa tcgcgcatca gccacgcgc ggtgaatacg ttcccgggcc   1320
ttgtacacac cgcccgtcaa gccatgaaag ccggggtac ctgaagtacg taaccgcg     1378

SEQ ID NO: 34         moltype = DNA    length = 1394
FEATURE               Location/Qualifiers
misc_feature          1..1394
                      note = K34
source                1..1394
                      mol_type = unassigned DNA
                      organism = unidentified
SEQUENCE: 34
cagtcgagcg aagcacttaa gtggatctct tcggattgaa acttattgtg actgagcggc    60
ggacgggtga gtaacgcgtg gtaacctgc ctcatacagg gggataacag ttagaaatgg    120
ctgctaatac cgcataagcg cacaggaccg catggtctgg tgtgaaaaac tccggtggta   180
tgagatggac ccgcgtctga ttagctagtt ggagggtaa cggcccacca aggcgacgat    240
cagtagccgg cctgagaggg tgaacggcca cattgggact gagacacggc ccagactcct   300
acgggaggca gcagtgggga atattgcaca atgggggaaa ccctgatgca gcgacgccgc   360
gtgaaggaag aagtatctcg gtatgtaaac ttctatcagc aggaagaaa atgacgtac    420
ctgactaaga agcccggct aactacgtgc cagcagccgc ggtaatacgt aggggggcaag   480
cgttatccgg atttactggg tgtaaaggga gcgtagacgg aagagcaagt ctgatgtgaa   540
aggctggggc ttaaccccag gactgcattg gaaactgttt ttctagagtg ccggagaggt   600
aagcggaatt cctagtgtag cggtgaaatg cgtagatatt aggaggaaca ccagtggcga   660
aggcggctta ctggacggta actgacgttg aggctcgaaa gcgtggggag caaacaggat   720
```

```
tagatacgcct ggtagtccac gccgtaaacg atgaatacta ggtgtcgggt ggcaaagcca    780
ttcggtgccg cagcaaacgc aataagtatt ccacctgggg agtacgttcg caagaatgaa    840
actcaaagga attgacgggg acccgcacaa gcggtggagc atgtggttta attcgaagca    900
acgcgaagaa ccttaccaag tcttgacatc ctctctgaccg gcccgtaacg gggccttccc    960
ttcgggggcag aggagacagg tggtgcatgg ttgtcgtcag ctcgtgtcgt gagatgttgg   1020
gttaagtccc gcaacgagcg caaccccctat ccttagtagc cagcaggtga agctgggcac   1080
tctagggaga ctgccgggga taacccggag aaggcgggg acgacgtcaa atcatcatgc    1140
cccttatgat ttgggctaca cacgtgctac aatggcgtaa acaaagggaa gcgagacagc   1200
gatgttgagc aaatcccaaa aataacgtcc cagttcggac tgcagtctgc aactcgactg   1260
cacgaagctg gaatcgctag taatcgcgaa tcagaatgtc gcggtgaata cgttcccggg   1320
tcttgtacac accgcccgtc acaccatggg agtcagtaac gcccgaagtc agtgacccaa   1380
ccttacagga ggga                                                     1394

SEQ ID NO: 35          moltype = DNA  length = 1392
FEATURE                Location/Qualifiers
misc_feature           1..1392
                       note = K35
variation              901
                       note = n is a, c, g, or t
source                 1..1392
                       mol_type = unassigned DNA
                       organism = unidentified
SEQUENCE: 35
cagtcgaacg gagctcagtt ttggaaactt tcttcgggag tggaattctc gacttagtgg     60
cggacgggtg agtaacgcgt gagcaatctg cctttaagag gggataacaa gtcggaaacg    120
gctgctaata ccgcataaag cattgaattc gcatgtttc gatgccaaag gagcaatccg    180
cttttagatg agctcgcgtc tgattagcta gttggcgggg taacggccca ccaaggcgac    240
gatcagtagc cggactgaga ggttgaacgg ccacattggg actgagacac ggcccagact    300
cctacgggag gcagcagtgg ggaatattgc gcaatggggg aaaccctgac gcagcaacgc    360
cgcgtgattg aagaaggcct tcggggtgta aagatctta atcagggacg aaacaaatga    420
cggtacctga agaataagct ccggctaact acgtgccagc agccgcggta atacgtaggg    480
agcaagcgtt atccggattt actgggtgta aagggcgcgc aggcgggccg caagttgga    540
agtgaaatct atgggcttaa cccataaact gctttcaaaa ctgctggtct tgagtgatgg    600
agaggcaggc ggaattccgt gtgtagcggt gaaatgcgta gatatacgga ggaacaccga    660
tggcgaaggc ggcctgctgg acattaactg acgctgaggc gcgaaagcgt gggagcaaa    720
caggattaga taccctggta gtccacgccg taaacgatgg atactaggtg tgggaggtat    780
tgaccccttc cgtgccgcag ttaacacaat aagtatccca cctggggagt acggccgcaa    840
ggttgaaact caaaggaatt gacgggggcc cgcacaagca gtggagtatg tggtttaatt    900
ngaagcaacg cgaagaacct taccagtct tgacatccg atgatccgct tagagataag    960
gctttttttc ggaacatcgg tgacaggtgg tgcatggttg tcgtcagctc gtgtcgtgag   1020
atgttgggtt aagtcccgca acgagcgcaa cccttacggt tagttgatac gcaagatcac   1080
tctagccgga ctgccgttga caaaacggag gaaggtgggg acgacgtcaa atcatcatgc   1140
cccttatgac ctgggctaca cacgtactac aatggcgtac atacagaggg aagcaaaacc   1200
gcgaggtgga gcaaatccct aaaagctgtc ccagttcaga ttgcaggctg caacccgcct   1260
gcatgaagtc ggaattgcta gtaatcgcgg atcagcatgc cgcggtgaat acgttccgg    1320
gccttgtaca caccgcccgt cacaccatga gagccgtcaa tacccgaagt ccgtagccta   1380
accttcttgg ag                                                       1392

SEQ ID NO: 36          moltype = DNA  length = 1394
FEATURE                Location/Qualifiers
misc_feature           1..1394
                       note = K36
variation              1068..1069
                       note = n is a, c, g, or t
source                 1..1394
                       mol_type = unassigned DNA
                       organism = unidentified
SEQUENCE: 36
agtcgaacga agcaattaaa atgaagtttt cggatggatt tttgattgac tgagtggcgg     60
acgggtgagt aacgcgtgga taacctgcct cacactgggg gataacagtt agaaatgact    120
gctaataccg cataagcgca cagtaccgca tggtacggtg tgaaaaactc cggtggtgtg    180
agatggatcc gcgtctgatt agccagttgg cggggtaacg gcccaccaaa gcgacgatca    240
gtagccgacc tgagagggtg accggccaca ttgggactga gacacggccc aaactcctac    300
gggaggcagc agtgggggaat attgcacaat gggcgcaagc ctgatgcagc gacgccgcgt    360
gagtgaagaa gtatttcggt atgtaaagct ctatcagcag gaagaaaat gacggtacct    420
gactaagaag ccccggctaa ctacgtgcca gcagccgcgg taatacgtag ggggcaagcg    480
ttatccggat ttactgggtg taaagggagc gtagacggcg aagcaagtct gaagtgaaaa    540
cccagggctc aaccctggga ctgctttgga aactgttttg ctagagtgtc ggagaggtaa    600
gtggaattcc tagtgtagcg gtgaaatgcg tagatattag gaggaacacc agtggcgaag    660
gcggcttact ggacgataac tgacgttgag gctcgaaagc gtgggagca acaggatta    720
gataccctgg tagtccacgc cgtaaacgat gaatgctagg tgttgggggg caaagccctt    780
cggtgccgtc gcaaacgcag taagcattcc acctggggag tacgttgcaa agaatgaaac    840
tcaaaggaat tgacggggac ccgcacaagc ggtggagcat gtggttaat tcgaagcaac    900
gcgaagaacc ttaccaagtc ttgacatcct cttgaccggc gtaacggc gccttccttt   960
cggggcaaga gagacaggtg gtgcatggtt gtcgtcagct cgtgtcgtga gatgttgggt   1020
taagtcccgc aacgagcgca accccttatcc ttagtagcca gcaggtanng ctggcactc   1080
tagggagact gccagggata acctggagga aggtggggat gacgtcaaat catcatgccc   1140
cttatgattt gggctacaca cgtgctacaa tggcgtaaac aaagggaagc aagacagtga   1200
tgtggagcaa atcccaaaaa taacgtccca gttcggactg tagtctgcaa cccgactaca   1260
```

```
cgaagctgga atcgctagta atcgcgaatc agaatgtcgc ggtgaatacg ttcccgggtc   1320
ttgtacacac cgcccgtcac accatgggag tcagcaacgc ccgaagtcag tgacccaact   1380
cgcaagagag ggag                                                    1394

SEQ ID NO: 37          moltype = DNA  length = 1371
FEATURE                Location/Qualifiers
misc_feature           1..1371
                       note = K37
source                 1..1371
                       mol_type = unassigned DNA
                       organism = unidentified
SEQUENCE: 37
cagtcgaacg agccgagggg agcttgctcc ccagagctag tggcggacgg gtgagtaaca   60
cgtgagcaac ctgcctttca gaggggggata acgtttggaa acgtgcta ataccgcata   120
```

```
cgaagctgga atcgctagta atcgcgaatc agaatgtcgc ggtgaatacg ttcccgggtc   1320
ttgtacacac cgcccgtcac accatgggag tcagcaacgc ccgaagtcag tgacccaact   1380
cgcaagagag ggag                                                    1394

SEQ ID NO: 37          moltype = DNA  length = 1371
FEATURE                Location/Qualifiers
misc_feature           1..1371
                       note = K37
source                 1..1371
                       mol_type = unassigned DNA
                       organism = unidentified
SEQUENCE: 37
cagtcgaacg agccgagggg agcttgctcc ccagagctag tggcggacgg gtgagtaaca   60
cgtgagcaac ctgcctttca gaggggggata acgtttggaa acgtgcta ataccgcata   120
acataccggg accgcatgat tctggtatca aaggagcaat ccgctgaaag atgggctcgc   180
gtccgattag ctagttggcg gggtaacggc ccaccaaggc gacgatcggt agccggactg   240
agaggttgat cggccacatt gggactgaga cacggcccag actcctacgg gaggcagcag   300
tggggggatat tgcacaatgg aggaaactct gatgcagcga cgccgcgtga gggaagacga   360
tcttcggatt gtaaacctct gtctttgggg acgataatga cggtacccaa ggaggaagct   420
ccggctaact acgtgccagc agccgcggta atacgtaggg agcgagcgtt gtccggaatt   480
actgggtgta agggagcgt aggcgggtc tcaagtcgaa tgttaaatct accggctcaa   540
ctggtagctg cgttcgaaac tggggctctt gagtgaagta aggcaggcg gaattcctag   600
tgtagcggtg aaatgcgtag atattaggag gaacaccagt ggcgaaggcg gcctgctggg   660
cttttactga cgctgaggct cgaaagcgtg gggagcaaac aggattagat accctggtag   720
tccacgccgt aaacgatgat tactaggtgt gggggggactg accccttccg tgccggagtt   780
aacacaataa gtaatccacc tggggagtac gaccgcaagg ttgaaactca aaggaattga   840
cggggggcccg cacaagcagt ggattatgtg gtttaattcg aagcaacgcg aagaacctta   900
ccaggtcttg acatcgagtg acggctctag agatagagct ttccttcggg acacaaagac   960
aggtggtgca tggttgtcgt cagctcgtgt cgtgagatgt tgggttaagt cccgcaacga   1020
gcgcaaccct tattattagt tgctacattc agttgagcac tctaatgaga ctgccgttga   1080
caaaacggag gaaggtgggg atgacgtcaa atcatcatgc cccttgtgac ctgggctaca   1140
cacgtaatac aatggcgatc aacagaggga agcaagaccg cgaggtggag caaaccccta   1200
aaagtcgtct cagttcggat tgcaggctgc aactcgcctg catgaagtcg gaattgctag   1260
taatcgcgga tcagcatgcc gcggtgaata cgttcccggg ccttgtacac accgcccgtc   1320
acaccatggg agtcggtaac acccgaagtc agtagcctaa ccgcaaggag g           1371

SEQ ID NO: 38          moltype = DNA  length = 1396
FEATURE                Location/Qualifiers
misc_feature           1..1396
                       note = K38
source                 1..1396
                       mol_type = unassigned DNA
                       organism = unidentified
SEQUENCE: 38
tgcagtcgaa cgctttgtaa aggagcttgc ttctttacga ggagtggcga acgggtgagt   60
aatacataag caatctgccc atcggcctgg ataacagtt ggaaacgact gctaataccg   120
gataggttag tttctggcat cagggactaa ttaaagttgg gatacaacac ggatggatga   180
gcttatggcg tattagctag taggtgaggt aacggcccac ctaggcgatg atacgtagcc   240
gacctgagag ggtgaccggc cacattggga ctgagacacg gcccaaactc ctacgggagg   300
cagcagtagg gaattttcgg caatgggcga aagcctgacc gagcaacgcc gcgtgagtga   360
agaaggcctt cgggttgtaa agctctgttg tgaaggaaga acggctcata gagggaatgc   420
tatgggagtg acggtacttt accagaaagc cacggctaac tacgtgccag cagccgcggt   480
aatacgtagg tggcgagcgt tatccggaat tattgggcgt aaagggtgcg caggcggttt   540
gaaaagttta aggtgaaagc gtggggctta acccctca gccttagaaa ctgtcagact   600
agagtacagg agagggcaat ggaattccat gtgtagcggt aaatgcgta gatatatgga   660
ggaacaccag tggcgaaggc ggttgcctgg cctgtaactg acgctcatgc acgaaagcgt   720
ggggagcaaa taggattaga taccctagta gtccacgccg taaacgatga gaactaagtg   780
ttgggggaaac tcagtgctgc agttaacgca ataagttctc cgcctgggga gtatgcacgc   840
aagtgtgaaa ctcaaaggaa ttgacggggg cccgcacaag cggtggagta tgtggtttaa   900
ttcgacgcaa cgcgaagaac cttaccaggt cttgacatac caggcaaagc tatagaatta   960
tagtggagga tatcctggat acaggtggtg catggttgtc gtcagctcgt gtcgtgagat   1020
gttgggttaa gtcccgcaac gagcgcaacc cttgtcttta gttactaaca ttaagttgag   1080
gactctagag agactgccgg tgacaaaccg gaggaaggtg gggatgacgt caaatcatca   1140
tgccccttat gacctgggct acacacgtac taatggcga gacaacgaga gcaagac   1200
agcaatgtgg agcaaacctc agaaagtccg tctcagttcg gattgaagtc tgcaacccga   1260
cttcatgaag ccggaatcgc tagtaatcgc ggatcagcat gccgcggtga atacgttctc   1320
gggccttgta cacaccgccc gtcaaaccat gagagttggc aatacccgaa gccggtggcc   1380
taaccctgca aaggga                                                  1396

SEQ ID NO: 39          moltype = DNA  length = 1399
FEATURE                Location/Qualifiers
misc_feature           1..1399
                       note = K39
source                 1..1399
                       mol_type = unassigned DNA
                       organism = unidentified
SEQUENCE: 39
cagtcgaacg gtaacaggaa gcagcttgct gctttgctga cgagtggcgg acgggtgagt   60
aatgtctggg aaactgcctg atggagggg ataactactg gaaacggtag ctaataccgc   120
```

```
ataacgtcgc aagaccaaag aggggggacct tagggcctct tgccatcgga tgtgcccaga    180
tgggattagc tagtaggtgg ggtaacggct cacctaggcg acgatcccta gctggtctga    240
gaggatgacc agccacactg gaactgagac acggtccaga ctcctacggg aggcagcagt    300
ggggaatatt gcacaatggg cgcaagcctg atgcagccat gccgcgtgta tgaagaaggc    360
cttcgggttg taaagtactt tcagcgggga ggaagggagt aaagttaata cctttgctca    420
ttgacgttac ccgcagaaga agcaccggct aactccgtgc cagcagccgc ggtaatacgg    480
agggtgcaag cgttaatcgg aattactggg cgtaaagcgc acgcaggcgg tttgttaagt    540
cagatgtgaa atcccgggc tcaacctggg aactgcatct gatactgcaa agcttgagtc    600
tcgtagaggg gggtagaatt ccaggtgtag cggtgaaatg cgtagagatc tggaggaata    660
ccggtggcga aggcggccc ctggacgaag actgacgctc aggtgcgaaa gcgtggggag    720
caaacaggat tagataccct ggtagtccac gccgtaaacg atgtcgactt ggaggttgtg    780
cccttgaggc gtggcttccg gagctaacgc gttaagtcga ccgcctgggg agtacggccg    840
caaggttaaa actcaaatga attgacgggg gcccgcacaa gcggtggagc atgtggttta    900
attcgatgca acgcgaagaa ccttacctgg tcttgacatc cacggaagtt ttcagagatg    960
agaatgtgcc ttcggaacc gtgagacagg tgctgcatgg ctgtcgtcag ctcgtgttgt   1020
gaaatgttgg gttaagtccc gcaacgagcg caacccttat cctttgttgc cagcggtccg   1080
gccgggaact caaggagac tgccagtgat aaactgagg aaggtgggga tgacgtcaag   1140
tcatcatggc ccttacgacc agggctacac acgtgctaca atggcagaag   1200
cgacctcgcg agagcaagcg gacctcataa agtgcgtcgt agtccggatt ggagtctgca   1260
actcgactcc atgaagtcgg aatcgctagt aatcgtggat cagaatgcca cggtgaatac   1320
gttcccgggc cttgtacaca ccgcccgtca ccatggga gtgggttgca aaagaagtag   1380
gtagcttaac cttcgggag                                                1399

SEQ ID NO: 40          moltype = DNA   length = 1384
FEATURE                Location/Qualifiers
misc_feature           1..1384
                       note = K40
source                 1..1384
                       mol_type = unassigned DNA
                       organism = unidentified
SEQUENCE: 40
agtcgaacgg ggttatttg gaaatctctt cggagatgga attcttaacc tagtggcgga     60
cgggtgagta acgcgtgagc aatctgcctt taggaggggg ataacagtcg gaacggctg    120
ctaatacgc ataatacgtt tgggaggcat ctcttgaacg tcaaagattt tatcgccttt    180
agatgagctc gcgtctgatt agctggttgg cggggtaacg gcccaccaag gcgacgatca    240
gtagccggac tgagaggttg aacgccaca ttgggactga gacacggccc agactcctac    300
gggaggcagc agtggggaat attgcgcaat ggggaaacc ctgacgcagc aacgccgcgt    360
gattgaagaa ggccttcggg ttgtaaagat ctttaatcag gacgaaaaa tgacggtacc    420
tgaagaataa gctccggcta actacgtgcc agcagccgc ggtaatacga ggagcaagc    480
gttatccgga tttactgggt gtaaagggcg cgcaggcggg ccggcaagtt gggagtgaaa    540
tcccggggct taaccccgga actgctttca aaactgctgg tcttgagtga tggagaggca    600
ggcggaattc cgtgtgtagc ggtgaaatgc gtagatatac ggaggaacac cagtggcgaa    660
ggcggcctgc tggacattaa ctgacgctga gcgcgaaag cgtggggagc aaacaggatt    720
agataccctg gtagtccacg ccgtaaacga tggatactag tgtgggagg tattgaccc    780
ttccgtgccg cagttaacac aataagtatc ccacctgggg agtacggccg caaggttgaa    840
actcaaagga attgacgggg gcccgcacaa gcagtggagt atgtggttta attcgaagca    900
acgcgaagaa ccttaccagg tcttgacatc ccgatgacg tagagatg acgccctctc    960
ttcgagcat cggtgacagg tggtgcatgg ttgtcgtcag ctcgtgtcgt gagatgttgg   1020
gttaagtccc gcaacgagcg caaccttac ggttagttga tacgcaagat cactctagcc   1080
ggactgccgt tgacaaaacg gaggaaggtg gggacgacgt caaatcatca tgccctat    1140
gacctgcct acacacgtac tacaatgcca gcatacaga gggaagcaat accgcgaggt    1200
ggagcaaatc cctaaaagct gtcccagttc agattgcagg ctgcaacccg cctgcatgaa   1260
gtcggaattg ctagtaatcg cggatcagca tgccgcggtg aatacgttcc cgggccttgt   1320
acacaccgcc cgtcacacca tgagagccgt caatacccga gtccgtagc ctaaccgcaa   1380
gggg                                                                1384

SEQ ID NO: 41          moltype = DNA   length = 1392
FEATURE                Location/Qualifiers
misc_feature           1..1392
                       note = K41
source                 1..1392
                       mol_type = unassigned DNA
                       organism = unidentified
SEQUENCE: 41
agtcgaacga agcactttat ttgatttcct tcgggactga ttattttgtg actgagtggc     60
ggacgggtga gtaacgcgtg ggtaacctgc cttgtacagg gggataacag ttggaaacgg    120
ctgctaatac cgcataagcg cacggcatcg catgatgcag tgtgaaaaac tccggtggta    180
taagatggac ccgcgttgga ttagctagtt ggtgaggtaa cggcccacca aggcgacgat    240
ccatagccga cctgagaggt tgaccggcca cattgggact gagacacggc ccaaactcct    300
acgggaggca gcagtgggga atattgcaca atgggcgaaa gcctgatgca gcgacgccgc    360
gtgagcgaag aagtatttcg gtatgtaaag ctctatcagc agggaagata atgacggtac    420
ctgactaaga agcaccggct aaatacgtgc cagcagccgc ggtaatacgt atggtgcaag    480
cgttatccgg atttactggg tgtaagggga gcgcaggcgg tgcggcaagt ctgatgtgaa    540
agcccggggc tcaaccccgg tactgcattg gaaactgtca tactagagtg tcggagggt    600
aagcggaatt cctagtgtag cggtgaaatg cgtagatatt aggaggaaca ccagtggcga    660
aggcggctta ctggacgata actgacgctg aggctcgaaa gcgtgggag caaacaggat    720
tagataccct ggtagtccac gccgtaaacg atgaatacta ggtgttggga agcattgctt    780
ctcggtgccg tcgcaaacgc agtaagtatt ccacctgggg agtacgttcg caagaatgaa    840
actcaaagga attgacgggg acccgcacaa gcggtggagc atgtggttta attcgaagca    900
```

```
acgcgaagaa ccttaccaag tcttgacatc cttctgaccg gtacttaacc gtaccttctc    960
ttcggagcag gagtgacagg tggtgcatgg ttgtcgtcag ctcgtgtcgt gagatgttgg   1020
gttaagtccc gcaacgagcg caacccttat ctttagtagc cagcggttcg gccgggcact   1080
ctagagagac tgccagggat aacctggagg aaggcgggga tgacgtcaaa tcatcatgcc   1140
ccttatgact tgggctacac acagtgctac atggcctaca caaagggaag caaagctgtg   1200
aagccgagca atctcaaaa ataacgtctc agttcggact gtagtctgca acccgactac   1260
acgaagctgg aatcgctagt aatcgcagat cagaatgctg cggtgaatac gttcccgggt   1320
cttgtacaca ccgcccgtca caccatggga gttgggaatg cccgaagcca gtgacctaac   1380
cgaaaggaag ga                                                        1392

SEQ ID NO: 42            moltype = DNA   length = 1397
FEATURE                  Location/Qualifiers
misc_feature             1..1397
                         note = K42
source                   1..1397
                         mol_type = unassigned DNA
                         organism = unidentified
SEQUENCE: 42
cagtcgaacg aagcatatag agacgagtat ttcggtatga gtaactatat gactgagtgg    60
cggacgggtg agtaacgcgt ggataacctg cctcatacag ggggataaca gttagaaatg   120
actgctaata ccgcataagc gcacagtgct gcatggcaca gtgtgaaaag ctccggcggt   180
atgagatgga tccgcgtttg attagctagt tggtggggta aggcctacc aaggcgacga   240
tcaatagccg acctgagagg gtgaccggcc acattgggac tgagacacgg cccaaactcc   300
tacgggaggc agcagtgggg aatattgcac aatgggggaa accctgatgc agcgacgccg   360
cgtgaaggaa gaagtatttc ggtatgtaaa cttctatcag cagggaagaa aatgacggta   420
cctgactaag aagccccggc taattacgtg ccagcagccg cggtaatacg taaggggcaa   480
gcgttatccg gatttactgg gtgtaaaggg agcgtagacg gcagtgcaag tctgatgtga   540
aagcccgggg ctcaaccccg ggactgcatt ggaaactgtg cagctagagt gtcggagagg   600
taagtggaat tcctagtgta gcggtgaaat gcgtagatat taggaggaac accagtggcg   660
aaggcggctt actggacgat aactgacgtt gaggctcgaa gcaaacagga   720
ttagataccc tggtagtcca cgccgtaaac gatgaatact aggtgtcggg cgccaaaggc   780
gttcggtgcc gcagcaaacg caataagtat tccacctggg gagtacgttc gcaagaatga   840
aactcaaagg aattgacggg gacccgcaca agcggtggag catgtggttt aattcgaagc   900
aacgcgaaga accttaccaa gtcttgacat ctgcctgacc ggtccgtaac aggaccctc   960
cttcgggaca ggcaagacag gtggtgcatg gttgtcgtca gctcgtgtcg tgagatgttg   1020
ggttaagtcc cgcaacgagc gcaacccttg tccttagtag ccagcaggta gagctgggca   1080
ctctaggag actgccaggg acaacctgga ggaaggtggg gatgacgtca atcatcatg   1140
cccccttatga tttgggctac acgtgctac aatggcgta aacaaaggga agcgaagggg   1200
tgacctgaag caaatcccaa aataacgtc tcagttcgga ttgtagtctg caactcgact   1260
acatgaagct ggaatcgcta gtaatcgcga atcagaatgc cggtgaat acgttcccgg   1320
gtcttgtaca caccgcccgt cacaccatgg gagtcggata tgcccgaagc cggtgaccga   1380
acccgaaagg gaaggag                                                   1397

SEQ ID NO: 43            moltype = DNA   length = 1388
FEATURE                  Location/Qualifiers
misc_feature             1..1388
                         note = K43
source                   1..1388
                         mol_type = unassigned DNA
                         organism = unidentified
SEQUENCE: 43
agtcgaacgg agcacccttg actgaggttt cggccaaatg ataggaatgc ttagtggcgg    60
actggtgagt aacgcgtgag gaacctgcct tccagagggg gacaacagtt ggaaacgact   120
gctaataccg catgacgcat gaccggggca tcccgggcat gtcaaagatt ttatcgctgg   180
aagatgcct cgcgtctgat tagctagatg gtggggtaac ggcctaccat ggcgacgatc   240
agtagccgga ctgagaggtt gaccggccac attgggactg agatacggcc cagactccta   300
cgggaggcag cagtggggaa tattgggcaa tggacgcaag tctgacccag caacgccgcg   360
tgaaggaaga aggctttcgg gttgtaaact tcttttgtca gggaagagta gaagacggta   420
cctgacgaat aagccacggc taactacgtg ccagcagccg cggtaatacg taggtggcaa   480
gcgttgtccg gatttactgg gtgtaaaggg cgtgcagccg gccggcaag tcagatgtga   540
aatctggagg cttaacctcc aaactgcatt tgaaactgta ggtcttgagt accggagagg   600
ttatcggaat tccttgtgta gcggtgaaat gcgtagatat aaggaagaac accagtggcg   660
aaggcggata actggacggc aactgacggt gaggcgcgaa agcgtgggga gcaaacagga   720
ttagataccc tggtagtcca cgctgtaaac gatgatact aggtgtcggg cgccaaggc   780
cctgcgtgcc gcagttaaca caataagtat cccacctggg gagtacgatc gcaaggttga   840
aactcaaagg aattgacggg ggcccgcaca agcggtggat tatgtggttt aattcgaagc   900
aacgcgaaga accttaccag ggcttgacat cctactaacg aagtagagat acatcaggtg   960
cccttcgggg aaagtagaga caggtggtgc atggttgtcg tcagctcgtg tcgtgagatg   1020
ttgggttaag tcccgcaacg agcgcaaccc ctattgttag ttgctacgca agacactct   1080
agcgagactg ccgttgacaa aacgaggaa ggtggggacg acgtcaaatc atcatgcccc   1140
ttatgtcctg ggctacacac gtaatacaat ggcggtcaac agagggaggc aaagccgcga   1200
ggcagagcaa accccccaaaa gccgtcccag ttcggatcgc aggctgcaac ccgcctgcgt   1260
gaagtcggaa tcgctagtaa tcgcggatca gcatgccgcg gtgaatacgt tcccgggcct   1320
tgtacaccac cgcccgtcaca ccatgagagt cgggaacacc cgaagtccgt agcctaaccg   1380
caaggagg                                                             1388

SEQ ID NO: 44            moltype = DNA   length = 1393
FEATURE                  Location/Qualifiers
misc_feature             1..1393
```

```
                      note = K44
source                1..1393
                      mol_type = unassigned DNA
                      organism = unidentified
SEQUENCE: 44
tgcagtcgaa cggagtgcct tagaaagagg attcgtccaa ttgataaggt tacttagtgg   60
cggacgggtg agtaacgcgt gaggaacctg cctcggagtg gggaataaca gaccgaaagg  120
cctgctaata ccgcatgatg cagttggacc gcatggtcct gactgccaaa gatttatcgc  180
tctgagatgg cctcgcgtct gattagcttg ttggcggggt aatggcccac caaggcgacg  240
atcagtagcc ggactgagag gttggccggc cacattggga ctgagacacg gcccagactc  300
ctacgggagg cagcagtggg gaatattggg caatgggcgc aagcctgacc cagcaacgcc  360
gcgtgaagga gaaggctttc ggggttgtaa acttctttc tcagggacga acaaatgacg  420
gtacctgagg aataagccac ggctaactac gtgccagcag ccgcggtaat acgtaggtgg  480
caagcgttat ccggatttac tgggtgtaaa gggcgtgtag gcgggaaggc aagtcagatg  540
tgaaaactat gggctcaacc catagcctgc atttgaaact gttttctctg agtgctggag  600
aggcaatcgg aattccgtgt gtagcggtga atgcgtaga tatacggagg aacaccagtg  660
gcgaaggcgg attgctggac agtaactgac gctgaggcgc gaaagcgtgg ggagcaaaca  720
ggattagata ccctggtagt ccacgctgta aacgatggat actaggtgtg gggggtctg   780
acccctccg tgccgcagtt aacacaataa gtatcccacc tggggagtac gatcgcaagg  840
ttgaaactca aaggaattga cggggcccca cacaagcggt ggagtatgtg gtttaattcg  900
aagcaacgcg aagaaccta ccaggggcttg acatcctact aacgaagcag agatgcatta  960
ggtgcccttc ggggaaagta gagacaggtg gtgcatggtt gtcgtcagct cgtgtcgtga 1020
gatgttgggt taagtcccgc aacgagcgca acccttattg ttagttgcta cgcaagagca 1080
ctctagcgag actgccgttg acaaaacgga ggaaggcggg gacgacgtca aatcatcatg 1140
ccccttatgt cctgggctac acacgtacta caatggtggt aaacagaggg aagcaagacc 1200
gcgaggtgga gcaaatccct aaaagccatc ccagttgtca ttgcaggctg aaaccgcgct 1260
gtatgaagtt ggaatcgcta gtaatcgcg atcagcatgc cgcggtgaat acgttcccgg 1320
gccttgtaca caccgcccgt cacaccatga gagtcgggaa caccgaagt ccgtagtcta 1380
accgcaaggg gga                                                    1393

SEQ ID NO: 45         moltype = DNA  length = 1409
FEATURE               Location/Qualifiers
misc_feature          1..1409
                      note = K45
source                1..1409
                      mol_type = unassigned DNA
                      organism = unidentified
SEQUENCE: 45
caagtagaac gctgactact ttagcttgct agagtagaag gagttgcgaa cgggtgagta   60
acgcgtaggt aacctgccta ctagcggggg ataactattg gaaacgatag ctaataccgc  120
ataacagtgt ttaacacatg ttagatgctt gaaagatgca attgcatcac tagtagatgg  180
acctgcgttg tattagctag ttggtggggt aacggcccac caaggcgacg atacatagcc  240
gacctgagag ggtgatcggc cacactggga ctgagacacg gcccagactc ctacgggagg  300
cagcagtagg gaatcttcgg caatgggggc aaccctgacc gagcaacgcc gcgtgagtga  360
agaaggtttt cggatcgtaa agctctgttg taagagaaga acgtgtgtga gagtggaaag  420
ttcacacagt gacggtaact taccagaaag ggacggctaa ctacgtgcca gcagccgcgg  480
taatacgtag gtcccgagcg ttgtccggat ttattgggcg taaagcgagc gcaggcggtt  540
taataagtct gaagttaaag gcagtggctt aaccattgtt cgctttggaa actgttaaac  600
ttgagtgcag aaggggagag tggaattcca tgtgtagcgg tgaaatgcgt agatatatgg  660
aggaacaccg gtggcgaaag cggctctctg gtctgtaact gacgctgagg ctcgaaagcg  720
tggggagcaa acaggattag ataccctggt agtccacgct gtaaacgatg agtgctagt   780
gttaggccct ttccggggct tagtgccgca gctaacgcat taagcactcc gcctgggag   840
tacgaccgca aggttgaaac tcaaaggaat tgacgggggc ccgcacaagc ggtggagcat  900
gtggtttaat tcgaagcaac gcgaagaacc ttaccaggtc ttgacatccc gatgctattt  960
ctagagatag aaagtttctt cggaacatcg tgtgacaggtg gtgcatggtt gtcgtcagct 1020
cgtgtcgtga gatgttgggt taagtcccgc aacgagcgca acccttattg ttagttgcca 1080
tcatttagtt gggcactcta gcgagactgc cggtaataaa ccgaggaag gtggggatga 1140
cgtcaaatca tcatgcccct tatgacctgg gctacacacg tgctacaatg gttggtacaa 1200
cgagtcgcaa gtcggtgacg gcaagcaaat ctcttaaagc caatctcagt tcggattgta 1260
ggctgcaact cgcctacatg aagtcggaat cgctagtaat cgcggatcag cacgccgcgg 1320
tgaatacgtt cccgggcctt gtacacaccg cccgtcacac cacgagagtt tgtaacaccc 1380
gaagtcggtg aggtaaccat ttaggagcc                                   1409

SEQ ID NO: 46         moltype = DNA  length = 1395
FEATURE               Location/Qualifiers
misc_feature          1..1395
                      note = K46
source                1..1395
                      mol_type = unassigned DNA
                      organism = unidentified
SEQUENCE: 46
caagtcgaac ggcagcgcgg ggagcttgct ccctggcggc gagtggcgca cgggtgagta   60
atacatcgga acgtgtcttc tagtgggga taactgcccg aaaggggcagc taataccgca  120
tgagacctga gggtgaaagc ggggatcgc aagcctgtgc gctggaagag cggccgatgt  180
ccgattagct agttggtgag gtaaaggctc accaaggcga cgatcggtag ctggtctgag  240
aggacgacca gccacactgg gactgagaca cggcccagac tcctacggga ggcagcagtg  300
gggaattttg gacaatgggg gcaacctga tccagccatg ccgcgtgcag gatgaaggtc  360
ttcggattgt aaactgcttt gtcagggac gaaaaggggat gcgataacac cgcattccgc  420
tgacggtacc tgaagaataa gcaccggcta actacgtgcc agcagccgcg gtaatacgta  480
```

```
gggtgcaagc gttaatcgga attactgggc gtaaagcgtg cgcaggcggt tctgtaagat    540
agatgtgaaa tccccgggct caacctggga attgcatata tgactgcagg acttgagttt    600
gtcagaggag ggtggaattc cacgtgtagc agtgaaatgc gtagatatgt ggaagaacac    660
cgatggcgaa ggcagccctc tgggacatga ctgacgctca tgcacgaaag cgtggggagc    720
aaacaggatt agataccctg gtagtccacg ccctaaacga tgtctactag ttgttgggga    780
cgatagtcct tggtaacgca gctaacgcgt gaagtagacc gcctgggagt acggtcgca    840
agattaaaac tcaaaggaat tgacggggac ccgcacaagc ggtggatgat gtggattaat    900
tcgatgcaac gcgaaaaacc ttacctagcc ttgacatgcc aggaaggcct gagagatcag    960
gccgtgcccg caagggaatc tggacacagg tgctgcatgg ctgtcgtcag ctcgtgtcgt   1020
gagatgttgg gttaagtccc gcaacgagcg caacccttgt cattagttgc tacgaaaggg   1080
cactctaatg agactgccgg tgacaaaccg gaggaaggtg gggatgacgt caagtcctca   1140
tggcccttat ggctagggcc tcacacgtca taatggtc ggaacagagg gaagcgaagc   1200
cgcgaggtga agcaatccc agaaaaccga tcgtagtccg gattgcagtc tgcaactcga   1260
ctgcatgaag tcggaatcgc tagtaatcgc ggatcagcat gccgcggtga atacgttccc   1320
gggtcttgta cacaccgccc gtcacaccat gggagtgggg ttcaccagaa gacgtttgcc   1380
caaccgaaag gaagg                                                    1395

SEQ ID NO: 47           moltype = DNA  length = 1384
FEATURE                 Location/Qualifiers
misc_feature            1..1384
                        note = K47
source                  1..1384
                        mol_type = unassigned DNA
                        organism = unidentified
SEQUENCE: 47
agtcgaacgg gatcccagga gcttgctcct gggtgagagt ggcgaacggg tgagtaatgc     60
gtgaccgacc tgcccatac accggaatag ctcctggaaa cggtggtaa tgccggatgc    120
tccagttgac cgcatggtcc tctgggaaag attctatcgg tatgggatgg ggtcgcgtcc    180
tatcagcttg atggcgggt aacggccac catggcttcg acgggtagcc ggcctgagag    240
ggcgaccggc cacattggga ctgagatacg cccagactc ctacgggagg cagcagtggg    300
gaatattgca caatgggcgc aagcctgatg cagcgacgcc gcgtgcggga tgacggcctt    360
cgggttgtaa accgcttttg actgggagca agccttcgg ggtgagtgta cctttcgaat    420
aagcaccggc taactacgtg ccagcagccg cggtaatacg tagggtgcaa gcgttatccg    480
gaattattgg gcgtaaaggg ctcgtaggcg gttcgtcgcg tccggtgtga aagtccatcg    540
cttaacggtg gatccgcgcc gggtacgggc gggcttgagt cggtaggggg agactggaat    600
tcccggtgta acgtggaat gtgtagatat cgggaagaac accaatggcg aaggcaggtc    660
tctgggccgt cactgacgct gaggagcgaa agcgtgggga gcgaacagga ttagataccc    720
tggtagtcca cgccgtaaac ggtggatgct ggatgtgggg accattccac ggtctccgtg    780
tcggagccaa cgcgttaagc atccccgcct gggagtacgg ccgcaaggct aaaactcaaa    840
gaaattgacg ggggcccgca caagcggcgg agcatgcgga ttaattcgat gcaacgcgaa    900
gaaccttacc tgggcttgac atgttcccga cagccgtaga gatacggtct cccttcgggg    960
cgggttcaca ggtggtgcat ggtcgtcgtc agctcgtgtc gtgagatgtt gggttaagtc   1020
ccgcaacgag cgcaaccctc gccctgtgtt gccagcacgt cgtggtggga actcacgggg   1080
gaccgccggg gtcaactcgg aggaaggtgg ggatgacgtc agatcatcat gccccttacg   1140
tccagggctt cacgcatgct acaatggccg gtacaacggg atgcgacatc gtgaggggga   1200
gcggatccct aaaaccggt ctcagttcgg attggagtct gcaacccgac tccatgaagg   1260
cggagtcgct agtaatcgcg gatcagcaac gccgcggtga atgcgttccc gggccttgta   1320
cacaccgccc gtcaagtcat gaaagtgggt agcacccgaa gccggtggcc caacctttttg   1380
gggg                                                                1384

SEQ ID NO: 48           moltype = DNA  length = 1387
FEATURE                 Location/Qualifiers
misc_feature            1..1387
                        note = K48
source                  1..1387
                        mol_type = unassigned DNA
                        organism = unidentified
SEQUENCE: 48
gtcgaacgga gctgctttga tgaagttttc ggatggattt aaaacagctt agtggcggac     60
gggtgagtaa cgcgtgggta acctgcctca cactggggga taacagttag aaatagctgc    120
taataccgca taagcgcaca gttccgcatg aacagtgtg aaaaactccg gtggtgtgag    180
atggaccgc gtctgattag ccagttggcg gggtaacggc ccaccaaagc gacgatcagt    240
agccggcctg agagggtgaa cggccacatt gggactgaga cacggcccaa actcctacgg    300
gaggcagcag tggggaatat tgcacaatgg gggaaaccct gatgcagcga cgccgcgtgg    360
gtgaagaagt atttcggtat gtaaagctct atcagcaggg aagaaagtga cggtacctga    420
ataagaagcc ccggctaact acgtgccagc agccgcggta atacgtaggg ggcaagcgtt    480
atccggattt actgggtgta aagggagcgt agacggcaag gcaagtctga gtgaaagcc    540
cggtgcttaa cgccgggact gctttggaaa ctgtttggct ggagtgccgg agaggtaagc    600
ggaattccta gtgtagcggt gaaatgcgta gatattagga ggaacaccag tggcgaaggc    660
ggcttactgg acgtaactg acgttgaggc tcgaaagcgt ggggagcaaa caggattaga    720
taccctggta gtccacgccg taaacgatga ttgctaggtg taggtgggta tggacccatc    780
ggtgccgcag ctaacgcaat aagcaatcca cctggggag tacgttcgca agaatgaaac    840
tcaaaggaat tgacggggac ccgcacaagc ggtggagcat gtggtttaat tcgaagcaac    900
gcgaagaacc ttaccaggtc ttgacatccc gatgaaaacc cctaacgag tggccctctt    960
cggagcatcg gagacaggtg gtgcatggtt gtcgtcagct cgtgtcgtga gatgttgggt   1020
taagtcccgc aacgagcgca acccttattc ttagtagcca gcaggtaaag ctgggcactc   1080
taaggagact gccggggata acccggagga aggtggggat gacgtcaaat catcatgccc   1140
cttatgatct gggctacaca cgtgctacaa tggcgtaaca aagggaagcg agcctgcgag   1200
ggtgagcgaa tcccaaaaaat aacgtcccag ttcggactgt agtctgcaac ccgactacac   1260
```

```
gaagctggaa tcgctagtaa tcgcgaatca gaatgtcgcg gtgaatacgt tcccgggtct   1320
tgtacacacc gcccgtcaca ccatgggagt cggaaatgcc cgaagtctgt gactcaaccg   1380
caaggag                                                              1387

SEQ ID NO: 49           moltype = DNA  length = 1368
FEATURE                 Location/Qualifiers
misc_feature            1..1368
                        note = K49
source                  1..1368
                        mol_type = unassigned DNA
                        organism = unidentified
SEQUENCE: 49
ttaaggagat tcttcggatg attcttgact gactgagcgg cggacgggtg agtaacgcgt    60
gggtgacctg ccccataccg ggggataaca gctggaaacg gctgctaata ccgcataagc   120
gcacagagct gcatggctcg gtgtgaaaaa ctccggtggt atgggatggg cccgcgtctg   180
attaggcagt tggcggggta acggcccacc aaaccgacga tcagtagccg gcctgagagg   240
gcgaccggcc acattgggac tgagacacgg cccaaactcc tacgggaggc agcagtgggg   300
aatattgcac aatgggggaa accctgatgc agcgacgccg cgtgagcgaa gaagtatttc   360
ggtatgtaaa gctctatcag cagggaagat aatgacggta cctgactaag aagcccccggc  420
taactacgtg ccagcagccg cggtaatacg tagggggcaa gcgttatccg gatttactgg   480
gtgtaaaggg agcgtagacg gcaaggcaag tctgatgtga aaacccaggg cttaaccctg   540
ggactgcatt ggaaactgtc tggctcgagt gccggagagg taagcggaat tcctagtgta   600
gcggtgaaat gcgtagatat taggaagaac accagtggcg aaggcggctt actggacggt   660
aactgacgtt gaggctcgaa agcgtgggga gcaaacagga ttagataccc tggtagtcca   720
cgccgtaaac gatgaatgct aggtgttggg agcaaagctc ttcggtgcc gccgcaaacgt   780
cattaagcat tccacctggg gagtacgttc gcaagaatga aactcaaagg aattgacggg   840
gacccgcaca agcggtggag catgtggttt aattcgaagc aacgcgaaga accttaccag   900
gtcttgacat cccgatgacc ggccgtaac ggggccttct cttcggagca ttggagacag   960
gtggtgcatg gttgtcgtca gctcgtgtcg tgagatgttg ggttaagtcc cgcaacgagc  1020
gcaaccctta tcctcagtag ccagcaggtc aagctggaca ctctgtggag actgccaggg  1080
ataacctgga ggaaggtggg gatgacgtca aatcatcatg cccttatga tctgggctac   1140
acacgtgcta caatgcgta aacaaaggga ggcaaagccg cgaggtggag caaatcccaa   1200
aaataacgtc tcagttcgga ctgcagtctg caactcgact gcacgaagct ggaatcgcta   1260
gtaatcgcga atcagaatgt cgcggtgaat acgttcccgg gtcttgtaca caccgcccgt   1320
cacaccatgg gagttggtaa cgcccgaagt cagtgaccca accttcag                1368

SEQ ID NO: 50           moltype = DNA  length = 1390
FEATURE                 Location/Qualifiers
misc_feature            1..1390
                        note = K50
source                  1..1390
                        mol_type = unassigned DNA
                        organism = unidentified
SEQUENCE: 50
gtcgagcgaa gcacttatga tgattcttcg gatgaatcat ttgtgactga gcggcggacg    60
ggtgagtaac gcgtgagtaa cctgcctcat acagggaat aacagttaga aatgactgct   120
aatgccgcat aagcgcacag ggccgcatgg cccggtgtga aaaactccgg tggtatgaga   180
tggactcgcg tctgattagc tagttggcag ggtaacggcc taccaaggcg acgatcagta   240
gccggcctga gaggtgaac ggccacattg gactgagac acgggcaaa ctcctacggg    300
aggcagcagt ggggaatatt gcacaatggg ggaaacctg atgcagcgac gccgcgtgag   360
tgaagaagta tttcggtatg taaagctcta tcagcaggaa agaaaatgac ggtacctgac   420
taagaagccc cggctaacta cgtgccagca gccgcggtaa tacgtagggg gcaagcgtta   480
tccggatttta ctgggtgtaa agggagcgta gacggctttg caagtctgac gtgaaactcc   540
ggggctcaac tccggaactg cgttggaaac tgtaaggctt gagtgccgga gaggtaagcg   600
gaattcctag tgtagcggtg aaatgcgtag atattaggag gaacaccagt ggcgaaggcg   660
gcttactgga cggcaactga cgttgaggct cgaaagcgtg gggagcaaac aggattagat   720
accctggtag tccacgcggt aaacgatgaa tactaggtgt tggggacaa agtccttcgg   780
tgccgccgca aacgcattaa gtattccacc tggggagta cgttcgcaag aatgaaactc   840
aaaggaattg acgggacccc gcacaagcgg tggagcatgt ggtttaattc gaagcaacgc   900
gaagaacctt accaagtctt gacatcgatt cgacggagt gtaatgactc ctttccctcc   960
ggggacgaag aagacaggtg gtgcatggtt gtcgtcagct cgtgtcgtga gatgttgggt  1020
taagtcccgc aacgagcgca acccttatct tcagtagcca gcgagtaagg tcgggcactc  1080
tggagagact gccaggaca acctggagga aggtgggat gacgtcaaat catcatgccc   1140
cttatgactt gggctacaca cgtgctacaa tggcgtaaa aagggaagc gaacctgtga   1200
gggtgggcaa atcccaaaaa taacgtctca gttcggattg tagtctgcaa ctcgactaca  1260
tgaagctgga atcgctagta atcgcgaatc agcatgtcgc ggtgaatacg ttcccggtc   1320
ttgtacacac cgcccgtcac accatgggag tcggtaacgc ccgaagtcag tgacccaacc  1380
gcaaggaggg                                                           1390

SEQ ID NO: 51           moltype = DNA  length = 1382
FEATURE                 Location/Qualifiers
misc_feature            1..1382
                        note = K51
source                  1..1382
                        mol_type = unassigned DNA
                        organism = unidentified
SEQUENCE: 51
gcagtcggac gcaatgcttc ggcattgagt ggcgaacggg tgagtaagac ataagcaacc    60
tgcccctgtg aggggataa ctgctggaaa cggcagctaa gaccgcatag gcatagagga   120
```

```
cgcatgtcga ctatgttaaa tatcccacgg gatagcacag ggatgggctt atgacgcatt    180
agccagctgg tgaggtaacg gctcaccagg gcgacgatgc gtagccgcc tgagagggtg     240
gacggccaca ctgggactga gacacggccc agactcctac gggaggcagc agtagggaat    300
tttcggcaat gggcgaaagc ctgaccgagc aacgccgcgt gaaggaagaa gtcattcgtg    360
atgtaaactt ctgttatgaa ggaagaacgg cagatggagg aatgccatg tgcgtgacgg     420
tacttcatga ggaagccacg gctaactacg tgccagcagc cgcggtaata cgtaggtggc    480
gagcgttatc cggaatcatt gggcgtaaag agggagcagg cggcagtgca ggtctgcggt    540
gaaagaccga agctaaactt cggtaagccg tggaaaccgc acagctagag agcatcagag    600
gatcgcggaa ttccatgtgt agcggtgaaa tgcgtagata tatggaggaa caccagtggc    660
gaaggcggcg gtctggggtg cagctgacgc tcagtcccga aagcgtgggg agcaaatagg    720
attagatacc ctagtagtcc acgccgtaaa cgatgagtgc taagtgttgg gggtcagacc    780
tcagtgctgg agttaacgca ataagcactc gcctgagta gtacgttcgc aagaatgaaa    840
ctcaaaggaa ttgacggggg cccgcacaaa gcggtgagc atgtggttta attcgaagca    900
acgcgaagaa ccttaccagg tcttgacatg gagataaagg ccctggagac agggagatag    960
atatatctca cacaggtggt gcatggttgt cgtcagctcg tgtcgtgaga tgttgggtta    1020
agtcccgcaa cgagcgcaac ccctgttgcc agttgccagc attaggttgg ggactctggc    1080
gagactgcct ctgcaaggag gaggaaggcg gggatgacgt caaatcatca tgccccttat    1140
gacctgggct acacacgtgc tacaatggac ggatcagagg gaggcgaagc cgcgaggtgg    1200
agcgaaaccc agaaaccccgt tcacagttcg gactgcagtc tgcaactcga ctgcacgaag    1260
ctggaatcgc tagtaatcgc gaatcagcat gtcgcggtga atacgttctc gggccttgta    1320
cacaccgccc gtcacaccat gagagttggt aacacccgaa gccggtggcc caaccgcaag    1380
ga                                                                  1382
SEQ ID NO: 52          moltype = DNA  length = 1388
FEATURE                Location/Qualifiers
misc_feature           1..1388
                       note = K52
source                 1..1388
                       mol_type = unassigned DNA
                       organism = unidentified
SEQUENCE: 52
agtcgaacgg gaaatatttt attgaaactt cggtggattt aatttatttc tagtggcgga    60
cgggtgagta acgcgtgggt aacctgcctt atactggggg ataacagcca gaaatgactg    120
ctaataccgc ataagcgcac agaaccgcat ggttcggtgt gaaaaactcc ggtggtataa    180
gatggacccg cgttggatta gctagttggc agggcagcgg cctaccaagg cgacgatcca    240
tagccggcct gagagggtga acggccacat tgggactgag acacggccca gactcctacg    300
ggaggcagca gtggggaata ttgcacaatg ggggaaaccc tgatgcagcg acgccgcgtg    360
aaggaagaag tatctcggta tgtaaacttc tatcagcagg gaagatataatg acggtacctg    420
actaagaagc cccggctaac tacgtgccaa cagccgcggt aatacgtagg gggcaagcgt    480
tatccggatt tactgggtgt aaagggagcg tagacggtgc agcaagtctg atgtgaaagg    540
caggggctta acccctggac tgcattggaa actgctgtgc ttgagtgccg gaggggtaag    600
cggaattcct agtgtagcgg tgaaatgcgt agatattagg aggaacacca gtggcgaagg    660
cggcttactg gacggtaact gacgttgagg ctcgaaagcg tgggagcaa acaggattag    720
ataccctggt agtccacgcc gtaaacgatg aatactaggt gtcagggagc acagctcttt    780
ggtgccgccg caaacgcatt aagtattcca cctggggagt acgttcgcaa gaatgaaact    840
caaaggaatt gacggggacc cgcacaagcg gtggagcatg tggtttaatt cgaagcaacg    900
cgaagaacct taccaaatct tgacatccct ctgaccggga cttaaccgtc cctttccttc    960
gggacagggg agacaggtgg tgcatggttg tcgtcagctc gtgtcgtgag atgttgggtt    1020
aagtcccgca acgagcgcaa ccccctatcct tagtagccag cacgcagtgg tgggcactct    1080
gaggagactg ccagggataa cctggaggaa ggcggggatg acgtcaaatc atcatgcccc    1140
ttatgatttg ggctacacac gtgctacaat ggcgtaaaca aagggaagcg aaccccgtga    1200
ggtgggcaaa tctcaaaaat aacgtccag ttcggactgc agtctgcaac tcgactgcac    1260
gaagctggaa tcgctagtaa tcgcggatca gaatgccgcg gtgaatacgt tcccgggtct    1320
tgtacacacc gcccgtcaca ccatgggagt cagtaacgcc cgaagtcagt gacctaaccg    1380
caagggag                                                            1388
SEQ ID NO: 53          moltype = DNA  length = 1385
FEATURE                Location/Qualifiers
misc_feature           1..1385
                       note = K53
source                 1..1385
                       mol_type = unassigned DNA
                       organism = unidentified
SEQUENCE: 53
cgaacgggaa ttatttcatt gagacttcgg tggatttgat ctatttctag tggcggacg    60
gtgagtaacg cgtgggtaac ctgccttata caggggata acagtcagaa atggctgcta    120
ataccgcata agcgcacaga gctgcatggc tcagtgtgaa aaactccggt ggtataagat    180
ggacccgcgt tggattagct tgttggtggg gtaacggccc accaaggcga cgatccatag    240
ccggcctgag agggtgaacg gccacattgg gactgagaca cggcccagac tcctacgggag    300
gcagcagtg gggaatattg cacaatgggg gaaaccctga tgcagcgacg ccgcgtgaag    360
gaagaagtat ctcggtatgt aaacttctat cagcagggaa gatagtgacg gtacctgact    420
aagaagcccc ggctaactac gtgccagcag ccgcggtaat acgtagggg caagcgttat    480
ccggatttac tgggtgtaaa gggagcgtag acggtgtggc aagtctgatg tgaaaggcat    540
gggctcaacc tgtgcagtgc attggaaact gtcatacttg agtgccggag gggtaagcgg    600
aattcctagt gtagcggtga atgcgtaga tattaggagg aacaccagtg gcgaaggcgg    660
cttactggac ggtaactgac gttgaggctc gaaagcgtgg ggagcaaaca ggattagata    720
ccctggtagt ccacgccgta aacgatgaat actaggtgtc ggggagcatg gctcttcggt    780
gccgtcgcaa acgcagtaag tattccacct ggggagtac gttcgcaaga atgaaactca    840
aaggaattga cggggacccg cacaagcggt ggagcatgtg gtttaattcg aagcaacgcg    900
```

-continued

```
aagaaccttaccaagtcttgacatccgcctgaccgatcctaatcggatcttttcttcgg 960
gacagacgagacaggtggtgcatgttgtcgtcagctcgtgtcgtgagatgttgggttaa 1020
gtcccgcaacgagcgcaaccctatcctcagtagccagcatttaaggtgggcactctggg 1080
gagactgccagggataacctggaggaaggcggggatgacgtcaaatcatcatgcccctta 1140
tgatttgggctacacacgtgctacaatggcgtaaacaaagggaagcgaatcgtgagatg 1200
gagcaaatcccaaaaataacgtcccagttcggactgtagtctgcaacccgactacacgaa 1260
gctggaatcgctagtaatcgcggatcagaatgccgcggtgaatacgttcccgggtcttgt 1320
acacaccgcccgtcacaccatgggagtcagtaacgcccgaagtcagtgacctaactgcaa 1380
agaag 1385

SEQ ID NO: 54           moltype = DNA   length = 1415
FEATURE                 Location/Qualifiers
misc_feature            1..1415
                        note = K54
source                  1..1415
                        mol_type = unassigned DNA
                        organism = unidentified
SEQUENCE: 54
gtcgaacggagaattttatttcggtagaattcttagtggcgaacgggtgagtaacgcgta 60
ggcaacctgcccttagacgggacaacatccgaaaggagtgctaatacggatgtgat 120
catcgtgccgcatggcaggatgaagaaagatggcctctacaagtaagctatcgctaaagg 180
atgggcctgcgtctgattagctagttggtagtgtaacggactaccaaggcgatgatcagt 240
agccggtctgagaggatgaacggccacattgggactgagacacggcccaaactcctacgg 300
gaggcagcagtggggaatcttccgcaatggacgaaagtctgacggagcaacgccgcgtga 360
gtgatgaaggatttcggtctgtaaagctctgttgtttatgacgaacgtgcagtgtgtgaa 420
caatgcattgcaatgacggtagtaaacgaggaagccacgctaactacgtgccagcagcc 480
gcggtaatacgtaggtggcgagcgttgtccggaattattgggcgtaaagagcatgtaggc 540
ggcttaataagtcgagcgtgaaaatgcgggctcaacccgtatggcgctggaaactgtt 600
aggcttgagtgcaggagaggaaaggggaattcccagtgtagcggtgaaatgcgtagatat 660
tggaggaacaccagtggcgaaggcgccttctggactgtgtctgacgctgagatgcgaa 720
agccagggtagcgaacgggattagataccccggtagtcctggccgtaaacgatgggtact 780
aggtgtaggaggtatcgacccttctgtgccggagttaacgcaataagtacccgcctgg 840
ggagtacggccgcaaggttgaaactcaaaggaattgacggggcccgcacaagcggtgga 900
gtatgtggtttaattcgacgcaacgcgaagaaccttaccaaggcttgacattgattgaac 960
gctctagagatagagctttccttcggggacaagaaaacaggtggtgcatggctgtcgtc 1020
agctcgtgtcgtgagatgttgggttaagtcccgcaacgagcgcaacccctatcctatgtt 1080
accagcaagtaaagttggggactcatggagactgccaggacaacctggaggaaggcgg 1140
ggatgacgtcaagtcatcatgccccttatgtcttgggctacacacgtactacaatggtcg 1200
gaaacagagggaagcgaagcgcgagcagagcaaaccgaagaaacccgatctcagttcga 1260
gatcgcaggctgcaacccgcctgcgtgaagtcgaatcgctagtaatcgcaggtcagcat 1320
actgcggtgaatacgttcccgggccttgtacacaccgcccgtcacaccacgaaagttggt 1380
aacacccgaagccggtgaggtaacctattaggagc 1415

SEQ ID NO: 55           moltype = DNA   length = 1366
FEATURE                 Location/Qualifiers
misc_feature            1..1366
                        note = K55
source                  1..1366
                        mol_type = unassigned DNA
                        organism = unidentified
SEQUENCE: 55
atgaggtagcaataccttgatggcgaccggcgcacgggtgagtaacgcgtatgcaacctg 60
cctgataccgggtatagccatggaaacgtggattaacaccccatagtacttttatcct 120
gcatgggatgtgagttaaatgttcaaggtatcggatgggcatgcgtcctattagttagtt 180
ggcgggtaacagcccaccaagacgatgataggtagggcgtctgagaggaggtcccca 240
cattggaactgagacacggtccaaactcctacgggaggcagcaggaatattggtca 300
atggacgagagtctgaaccagccaagtcgcgtgagggaagactgccctatgggttggtaaa 360
cctctttttataagggaagaataagttctacgtgtagaatgatgcctgtacttatgaata 420
agcatcggctaactccgtgccagcagccgcggtaatacggaggatgcgagcgttatccgg 480
atttattgggtttaaagggtgcgtaggcggtttattagttagtgcgtaaatatttgagc 540
taaactcaattgtgccattaatactggtaaactggagtacagacgaggtaggcggaataa 600
gttaagtagcggtgaaatgcatagatataacttagaactcgatagcgaaggcagcttac 660
cagactgtaactgacgctgatgcacgagagcgtgggtagcgaacaggattagataccctg 720
gtagtccacgccgtaaacgatgctcactggtttctgtgatatattgtacccggactaagc 780
gaaagtattaagtgagccactgggggagtacgtcggcaacgatgaaactcaaaggaattg 840
acgggggcccgcacaagcggaggaacatgtggtttaattcgatgatacgcgaggaacctt 900
acctgggtttaaatgggaaatgtcgtatttggaaacagattctcttcgagcgttttt 960
caaggtgtcgcatggttgtcgtcagctcgtgccgtgaggtgtcgggttaagtcccataac 1020
gagcgcaaccttaccgttagttgctagcatgtaatgatgagcactctaacgggactgcc 1080
accgtaaggtgagaggaaggcggggatgacgtcaaatcagcacggcccttacacccaggg 1140
ctacacacgtgttacaatggccggtacagagggccgctacaggtgactggatgccaatc 1200
tcaaaagccgtcgtagttcggattggagtctgtaacccgactccatgaagttggattcg 1260
ctagtaatcgcgcatcagccatggcgcggtgaatacgttcccgggccttgtacacaccgc 1320
ccgtcaagccatgaagccggggtgcctgaagtccgtaaccgcga 1366

SEQ ID NO: 56           moltype = DNA   length = 1364
FEATURE                 Location/Qualifiers
misc_feature            1..1364
                        note = K56
```

| variation | 923..924 |
| | note = n is a, c, g, or t |
| variation | 1349 |
| | note = n is a, c, g, or t |
| variation | 1351..1352 |
| | note = n is a, c, g, or t |
| source | 1..1364 |
| | mol_type = unassigned DNA |
| | organism = unidentified |

SEQUENCE: 56

```
tcgaacgagc gagagagagc ttgctttctc gagcgagtgg cgaacgggtg agtaacgcgt   60
gaggaacctg cctcaaagag ggggacaaca gttggaaacg actgctaata ccgcataagc  120
ccacgggtcg gcatcgacca gagggaaaag gagcaatccg ctttgagatg gcctcgcgtc  180
cgattagcta gttggtgagg taacggccca ccaaggcgac gatcggtagc cggactgaga  240
ggttgaacgg ccacattggg actgagacac ggcccagact cctacgggag gcagcagtgg  300
ggaatattgc acaatggggg aaaccctgat gcagcgacgc cgcgtggagg aagaaggtct  360
tcggattgta aactcctgtt gttggggaag ataatgacgg tacccaacaa ggaagtgacg  420
gctaactacg tgccagcagc cgcggtaaaa cgtaggtcac aagcgttgtc cggaattact  480
gggtgtaaag ggagcgcagg cgggaagaca agttggaagt gaaatctatg ggctcaaccc  540
ataaactgct ttcaaaactg ttttcttga gtagtgcaga ggtaggcgga attcccggtg  600
tagcggtgga atgcgtagat atcggagga acaccagtgg cgaaggcggc ctactgggca  660
ccaactgacg ctgaggctcg aaagtgtggg tagcaaacag gattagatac cctggtagtc  720
cacaccgtaa acgatgatta ctaggtgttg gaggattgac cccttcagtg ccgcagttaa  780
cacaataagt aatccacctg gggagtacga ccgcaaggtt gaaactcaaa ggaattgacg  840
ggggcccgca caagcagtgg agtatgtggt ttaattcgac gcaacgcgaa gaaccttacc  900
aagtcttgac atcccttgac agnnataaga atatgtttc tcttcggagc aaggagacag  960
gtggtgcatg gttgtcgtca gctcgtgtcg tgagatgttg ggttaagtcc cgcaacgagc 1020
gcaacccta tggtcagtta ctacgcaaga ggactctggc cagactgccg ttgacaaaac 1080
ggaggaaggt ggggatgacg tcaaatcatc atgccctta tgacttgggc tacacacgta 1140
ctacaatggc gttaaacaaa gagaagcaag accgcgaggt gcagcaaaac tcagaaacaa 1200
cgtcccagtt cggactgcag gctgcaactc gcctgcacga agtcggaatt gctagtaatc 1260
gtggatcagc atgccacggt gaatacgttc ccgggccttg tacacaccgc ccgtcacacc 1320
atgagagccg gggggacccg aagtcggtng nntaaccgca agga            1364
```

| SEQ ID NO: 57 | moltype = DNA   length = 1391 |
| FEATURE | Location/Qualifiers |
| misc_feature | 1..1391 |
| | note = K57 |
| source | 1..1391 |
| | mol_type = unassigned DNA |
| | organism = unidentified |

SEQUENCE: 57

```
tgcagtcgaa cggagtgctc atgacagagg attcgtccaa tggagtgagt tacttagtgg   60
cggacgggtg agtaacgcgt gagtaacctg ccttggagtg gggaataaca ggtgaaaaca  120
tctgctaata ccgcatgatg cagttgggtc gcatggctct gactgccaaa gatttatcgc  180
tctgagatg actcgcgtct gattagctgg ttggcgggt aacggccac caaggcgacg  240
atcagtagcc ggactgagag gttggccggc cacattggga ctgagacacg gcccagactc  300
ctacgggagg cagcagtggg gaatattggg caatgggcgc aagcctgacc cagcaacgcc  360
gcgtgaagga gaaggctttc ggggttgtaa acttctttc tcaggacga agcaagtgac  420
ggtacctgag gaataagcca cggctaacta cgtgccagca gccgcggtaa tacgtaggtg  480
gcgagcgtta tccggattta ctgggtgtaa agggcgtgta gccgggactg caagtcgat  540
gtgaaaacca tgggctcaac ctgtggcctg catttgaaac tgtagttctt gagtactgga  600
gaggcagacg gaattcctag tgtagcggtg aaatgcgtag atattaggag gaacaccagt  660
ggcgaaggcg gtctgctgga cagcaactga cgctgaggcg cgaaagcgtg gggagcaaac  720
aggattagat accctggtag tccacgctgt aaacgatgga tactaggtgt ggggggctctg  780
acccctccg tgccgcagtt aacacaataa gtatcccacc tggggagtac gatccgcaagg  840
ttgaaactca aaggaattga cggggggccc cacaagcggt ggagtatgtg gtttaattcg  900
aagcaacgcg aagaaccta ccagggcttg acatccggt gaccggtgta gagatacacc  960
ttcttcttcg gaagcgccgg tgacaggtgg tgcatggttg tcgtcagctc gtgtcgtgag 1020
atgttgggtt aagtcccgca acgagcgcaa ccctttattgt tagttgctac gcaagagcac 1080
tctagcgaga ctgccgttga caaaacggag gaaggtgggg acgacgtcaa atcatcatgc 1140
cccttatgtc ctgggccaca cacgtactac aatggtggtc aacagaggga agcaagaccc 1200
cgaggtggag caaacccta aaagccatcc cagttcggat gcaggctgc aactcgcctg 1260
tatgaagttg gaatcgctag taatcgcgga tcagcatgcc gcggtaata cgttcccggg 1320
ccttgtacac accgcccgtc acaccatgag agtcgggaac accgaagtc cgtagcctaa 1380
ccgcaagggg g                                                     1391
```

| SEQ ID NO: 58 | moltype = DNA   length = 1377 |
| FEATURE | Location/Qualifiers |
| misc_feature | 1..1377 |
| | note = K58 |
| source | 1..1377 |
| | mol_type = unassigned DNA |
| | organism = unidentified |

SEQUENCE: 58

```
gcaagtcgag cgagaagctt tgaactgacg cttcggttga tgatcaaagt ggaaagcggc   60
ggacgggtga gtaacgcgta ggcaacctgc cctttgcaga gggatagcct cgggaaaccg  120
ggattaaaac ctcataacgc acaactgaga catcttggat gtgccaaaga tttatcgca  180
gaggatgggc ctgcgtctga ttagttagtt ggtgggtaa cggcctacca aggcgacgat  240
```

```
cagtagccga cctgagaggg tgatcggcca cattggaact gagacacggt ccaaactcct  300
acgggaggca gcagtgggga atattgcaca atgggggaaa ccctgatgca gcaacgccgc  360
gtgaaggatg aaggcccttg ggtcgtaaac ttctgttcta ggggaagata gtgacggtac  420
cttaggagca agtcccggct aactacgtgc cagcagccgc ggtaatacgt agggggcaag  480
cgttatccgg aattattggg cgtaaagagt acgtaggtgg ttacctaagc aaggggttta  540
aggcaatggc ttaactattg ttcgcccctt gaactgggct acttgagtgc aggagaggaa  600
agcggaattc ctagtgtagc ggtgaaatgc gtagatatta ggaggaacac cagtggcgaa  660
ggcggctttc tggactgtaa ctgacactga ggtacgaaag cgtggggagc aaacaggatt  720
agataccctg gtagtccacg ccgtaaacga tgagcactag gtgtcgggtc cgcaagactt  780
cggtgccgca gttaacgcaa taagtgctcc gcctggggag tacgttcgca agaatgaaac  840
tcaaaggaat tgacggggac ccgcacaagc agcggagcat gtggtttaat tcgaagcaac  900
gcgaagaacc ttaccagggc ttgacatctt cctgacagac ccttaaacgg tccttcttc   960
ggacaggaaa gacaggtggt gcatggttgt cgtcagctcg tgtcgtgaga tgttgggtta 1020
agtcccgcaa cgagcgcaac ccttgctgtt agttgccatc attaagttgg gcactcaac  1080
gggactgccg gggataactc ggaggaaggt ggggatgacg tcaaatcatc atgccccta  1140
tgttctgggc tacacacgtg ctacaatggc cggtacaaag aggaagcgag accgcgaggt 1200
ggagcgaatc tcaaaagccg gtcccagttc ggattgcagg ctgcaactcg cctgcatgaa 1260
gtcggagttg ctagtaatcg cgaatcagaa tgtcgcggtg aatgcgttcc cgggtcttgt 1320
acacaccgcc cgtcacacca tggaagttgg gggcgcccga agttggcagg caaatat    1377

SEQ ID NO: 59           moltype = DNA   length = 1373
FEATURE                 Location/Qualifiers
misc_feature            1..1373
                        note = K59
source                  1..1373
                        mol_type = unassigned DNA
                        organism = unidentified
SEQUENCE: 59
cgaggggcag cgcggagagt agcaatactt tggaggcgac cggcgcacgg gtgcgtaacg   60
cgtatgcaac ctacctttaa caggggcata cactgtagaa attggtacta attccccata  120
acattcgaga aggcatcttc ttgggttaaa aactccggtg gttaaagatg gcatgcgtt   180
gtattagcta gttggtgagg taacggctca ccaaggcgac gatacatagg gggactgaga  240
ggttaacccc ccacattggt actgagacac ggaccaaact cctacgggag gcagcagtga  300
ggaatattgg tcaatggacg caagtctgaa ccagccatgc cgcgtgcagg aagacggctc  360
tatgagttgt aaactgcttt tgtactaggg taaacgcttc tacgtgtagg agtctgaaag  420
tatagtacga ataaggatcg gctaactccg tgccagcagc cgcggtaata cggaggatcc  480
aagcgttatc cggatttatt gggtttaaag ggtgcgtagg cggtttgata agttagaggt  540
gaaataccgg ggctcaactc cggaactgcc tctaatactg ttgaactaga gagtagttgc  600
ggtaggcgga atgtatggtg tagcggtgaa atgcttaaga atcatacaga acaccgattg  660
cgaaggcagc ttaccaaact atatctgacg ttgaggcacg aaagcgtggg gagcaaacag  720
gattagatac cctggtagtc cacgcagtaa acgatgataa ctcgttgtcg gcgatacaca  780
gtcggtgact aagcgaaagc gataagttat ccacctgggg agtacgttcg caagaatgaa  840
actcaaagga attgacgggg gcccgcacaa gcggaggaac atgtggttta attcgatgat  900
acgcgaggaa ccttacccgg gcttgaaagt tagtgacgat tctggaaaca ggatttccct  960
tcggggcacg aaactaggtg ctgcatggtt gtcgtcagct cgtgccgtga ggtgtcgggt 1020
taagtcccat aacgagcgca accccctaccg ttagttgcca tcaggtcaag ctgggcactc 1080
tggcgggact gccggtgtaa gccgagagga aggtgggact gacgtcaaat cagcacggcc 1140
cttacgtccg gggctacaca cgtgttacaa tggtaggtac agagggccgc taccccgcga 1200
ggggatgcca atctcgaaag cctatctcag ttcggatcgg aggctgaaac ccgcctccgt 1260
gaagttggat tcgctagtaa tcgcgcatca gccatgcgc ggtgaatacg ttcccggggcc 1320
ttgtacacac cgcccgtcaa gccatggaag ctggggtgc ctgaagttcg tga         1373

SEQ ID NO: 60           moltype = DNA   length = 1384
FEATURE                 Location/Qualifiers
misc_feature            1..1384
                        note = K60
source                  1..1384
                        mol_type = unassigned DNA
                        organism = unidentified
SEQUENCE: 60
gtcgaacgga gctgttttct ctgaagtttt cggatggaag agagttcagc ttagtggcga   60
acgggtgagt aacacgtgag caacctgcct ttcagtgggg gacaacattt ggaaacgaat  120
gctaataccg cataagacca cagtgtcgca tggcacaggg tcaaaggat ttatccgctg   180
aaagatgggc tcgcgtccga ttagctagat ggtgaggtaa cggcccacca tggcgacgat  240
cggtagccgg actgagaggt tgaacggcca cattggact gagacacggc ccagactcct  300
acgggaggca gcagtgggga atattgcaca atgggggaaa ccctgatgca gcgacgccgc  360
gtggaggaag aaggtcttcg gattgtaaac tcctgtccca ggggacgata atgacggtac  420
cctggggagga agcaccggct aactacgtgc cagcagccgc ggtaaaacgt agggtgcaag  480
cgttgtccgg aattactggg tgtaaaggga gcgcaggcgg attggcaagt tgggagtgaa  540
atctatgggc tcaacccata aattgctttc aaaactgtca gtcttgagtg gtgtagaggt  600
aggcggaatt cccggtgtag cggtggaatg cgtagatatc gggaggaaca ccagtggcga  660
aggcggccta ctgggcacta actgacgctg aggctcgaaa gcatgggtag caaacaggat  720
tagataccct ggtagtccat gccgtaaacg atgattacta ggtgtgggag gattgacccc  780
tccgtgccg cacgttaacac aataagtaat ccacctgggg agtacgaccg caaggttgaa  840
actcaaagga attgacgggg gcccgcacaa gcagtggagt atgtggttta attcgaagca  900
acgcgaagaa ccttaccagg tcttgacatc ggatgcatac ctaagagatt agggaagtcc  960
ttcgggacat ccagacaggt ggtgcatggt tgtcgtcagc tcgtgtcgtg agatgttggg 1020
ttaagtcccg caacgagcgc aacccttatc gttagttact acgcaagagg actctagcga 1080
gactgccgtt gacaaaacgg aggaaggtgg ggatgacgtc aaatcatcat gccctttatg 1140
```

```
acctgggcta cacacgtact acaatggcta ttaacagaga gaagcgatac cgcgaggtgg   1200
agcaaacctc acaaaaatag tctcagttcg gatcgcaggc tgcaacccgc ctgcgtgaag   1260
ccggaattgc tagtaatcgc ggatcagcat gccgcggtga atacgttccc gggccttgta   1320
cacaccgccc gtcacaccat gagagccggg gggacccgaa gtcggtagtc taaccgcaag   1380
gagg                                                                1384

SEQ ID NO: 61           moltype = DNA   length = 1394
FEATURE                 Location/Qualifiers
misc_feature            1..1394
                        note = K61
source                  1..1394
                        mol_type = unassigned DNA
                        organism = unidentified
SEQUENCE: 61
agtcgaacga agttgctctt tgtgaagccc tcgggtggaa ctgcgagtat acttagtggc   60
ggacgggtga gtaacgcgtg agcaatctgc cctgcaatgg gggacaacag ttggaaacga   120
ctgctaatac cgcatgagac cacgaaaccg catggttttg aggtaaaagg atttattcga   180
tgcaggatga gctcgcgtcc cattagatag ttggtgaggt aacggcccac caagtcaacg   240
atgggtagcc gacctgagag ggtgatcggc cacactggaa ctgagacacg gtccagactc   300
ctacgggagg cagcagtggg gaatattggg caatggggga aaccctgacc cagcaacgcc   360
gcgtgaggga agaaggtctt cggattgtaa acctttgtcc tatgggacga aacaaatgac   420
ggtaccatag gaggaagctc cggctaacta cgtgccagca gccgcggtaa tacgtaggga   480
gcaagcgttg tccggaatta ctgggcgtaa agggtgcgta ggtggctatg taagtcagat   540
gtgaaagacc gggggcttaac cccggggttg catttgaaac tgtgtggctt gagtacagga   600
gagggaagtg gaattcctag tgtagcggtg aaatgcgtag atattaggag gaacaccagt   660
ggcgaaggcg actttctgga ctgtaactga cactgaagca cgaaagcgtg gggagcaaac   720
aggattagat accctggtag tccacgccgt aaacgatgga tactaggtgt ggggcccgat   780
agggttccgt gccgaagcta acgcattaag tatcccgcct ggggagtacg atcgcaaggt   840
tgaaactcaa aggaattgac gggggcccgc acaagcagcg gagcatgtgg tttaattcga   900
agcaacgcga agaaccttac caaggcttga catcctctga cgactgtaga gatacagtgt   960
cccttcgggg cagagagaca ggtggtgcat ggttgtcgtc agctcgtgtc gtgagatgtt   1020
gggttaagtc ccgcaacgag cgcaacccctt attgctagtt gccagcgcgt aaaggcggga   1080
actctagtga gactgccggg gacaactcgg aggaaggtgg ggacgacgtc aaatcatcat   1140
gccccttatg tcttgggcta cacacgtgct acaatggccg gtacaaaggg cagcgaaccc   1200
gtaaggggaa gcgaatctca aaaagccggt cccagttcgg attgtgggct gcaacccgcc   1260
cacatgaagt cggagttgct agtaatcgcg aatcagcatg tcgcggtgaa tgcgttcccg   1320
ggccttgtac acaccgcccg tcacaccacg gaagttggga gcacccgaag ccagtggctt   1380
aaccgtaagg agag                                                     1394

SEQ ID NO: 62           moltype = DNA   length = 1388
FEATURE                 Location/Qualifiers
misc_feature            1..1388
                        note = K62
source                  1..1388
                        mol_type = unassigned DNA
                        organism = unidentified
SEQUENCE: 62
aacgaagcgc ttccgcctga ttttcttcgg agatgaaggc ggctgcgact gagtggcgga   60
cgggtgagta acgcgtgggc aacctgcctt gcactggggg ataacagcca gaaatggctg   120
ctaataccgc ataagaccga agcgccgcat ggcgctgcgg ccaaagcccc ggcggtgcaa   180
gatgggcccg cgtctgatta ggtagttggc ggggtaacgg cccaccaagc cgacgatcag   240
tagccgacct gagagggtga ccggccacat tgggactgag acacggccca gactcctacg   300
ggaggcagca gtgggaata ttgcacaatg ggggaaaccc tgatgcagcg acgccgcgtg   360
aaggatgaag tatttcggta tgtaaacttc tatcagcagg gaagaagatg acggtacctg   420
actaagaagc cccggctaac tacgtgccag cagccgcggt aatacgtagg ggcaagcgtt   480
tatccggatt tactgggtgt aaagggagcg tagacgcgga tgcaagccag atgtgaaagc   540
ccggggctca accccgggac tgcatttgga actgcgttgg ctggagtgtcg gagaggcagg   600
cggaattcct agtgtagcgg tgaaatgcgt agaatattag gaggaacacc agtggcgaag   660
gcggcctgct ggacgatgac tgacgttgag gctcgaaagc gtggggagca aacaggatta   720
gataccctgg tagtccacgc cgtaaacgat gactactagg tgtgcgggtgg caaggccatt   780
cggtgccgca gcaaacgcaa taagtagtcc acctggggga gtacgttcgc aagaatgaaa   840
ctcaaaggaa ttgacgggga cccgcacaag cggtggagca tgtggtttaa ttcgaagcaa   900
cgcgaagaac cttacctgat cttgacatcc cgatgccaaa gcgcgtaacg cgtctttct   960
tcggaacatc ggtgacaggt ggtgcatggt tgtcgtcagc tcgtgtcgtg agatgttggg   1020
ttaagtcccg caacgagcgc aaccccctatc ttcagtagcc agcattcgg atgggcactc   1080
tggagagact gccaggacac acctggagga aggtggggat gacgtcaaat catcatgccc   1140
cttatgacca gggctacaca cgtgctacaa tggcgtaaac aaagggaggc gaacccgcga   1200
gggtgggcaa atcccaaaaa taacgtctca gttcggattg tagtctgcaa ctcgactaca   1260
tgaagctgga atcgctagta atcgcgaatc agaatgtcgc ggtgaatacg ttcccgggtc   1320
ttgtacacac cgcccgtcac accatgggag tcagtaacgc ccgaagccgg tgacccaacc   1380
cgcaaggg                                                             1388

SEQ ID NO: 63           moltype = DNA   length = 1415
FEATURE                 Location/Qualifiers
misc_feature            1..1415
                        note = K63
source                  1..1415
                        mol_type = unassigned DNA
                        organism = unidentified
```

```
SEQUENCE: 63
agtcgaacgc ttctttcctc ccgagtgctt gcactcaatt ggaaagagga gtggcggacg    60
ggtgagtaac acgtgggtaa cctacccatc agagggggat aacacttgga aacaggtgct   120
aataccgcat aacagtttat gccgcatggc ataagagtga aaggcgcttt cggtgtcgc   180
tgatggatgg acccgcggtg cattagctag ttggtgaggt aacggctcac caaggccacg   240
atgcatagcc gacctgagag ggtgatcggc cacactggga ctgagacacg gcccagactc   300
ctacgggagg cagcagtagg gaatcttcgg caatggacga aagtctgacc gagcaacgcc   360
gcgtgagtga agaaggtttt cggatcgtaa aactctgttg ttagagaaga caaggacgt   420
tagtaactga acgtcccctg acggtatcta accagaaagc cacggctaac tacgtgccaa   480
cagccgcggt aatacgtagg tggcaagcgt tgtccggatt tattgggcgt aaagcgagcg   540
caggcggttt cttaagtctg atgtgaaagc ccccggctca accggggagg gtcattggaa   600
actgggagac ttgagtgcag aagaggagag tggaattcca tgtgtagcgg tgaaatgcgt   660
agatatatgg aggaacacca gtggcgaagg cggctctctg gtctgtaact gacgctgagg   720
ctcgaaagcg tggggagcaa acaggattag ataccctggt agtccacgcc gtaaacgatg   780
agtgctaagt gttggagggt ttccgccctt cagtgctgca gcaaacgcat taagcactcc   840
gcctggggag tacgaccgca aggttgaaac tcaaaggaat tgacggggc ccgcacaagc   900
ggtggagcat gtggtttaat tcgaagcaac gcgaagaacc ttaccaggtc ttgacatcct   960
ttgaccactc tagagataga gctttccctt cgggacaaa gtgacaggtg gtgcatggtt  1020
gtcgtcagct cgtgtcgtga gatgttgggt taagtcccgc aacgagcgca acccttattg  1080
ttagttgcca tcatttagtt gggcactcta gcgagactgc cggtgacaaa ccggaggaag  1140
gtggggatga cgtcaaatca tcatgcccct tatgacctgg gctacacacg tgctacaatg  1200
ggaagtacaa cgagtcgcta gaccgcgagg tcatgcaaat ctcttaaagc ttctctcagt  1260
tcggattgca ggctgcaact cgcctgcatg aagccgaat cgctagtaat cgcggatcag  1320
cacgccgcgg tgaatacgtt cccgggcctt gtacacaccg cccgtcacac cacgagagtt  1380
tgtaacaccc gaagtcggtg aggtaacctt tttgg                             1415

SEQ ID NO: 64               moltype = DNA   length = 1392
FEATURE                     Location/Qualifiers
misc_feature                1..1392
                            note = K64
source                      1..1392
                            mol_type = unassigned DNA
                            organism = unidentified
SEQUENCE: 64
agtcgagcga agcgctaaga caggatttct tcggattgaa gtctttgtga ctgagcggcg    60
gacgggtgag taacgcgtgg gtaacctgcc tcatacaggg ggataacagt tagaaatgac   120
tgctaatacc gcataagcgc acaggaccgc atggtctggt gtgaaaaact ccggtggtat   180
gagatggacc cgcgtctgat tagctagttg gaggggtaac ggcccaccaa ggcgacgatc   240
agtagccggc ctgagagggt gaacgccac atttgggactg agacacggc cagactccta   300
cgggaggcag cagtgggaa tattgcacaa tgggggaaac cctgatgcag cgacgccgcg   360
tgaaggaaga agtatctcgg tatgtaaact tctatcagca gggaagaaaa tgacggtacc   420
tgactaagaa gccccggcta actacgtgcc agcagccgcg gtaatacgta gggggcaagc   480
gttatccgga tttactgggt gtaaagggag cgtagacgga gagcaagtc tgatgtgaaa   540
ggctggggct taaccccagg actgcattgg aaactgttgt tctagagtgc ggagaggta   600
agcggaattc ctagtgtagc ggtgaaatgc gtagatatta ggaggaacac cagtggcgaa   660
ggcggcttac tggacggtaa ctgacgttga ggctcgaaag cgtggggagc aaacaggatt   720
agataccctg gtagtccacg ccgtaaacga tgaatactag gtgtcggggt gcaaagccat   780
tcggtgccgc agcaaacgca ataagtattc cacctgggga gtacgttcgc aagaatgaaa   840
ctcaaaggaa ttgacgggga cccgcacaag cggtggagca tgtggtttaa ttcgaagcaa   900
cgcgaagaac cttaccaagt cttgacatcc tctctgaccgt cccgtaacgg ggcttccct   960
tcggggacaga ggagacaggt ggtgcatggt tgtcgtcagc tcgtgtcgtg agatgttgggt  1020
ttaagtcccg caacgagcgc aacccttatc cttagtagcc agcacatgat ggtgggcact  1080
ctagggagac tgccggggat aaccggagg aaggcgggga cgacgtcaaa tcatcatgcc  1140
ccttatgatt gggctacaca cgtgctacaa tggcgtaaaa caagggaag cgagacagcg  1200
atgttgagcg aatcccaaaa ataacgtccc agttcggact gcagtctgca actcgactgc  1260
acgaagctgg aatcgctagt aatcgcggat cagaatgccg cggtgaatac gttcccgggt  1320
cttgtacaca ccgcccgtca ccatgggagt gtcagtaacg cccgaagtca gtgacctaac  1380
cgaaaggaag ga                                                      1392

SEQ ID NO: 65               moltype = DNA   length = 1388
FEATURE                     Location/Qualifiers
misc_feature                1..1388
                            note = K65
source                      1..1388
                            mol_type = unassigned DNA
                            organism = unidentified
SEQUENCE: 65
aagtcgaggg gcagcggatg gagtgcttcg gtactcctgc cggcgaccgg cggacgggtg    60
cgtaacgcgt atgcaacctg ccttcaacag ggggataatc cgaagaaatt tggtctaata   120
ccccataata ttccgacagg catctgtcgg agttgaaagc ttcggtggtt ggagatgggc   180
atgcgttgta ttagctggat ggtgaggtaa cggctcacca tggcgatgat acataggggg   240
actgagaggt tttcccccca cactggtact gagacacgga ccagactcct acggaggca   300
gcagtgagga atattggtca atggacgaaa gtctgaacca gccatgccgc gtgcaggatg   360
aatgtgctat gcattgtaaa ctgcttttgt acgagggtaa accagatac gctatctga   420
ttgaaagtat cgtacgaata aggatcggct aactccgtgc cagcagccgc ggtaatacgg   480
aggatccgag cgttatccgg atttattggg tttaaagggt gcgtaggctg ttttttaagt   540
tagaggtgaa agctcgacgc tcaacgtcga aattgcctct gatactgaga gactagagtg   600
tagttgcgga aggcggaatg tgtggtgtag cggtgaaatg cttagatatc acacagaaca   660
ccgattgcga aggcagcttt ccaagctatt actgacgctg aggcacgaaa gcgtggggag   720
```

```
cgaacaggat tagataccct ggtagtccac gcagtaaacg atgataactc gttgccggcg   780
atacacagtc ggtgacttag cgaaagcgtt aagttatcca cctggggggag tacgttcgca   840
agaatgaaac tcaaaggaat tgacgggggc ccgcacaagc ggaggaacat gtggtttaat   900
tcgatgatac gcgaggaacc ttacccgggc ttgaaagtta gcgacggatc gagaaatcgg   960
tcttccctac ggggcgcgaa actaggtgct gcatggttgt cgtcagctcg tgccgtgagg  1020
tgtcgggtta agtcccataa cgagcgcaac ccctaccgtt agttgccatc aggtcaagct  1080
gggcactcta gcgggactgc cggtgtaagc cgagaggaag gtgggggatga cgtcaaatca  1140
gcacggccct tacgtccggg gcgacacacg tgttacaatg gccggtacag agggtagcta  1200
cctggtgaca ggatgccaat ctcgaaagcc ggtctcagtt cggattggag gctgaaactc  1260
gcctccatga agttggattc gctagtaatc gcgcatcagc catggcgcgg tgaatacgtt  1320
cccgggcctt gtacacaccg cccgtcaagc catgggagtt ggggggtgcct gaagtacgtg  1380
accgcaag                                                            1388

SEQ ID NO: 66           moltype = DNA  length = 1388
FEATURE                 Location/Qualifiers
misc_feature            1..1388
                        note = K66
source                  1..1388
                        mol_type = unassigned DNA
                        organism = unidentified
SEQUENCE: 66
gtcgaacgga gcacccctga cggagttttc ggacaacgaa agggaatgct tagtggcgga    60
cgggtgagta acgcgtgagt aacctgcctt ggagtgggga ataacagccg gaaacggctg   120
ctaataccgc atgatgtatc tggatcgcat ggttctggat accaaagatt tatcgctctg   180
agatggactc gcgtctgatt agctagttgg tgaggtaatg gctcaccaag gcgacgatca   240
gtagccggac tgagaggttg gccgccaca ttgggactga gacacggccc agactcctac   300
gggaggcagc agtggggaat attgggcaat gggcgaaagc ctgacccagc aacgccgcgt   360
gaaggaagaa ggcccctggg ttgtaaactt cttttgtcag ggacgaagca agtgacggta   420
cctgacgaat aagccacggc taactacgtg ccagcagccg cggtaatacg taggtggcaa   480
gcgttatccg gatttactgg gtgtaaaggg cgtgtaggcg ggtgcaa tcagatgctg   540
aaactatggg ctcaacccat agcctgcatt tgaaactgta cttcttgagt gatggagagg   600
caggcggaat tccctgtgta gcggtgaaat gcgtagatat aggaggaac accagtggcg   660
aaggcggcct gctggacatt aactgacgct gaggcgcgaa agcgtgggga gcaaacagga   720
ttagataccc tggtagtcca cgccgtaaac gatggatact aggtgtgggg ggtctctgaccc   780
cctccgtgcc gcagttaaca caataagtat cccacctggg gagtacgatc gcaaggttga   840
aactcaaagg aattgacggg ggcccgcaca gcggtggag tatgtggttt aattcgaagc   900
aacgcgaaga accttaccag gacttgacat cctactaacg aagcagagat gcataaggtg   960
cccttcgggg aaagtagaga caggtggtgc atggttgtcg tcagctcgtg tcgtgagatg  1020
ttgggttaag tcccgcaacg agcgcaaccc ttattgtta ttgctacgca agagcactct  1080
agcgagactg ccgttgacaa aacgaggaa ggtggggacg acgtcaaatc atcatgcccc  1140
ttatgtcctg ggccacacac gtactacaat ggcggtcaac agagggaagc aaagccgcga  1200
ggtggagcaa atccctaaaa gccgtccag ttcggattgc aggctgaaac tcgcctgtat  1260
gaagtcggaa tcgctagtaa tcgcggatca gcatgccgcg gtgaatacgt tcccgggcct  1320
tgtacacacc gcccgtcaca ccatgagagt cgggaacacc cgaagtccgt agcctaacag  1380
caatgggg                                                            1388

SEQ ID NO: 67           moltype = DNA  length = 1380
FEATURE                 Location/Qualifiers
misc_feature            1..1380
                        note = K67
source                  1..1380
                        mol_type = unassigned DNA
                        organism = unidentified
SEQUENCE: 67
tcgagggca gcatgaactt agcttgctaa gtttgatggc gaccggcgca cgggtgagta    60
acacgtatcc aacctgccga tgactcgggg atagcctttc gaaagaaaga ttaatacccg   120
atggcataat tcttccgcat ggtagaacta ttaaagaatt tcggtcatcg atggggatgc   180
gttccattag gttgttggcg gggtaacggc ccaccaagcc ttcgatggat agggggttctg   240
agaggaaggt cccccacatt ggaactgaga cacggtccaa actcctacgg gaggcagcag   300
tgaggaatat tggtcaatgg acgagagtct gaaccagcca agtagcgtga aggatgactg   360
ccctatgggt tgtaaactc ttttatacgg gaataaagtg aggcacgtgt gccttttttgt   420
atgtaccgta tgaataagga tcggctaact ccgtgccagc agccgcggta atacggagga   480
tccgagcgtt atccggattt attgggttta aagggagcgt aggcggacgc ttaagtcagt   540
tgtgaaagtt tgcggctcaa ccgtaaaatt gcagttgata ctgggtgtct tgagtacagt   600
agaggcaggc ggaattcgtg gtgtagcggt gaaatgctta gatatcacga gaactccga   660
ttgcgaaggc agcttgctgg actgtaactg acgctgatgc tcgaaagtgt gggtatcaaa   720
caggattaga taccctggta gtccacacag taaacgatga atactcgctg tttgcgatat   780
acagtaagcg gccaagcgaa agcgttaagt attccacctg ggaagtacgc cggcaacggt   840
gaaactcaaa ggaattgacg ggggcccgca caagcggagg aacatgtgtt ttaattcgat   900
gatacgcgag gaaccttacc cgggcttgaa ttgcaactga atgatgtgga gacatgtcag   960
ccgcaaggca gttgtgaagg tgctgcatgg ttgtcgtcag ctcgtgccgt gaggtgtcgg  1020
cttaagtgcc ataacgagcg caaccctat cgatagttac catcaggtta tgctgggggac  1080
tctgtcgaga ctgccgtcgt aagatgtgag gaaggtgggg atgacgtcaa atcagcacgg  1140
ccccttacgtc cggggctaca cacgtgttac aatggggggt acagaaggca gctacgtgg  1200
gacgtgatgc taatccctaa agcctctctc agttcggatt ggagtctgca acccgactcc  1260
atgaagctgg attcgctagt aatcgcgcat cagccacggc gcggtgaata cgttcccggg  1320
ccttgtacac accgcccgtc aagccatgaa agccgggggt acctgaagtg cgtaaccgca  1380

SEQ ID NO: 68           moltype = DNA  length = 1370
```

```
FEATURE                 Location/Qualifiers
misc_feature            1..1370
                        note = K68
variation               6
                        note = n is a, c, g, or t
variation               1352
                        note = n is a, c, g, or t
source                  1..1370
                        mol_type = unassigned DNA
                        organism = unidentified
SEQUENCE: 68
agtcgnacga gagaattgct agcttgctaa taattctcta gtggcgcacg ggtgagtaac   60
acgtgagtaa cctgccccca agagtgggat agccccggga aactgggatt aataccgcat  120
aaaatcgcaa gattaaagca gcaatgcgct tggggatggg ctcgcgtcct attagttagt  180
tggtgaggta acggctcacc aaggcgatga cgggtagccg gtctgagagg atgtccggcc  240
acactggaac tgagacacgg tccagacacc tacgggtggc agcagtcgag aatcattcac  300
aatggggaa  accctgatgg tgcgacgccg cgtggggaa  tgaaggtctt cggattgtaa  360
accccctgtca tgtgggagca aattaaaaag atagtaccac aagaggaaga gacggctaac  420
tctgtgccag cagccgcggt aatacagagg tctcaagcgt tgttcggaat cactgggcgt  480
aaagcgtgcg taggcggttt cgtaagtcgt gtgtgaaagg cggggctca acccccggac  540
tgcacatgat actgcgagac tagagtaatg agggggaac cggaattctc ggtgtagcag  600
tgaaatgcgt agatatcgag aggaacactc gtggcgaagg cgggttcctg gacattaact  660
gacgctgagg cacgaaggcc aggggagcga aagggattag ataccccgt agtcctggca  720
gtaaacggtg cacgcttggt gtgcgggaa  tcgacccct gcgtgccgga gctaacgcgt  780
taagcgtgcc gcctggggga gtacggtcgc aagattaaaa ctcaaagaaa ttgacgggga  840
cccgcacaag cggtggagta tgtggcttaa ttcgatgcaa cgcgaagaac cttacctggg  900
cttgacatgt aatgaacaac atgtgaaagc atgcgactct tcggaggcgt tacacaggtg  960
ctgcatggcc gtcgtcagct cgtgtcgtga gatgtttggt taagtccagc aacgagcgca 1020
acccctgttg ccagttacca gcacgtaaag gtggggactc tggcgagact gcccagatca 1080
actgggagga aggtgggac gacgtcaggt cagtatgccc cttatgccca gggctgcaca 1140
cgtactacaa tgcccagtac agaggggggcc gaagccgcga ggcggaggaa atcctaaaaa 1200
ctgggcccag ttcggactgt aggctgcaac ccgcctacac gaagccggaa tcgctagtaa 1260
tggcgcatca gctacggcgc cgtgaatacg ttccgggtc  ttgtacacac cgcccgtcac 1320
atcatggaag ccggtcgcac ccgaagtatc tnaagccaac cgcaaggagg           1370

SEQ ID NO: 69           moltype = DNA  length = 1382
FEATURE                 Location/Qualifiers
misc_feature            1..1382
                        note = F01
source                  1..1382
                        mol_type = unassigned DNA
                        organism = unidentified
SEQUENCE: 69
cagtcgaacg ggatccatca ggcttttgctt ggtggtgaga gtggcgaacg ggtgagtaat   60
gcgtgaccga cctgccccat acaccggaat agctcctgga aacgggtggt aatgccggat  120
gctccagttg atcgcatggt cttctgggaa agctttcgcg gtatgggatg gggtcgcgtc  180
ctatcagctt gacggcgggg taacggccca ccgtggcttc gggcctgaga  240
gggcgaccgg ccacattggg actgagatac ggcccagact cctacgggag gcagcagtgg  300
ggaatattgc acaatgggcg caagcctgat gcagcgacgc cgcgtgaggg atggaggcct  360
tcgggttgta aacctctttt atcggggagc aagcgagagt gagtttaccc gttgaataag  420
caccggctaa ctacgtgcca gcagccgcgg taatacgtag ggtgcaagcg ttatcggaat  480
ttattgggcg taaagggctc gtaggcggtt cgtcgcgtcc ggtgtgaaag tccatcgctt  540
aacggtggat ccgcgccggg tacggcggg  cttgagtgcg gtaggggaga ctggaattcc  600
cggtgtaacg gtgaatgtg  tagatatcgg gaagaacacc aatggcgaag gcaggtctct  660
gggccgttac tgacgctgag gagcgaaagc gtggggagcg aacaggatta gataccctgg  720
tagtccacgc cgtaaacggt ggatgctgga tgtggggccc gttccacggg ttccgtgtcg  780
gagctaacgc gttaagcatc ccgcctgggg agtacggccg caaggctaaa actcaaagaa  840
attgacgggg gcccgcacaa gcggcggagc atgcggatta ttcgatgca  acgcgaagaa  900
ccttacctgg gcttgacatg ttcccgacgg tcgtagagat acggcttccc ttcggggcgg  960
gttcacaggt ggtgcatggt cgtcgtcagc tcgtgtcgtg agatgttggg ttaagtcccg 1020
caacgagcgc aaccctcgcc ccgtgttgcc agcggattat gccggaact cacggggac  1080
cgccggggtt aactcggagg aaggtgggga tgacgtcaga tcatcatgcc cttacgtcc  1140
agggcttcac gcatgctaca atggccggta caacgggatg cgacgcggcg acgcggagcg 1200
gatccctgaa aaccggtctc agttcggatc gcagtctgca actgactgc  gtgaagggcg 1260
agtcgctagt aatcgcgaat cagcaacgtc gcggtgaatg cgttcccggg ccttgtacac 1320
accgcccgtc aagtcatgaa agtgggcagc acccgaagcc ggtggcctaa ccccttgtgg 1380
ga                                                                1382

SEQ ID NO: 70           moltype = DNA  length = 1382
FEATURE                 Location/Qualifiers
misc_feature            1..1382
                        note = F02
source                  1..1382
                        mol_type = unassigned DNA
                        organism = unidentified
SEQUENCE: 70
tcgagggca  gcattttagt ttgcttgcaa actaaagatg gcgaccggcg cacgggtgag   60
taacacgtat ccaacctgcc gataactcgg ggatagcctt cgaaagaaa  gattaatatc  120
cgatagtata ttaaaaccgc atggttttac tattaaagaa tttcggttat cgatggggat  180
```

```
gcgttccatt agtttgttgg cggggtaacg gcccaccaag actacgatgg atagggttc   240
tgagaggaag gtcccccaca ttggaactga gacacggtcc aaactcctac gggaggcagc  300
agtgaggaat attggtcaat ggacgagagt ctgaaccagc caagtagcgt gaaggatgac  360
tgccctatgg gttgtaaact tcttttatat gggaataaag tattccacgt gtgggatttt  420
gtatgtacca tatgaataag gatcggctaa ctccgtgcca gcagccgcgg taatacggag  480
gatccgagcg ttatccggat ttattggtt  taaaggagc gtaggtggat tgttaagtca   540
gttgtgaaag tttgcggctc aaccgtaaaa ttgcagttga aactggcagt cttgagtaca  600
gtagaggtgg gcggaattcg tggtgtagcg gtgaaatgct tagatatcac gaagaactcc  660
gattgcgaag gcagctcact agactgcaac tgacactgat gctcgaaagt gtgggtatca  720
aacaggatta gataccctgg tagtccacac agtaaacgat gaatactcgc tgtttgcgat  780
atacagtaag cggccaagcg aaagcattaa gtattccacc tggggagtac gccggcaacg  840
gtgaaactca aaggaattga cggggcccca cacaagcgga ggaacatgtg gtttaattcg  900
atgatacgcg aggaacctta cccgggctta aattgcattt gaataatctg gaaacaggtt  960
agccgcaagg caaatgtgaa ggtgctgcat ggttgtcgtc agctcgtgcc gtgaggtgtc 1020
ggcttaagtg ccataacgag cgcaaccctt atctttagtt actaacaggt catgctgagg 1080
actctagaga gactgccgtc gtaagatgtg aggaaggtgg ggatgacgtc aaatcagcac 1140
ggcccttacg tccggggcta cacacgtgtt acaatggggg tacagaagg cagctacctg  1200
gcgacaggat gctaatccca aaaacctctc tcagttcgga tcgaagtcgc caacccgact 1260
tcgtgaagct ggattcgcta gtaatcgcgc atcagccatg gcgcggtgaa tacgttcccg 1320
ggccttgtac acaccgcccg tcaagccatg aaagccgggg gtacctgaag tacgtaaccg 1380
ca                                                                1382

SEQ ID NO: 71         moltype = DNA   length = 1386
FEATURE               Location/Qualifiers
misc_feature          1..1386
                      note = F03
source                1..1386
                      mol_type = unassigned DNA
                      organism = unidentified
SEQUENCE: 71
aagtcgaggg gcatcaggaa gaaagcttgc tttctttgct ggcgaccggc gcacgggtga   60
gtaacacgta tccaacctgc cctttactcg gggatagccc ttcgaaagaa agattaatac  120
ccgatggtat aattattccg catggtttga ttattaaagg attccggtaa aggatgggga  180
tgcgttccat taggttgttg gtgaggtaac ggctcaccaa gccttcgatg gatagggtt   240
ctgagaggaa ggtcccccac attggaactg agacacggtc caaactccta cggggaggcag 300
cagtgaggaa tattggtcaa tgggcgatgg cctgaaccag ccaagtagcg tgaaggatga  360
aggctctatg ggtcgtaaac ttcttttata ttagaataaa gtgcagtatg tatactgttt  420
tgtatgtata atatgaataa ggatcggcta actccgtgcc agcagccgcg gtaatacgga  480
ggatccgagc gttatccgga tttattggggt ttaaagggag cgtaggtgga ctggtaagtc 540
agttgtgaaa gtttgcggct caaccgtaaa attgcagttg atactgtcag tcttgagtac  600
agtagaggtg ggcggaattc gtggtgtagc ggtgaaatgc ttagatatca cgaagaactc  660
cgattgcgaa ggcagctcac tggactgcaa ctgacactga tgctcgaaag tgtgggtatc  720
aaacaggatt agataccctg gtagtccaca cagtaaacga tgaatactcg ctgtttgcga  780
tatacagtaa gcggccaagc gaaagcatta gtattccac ctggggagta cgccggcaac   840
ggtgaaactc aaaggaattg acggggcccc gcacaagcgg aggaacatgt ggtttaattc  900
gatgatacgc gaggaacctt acccgggctt aaattgcagt ggatgatgt ggaaacatgt   960
cagtgagcaa tcaccgctgt gaaggtgctg catggttgtc gtcagctcgt gccgtgaggt 1020
gtcggcttaa gtgccataac gagcgcaacc cttatctta gttactaaca ggtcatgctg  1080
aggactctag agagactgcc gtcgtaagat gtgaggaagg tggggatgac gtcaaatcag 1140
cacggccctt acgtccgggg ctacacacgt gttacaatgg ggtacagaa ggcagctac   1200
ctgtgacag gatgctaatc ccaaaaagcc tctcagttc ggatcgaagt ctgcaaccgc   1260
acttcgtgaa gctggattcg ctagtaatcg cgcatcagcc acggcgcggt gaatacgttc 1320
ccgggccttg tacacaccgc ccgtcaagcc atgggagccg ggggtacctg aagtacgtaa 1380
ccgcaa                                                            1386

SEQ ID NO: 72         moltype = DNA   length = 1380
FEATURE               Location/Qualifiers
misc_feature          1..1380
                      note = F04
source                1..1380
                      mol_type = unassigned DNA
                      organism = unidentified
SEQUENCE: 72
tcgaggggca gcatgaactt agcttgctaa gtttgatggc gaccggcgca cgggtgagta   60
acacgtatcc aacctgccga tgactcgggg atagcctttc gaaagaaaga ttaatacccg  120
atggcataat tcttccgcat ggtagaatta ttaaagaatt tcggtcatcg atggggatgc  180
gttccattag gttgttggcg gggtaacggc ccaccaagcc ttcgatggat aggggttctg  240
agaggaaggt cccccacatt ggaactgaga cacggtccaa actcctacgg gaggcagcag  300
tgaggaatat tggtcaatgg acgagagtct gaaccagcca agtagcgtga aggatgactg  360
ccctatgggt tgtaaacttc ttttatacgg gaataaagtg aggcacgtgt gccttttgt   420
atgtaccgta tgaataagga tcggctaact ccgtgccagc agccgcgta atacgggaga  480
tccgagcgtt atccggattt attggttta  aaggagcgt aggcggacgc ttaagtcagt   540
tgtgaaagtt tgcggctcaa ccgtaaaatt gcagttgata ctgggtgtct tgagtacagt  600
agaggtggaa ttcgtg gtgtagcggt gaaatgctta gatatcacga agaactcgt      660
tgcgaaggc agcttgctgg actgtaactg acgctgatgc tcgaaagtgt gggtatcaaa   720
caggattaga taccctggta gtccacacag taaacgatga atactcgctg tttgcgatat  780
acagtaagcg gccaagcgaa agcgttaagt attccacctg gggagtacgc ggcaacggt   840
gaaactcaaa ggaattgacg ggggcccgca agcggagg aacatgtggt ttaattcgat   900
gatacgcgag gaaccttacc cgggcttgaa ttgcaactga atgatgtgga gacatgtcag  960
```

```
ccgcaaggca gttgtgaagg tgctgcatgg ttgtcgtcag ctcgtgccgt gaggtgtcgg   1020
cttaagtgcc ataacgagcg caacccttat cgatagttac catcaggtta tgctggggac   1080
tctgtcgaga ctgccgtcgt aagatgtgag gaaggtgggg atgacgtcaa atcagcacgg   1140
cccttacgtc cggggctaca cacgtgttac aatgggggt acagaaggca gctacacggc    1200
gacgtgatgc taatcccgaa agcctctctc agttcggatt ggagtctgca acccgactcg   1260
atgaagctgg attcgctagt aatcgcgcat cagccacggc gcggtgaata cgttcccggg   1320
ccttgtacac accgcccgtc aagccatgaa agcgggggt acctgaagtg cgtaaccgca    1380

SEQ ID NO: 73            moltype = DNA   length = 1384
FEATURE                  Location/Qualifiers
misc_feature             1..1384
                         note = F05
source                   1..1384
                         mol_type = unassigned DNA
                         organism = unidentified
SEQUENCE: 73
agtcgagggg cagcatttca gtttgcttgc aaactggaga tggcgaccgg cgcacgggtg   60
agtaacacgt atccaacctg ccgataactc ggggatagcc tttcgaaaga aagattaata   120
cccgatggta taatcagacc gcatggtctt gttattaaag aatttcggtt atcgatgggg   180
atgcgttcca ttaggcagtt ggtgaggtaa cggctcacca aaccttcgat ggataggggt   240
tctgagagga aggtccccca cattggaact gagacacggt ccaaactcct acgggaggca   300
gcagtgagta atattggtca atgggcgcag gcctgaacca gccaagtagc gtgaaggatg   360
actgccctat gggttgtaaa cttctttttat atgggaataa agttttccac gtgtggaatt   420
ttgtatgtac catatgaata aggatcggct aactccgtgc cagcagccgc ggtaatacgg   480
aggatccgag cgttatccgg atttattggg tttaaaggga gcgtaggtgg acagttaagt   540
cagttgtgaa agtttgcggc tcaaccgtaa aattgcagt gatactggct gtcttgagta    600
cagtagaggt gggcggaatt cgtggtgtag cggtgaaatg cttagatatc acgaagaact   660
ccgattgcga aggcagctca ctggactgca actgacactg atgctcgaaa gtgtgggtat   720
caaacaggat tagataccct ggtagtccac acagtaaacg atgaatactc gctgtttgcg   780
atatacagta agcggccaag cgaaagcatt aagtattcca cctggggagt acgccggcaa   840
cggtgaaact caaaggaatt gacggggggc cgcacaagcg gaggaacatg tggtttaatt   900
cgatgatacg cgaggaacct tacccgggct taaattgcat ttgaatatat tggaaacagt   960
atagccgtaa ggcaaatgtg aaggtgctgc atggttgtcg tcagctcgtg ccgtgaggtg   1020
tcggcttaag tgccataacg agcgcaaccc ttatcttttag ttataacag gtcatgctga   1080
ggactctaga gagactgccg tcgtaagatg tgaggaaggt ggggatgacg tcaaatcagc   1140
acggccctta cgtccggggc tacacacgtg ttacaatggg gggtacagaa ggcagctacc   1200
tggtgacagg atgctaatcc caaaagcctc tctcagttcg gatcgaagtc tgcaacccga   1260
cttcgtgaag ctggattcgc tagtaatcgc gcatcagcca tggcgcggtg aatacgttcc   1320
cgggccttgt acacaccgcc cgtcaagcca tgaaagccgg ggtacctga agtacgtaac    1380
cgca                                                                1384

SEQ ID NO: 74            moltype = DNA   length = 1383
FEATURE                  Location/Qualifiers
misc_feature             1..1383
                         note = F06
source                   1..1383
                         mol_type = unassigned DNA
                         organism = unidentified
SEQUENCE: 74
agtcgagggg cagcatgaac ttagcttgct aagtttgatg gcgaccggcg cacgggtgag   60
taacacgtat ccaacctgcc gatgactcgg ggatagcctt tcgaaagaaa gattaatacc   120
cgatggcata attcttccgc atggtagaat tattaaagaa tttcggtcat cgatggggat   180
gcgttccatt aggttgttgg cggggtaacg gcccaccaag ccttcgatgg ataggggttc   240
tgagaggaag gtcccccaca ttggaactga gacacggtcc aaactcctac gggaggcagc   300
agtgaggaat attggtcaat ggacgagagt ctgaaccagc caagtagcgt gaaggatgac   360
tgccctatgg gttgtaaact tcttttatac gggaataaag tgaggcacgt gtgcctttt    420
gtatgtaccg tatgaataag gatcggctaa ctccgtgcca gcagccgcgg taatacggag   480
gatccgagcg ttatccggat ttattgggtt taaagggagc gtaggcggac gcttaagtca   540
gttgtgaaag tttgcggctc aaccgtaaaa ttgcagttga tactgggtgt cttgagtaca   600
gtagaggcag gcggaattcg tggtgtagcg gtgaaatgct tagatatcac gaagaactcc   660
gattgcgaag gcagcttgct ggactgtaac tgacgctgat gctcgaaagt gtgggtatca   720
aacaggatta gataccctgg tagtccacac agtaaacgat gaatactcgc tgtttgcgat   780
atacagtaag cggccaagcg aaagcgtaa gtattccacc tggggagtac gccggcaacg   840
gtgaaactca aaggaattga cggggccccg cacaagcgga ggaacatgt gtttaattcg    900
atgatacgcg aggaacctta cccgggcttg aattgcaact gaatgatgtg agacatgtc    960
agccgcaagg cagttgtgaa ggtgctgcat ggttgtcgtc agctcgtgcc gtgaggtgtc   1020
ggcttaagtg ccataacgag cgcaaccctt atcgatagtt accatcaggt tatgctgggg   1080
actctgtcga gactgccgtc gtaagatgtg aggaaggtgg ggatgacgtc aaatcagcac   1140
ggcccttacg tccggggcta cacacgtgtt acaatgggg tacagaaggc agctacacgg    1200
gcgacgtgat gctaatcccg aaagcctctc tcagttcgga ttggagtctg caacccgact   1260
ccatgaagct ggattcgcta gtaatcgcgc atcagccacg gcgcggtgaa tacgttcccg   1320
ggccttgtac acaccgcccg tcaagccatg aaagccgggg tacctgaag tgcgtaaccg    1380
caa                                                                 1383

SEQ ID NO: 75            moltype = DNA   length = 1382
FEATURE                  Location/Qualifiers
misc_feature             1..1382
                         note = F07
source                   1..1382
```

```
                          mol_type = unassigned DNA
                          organism = unidentified
SEQUENCE: 75
cgaggggcag catttcagtt tgcttgcaaa ctggagatgg cgaccggcgc acgggtgagt    60
aacacgtatc caacctgccg ataactcggg gatagccttt cgaaagaaag attaatatcc   120
gatggtatat ttctcccgca tgagagagat attaaagaat ttcgttatc gatggggatg    180
cgttccatta gtttgttggc ggggtaacgg cccaccaaga ctacgatgga tagggggttct  240
gagaggaagg tcccccacat tggaactgag acacggtcca aactcctacg ggaggcagca   300
gtgaggaata ttggtcaatg gacgagagtc tgaaccagcc aagtagcctg aaggatgact   360
gccctatggg ttgtaaactt cttttatatg ggaataaaat gttccacgtg tgggattttg   420
tatgtaccat atgaataagg atcggctaac tccgtgccag cagccgcggt aatacgaggc   480
atccgagcgt tatccggatt tattgggttt aaagggagcg taggtggatt gttaagtcag   540
ttgtgaaagt ttgcggctca accgtaaaat tgcagttgaa actggcagtc ttgagtacag   600
tagaggtggg cggaattcgt ggtgtagcgg tgaaatgctt agatatcacg aagaactccg   660
attgcgaagg cagctcacta gactggtcac tgacactgag gctcgaaagt gtgggtatca   720
aacaggatta gataccctgg tagtccacac agtaaacgat gaatactcgc tgtttgcgat   780
atacagcaag cggccaagcg aaagcattaa gtattccacc tggggagtac gccggcaacg   840
tgaaactcaa aaggaattga cggggggccc cacaagcgga gaacatgtgg tttaattcg   900
atgatacgcg aggaacctta cccgggctta aattgcattt gaatatagtg gaaacattat   960
agccgcaagg caaatgtgaa ggtgctgcat ggttgtcgtc agctcgtgcc gtgaggtgtc  1020
ggcttaagtg ccataacgag cgcaacccctt atcttcagtt actaacaggt catgctgagg  1080
actctggaga gactgccgtc gtaagatgtg aggaaggtg ggatgacgtc aaatcagcac   1140
ggcccttacg tccggggcta cacacgtgtt acaatggggg gtacagaagg ccgctacctg  1200
gtgacaggat gccaatccca aaaacctctc tcagttcgga tcgaagtctg caacccgact  1260
tcgtgaagct ggattcgcta gtaatcgcgc atcagccatg gcgcggtgaa tacgttcccg  1320
ggccttgtac acaccgcccg tcaagccatg aaagccgggg gtacctgaag tacgtaaccg  1380
ca                                                                 1382

SEQ ID NO: 76             moltype = DNA   length = 1386
FEATURE                   Location/Qualifiers
misc_feature              1..1386
                          note = F08
source                    1..1386
                          mol_type = unassigned DNA
                          organism = unidentified
SEQUENCE: 76
gtcgaggggc atcaggaaga aagcttgctt tctttgctgg cgaccggcgc acgggtgagt    60
aacacgtatc caacctgccc tttactcggg gatagccttt cgaaagaaag attaataccc   120
gatggtataa ttattccgca tggtttgatt attaaagat tccggtaaag gatgggatg     180
cgttccatta ggttgttggt gaggtaacgg ctcaccaagc cttcgatgga tagggggttct  240
gagaggaagg tcccccacat tggaactgag acacggtcca aactcctacg ggaggcagca   300
gtgaggaata ttggtcaatg ggcgatggcc tgaaccagcc aagtagcgtg aaggatgaag   360
gctctatggg tcgtaaactt cttttatatt agaataagc cagtatgta tactgtttg     420
tatgtataat atgaataagg atcggctaac tccgtgccag cagccgcggt aatacgagc    480
atccgagcgt tatccggatt tattgggttt aagggagcg taggtggact ggtaagtcag    540
ttgtgaaagt ttgcggctca accgtaaaat tgcagttgat actgtcagtc ttgagtacag   600
tagaggtggg cggaattcgt ggtgtagcgg tgaaatgctt agatatcacg aagaactccg   660
attgcgaagg cagctcactg gactgcaact gacactgatg ctcgaaagt tgggtatcaa    720
acaggattag ataccctggt agtccacaca gtaaacgatg aatactgct gtttgcgata    780
tacagtaagc ggcaagcga aagcattaag tattccacct ggggagtacg ccggcaacg     840
tgaaactcaa aggaattgac gggggccgc acaagcggga ggacatgtgg tttaattgca    900
tgatacgcga ggaacccttac ccgggcttaa attgcagtgg aatgatgtgg aaacatgtca   960
gtgagcaatc accgctgtga aggtgctgca tggttgtcgt cagctcgtgc cgtgaggtgt   1020
cggcttaagt gccataacga cgcaaccct tatctttagt tactaacagg tcatgctgag    1080
gactctagag agactgccgt cgtaagatgt gaggaaggtg gggatgacgt caaatcagca   1140
cggcccttac gtccggggct acacacgtgt tacaatgggg gtacagaag cagctacct    1200
ggtgacagga tgctaatccc aaaagcctct ctcagttcgg atcgaagtct gcaacccgac   1260
ttcgtgaagc tggattcgct agtaatcgcg catcagccac ggcgcggtga atacgttccc   1320
gggccttgta cacaccgccc gtcaagccat gggagcgggg gtacctgaa gtacgtaacc    1380
gcaagg                                                             1386

SEQ ID NO: 77             moltype = DNA   length = 1384
FEATURE                   Location/Qualifiers
misc_feature              1..1384
                          note = F09
source                    1..1384
                          mol_type = unassigned DNA
                          organism = unidentified
SEQUENCE: 77
gtcgagggggc agcacgatgt agcaatacat tggtggcgac cggcgcacgg gtgagtaacg    60
cgtatgcaac ctacctatca gaggggaata acccggcgaa agtcggacta ataccgcata   120
aaacagggt tccacatgga aatatttgtt aaagaattat cgctgataga tgggcatgcg   180
ttccattaga tagttggtga ggtaacggct caccaagtcc acgatggata ggggttctga   240
gaggaagtc ccccacactg gtactgagac acggaccaga ctcctacggg aggcagcagt   300
gaggaatatt ggtcaatggg cgagagcctg aaccagccaa gtcgcgtgaa ggatgaagga   360
tctatggttt gtaaacttct tttatatggg aataaagtga gaacgtgttc cttttgta    420
tgtaccatat gaataagcat cggctaactc cgtgccagca gccgcggtaa tacgaggat    480
gcgagcgtta tccggattta ttgggttaa agggtgcgta ggtggttaat taagtcagcg    540
gtgaaagttt gtggctcaac cataaaattg ccgttgaaac tggttgactt gagtatattt   600
```

```
gaggtaggcg gaatgcgtgg tgtagcggtg aaatgcatag atatcacgca gaactccgat    660
tgcgaaggca gcttactaaa ctataactga cactgaagca cgaaagcgtg gggatcaaac    720
aggattagat accctggtag tccacgcagt aaacgatgat tactagctgt ttgcgataca    780
cagtaagcgc cacagcgaaa gcgttaagta atccacctgg ggagtacgcc ggcaacggtg    840
aaactcaaag gaattgacgg gggcccgcac aagcggagga acatgtggtt taattcgatg    900
atacgcgagg aaccttaccc gggtttgaac gcattcggac cggagtggaa acacttcttc    960
tagcaatagc cgtttgcgag gtgctgcatg gttgtcgtca gctcgtgccg tgaggtgtcg   1020
gcttaagtgc cataacgagc gcaaccctta tcactagtta ctaacaggtc atgctgagga   1080
ctctagtgag actgccagcg taagctgtga ggaaggtggg gatgacgtca aatcagcacg   1140
gcccttacat ccggggcgac acacgtgtta caatggtggg gacaaagggc agctaccgtg   1200
tgagcggatg ctaatctcca aaccccatct cagttcggat cgaagtctgc aacccgactt   1260
cgtgaagctg gattcgctag taatcgcgca tcagccatgg cgcggtgaat acgttcccgg   1320
gccttgtaca caccgcccgt caagccatgg gagttggggg tacctaaagt ccgtaaccgc   1380
aagg                                                                1384

SEQ ID NO: 78          moltype = DNA  length = 1387
FEATURE                Location/Qualifiers
misc_feature           1..1387
                       note = F10
source                 1..1387
                       mol_type = unassigned DNA
                       organism = unidentified
SEQUENCE: 78
gtcgagcgaa gcaccttgac ggatttcttc ggattgaagc cttggtgact gagcggcgga     60
cgggtgagta acgcgtgggt aacctgcctc atacaggggg ataacagttg gaaacggctg    120
ctaataccgc ataagcgcac agtaccgcat ggtacggtgt gaaaaactcc ggtggtatga    180
gatggacccg cgtctgatta ggtagttggt ggggtaacgg cctaccaagc cgacgatcag    240
tagccgacct gagagggtga ccggccacat tgggactgag acacgcccca aactcctacg    300
ggaggcagca gtggggaata ttgcacaatg ggggaaaccc tgatgcagcg acgccgcgtg    360
agcgatgaag tatttcggta tgtaaagctc tatcagcagg gaagaaaatg acggtacctg    420
actaagaagc cccggctaac tacgtgccaa cagccgcggt aatacgtagg gggcaagcgt    480
tatccggatt tactggtgtg aaagggagcg tagacggcat ggcaagccag atgtgaaagc    540
ccggggctca accccgggac tgcatttgga actgtcaggc tagagtgtcg gagaggaaag    600
cggaattcct agtgtagcgg tgaaatgcgt agatattagg aggaacacca gtggcgaagg    660
cggcttttctg gacgatgact gacgttgagg ctcgaaagcg tggggagcaa caggattag    720
ataccctggt agtccacgcc gtaaacgatg aatactaggt gtcgggtggc aaagccattc    780
ggtgccgcag caaacgcaat aagtattcca cctggggagt acgttcgcaa gaatgaaact    840
caaaggaatt gacggggacc cgcacaagcg gtggagcatg tggtttaatt cgaagcaacg    900
cgaagaacct tacctggtct tgacatccct ctgaccgctc tttaatcgga gctttccttc    960
gggacagagg agacaggtgg tgcatggttg tcgtcagctc gtgtcgtgag atgttgggtt   1020
aagtcccgca acgagcgcaa ccccatcttt tagtagccag catttggatg ggcactcta   1080
gagagactgc cagggataac ctggaggaag gtggggatga cgtcaaatca tcatgcccct   1140
tatgaccagg gctacacacg tgctacaatg gcgtaaacaa ggaagcgaga cccgcgagg   1200
gggagcaaat cccaaaaata acgtctcagt tcggattgta gtctgcaact cgactacatg   1260
aagctggaat cgctagtaat cgcgaatcag aatgtcgcgg tgaatacgtt cccgggtctt   1320
gtacacaccg cccgtcacac catgggagtc agtaacgccc gaagtcagtg acccaaccgc   1380
aaggagg                                                             1387

SEQ ID NO: 79          moltype = DNA  length = 1392
FEATURE                Location/Qualifiers
misc_feature           1..1392
                       note = F11
source                 1..1392
                       mol_type = unassigned DNA
                       organism = unidentified
SEQUENCE: 79
cagtcgaacg ggaatcactt cattgagact tcggtggatt tgatttagat tctagtggcg     60
gacgggtgag taacgcgtgg gtaacctgcc ttatacaggg gataacagt cagaaatgac    120
tgctaatacc gcataagcgc acaggaccgc atggtccggt gtgaaaaact ccggtggtat    180
aagatggacc cgcgttggat tagcttgttg gtggggtaaa ggcccaccaa ggcgacgatc    240
catagccggc ctgagagggt gaacggccac attgggactg agacacggcc cagactccta    300
cgggaggcag cagtggggaa tattgcacaa tgggggaaac cctgatgcag cgacgccgcg    360
tgaaggaaga agtatctcgg tatgtaaact tctatcagca gggaagatag tgacggtacc    420
tgactaagaa gccccggcta actacgtgcc agcagccgcg gtaatacgta ggggcaagc    480
gttatccgga tttactgggt gtaaagggag cgtagacggt gtggcaagtc tgatgtgaaa    540
ggcatgggct caacctgtgg actgcattgg aaactgtcat acttgagtgc ggagggta    600
agcggaattc tagtgtagc ggtgaaatgc gtagatatta ggaggaacac cagtggcgaa    660
ggcggcttac tggacggtaa ctgacgttga ggctcgaaag cgtgggagc aaacaggatt    720
agataccctg gtagtccacg ccgtaaacga tgaatactag gtgtcggggg catggccat    780
tcggtgccgt cgcaaacgca gtaagtattc cacctgggga gtacgttcgc aagaatgaaa    840
ctcaaaggaa ttgacgggga cccgcacaag cggtggagca tgtggtttaa ttcgaagcaa    900
cgcgaagaac cttaccaagt cttgacatcc tctgaccga ctcttaaccg agtctttcct    960
tcgggacaga ggagacaggt ggtgcatggt tgtcgtcagc tcgtgtcgtg agatgttggg   1020
ttaagtcccg caacgagcgc aaccccctatc tcagtagcgc agcaagttaa gttgggcact   1080
ctgtggagac tgccagggat aacctggagg aaggcgggga tgacgtcaaa tcatcatgcc   1140
ccttatgatt gggctacac acgtgctaca atggcgtaaa caagggaag cgagattgtg   1200
agatggagca atcccaaaaa taacgtccc agttcggact gtagtctgca acccgactac   1260
acgaagctgg aatcgctagt aatcgcggat cagaatgccg cggtgaatac gttcccgggt   1320
cttgtacaca ccgcccgtca caccatggga gtcagtaacg cccgaagtca gtgacctaac   1380
```
tgcaaagaag ga                                                                1392

SEQ ID NO: 80           moltype = DNA   length = 1388
FEATURE                 Location/Qualifiers
misc_feature            1..1388
                        note = F12
source                  1..1388
                        mol_type = unassigned DNA
                        organism = unidentified
SEQUENCE: 80
gtcgaacgaa gcacttgaat ggaattcttc ggaaggaagc tcaagtgact gagtggcgga    60
cgggtgagta acgcgtgggt aacctgcctc atacagggggg ataacagtta gaaatgactg   120
ctaataccgc ataagcacac gtgatcgcat gatcgagtgt gaaaaactcc ggtggtatga   180
gatggaccccg cgtctgatta gctagttggt ggggtaatgg cccaccaagg cgacgatcag   240
tagccggcct gagagggtga acggccacat tgggactgag acacggccca aactcctacg   300
ggaggcagca gtggggaata ttgcacaatg ggggaaaccc tgatgcagcg acgccgcgtg   360
aaggatgaag tatttcggta tgtaaacttc tatcagcagg aagaaaatg acggtacctg    420
actaagaagc cccggctaac tacgtgccag cagccgcggt aatacgtagg gggcaagcgt   480
tatccggatt tactgggtgt aaagggagcg tagacggcag tgcaagtctg aagtgaaagc   540
ccggggctca accccgggac tgctttggaa actgtgcagc tagagtgtcg gagaggcaag   600
cggaattcct agtgtagcgg tgaaatgcgt agatattagg aggaacacca gtggcgaagg   660
cggcttgctg gacgatgact gacgttgagg ctcgaaagcg tggggagcaa acaggattag   720
ataccctggt agtccacgcc gtaaacgatg actactaggt gtcggggagc aaagctcttc   780
ggtgccgcag ccaacgcaat aagtagtcca cctggggagt acgttcgcaa gaatgaaact   840
caaaggaatt gacggggacc cgcacaagcg gtggagcatg tggtttaatt cgaagcaacg   900
cgaagaacct tacctgctct tgacatccct ctgaccgctc tttaatcgga gctttccttc   960
gggacagagg agacaggtgg tgcatggttg tcgtcagctc gtgtcgtgag atgttgggtt  1020
aagtcccgca acgagcgcaa cccctatctt cagtagccag cggcaaggcc gggcactctg  1080
gagagactgc cagggataac ctggaggaag gtggggatga cgtcaaatca tcatgcccct  1140
tatgagcagg gctacacacg tgctacaatg gcgtaaacaa agggaagcga agtcgtgagg  1200
ccgagcaaat cccaaaaata acgtctcagt tcggattgta gtctgcaact cgactacatg  1260
aagctggaat cgctagtaat cgcgaatcag aatgtcgcgg tgaatacgtt cccgggtctt  1320
gtacacaccg cccgtcacac catgggagtc agtaacgccc gaagtcagtg acccaaccgc  1380
aaggaggg                                                            1388

SEQ ID NO: 81           moltype = DNA   length = 1380
FEATURE                 Location/Qualifiers
misc_feature            1..1380
                        note = F13
source                  1..1380
                        mol_type = unassigned DNA
                        organism = unidentified
SEQUENCE: 81
gagcgaagcg gtctggagga agttttcgga tggaatccgg attgactgag cggcggacgg    60
gtgagtaacg cgtgggtaac ctgcctcata caggggggata acagttagaa atggctgcta   120
ataccgcata agcgcacagc ttcgcatgga gcagtgtgaa aaactccggt ggtatgagat   180
ggaccgcgt ctgattagct ggttggtaag gtaacgcgtt accaaggcga cgatcagtag   240
ccgacctgag agggtgaccg gccacattgg gactgagaca cggcccaaac tcctacggga   300
ggcagcagtg ggaatattg cacaatgggg gaaaccctga tgcagcgacg ccgcgtgagt   360
gaagaagtat ttcggtatgt aaagctctat cagcagggaa gaaaatgacg gtacctgact   420
aagaagcccc ggctaactac gtgccagcag ccgcggtaat acgtaggggg caagcgttac   480
ccggatttac tgggtgtaaa gggagcgtag acggcatagc aagtctggag tgaaagcccg   540
gggctcaacc ccgtactgc tttgaaaact gttaagctag agtgctggag aggtaagtgg   600
aattcctagt gtagcggtga aatgcgtaga tattaggagg aacaccagtg gcgaaggcgg   660
cttactggac agtaactgac gttgaggctc gaaagcgtgg ggagcaaaca ggattagata   720
ccctggtagt ccacgccgta aacgatgaat actaggtgtt ggtgggcaaa gcccatcggt   780
gccgccgcaa acgcaataag tattccacct ggggagtacg ttcgcaagaa tgaaactcaa   840
aggaattgac ggggaccccgc acaagcggtg gagcatgtgg tttaattcga agcaacgcga   900
agaaccttac caagtcttga catcggaatg accgggagtg aatgttccct tctctacgga   960
gcattctaga caggtggtgc atggttgtcg tcagctcgtg tcgtgagatg ttgggttaag  1020
tcccgcaacg agcgcaaccc ttatccttag tagccagcag taagatgggc actctaggga  1080
gactgccagg gataacctgg aggaaggtgg ggatgacgtc aaatcatcat gcccttatg   1140
atttgggcta cacacgtgct acaatggcgt aaacaaagag gcgagcct gcgaggggga   1200
gcgaatctca aaaataacgt cccagttcgg actgtagtct gcaaccgac tacacgaagc   1260
tggaatcgct agtaatcgcg aatcagaatg tcgcggtgaa tacgttcccg ggtcttgtac  1320
acaccgcccg tcacaccatg ggagtcagca acgcccgaag tcagtgactc aaccgaaagg  1380

SEQ ID NO: 82           moltype = DNA   length = 1388
FEATURE                 Location/Qualifiers
misc_feature            1..1388
                        note = F14
source                  1..1388
                        mol_type = unassigned DNA
                        organism = unidentified
SEQUENCE: 82
agtcgaacga agcgcttaaa cggatttctt cggattgaag tttttgtgac tgagtggcgg    60
acgggtgagt aacgcgtggg taacctgcct catacagggg gataacagtt agaaatgact   120
gctaataccg cataagcgca cagtgctgca tggcacagtg tgaaaaactc cggtggtatg   180
agatggaccc gcgtctgatt agctagttgg tggggtaacg gcctaccaag gcgacgatca   240

```
gtagccggcc tgagagggtg aacggccaca ttgggactga gacacggccc aaactcctac   300
gggaggcagc agtggggaat attgcacaat gggggaaacc ctgatgcagc gacgccgcgt   360
gagcgaagaa gtatttcggt atgtaaagct ctatcagcag ggaagaaaat gacggtacct   420
gactaagaag caccggctaa atacgtgcca gcagccgcgg taatacgtat ggtgcaagcg   480
ttatccggat ttactgggtg taaagggagc gtagacggtt gtgtaagtct gatgtgaaag   540
cccggggctc aaccccggga ctgcattgga aactatgtaa ctagagtgtc ggagaggtaa   600
gcggaattcc tagtgtagcg gtgaaatgcg tagatattag gaggaacacc agtggcgaag   660
gcggcttact ggacgatcac tgacgttgag gctcgaaagc gtggggagca aacaggatta   720
gataccctgg tagtccacgc cgtaaacgat gactactgag tgtcggggag caaagctctt   780
cggtgccgca gcaaacgcaa taagtagtcc acctggggag tacgttcgca agaatgaaac   840
tcaaaggaat tgacggggac ccgcacaagc ggtggagcat gtggtttaat tcgaagcaac   900
gcgaagaacc ttacctggtc ttgacatccc ggtgaccggc aagtaatgtt gcctttcctt   960
cgggacaccg tgacaggtg gtgcatggtt gtcgtcagct cgtgtcgtga gatgttgggt  1020
taagtcccgc aacgagcgca accccctatct tcagtagcca gcatttaagg tgggcactct  1080
ggagagactg ccaggaataa cctggaggaa ggtggggatg acgtcaaatc atcatgcccc  1140
ttatgaccag ggctacacac gtgctacaat ggcgtaaaca aagggaagcg aacctgtgag  1200
gggaagcaaa tctcaaaaat aacgtctcag ttcggattgt agtctgcaac tcgactacat  1260
gaagctggaa tcgctagtaa tcgcgaatca gcatgtcgcg gtgaatacgt tcccgggtct  1320
tgtacacacc gcccgtcaca ccatgggagt cagtaacgcc cgaagtcagt gacccaaccg  1380
taaggagg                                                          1388

SEQ ID NO: 83         moltype = DNA  length = 1391
FEATURE               Location/Qualifiers
misc_feature          1..1391
                      note = F15
source                1..1391
                      mol_type = unassigned DNA
                      organism = unidentified
SEQUENCE: 83
cagtcgagcg aagcaccttg acggatttct tcggattgaa gccttggtga ctgagcggcg    60
gacgggtgag taacgcgtgg gtaacctgcc tcatacaggg ggataacagt tggaaacggc   120
tgctaatacc gcataagcgc acagtaccgc atggtacggt gtgaaaaact ccggtggtat   180
gagatggacc cgcgtctgat taggtagttg gtggggtaac ggcctaccaa gccgacgatc   240
agtagccgac ctgagagggt gaccggccac attgggactg agacacggcc caaactccta   300
cgggaggcag cagtggggaa tattgcacaa tgggggaaac cctgatgcag cgacgccgcg   360
tgagcgatga agtatttcgg tatgtaaagc tctatcagca gggaagaaaa tgacggtacc   420
tgactaagaa gccccggcta actacgtgcc agcagccgcg gtaatacgta gggggcaagc   480
gttatccgga tttactgggt gtaaagggag cgtagacggc atggcaagcc agatgtgaaa   540
gcccggggct caaccccggg actgcatttg gaactgctag tagtgtcgga gaggaagaa   600
agcggaattc ctagtgtagc ggtgaaatgc gtagatatta ggaggaacac cagtggcgaa   660
ggcggctttc tggacgatga ctgacgttga ggctcgaaag cgtggggagc aaacaggatt   720
agataccctg gtagtccacg ccgtaaacga tgaatactag gtgtcgggtg caaagccat   780
tcggtgccgc agcaaacgca ataagtattc cacctgggga gtacgttcgc aagaatgaaa   840
ctcaaaggaa ttgacgggga cccgcacaag cggtggagca tgtggtttaa ttcgaagcaa   900
cgcgaagaac cttacctggt cttgacatcc tctgaccgc tctttaatcg gagctttcct   960
tcgggacaga ggagacaggt ggtgcatggt tgtcgtcagc tcgtgtcgtg agatgttggg  1020
ttaagtcccg caacgagcgc aaccccctatc tttagtagcc agcattttgg atgggcactc  1080
tagagagact gccagggata acctggagga aggtggggat gacgtcaaat catcatgccc  1140
cttatgacca gggctacaca cgtgctacaa tggcgtaaac aaagggaagc gagcccgcga  1200
gggggagcaa atcccaaaaa taacgtctca gttcggatt tagtctgcaa ctcgactaca  1260
tgaagctgga atcgctagta atcgcgaatc agaatgtcgc ggtgaatacg ttcccggtc  1320
ttgtacacac cgcccgtcac accatgggag tcagtaacgc cgaagtcag tgacccaacc  1380
gcaaggaggg a                                                      1391

SEQ ID NO: 84         moltype = DNA  length = 1391
FEATURE               Location/Qualifiers
misc_feature          1..1391
                      note = F16
source                1..1391
                      mol_type = unassigned DNA
                      organism = unidentified
SEQUENCE: 84
agtcgaacga aacaccttat ttgattttct tcggaactga agatttggtg attgagtggc    60
ggacgggtga gtaacgcgtg gtaacctgc cctgtacagg gataacag tcagaaatga   120
ctgctaatac cgcataagac cacagcaccg catggtgcag gggtaaaaac tccggtggta   180
caggatggac ccgcgtctga ttagctggtt ggtgaggtaa cggctcacca aggcgacgat   240
cagtagccgg cttgagagag tgaacggcca cattgggact gagacacggc ccaaactcct   300
acgggaggca gcagtgggga atattgcaca atgggggaaa ccctgatgca gcgacgccgc   360
gtgagtgaag aagtatttcg gtatgtaaag ctctatcagc agggaagaaa atgacggtac   420
ctgactaaga agccccggct aactacgtgc cagcagccgc ggtaatacgt agggggcaag   480
cgttatccgg aattactggg tgtaaagggt gcgtaggtgg tatggcaagt cagaagtgaa   540
aacccagggc ttaactctgg gactgctttt gaaactgtca gactagagtg caggagaggt   600
aagcggaatt cctagtgtag cggtgaaatg cgtagatatt aggaggaaca tcagtggcga   660
aggcggctta ctggactgaa actgacactg aggcacgaaa gcgtggggag caaacaggat   720
tagatacccct ggtagtccac gccgtaaacg atgaatacta ggtgtcgggg ccgtagaggc   780
ttcggtgccg cagccaacgc agtaagtatt ccacctgggg agtacgttcg caagaatgaa   840
actcaaagga attgacgggg acccgcacaa gcggtggagc atgtggttta attcgaagca   900
acgcgaagaa ccttacctgg tcttgacatc cttctgaccg gtccttaacc ggacctttcc   960
ttcgggacag gagtgacagg tggtgcatgg ttgtcgtcag ctcgtgtcgt gagatgttgg  1020
```

```
gttaagtccc gcaacgagcg caaccccctat ctttagtagc cagcatataa ggtgggcact   1080
ctagagagac tgccagggat aacctggagg aaggtgggga cgacgtcaaa tcatcatgcc   1140
ccttatgacc agggctacac acgtgctaca atggcgtaaa cagagggaag cagcctcgtg   1200
agagtgagca aatcccaaaa ataacgtctc agttcggatt gtagtctgca actcgactac   1260
atgaagctgg aatcgctagt aatcgcgaat cagaatgtcg cggtgaatac gttcccgggt   1320
cttgtacaca ccgcccgtca caccatggga gtcagtaacc cccgaagtca gtgacccaac   1380
cgtaaggagg g                                                        1391
```

SEQ ID NO: 85          moltype = DNA   length = 1423
FEATURE                Location/Qualifiers
source                 1..1423
                       mol_type = unassigned DNA
                       organism = unidentified
misc_feature           1..1423
                       note = F17
variation              965..966
                       note = n is a, c, g, or t
variation              974..976
                       note = n is a, c, g, or t
variation              984..986
                       note = n is a, c, g, or t
variation              990..991
                       note = n is a, c, g, or t
variation              998..1000
                       note = n is a, c, g, or t
variation              1002..1004
                       note = n is a, c, g, or t
variation              1101..1103
                       note = n is a, c, g, or t
SEQUENCE: 85

```
caggatgaac gctggcggcg tgcttaacac atgcaagtcg aacggggaac attttatgga    60
agcttcggtg gaaatagctt gttcctagtg gcggacgggt gagtaacgcg tgggtaacct   120
gcctcacact gggggataac agtcagaaat gactgctaat accgcataag cgcacaggac   180
tgcatgattc agtgtgaaaa actccggtgg tgtgagatgg acccgcgttg gattagccag   240
ttggcagggt aacggcctac caaagcgacg atccatagcc ggcctgagag gggatattgca  300
cacattggga ctgagacacg gcccagactc ctacgggagg cagcagtggg gaatattgca   360
caatggggga aaccctgatg cagcgacgcc gcgtgaagga agaagtatct cggtatgtaa   420
acttctatca gcagggaaga aaatgacggt acctgactaa gaagcccggg ctaactacgt   480
gccagcagcc gcggtaatac gtagggggca agcgttatcc ggatttactg ggtgtaaagg   540
gagcgtagac ggagcagcaa gtctgatgtg aaaggcgggg gctcaacccc cggactgcat   600
tggaaactgt tgatcttgag taccggagag gtaagcggaa ttcctagtgt agcggtgaaa   660
tgcgtagata ttaggaggaa caccagtggc gaaggcggct tactgacgg taactgacgt    720
tgaggctcga aagcgtgggg agcaaacagg attagatacc ctggtagtcc acgccgtaaa   780
cgatgaatac taggtgtcgg gtggcagagc cattcggtgc cgcagcaaac gcagtaagta   840
ttccacctgg ggagtacgtt cgcaagaatg aaactcaaag gaattgacgg gacccgcac    900
aagcggtgga gcatgtggtt taattcgaag caacgcgaag aaccttacca agtcttgaca   960
tcccnntgac cggnnngtaa cgtnnncttn ncttcggnnn annngagaca ggtggtgcat  1020
ggttgtcgtc agctcgtgtc gtgagatgtt gggttaagtc cgcaacgagc gcaaccccct  1080
atccttagta gccagcggtt nnnccgggca ctctgaggag actgccaggg ataacctgga  1140
ggaaggcggg gatgacgtca aatcatcatg cccccttatg atttgggcta cacgtgctca  1200
caatggacga aacaaaggga agcgagagtg tgagcttaag caaatcccaa aaataacgtc   1260
ccagttcgga ctgcagtctg caactcgact gcacgaagct ggaatcgcta gtaatcgcgg  1320
atcagaatgc cgcggtgaat acgttcccgg gtcttgtaca caccgcccgt cacaccatgg  1380
gagtcagtaa cgcccgaagt cagtgaccga accgaaagga cgg                     1423
```

SEQ ID NO: 86          moltype = DNA   length = 1426
FEATURE                Location/Qualifiers
misc_feature           1..1426
                       note = F18
source                 1..1426
                       mol_type = unassigned DNA
                       organism = unidentified
SEQUENCE: 86

```
aggatgaacg ctggcggcgt gcctaacaca tgcaagtcga acgaagcaat taaaatgaag    60
ttttcggatg gatttttgat tgactgagtc gcggacgggt gagtaacgcg tggataacct   120
gcctcacact gggggataac agttagaaat gactgctaat accgcataag cgcacagtac   180
cgcatggtac ggtgtgaaaa actccggtgg tgtgagatgg atccgcgtct gattagccag   240
ttggcggggt aacggcccac caaagcgacg atcagtagcc gacctgagag ggtgaccggc   300
cacattggga ctgagacacg gcccaaactc ctacgggagg cagcagtggg gaatattgca   360
caatgggcga aagcctgatg cagcgacgcc gcgtgagtga agaagtattt cggtatgtaa   420
agctctatca gcagggaaga aaatgacggt acctgactaa gaagcccggg ctaactacgt   480
gccagcagcc gcggtaatac gtagggggca agcgttatcc ggatttactg ggtgtaaagg   540
gagcgtagac ggcgaagcaa gtctgaagtg aaacccagg gctcaaccct gggactgctt   600
tggaaactgt tttgctagag tgtcggagag gtaagtggaa ttcctagtgt agcggtgaaa   660
tgcgtagata ttaggaggaa caccagtggc gaaggcggct tactggacga taactgacgt   720
tgaggctcga aagcgtgggg agcaaacagg attagatacc ctggtagtcc acgccgtaaa   780
cgatgaatag taggtgttgg ggggcaaagc ccttcggtgc cgtcgcaaac gcagtaagca   840
ttccacctgg ggagtacgtt cgcaagaatg aaactcaaag gaattgacgg gacccgcac    900
aagcggtgga gcatgtggtt taattcgaag caacgcgaag aaccttacca agtcttgaca   960
```

-continued

```
tcctcttgac cggcgtgtaa cggcgccttc ccttcggggc aagagagaca ggtggtgcat   1020
ggttgtcgtc agctcgtgtc gtgagatgtt gggttaagtc ccgcaacgag cgcaacccTT   1080
atccttagta gccagcaggt agagctgggc actctaggga gactgccagg gataacctgg   1140
aggaaggtgg ggatgacgtc aaatcatcat gccccttatg atttgggcta cacacgtgct   1200
acaatggcgt aaacaaaggg aagcaagaca gtgatgtgga gcaaatccca aaaataacgt   1260
cccagttcgg actgtagtct gcaacccgac tacacgaagc tggaatcgct agtaatcgcg   1320
aatcagaatg tcgcggtgaa tacgttcccg ggtcttgtac accgcccgt cacaccatg    1380
ggagtcagca acgcccgaag tcagtgaccc aactcgcaag agaggg                 1426
```

SEQ ID NO: 87           moltype = DNA  length = 1420
FEATURE                 Location/Qualifiers
misc_feature            1..1420
                        note = F19
variation               1402
                        note = n is a, c, g, or t
source                  1..1420
                        mol_type = unassigned DNA
                        organism = unidentified
variation               1404
                        note = n is a, c, g, or t
SEQUENCE: 87

```
cggatgaacg ctggcggcgt gcttaacaca tgcaagtcga acggggatta ttttgacaga     60
gacttcggtt gaagtcgtta taatcctagt ggcggacggg tgagtaacgc gtgggtaacc   120
tgcctcacac tgggggataa cagtcagaaa tgactgctaa taccgcataa gcgcacggga   180
ctgcatggtt cagtgtgaaa aactccggtg gtgtgagatg gacccgcgtt ggattagcca   240
gttggcagtg taacggccta ccaaagcgac gatccatagc cggcctgaga gggtggacgg   300
ccacattggg actgagacac ggcccagact cctacgggag gcagcagtgg ggaatattgc   360
acaatggggg aaaccctgat gcagcgacgc cgcgtgaagg aagaagtatc tcggtatgta   420
aacttctatc agcaggaag aaaatgacgg tacctgacta gaagccccg gctaactacg    480
tgccagcagc cgcggtaata cgtaggggggc aagcgttact gggtgtaaag                540
ggagcgtaga cggagcagca agtctgatgt gaaaggcggg ggctcaaccc ccggactgca   600
ttggaaactg ttgatcttga gtaccggaga ggtaagcgga attcctagtg tagcggtgaa   660
atgcgtagat attaggagga acaccagtgg cgaaggcggc ttactggacg gtaactgacg   720
tgaggctcga aagcgtggga gcaaacagga ttagataccc tggtagtcca cgccgtaaac   780
gatgaatact aggtgtcggg tggcagagcc attcggtgcc gcagcaaacg cagtaagtat   840
tccacctggg gagtacgttc gcaagaatga aactcaaagg aattgacggg acccgcaca    900
agcggtggag catgtggttt aattcgaagc aacgcgaaga accttaccaa gtcttgacat   960
ccctctgacc ggtgagtaac gtcacctttc cttcgggaca gaggagacag gtggtgcatg  1020
gttgtcgtca gctcgtgtcg tgagatgttg ggttaagtcc cgcaacgagc gcaacccta   1080
tccttagtag ccagcggttt ggccgggcac tctgaggaga ctgccaggga taacctggag  1140
gaaggcgggg atgacgtcaa atcatcatgc ccttatgat ttgggctaca cacgtgctac   1200
aatgcgtaa acaagggaa gcgagagtgt gagcttaagc aaatcccaaa ataacgtcc    1260
cagttcggac tgcagtctgc aactgactg cacgaagctg gaatcgctag taatcgcgga   1320
tcagaatgcc gcggtgaata cgttcccggg tcttgtacac accgcccgtc acaccatggg  1380
agtcagtaac gcccgaagtc antnaccgaa ccgaaaggac                        1420
```

SEQ ID NO: 88           moltype = DNA  length = 1397
FEATURE                 Location/Qualifiers
misc_feature            1..1397
                        note = F20
variation               945
                        note = n is a, c, g, or t
variation               947
                        note = n is a, c, g, or t
source                  1..1397
                        mol_type = unassigned DNA
                        organism = unidentified
variation               953
                        note = n is a, c, g, or t
variation               965..968
                        note = n is a, c, g, or t
SEQUENCE: 88

```
agtcgaacga agtttcgagg aagcttgctt ccaaagagac ttagtggcga acgggtgagt     60
aacacgtagg taacctgccc atgtgtccgg gataactgct ggaaacggta gctaaaccg    120
gataggtata cagagcgcat gctcagtata ttaaagcgcc catcaaggcg tgaacatgga   180
tggacctgcg gcgcattagc tagttggtga ggtaacggcc caccaaggcg atgatgcgta   240
gccggcctga gagggtaaac ggccacattg ggactgagac acggcccaaa ctcctacggg   300
aggcagcagt agggaatttt cgtcaatggg ggaaaccctg aacgagcaat gccgcgtgag   360
tgaagaaggt cttcggatcg taaagctctg ttgtaagtga agaacggctc atagaggaaa   420
tgctatggga gtgacggtag cttaccagaa agccacggct aactacgtgc cagcagccgc   480
ggtaatacgt aggtggcaag cgttatccgg aatcattggg cgtaaagggt gcgtaggtgg   540
cgtactaagt ctgtagtaaa aggcaatggc tcaaccattg taagctatgg aaactggtat   600
gctggagtgc agaagagggc gatggaattc catgtgtagc ggtaaaatgc gtagatatat   660
ggaggaacac cagtggcgaa ggcggtcgcc tggtctgtaa ctgacactga gcacgaaag    720
cgtgggagc aaataggatt agataccta gtagtccacg ccgtaaacga tgagaactaa    780
gtgttggagg aattcagtgc tgcagttaac gcaataagtt ctccgcctgg ggagtatgca   840
cgcaagtgtg aaactcaaag gaattgacgg gggcccgcac aagcggtgga gtatgtggtt   900
taattcgaag caacgcgaag aaccttacca ggccttgaca tggananaaa tantctgag    960
atagnnnnat aattatggat cacacaggtg gtgcatggtt gtcgtcagct cgtgtcgtga  1020
```

```
gatgttgggt taagtcccgc aacgagcgca acccttgtcg catgttacca gcatcaagtt   1080
ggggactcat gcgagactgc cggtgacaaa ccggaggaag gtggggatga cgtcaaatca   1140
tcatgcccct tatggcctgg gctacacacg tactacaatg gcgaccacaa agagcagcga   1200
cacagtgatg tgaagcgaat ctcataaagg tcgtctcagt tcggattgaa gtctgcaact   1260
cgacttcatg aagtcggaat cgctagtaat cgcagatcag catgctgcgg tgaatacgtt   1320
ctcgggcctt gtacacaccg cccgtcaaac catgggagtc agtaatacccc gaagccggtg   1380
gcataaccgt aaggagt                                                  1397

SEQ ID NO: 89              moltype = DNA   length = 1392
FEATURE                    Location/Qualifiers
misc_feature               1..1392
                           note = F21
source                     1..1392
                           mol_type = unassigned DNA
                           organism = unidentified
SEQUENCE: 89
agtcgagcga agcacttaag tggatctctt cggattgaag cttatttgac tgagcggcgg    60
acgggtgagt aacgcgtggg taacctgcct catacagggg gataacagtt agaaatgact   120
gctaataccg cataagcgca caggaccgca tggtctggtg tgaaaaactc cggtggtatg   180
agatggaccc gcgtctgatt agctagttgg aggggtaacg gcccaccaag gcgacgatca   240
gtagccggcc tgagagggtg aacggccaca ttggactgag acacggccc agactcctac    300
gggaggcagc agtggggaat attgcacaat gggggaaacc ctgatgcagc gacgccgcgt   360
gaaggaagaa gtatctcggt atgtaaactt ctatcagcag ggaagaaaat gacggtacct   420
gactaagaag cccccggcta actacgtgcca gcagccgcgg taatacgtag ggggcaagcg   480
ttatccggat ttactgggtg taaagggagc gtagacggaa gagcaagtct gatgtgaaag   540
gctggggctt aaccccagga ctgcattgga aactgttttt ctagagtgcc gggagggtaa   600
gcggaattcc tagtgtagcg gtgaaatgcg tagatattag gaggaacacc agtggcgaag   660
gcggcttact ggacggtaac tgacgttgag gctcgaaagc gtggggagca aacaggatta   720
gataccctgg tagtccacgc cgtaaacgat gaatactagg tgtcgggtgg caaagccatt   780
cggtgccgca gcaaacgcaa taagtattcc acctggggag tacgttcgca agaatgaaac   840
tcaaaggaat tgacggggac ccgcacaagc ggtggagcat gtggtttaat tcgaagcaac   900
gcgaagaacc ttaccaagtc ttgacatccc tctgaccggc ccgtaacggg gccttccctt   960
cggggcagag gagacaggtg gtgcatggtt gtcgtcagct cgtgtcgtga gatgttgggt   1020
taagtcccgc aacgagcgca accccctatcc ttagtagcca gcaggtgaag ctgggcactc   1080
tagggagact gccggggata acccggagga aggtgggggat gacgtcaaat catcatgccc   1140
cttatgattt gggctacaca cgtgctacaa tggcgtaaac aaaggggaagc gagacagcga   1200
tgttgagcaa atcccaaaaa taacgtccca gttcggactg cagtctgcaa ctcgactgca   1260
cgaagctgga atcgctagta atcgcggatc agaatgtcgc ggtgaatacg ttcccgggtc   1320
ttgtacacac cgcccgtcac accatgggag tcagtaacgc ccgaagtcag tgacccaacc   1380
ttataggagg ga                                                       1392

SEQ ID NO: 90              moltype = DNA   length = 1382
FEATURE                    Location/Qualifiers
misc_feature               1..1382
                           note = F22
source                     1..1382
                           mol_type = unassigned DNA
                           organism = unidentified
SEQUENCE: 90
gaacgaagca ttttaggatg aagttttcgg atgcattctg agatgactga gtggcggacg    60
ggtgagtaac acgtggataa cctgcctcac actggggggac aacagttaga aatgactgct   120
aataccgcat aagcgcacag taccgcatgg tacggtgtga aaaactccgg tggtgtgaga   180
tggatccgcg tctgattagc cagttggcgg ggtaacggcc caccaaagcg acgatcagta   240
gccgacctga gaggtgacc ggccacattg gactgagac acggcccaaa ctcctacggg    300
aggcagcagt ggggaatatt gcacaatggg cgaaagcctg atgcagcgac gccgcgtgag   360
tgaagaagta tttcggtatg taaagctcta tcagcaggga agataatgac ggtacctgac   420
taagaagccc cggctaacta cgtgccagca gccgcggtaa tacgtagggg gcaagcgtta   480
tccggattta ctgggtgtaa agggagcgta gacggcatgg caagtctgaa gtgaaaaccc   540
agggctcaac cctgggactg ctttggaaac tgtcaagctg gagtgcagga gaggtaagtg   600
gaattcctag tgtagcggtg aaatgcgtag atattaggag gaacaccagt ggcgaaggcg   660
gcttactgga ctgtaactga cgttgaggct cgaaagcgtg gggagcaaac aggattagat   720
accctggtag tccacgccgt aaacgatgag tgctaggtgt tgggggcaa gcccttcgg    780
tgccgtcgca aacgcaataa gcactccacc tggggagtac gttcgcaaga atgaaactca   840
aaggaattga cggggacccg cacaagcggt ggagcatgtg gtttaattcg aagcaacgcg   900
aagaacctta ccaagtcttg acatcctctt gaccggcgtg taacggcgcc tttccttcgg   960
gacaagagag acaggtggtg catggttgtc gtcagctcgt gtcgtgagat gttgggttaa   1020
gtcccgcaac gagcgcaacc cttatcctta gtagccagca ttaagatggg cactctaggg   1080
agactgccag ggacaaacctg gaggaaggtg gggatgacgt caaatcatca tgccccttat   1140
gatttgggct acacacgtgc tacaatggcg taaacaaagg gaagcgaccc tgcgaaggtg   1200
agcaaatctc aaaaataacg tcccagttcg gactgtagtc tgcaacccga ctacacgaag   1260
ctggaatcgc tagtaatcgc gaatcagaat cgcggtga atacgttccc gggtcttgta   1320
cacaccgccc gtcacaccat gggagtcagc aacgcccgaa gtcagtgacc caaccgaaag   1380
ga                                                                 1382

SEQ ID NO: 91              moltype = DNA   length = 1386
FEATURE                    Location/Qualifiers
misc_feature               1..1386
                           note = F23
source                     1..1386
```

```
                        mol_type = unassigned DNA
                        organism = unidentified
SEQUENCE: 91
tcgaacgaag cactttaccg gatttcttcg ggatgaaagt tttgtgactg agtggcggac    60
gggtgagtaa cgcgtgggta acctgcctca tacagggga taacagttag aaatgactgc   120
taataccgca taagaccaca ggattgcatg atccggtggt aaaaactccg gtggtatgag   180
atggacccgc gtctgattag gtagttggtg gggtaacggc tcaccaagcc gacgatcagt   240
agccgacctg agagggtgac cggccacatt gggactgaga cacggcccaa actcctacgg   300
gaggcagcag tgggaatat tgcacaatgg gggaaaccct gatgcagcga cgccgcgtga    360
gcgatgaagt atttcggtat gtaaagctct atcagcaggg aagaaaatga cggtacctga   420
ctaagaagca ccggctaaat acgtgccagc agccgcggta atacgtatgg tgcaagcgtt   480
atccggattt actgggtgta aagggagcgt agacggagag caagtctgat gtgaaaacc   540
cggggctcaa ccccgggact gcattggaaa ctgtttttct agagtgtcgg agaggtaagt   600
ggaattccta gtgtagcggt gaaatgcgta gatattagga ggaacaccag tggcgaaggc   660
ggcttactgg acgatgactg acgttgaggc tcgaaagcgt ggggagcaaa caggattaga   720
taccctggta gtccacgccg taaacgatga ctgctaggtg tcgggaggca aagcctttcg   780
gtgccgcagc aaacgcaata agcagtccac tggggagta cgttcgcaag aatgaaactc    840
aaaggaattg acggggaccc gcacaagcgg tggagcatgt ggtttaattc gaagcaacgc   900
gaagaacctt acctgcccct gacatccggc tgaccggcga gtaatgtcgc ttttccttcg   960
ggacagccga gacaggtggt gcatggttgt cgtcagctcg tgtcgtgaga gttgggtta   1020
agtcccgcaa cgagcgcaac ccttatcttt agtagccagc atttcggatg ggcactctag  1080
agagactgcc agggataacc tggaggaagg tgggatgac gtcaaatcat catgcccctt   1140
atgggcaggg ctacacacgt gctacaatgg cgtaaacaaa gggaggcaag cctgcgaggg  1200
tgagcaaatc ccaaaaataa cgtctcagtt cggattgtag tctgcaactc gactacatga  1260
agctggaatc gctagtaatc gcgaatcaga atgtcgcggt gaatacgttc ccgggtcttg  1320
tacacaccgc ccgtcacacc atgggagttg gtaacgcccg aagtcagtga cccaaccgta  1380
aggagg                                                             1386

SEQ ID NO: 92          moltype = DNA  length = 1391
FEATURE                Location/Qualifiers
misc_feature           1..1391
                       note = F24
variation              931
                       note = n is a, c, g, or t
variation              936..940
                       note = n is a, c, g, or t
source                 1..1391
                       mol_type = unassigned DNA
                       organism = unidentified
variation              948..950
                       note = n is a, c, g, or t
variation              953..957
                       note = n is a, c, g, or t
variation              968..970
                       note = n is a, c, g, or t
variation              1068
                       note = n is a, c, g, or t
SEQUENCE: 92
gtcgaacgaa gttacgacag aggaagtttt cggatggaat cggtataact tagtggcgga    60
cgggtgagta acgcgtggga aacctgccct gtaccggggg ataacactta gaaataggtg   120
ctaataccgc ataagcgcac ggaaccgcat ggttgtcgtg aaaaactccg ggtggtacag   180
gatggtcccg cgtctgatta gccagttggc agggtaacgg cctaccaaag cgacgatcag   240
tagccggcct gagagggtga acggccacat tgggactgag acacggccca aactcctacg   300
ggaggcagca gtgggaata ttgcacaatg ggggaaaccc tgatgcagcg acgccgcgtg    360
agtgaagaag tatttcggta tgtaaagctc tatcagcagg gaagaaaatg acggtacctg   420
actaagaagc cccggctaac tacgtgccag cagccgcggt aatacgtagg ggcaagcgt   480
tatccggatt tactgggtgt aaagggagcg tagacggcat ggcaagccag atgtgaaaac   540
ccagggctca accttgggat tgcatttgga actgccaggc tggagtgcag gagaggtaag   600
cggaattcct agtgtagcgg tgaaatgcgt agatattagg aggaacacca gtggcgaagg   660
cggcttactg gactgtaact gacgttgagg ctcgaaagcg tggggagcaa acaggattag   720
atacccctggt agtccacgcg gtaaacgatg attgctaggt gtaggtgggt atggaccat   780
cggtgccgca gctaacgcaa taagcaatcc acctggggag tacgttcgca agaatgaaac   840
tcaaaggaat tgacggggac ccgcacaagc ggtggagcat gtggtttaat tcgaagcaac   900
gcgaagaacc ttaccaagtc ttgacatccc nttgannnnn ttgtaaannn gcnnnnnctt   960
cgggacannn gagacaggtg gtgcatggtt gtcgtcagct cgtgtcgtga gatgttgggt  1020
taagtcccgc aacgagcgca acccttattc ttagtagcca gcaggtgnag ctgggcactc  1080
taaggagact gccggggata acccggagga aggcgggat gacgtcaaat catcatgccc  1140
cttatgattt gggctacaca cgtgctacaa tggcgtaaac aaagggaagc gagacagtga  1200
tgtggagcaa atcccagaaa taacgtctca gttcggattg tagtctgcaa ctcgactaca  1260
tgaagctgga atcgctagta atcgcgaatc agcatgtcgc ggtgaatacg ttcccgggtc  1320
ttgtacacac cgcccgtcac accatgggag ttggaaatgc ccgaagtctg tgacctaacc  1380
gaaagggagg a                                                       1391

SEQ ID NO: 93          moltype = DNA  length = 1388
FEATURE                Location/Qualifiers
misc_feature           1..1388
                       note = F25
source                 1..1388
                       mol_type = unassigned DNA
```

```
                        organism = unidentified
SEQUENCE: 93
gtcgaacgaa gcactttacc ggatttcttc gggatgaaag ttttgtgact gagtggcgga    60
cgggtgagta acgcgtgggt aacctgcctc atacaggggg ataacagtta gaaatgactg   120
ctaataccgc ataagaccac aggattgcat gatccggtgg taaaaactcc ggtggtatga   180
gatggacccg cgtctgatta ggtagttggt ggggtaacgg ctcaccaagc cgacgatcag   240
tagccgacct gagagggtga ccggccacat tgggactgag acacggccca aactcctacg   300
ggaggcagca gtggggaata ttgcacaatg ggggaaaccc tgatgcagcg acgccgcgtg   360
agcgatgaag tatttcggta tgtaaagctc tatcagcagg gaagaaaatg acggtaccctg   420
actaagaagc accggctaaa tacgtgccag cagccgcggt aatacgtatg gtgcaagcgt   480
tatccggatt tactgggtgt aaagggagcg tagacggaga ggcaagtctg atgtgaaaac   540
ccggggctca accccgggac tgcattggaa actgtttttc tagagtgtcg gagaggtaag   600
tggaattcct agtgtagcgg tgaaatgcgt agatattagg aggaacacca gtggcgaagg   660
cggcttactg gacgatgact gacgttgagg ctcgaaagcg tggggagcaa acaggattag   720
ataccctggt agtccacgcc gtaaacgatg actgctaggt gtcggaggc aaaagccttc    780
ggtgccgcag caaacgcaat aagcagtcca cctgggagt acgttcgcaa gaatgaaact   840
caaaggaatt gacgggacc cgcacaagcg gtggagcatg tggtttaatt cgaagcaacg   900
cgaagaacct taccctgccct tgacatccgg ctgaccggca gtaatgtcg cctttccttc    960
gggacagccg agacaggtgg tgcatggttg tcgtcagctc gtgtcgtgag atgttgggtt  1020
aagtcccgca acgagcgcaa cccttatctt tagtagccag catttcggat gggcactcta  1080
gagagactgc cagggataac ctggaggaag tggggatga cgtcaaatca tcatgcccct  1140
tatgggcagg gctacacacg tgctacaatg gcgtaaacaa gggaggcaa gcctgcgagg  1200
gtgagcaaat cccaaaaata acgtctcagt tcggattgta gtctgcaact cgactacatg  1260
aagctggaat cgctagtaat cgcgaatcag aatgtcgcgg tgaatacgtt cccgggtctt  1320
gtacacaccg cccgtcacac catggagagtt ggtaacgccc gaagtcagtg acccaaccgt  1380
aaggaggg                                                            1388

SEQ ID NO: 94           moltype = DNA   length = 1386
FEATURE                 Location/Qualifiers
misc_feature            1..1386
                        note = F26
source                  1..1386
                        mol_type = unassigned DNA
                        organism = unidentified
SEQUENCE: 94
tcgaacgggg tgctcatgac ggaggattcg tccaacggat tgagttacct agtggcggac    60
gggtgagtaa cgcgtgagga acctgccttg gagaggggaa taacactccg aaaggagtgc   120
taataccgca tgatgcagtt gggtcgcatg gctctgactg ccaaagattt atcgctctga   180
gatggacctc cgtctgatta gctagtaggc ggggtaacgg cccacctagg cgacgatcag   240
tagccggact gagaggttga ccggccacat tgggactgag acacggccca gactcctacg   300
ggaggcagca gtggggaata ttgggcaatg gcgcaagcc tgacccagca acgccgcgtg   360
aaggaagaag gctttcgggt tgtaaacttc ttttgtcggg gacgaaacaa atgacggtac   420
ccgacgaata agcacggct aactacgtgc cagcagccgc ggtaatacgt aggtggcaag   480
cgttatccgg atttactggg tgtaaagggc gtgtaggcgg gattgcaagt cagatgtgaa   540
aactgggggc tcaacctcca gcctgcatttt gaaactgtag ttcttgagtg ctggagaggc   600
aatcggaatt ccgtgtgtag cggtgaaatg cgtagatata cggaggaaca ccagtggcga   660
aggcggattg ctggacagta actgacgctg aggcgcgaaa gcgtggggag caaacaggat   720
tagataccct ggtagtccac gccgtaaacg atggatacta ggtgtgggg gtctgacccc   780
ctccgtgccg cagttaacac aataagtatc ccacctgggg agtacgatcg caaggttgaa   840
actcaaagga attgacgggg gcccgcacaa gcggtggagt atgtggttta attcgaagca   900
acgcgaagaa ccttaccagg gcttgacatc ccactaacga agcagagatg cattaggtgc   960
ccttcgggga aagtggagac aggtggtgca tggttgtcgt cagctcgtgt cgtgagatgt  1020
tgggttaagt cccgcaacga gcgcaaccct tattgttagt tgctacgcaa gagcactcta  1080
gcgagactgc cgttgacaaa acggaggaag tggggacga cgtcaaatca tcatgcccct  1140
tatgtcctgg gccacacacg tactacaatg gtggttacaa gagggagcga ataccgcagg  1200
gtggagcaaa tccctaaaag ccatcccagt tcggattgca ggctgaaacc cgcctgtatg  1260
aagttggaat cgctagtaat cgcggatcag catgccgcgg tgaatacgtt cccgggcctt  1320
gtacacaccg cccgtcacac catgagagtc gggaacaccc gaagtccgta gcctaaccgc  1380
aaggag                                                              1386

SEQ ID NO: 95           moltype = DNA   length = 1392
FEATURE                 Location/Qualifiers
misc_feature            1..1392
                        note = F27
source                  1..1392
                        mol_type = unassigned DNA
                        organism = unidentified
SEQUENCE: 95
cagtcgaacg ggaatcactt cattgagact tcggtggatt tgatttagat tctagtggcg    60
gacgggtgag taacgcgtgg gtaacctgcc tttatacaggg ggataacagt cagaaatgac   120
tgctaatacc gcataagcgc acaggaccgc atggtccggt gtgaaaaact ccggtggtat   180
aagatgacc cgcgttggat tagcttgttg gtggggtaac ggcccaccaa ggcgacgatc   240
catagccggc ctgagagggt gaacggccac attgggactg agacacgcc cagactccta   300
cgggaggcag cagtgggaa tattgcacaa tgggggaaac cctgatgcag cgacgccgcg   360
tgaaggaaga gtatctcgg tatgtaaact tctatcagca gggaagatag tgacggtacc   420
tgactaagaa gccccggcta actacgtgcc agcagccgcg gtaatacgta ggggcaagc   480
gttatccgga tttactgggt gtaaagggag cgtagacggt gtggcaagtc tgatgtgaaa   540
ggcatgggct caacctgtgg actgcattgg aaactgtcat acttgagtgc ggaggggta   600
agcggaattc tagtgtagcg gtgaaatgcg tagatattag gaggaacaca cagtggcgaa   660
```

```
ggcggcttac tggacggtaa ctgacgttga ggctcgaaag cgtgggagc aaacaggatt   720
agatacctg  gtagtccacg ccgtaaacga tgaatactag gtgtcgggtg gcatggccat   780
tcggtgccgt cgcaaacgca gtaagtattc cacctggggg agtacgttcg caagaatgaa   840
actcaaagga attgacgggg acccgcacaa gcggtggagc atgtggttta attcgaagca   900
acgcgaagaa ccttaccaag tcttgacatc cctctgaccg actcttaacc gagtctttcc  960
ttcgggacag aggagacagg tggtgcatgg ttgtcgtcag ctcgtgtcgt gagatgttga  1020
gttaagtccc gcaacgagcg caaccccttat cctcagtagc cagcaagtta agttgggcac 1080
tctgtgagac tgccaggga  taacctggag gaaggcgggg atgacgtcaa atcatcatgc  1140
cccttatgat ttgggctaca cacgtgctac aatggcgtaa acaaagggaa gcgagattgc  1200
gagatggagc aaatcccaaa aataacgtcc cagttcggac tgtagtctgc aacccgacta  1260
cacgaagctg gaatcgctag taatcgcgga tcagaatgcc gcggtgaata cgttcccggg  1320
tcttgtacac accgcccgtc acaccatggg agtcagtaac gcccgaagtc agtgacctaa  1380
ctgcaaagaa gg                                                    1392

SEQ ID NO: 96              moltype = DNA   length = 1394
FEATURE                    Location/Qualifiers
misc_feature               1..1394
                           note = F28
variation                  25
                           note = n is a, c, g, or t
source                     1..1394
                           mol_type = unassigned DNA
                           organism = unidentified
SEQUENCE: 96
tgcagtcgag cgatactctt cgganaagag cggcggacgg gtgagtaacg cgtgggtaac    60
ctgccctgta cacacggata acataccgaa aggtatgcta atacgggata acataagaaa   120
ttcgcatgtt tttcttatca aagctccggc ggtacaggat ggacccgcgt ctgattagct   180
agttggtgag gtaacggctc accaaggcga cgatcagtag ccgacctgag agggtgatcg   240
gccacattgg aactgagaca cggtccaaac tcctacggga ggcagcagtg gggaatattg   300
cacaatgggc gaaagcctga tgcagcaacg ccgcgtgagc gatgaaggcc ttcgggtcgt   360
aaagctctgt cctcaaggaa gataatgacg gtacttgagg aggaagcccc ggctaactac   420
gtgccagcag ccgcggtaat acgtaggggg ctagcgttat ccggatttac tgggcgtaaa   480
gggtgcgtag gcggtctttt aagtcaggag tgaaaggcta cggctcaacc gtagtaagct   540
cttgaaactg gaggacttga gtgcaggaga ggagagtgga attcctagtg tagcggtgaa   600
atgcgtagat attaggagga acaccagtag cgaaggcggc tctctggact gtaactgacg   660
ctgaggcacg aaagcgtggg gagcaaacag gattagatac cctggtagtc cacgccgtaa   720
acgatgagta ctagctgtcg gaggttaccc ccttcggtgg cgcagctaac gcattaagta   780
ctccgcctgg ggagtacgct cgcaagagtg aaactcaaag gaattgacgg ggacccgcac   840
aagtagcgga gcatgtggtt taattcgaag caacgcgaag aaccttacct aagcttgaca   900
tccttttgac cgatgcctaa tcgcatcttt cccttcgggg acagaagtga caggtggtgc   960
atggttgtcg tcagctcgtg tcgtgagatg ttgggttaag tcccgcaacg agcgcaaccc  1020
ttgcctttag ttgccatcat taagttgggc actctagagg gactgccagg gataacctgg  1080
aggaaggtgg ggatgacgtc aaatcatcat gccccttatg cttagggcta cacacgtgca  1140
acaatgggtg gtacagaggg cagcgaagtc gtgaggccaa gctaatccct taaagccatt  1200
ctcagttcgg attgtaggct gaaactcgcc tacatgaagc tggagttact agtaatcgca  1260
gatcaaaatg ctgcggtgaa tgcgttcccg ggtcttgtac acaccgcccg tcacaccatg  1320
ggagttgggg gcgcccgaag ccggctagct aacctttgg aagcggtcgt cgaaggtgaa  1380
accaataact gggg                                                   1394

SEQ ID NO: 97              moltype = DNA   length = 1392
FEATURE                    Location/Qualifiers
misc_feature               1..1392
                           note = F29
source                     1..1392
                           mol_type = unassigned DNA
                           organism = unidentified
variation                  1046
                           note = n is a, c, g, or t
variation                  1071..1072
                           note = n is a, c, g, or t
SEQUENCE: 97
cagtcgagcg aagcactttt gcggatttct tcggattgaa gcaattgtga ctgagcggcg    60
gacgggtgag taacgcgtgg gtaacctgcc tcatacaggg gataacagt tggaaacggc   120
tgctaatacc gcataagcgc acagtaccgc atggtaccgt agaaaaact ccggtggtat   180
gagatggacc cgcgtctgat tagctagttg tgggggtaac ggcctaccaa ggcgacgatc   240
agtagccgac ctgagagggt gaccggccac attgggactg agacacggcc caaactccta   300
cgggaggcag cagtggggaa tattgcacaa tgggggaaac cctgatgcag cgacgccgcg   360
tgagcgatga agtattcgg tatgtaaagc tctatcagca gggagaaaa tgacggtacc   420
tgactaagaa gccccgccta actacgtgcc agcagccgcg gtaatacga gggggcaagc   480
gttatccgga tttactgggt gtaaaggag cgtagacggc atggcaagcc agatgtgaaa   540
gcccggggct caaccccggg actgcatttg gaactgtcag gctagagtgt cggagggaa   600
agcggaattc ctagtgtagc ggtgaaatgc gtagatatta ggaggaacac cagtggcgaa   660
ggcggctttc tggacgatga ctgacgttga ggctcgaaag cgtggggagc aaacaggatt   720
agatacctg gtagtccacg ccgtaaacga tgaatactag gtgtcggtg gcaaagccat   780
tcggtgccgt agcaaacgca ataagtattc cacctggggg gtacgttcgc aagaatgaa   840
ctcaaaggaa ttgacgggga cccgcacaag cggtggagca tgtggtttaa ttcgaagcaa   900
cgcgaagaac cttacctggt cttgacatcc ctctgaccgc tctttaatcg agctttcct   960
tcgggacaga ggagacaggt ggtgcatggt tgtcgtcagc tcgtgtcgtg agatgttggg  1020
ttaagtcccg caacgagcgc aacccntatc tttagtagcc agcatttaag nngggcactc  1080
```

```
tagagagact gccagggata acctggagga aggtggggat gacgtcaaat catcatgccc   1140
cttatgacca gggctacaca cgtgctacaa tggcgtaaac aaagggaagc gagcccgcga   1200
gggggagcaa atcccaaaaa taacgtctca gttcggattg tagtctgcaa ctcgactaca   1260
tgaagctgga atcgctagta atcgcgaatc agaatgtcgc ggtgaatacg ttcccgggtc   1320
ttgtacacac cgcccgtcac accatgggag tcagtaacgc ccgaagtcag tgacccaacc   1380
gcaaggaggg ag                                                      1392

SEQ ID NO: 98           moltype = DNA   length = 1378
FEATURE                 Location/Qualifiers
misc_feature            1..1378
                        note = F30
source                  1..1378
                        mol_type = unassigned DNA
                        organism = unidentified
SEQUENCE: 98
gtcggacgca atgcttcggc attgagtggc gaacgggtga gtaagacata agcaacctgc    60
ccctgtgagg gggataactg ctggaaacgg cagctaagac cgcataggca tagaggacgc   120
atgtcgacta tgttaaatat cccacgggat agcacaggga tgggcttatg acgcattagc   180
cagctggtga ggtaacggct caccaggggcg acgatgcgta gccggcctga gagggtggac   240
ggccacactg ggactgagac acggcccaga ctcctacggg aggcagcagt agggaatttt   300
cggcaatggg cgaaagcctg accgagcaac gccgcgtgaa ggaagaagtc attcgtgatg   360
taaacttctg ttatgaagga agaacgcag atggagggaa tgccatgtgc gtgacggtac   420
ttcatgagga agccacggct aactacgtgc cagcagccgc ggtaatacgt aggtggcgag   480
cgttatccgg aatcattggg cgtaaagagg gagcaggcgg cagtgcaggt ctgcggtgaa   540
agaccggagc taaacttcgg taagccgtgg aaaccgcaca gctagagagc atcagaggat   600
cgcggaattc catgtgtagc ggtgaaatgc gtagatatat gggaggaacac cagtggcgaa   660
ggcggcggtc tggggtgcag ctgacgctca gtcccgaaag cgtggggagc aaataggatt   720
agataccccta gtagtccacg ccgtaaacga tgagtgctaa gtgttggggg tcagacctca   780
gtgctggagt taacgcaata agcactccgc ctgagtagta cgttcgcaag aatgaaactc   840
aaaggaattg acgggggccc gcacaagcgg tggagcatgt ggtttaattc gaagcaacgc   900
gaagaaccttt accaggtctt gacatggaga taaaggccct ggagacaggg agatagatat   960
atctcacaca ggtggtgcat ggttgtcgtc agctcgtgtc gtgagatgtt gggttaagtc  1020
ccgcaacgag cgcaacccct gttgccagtt gccagcatta ggttgggac tctggcgaga  1080
ctgcctctgc aaggaggagg aaggcgggga tgacgtcaaa tcatcatgcc ccttatgacc  1140
tgggctacac acgtgctaca atggacggat cagagggagg cgaagccgcg aggtggagcg  1200
aaacccagaa acccgttcac agttcggact gcagtctgca actcgactgc acgaagctgg  1260
aatcgctagt aatcgcgaat cagcatgtcg cggtgaatac gttctcgggc cttgtacaca  1320
ccgcccgtca caccatgaga gttggtaaca cccgaagccg gtggcccaac cgcaagga    1378

SEQ ID NO: 99           moltype = DNA   length = 1392
FEATURE                 Location/Qualifiers
misc_feature            1..1392
                        note = F31
source                  1..1392
                        mol_type = unassigned DNA
                        organism = unidentified
SEQUENCE: 99
gtcgaacgaa gcattttgga aggaagtttt cggatggaat tccttaatga ctgagtggcg    60
gacgggtgag taacgcgtgg ggaacctgcc ctatacaggg ggataacagc tggaaacggc   120
tgctaatacc gcataagcgc acagaatcgc atgattcggt gtgaaaagct ccggcagtat   180
aggatggtcc cgcgtctgat tagctggttg gcggggtaac ggcccaccaa ggcgacgatc   240
agtagccggc ttgagagagt ggacggccac attgggactg agacacggcc caaactccta   300
cgggaggcag cagtggggaa tattgcacaa tgggggaaac cctgatgcag cgacgccgcg   360
tgagtgaaga agtatttcgg tatgtaaagc tctatcagca gggaagaaaa aagacggtac   420
ctgactaaga agccccggct aactacgtgc cagcagccgc ggtaatacgt aggggcaag   480
cgttatccgg aattactggg tgtaaagggt gcgtaggtgg catggtaagt cagaagtgaa   540
agcccggggc ttaacccccgg gactgcttt gaaactgtca tgctgagtg caggagaggt   600
aagcggaatt cctagtgtag cggtgaaatg cgtagatatt aggaggaaca ccagtggcga   660
aggcggctta ctggactgtc actgacatgc atgcacgaaa gcgtgggggag caaacaggat   720
tagatacccct ggtagtccac gccgtaaacg atgaatacta ggtgtcgggtg ccgtagaggo   780
ttcggtgccg cagcaaacgc agtaagtatt ccacctgggg agtacgttcg caagaatgaa   840
actcaaagga attgacgggg acccgcacaa gcggtggagc atgtggttta attcgaagca   900
acgcgaagaa ccttacctgg tcttgacatc taactgaccg gttcgtaatg gaccttttcc   960
ttcgggacag ttaagacagg tggtgcatgg ttgtcgtcag ctcgtgtcgt gagatgttgg  1020
gttaagtccc gcaacgagcg caaccccctat ctttagtagc cagcatataa ggtgggcact  1080
ctagagagac tgccagggat aacctggagg aaggtgggga cgacgtcaaa tcatcatgcc  1140
ccttatggcc agggctacac acgtgctaca atggcgtaaa caaagggaag cgaagtcgtg  1200
aggcgaagca aatcccagaa ataacgtctc agttcggatt gtagtctgca actcgactac  1260
atgaagctgg aatcgctagt aatcgtgaat cagaatgtca cggtgaatac gttcccgggt  1320
cttgtacaca ccgcccgtca caccatggga gtcagtaacg cccgaagtca gtgacccaac  1380
cttataggag gg                                                      1392

SEQ ID NO: 100          moltype = DNA   length = 1391
FEATURE                 Location/Qualifiers
misc_feature            1..1391
                        note = F32
source                  1..1391
                        mol_type = unassigned DNA
                        organism = unidentified
```

| variation | 951..952 |
| --- | --- |
| | note = n is a, c, g, or t |

SEQUENCE: 100

```
gtcgagcgaa gcactaagac ggatttcttc ggattgaagt ctttgtgact gagcggcgga   60
cgggtgagta acgcgtgggt aacctgcctc atacaggggg ataacagtta gaaatgactg  120
ctaataccgc ataagcgcac aggaccgcat ggtctggtgt gaaaaactcc ggtggtatga  180
gatggacccg cgtctgatta gctagttgga ggggtaacgg cccaccaagg cgacgatcag  240
tagccggcct gagagggtga acggccacat tgggactgag acacggccca gactcctacg  300
ggaggcagca gtggggaata ttgcacaatg ggggaaaccc tgatgcagcg acgccgcgtg  360
aaggaagaag tatctcggta tgtaaacttc tatcagcagg gaagaaaatg acggtacctg  420
actaagaagc cccggctaac tacgtgccag cagccgcggt aatacgtagg gggcaagcgt  480
tatccggatt tactgggtgt aaagggagcg tagacgaagc agtcaagtctg atgtgaaagg  540
ctggggctta accccaggac tgcattggaa actgttgttc tagagtgccg gagaggtaag  600
cggaattcct agtgtagcgg tgaaatgcgt agatattagg aggaacacca gtggcgaacg  660
cggcttactg gacggtaact gacgttgagg ctcgaaagcg tggggagcaa acaggattag  720
ataccctggt agtccacgcc gtaaacgatg aatactaggt gtcgggtggc aaagccattc  780
ggtgccgcag caaacgcaat aagtattcca cctggggagt acgttcgcaa gaatgaaact  840
caaaggaatt gacggggacc cgcacaagcg gtggagcatg tgttttaatt cgaagcaacg  900
cgaagaacct taccaagtct tgacatccct ctgaccgtcc cgtaacgggg nnttcccttc  960
ggggcagagg agacaggtgg tgcatggttg tcgtcagctc gtgtcgtgag atgttgggtt 1020
aagtcccgca acgagcgcaa cccttatcct tagtagccag cacatgatgg tgggcactct 1080
agggagactg ccggggataa cccggaggaa ggcggggacg acgtcaaatc atcatgcccc 1140
ttatgatttg ggctacacac gtgctacaat ggcgtaaaca aagggaagcg agacagcgat 1200
gttgagcgaa tccaaaaaat aacgtccag ttcggactgc agtctgcaac tcgactgcac 1260
gaagctggaa tcgctagtaa tcgcggatca gaatgccgcg gtgaatacgt tcccgggtct 1320
tgtacacacc gcccgtcaca ccatgggagt cagtaacgcc cgaagtcagt gacctaaccg 1380
aaaggaagga g                                                     1391
```

| SEQ ID NO: 101 | moltype = DNA length = 1381 |
| --- | --- |
| FEATURE | Location/Qualifiers |
| misc_feature | 1..1381 |
| | note = F33 |
| source | 1..1381 |
| | mol_type = unassigned DNA |
| | organism = unidentified |

SEQUENCE: 101

```
agtcgaacgc gagcacttgt gctcgagtgg cgaacgggtg agtaatacat aagtaacctg   60
ccctagacag ggggataact attggaaacg atagctaaga ccgcataggt acggacactg  120
catggtgacc gtattaaaag tgcctcaaag cactggtaga ggatggactt atggcgcatt  180
agctggttgg cggggtaacg gcccaccaag gcgacgatgc gtagccgacc tgagagggtg  240
accggccaca ctgggactga gacacggccc agactcctac gggaggcagc agtagggaat  300
tttcggcaat ggggggaaacc ctgaccgagc aacgccgcgt gaaggaagaa ggttttcgga  360
ttgtaaactt ctgttataaa ggaagaacgg cggctacaag tgagtgacgg  420
tactttatta gaaagccacg gctaactacg tgccagcagc cgcggtaata cgtaggtggc  480
aagcgttatc cggaattatt gggcgtaaag agggagcagg cggcagcaag ggtctgtggt  540
gaaagccctga agcttaactt cagtaagcca tagaaaccag gcagctagag tgcaggagag  600
gatcgtggaa ttcatcatgt agcggtgaaa tgcgtagata tatggaggaa caccagtggc  660
gaaggcgacg atctggcctg caactgacgc tcagtcccga aagcgtgggg agcaaatagg  720
attagatacc ctagtagtcc acgccgtaaa cgatgagtac taagtgttgg atgtcaaagt  780
tcagtgctga gttaacgcag ataagtactc cgcctgagta gtacgttcgc aagaatgaaa  840
ctcaaaggaa ttgacggggg cccgcacaag cggtggagca tgtggtttaa ttcgaagcaa  900
cgcgaagaac cttaccaggt cttgacatac tcataaaggc tccagagatg gagagatagc  960
tatatgagat acaggtggtg catggttgtc gtcagctcgt gtcgtgagat gttgggttaa 1020
gtcccgcaac gagcgcaacc cttatcgtta gttaccatca ttaagttggg gactctagcg 1080
agactgccag tgacaagctg gaggaaggcg gggatgacg caaatcatca tgcccctat  1140
gacctgggct acacacgtgc tacaatggat ggtgcagagg gaagcgaagc cgcgaggtga 1200
agcaaaaccc ataaaaccat tctcagttcg gattgtagtc tgcaactcga ctacatgaag 1260
ttggaatcgc tagtaatcgc gaatcagcat gtcgcggtga atacgttctc gggccttgta 1320
cacaccgccc gtcacaccac gagagttgat aacacccgaa gccggtggcc taaccgcaag 1380
g                                                                1381
```

| SEQ ID NO: 102 | moltype = DNA length = 1424 |
| --- | --- |
| FEATURE | Location/Qualifiers |
| misc_feature | 1..1424 |
| | note = F34 |
| variation | 170 |
| | note = n is a, c, g, or t |
| variation | 554..555 |
| | note = n is a, c, g, or t |
| source | 1..1424 |
| | mol_type = unassigned DNA |
| | organism = unidentified |

SEQUENCE: 102

```
gcagtcgaac gaagagcgat ggaagcttgc ttctatcaat cttagtgcg aacgggtgag   60
taacgcgtaa tcaacctgcc cttcagaggg ggacaacagt tggaaacgac tgctaatacc  120
gcatacgatc taatctcggc atcgaggata gatgaaaggt ggcctctacn tgtaagctat  180
cactgaagga ggggattgcg tctgattagc tagttgagg ggtaacggcc caccaaggcg  240
atgatcagta gccggtctga gaggatgaac ggccacattg gactgagac acggcccaga  300
ctcctacggg aggcagcagt ggggaatctt ccgcaatgga cgaaagtctg acggagcaac  360
```

```
gccgcgtgag tgatgacggc cttcgggttg taaagctctg ttaatcggga cgaaaggcct   420
tcttgcgaat agtgagaagg attgacggta ccgaataga aagccacggc taactacgtg   480
ccagcagccg cggtaatacg taggtggcaa gcgttgtccg gaattattgg gcgtaaagcg   540
cgcgcaggcg gatnngtcag tctgtcttaa aagttcgggg cttaacccg tgatgggatg   600
gaaactgctg atctagagta tcggagagga aagtggaatt cctagtgtag cgtgaaatg   660
cgtagatatt aggaagaaca ccagtggcga aggcgacttt ctggacgaaa actgacgctg   720
aggcgcgaaa gccaggggag cgaacgggat tagataccc ggtagtcctg gccgtaaacg   780
atgggtacta ggtgtaggag gtatcgaccc cttctgtgcc ggagttaacg caataagtac   840
cccgcctggg gagtacgacc gcaaggttga aactcaaagg aattgacggg ggcccgcaca   900
agcggtggag tatgtggttt aattcgacgc aacgcgaaga accttaccag gtcttgacat   960
tgatggacag aaccagagat ggttcctctt cttcggaagc cagaaaacag gtggtgcacg  1020
gttgtcgtca gctcgtgtcg tgagatgttg ggttaagtcc cgcaacgagc gcaacccta  1080
tcttatgttg ccagcactta aaggtgggaa ctcatgagag actgccgcag acaatgcgga  1140
ggaaggcggg gatgacgtca aatcatcatg cccttatga cctgggctac acacgtacta  1200
caatgggagt aatagacgg aagcgagatc gcgagatgga gcaaaccga gaaacactct  1260
ctcagttcgg atcgtaggct gcaactcgcc tacgtgaagt cggaatcgct agtaatcgca  1320
ggtcagcata ctgcggtgaa tacgttcccg ggccttgtac acaccgcccg tcacaccacg  1380
aaagtcggaa gtgcccaaag ccggtggggt aaccttcggg agcc                  1424

SEQ ID NO: 103        moltype = DNA   length = 1361
FEATURE               Location/Qualifiers
misc_feature          1..1361
                      note = F35
source                1..1361
                      mol_type = unassigned DNA
                      organism = unidentified
SEQUENCE: 103
gtctacttga tccttcgggt gaaggtggcg gacgggtgag taacgcgtaa agaacttgcc   60
ttacagactg gacaacatt tggaaacgaa tgctaatacc ggatattatg attgggtcgc  120
atgatctggt tatgaaagct atatgcgctg tgagagagct ttgcgtccca ttagttagtt  180
ggtgaggtaa cggctcacca agacgatgat gggtagccgg cctgagaggg tgaacgcca   240
caaggggact gagacacggc ccttactcct acgggaggca gcagtgggga atattggaca  300
atggaccaaa agtctgatcc agcaattctg tgtgcacgat gaagttttc ggaatgtaaa  360
gtgcttcag ttgggaagaa gtcagtgacg gtaccaacag aagaagcgac ggctaaatac  420
gtgccagcag ccgcggtaat acgtatgtcg caagcgttat ccggatttat tgggcgtaaa  480
gcgcgtctag gcggcttagt aagtctgatg tgaaaatgcg gggctcaacc ccgtattgcg  540
ttggaaactg ctaaactaga gtactggaga ggtaggcgga actacaagtg tagaggtgaa  600
attcgtagat atttgtagga atgccgatgg ggaagccagc ctactggaca gatactacg   660
ctaaagcgcg aaagcgtggg tagcaaacag gattagatac cctggtagtc cacgccgtaa  720
acgatgatta ctaggtgttg ggggtcgaac ctcagcgccc aagctaacgc gataagtaat  780
ccgcctgggg agtacgtacg caagtatgaa actcaaagga attgacgggg accccgcaca  840
gcggtggagc atgtggttta attcgacgca acgcgaggaa ccttaccagc gtttgacatc  900
ccaagaagtt aacagagatg ttttcgtgcc tcttcggaag caggtggtac ggggctgtcg  960
atggctgtcg tcagctcgtg tcgtgagatg ttgggttaag tcccgcaacg agcgcaaccc 1020
ctttcgtatgt ttaccatcat taagttggga actcatgcga gactgcctgc gatgagcagg 1080
aggaaggtgg ggatgacgtc aagtcatcat gcccccttata cgctgggcta cacacgtgct 1140
acaatgggga gtacagagag ctgcaaacct gcgagggtaa gctaatctca taaaaactatt 1200
cttagttcgg attgtactct gcaactcgag tacatgaagt tggaatcgct agtaatcgca 1260
aatcagctat gttgcggtga atacgttctc gggtcttgta cacaccgccc gtcacaccac 1320
gagagttggt tgcacctgaa gtaacaggcc taaccgtaag g                    1361

SEQ ID NO: 104        moltype = DNA   length = 1362
FEATURE               Location/Qualifiers
misc_feature          1..1362
                      note = F36
source                1..1362
                      mol_type = unassigned DNA
                      organism = unidentified
SEQUENCE: 104
agtctacttg atccttcggg tgaaggtggc ggacgggtga gtaacgcgta agaacttgc   60
cttacagact gggacaacat ttggaaacga atgctaatac cggatattat gattgggtcg  120
catgatctgg ttatgaaagc tatatgcgct gtgagagagc tttgcgtccc attagtagt  180
tggtgaggta acggctcacc aagacgatga tgggtagccg gctgagagg gtgaacggcc  240
acaaggggac tgagacacgg cccttactcc tacgggagcg agcagtgggga atattggac   300
aatggaccaa agtctgatc cagcaattct gtgtgcacga tgaagttttt cggaatgtaa  360
agtgctttca gttgggaaga gtcagtgacg gtaccaacag aagaagcgac ggctaaata  420
cgtgccagca gccgcggtaa tacgtatgtc gcaagcgtta tccggattta ttgggcgtaa  480
agcgcgtcta ggcggcttag taagtctgat gtgaaaatgc ggggctcaac ccgtattgc  540
gttggaaact gctaaactag aactactgag aggtaggcgg aactacaagt gtagaggtga a  600
aattcgtaga tatttgtagg aatgccgatg gggaagccag cctactggac agatactgac   660
gctaaagcgc gaaagcgtgg gtagcaaaca ggattagata ccctggtagt ccacgccgta  720
aacgatgatt actaggtgtt gggggtcgaa cctcagcgcc caagctaacg cgataagtaa  780
tccgcctggg gagtacgtac gcaagtatga aactcaaagg aattgacggg gacccgcaca  840
agcggtggag catgtggttt aattcgacgc aacgcgaaga accttaccag cgtttgacat  900
cccaagaagt taacagagat gttttcgtgc ctcttcggag aacttggtg acaggtggta   960
catggctgtc gtcagctcgt gtcgtgagat gttgggttaa gtcccgcaac gagcgcaacc 1020
cctttcgtat gttaccatca ttaagttggg gactcatgcg agactgcctg cgatgagcag 1080
gaggaaggtg gggatgacgt caagtcatca tgccccttat acgctgggct acacacgtgc 1140
tacaatgggg agtacagaga gctgcaaacc tgcgagggta agctaatctc ataaaactat 1200
```

```
tcttagttcg gattgtactc tgcaactcga gtacatgaag ttggaatcgc tagtaatcgc   1260
aaatcagcta tgttgcggtg aatacgttct cgggtcttgt acacaccgcc cgtcacacca   1320
cgagagttgg ttgcacctga agtaacaggc ctaaccgtaa gg                      1362
```

```
SEQ ID NO: 105           moltype = DNA   length = 1397
FEATURE                  Location/Qualifiers
misc_feature             1..1397
                         note = F37
source                   1..1397
                         mol_type = unassigned DNA
                         organism = unidentified
SEQUENCE: 105
agtcgaacgg taacaggaag cagcttgctg ctttgctgac gagtggcgga cgggtgagta    60
atgtctggga aactgcctga tggaggggga taactactgg aaacggtagc taataccgca   120
taacgtcgca agaccaaaga gggggacctt cgggcctctt gccatcggat gtgcccagat   180
gggattagct agtaggtggg gtaacggctc acctaggcga cgatccctag ctggtctgag   240
aggatgacca gccacactgg aactgagaca cggtccagac tcctacggga ggcagcagtg   300
gggaatattg cacaatgggc gcaagcctga tgcagccatg ccgcgtgtat gaagaaggcc   360
ttcgggttgt aaagtacttt cagcggggag gaagggagta aagttaatac ctttgctcat   420
tgacgttacc cgcagaagaa gcaccggcta actccgtgcc agcagccgcg gtaatacgga   480
gggtgcaagc gttaatcgga attactgggc gtaaagcgca cgcaggcggt ttgttaagtc   540
agatgtgaaa tccccgggct caacctggga actgcatctg atactggcaa gcttgagtct   600
cgtagagggg ggtagaattc caggtgtagc ggtgaaatgc gtagagatct ggaggaatac   660
cggtggcgaa ggcggcccc tgacgaaga ctgacgctca ggtgcgaaag cgtggggagc   720
aaacaggatt agataccctg gtagtccacg ccgtaaacga tgtcgacttg gaggttgtgc   780
ccttgaggcg tggcttccgg agctaacgcg ttaagtcgac cgcctgggga gtacggccgc   840
aaggttaaaa ctcaaatgaa ttgacggggg cccgcacaag cggtggagca tgtggtttaa   900
ttcgatgcaa cgcgaagaac cttacctggt cttgacatcc acggaagttt tcagagatga   960
gaatgtgcct tcgggaaccg tgagacaggt gctgcatggc tgtcgtcagc tcgtgttgtg  1020
aaatgttggg ttaagtcccg caacgagcgc aaccctatc ctttgttgcc agcggtccgg  1080
ccgggaactc aaaggagact gccagtgata aactggagga aggtggggat gacgtcaagt  1140
catcatggcc cttacgacca gggctacaca cgtgctacaa tggcgcatac aaagagaagc  1200
gacctcgcga gagcaagcgg acctcataaa gtgcgtcgta gtccggattg gagtctgcaa  1260
ctcgactcca tgaagtcgga atcgctagta atcgtggatc agaatgccac ggtgaatacg  1320
ttcccgggcc ttgtacacac cgcccgtcac accatgggag tgggttgcaa aagaagtagg  1380
tagcttaacc ttcggga                                                 1397
```

```
SEQ ID NO: 106           moltype = DNA   length = 1339
FEATURE                  Location/Qualifiers
misc_feature             1..1339
                         note = I01
source                   1..1339
                         mol_type = unassigned DNA
                         organism = unidentified
variation                139
                         note = n is a, c, g, or t
variation                237
                         note = n is a, c, g, or t
variation                248
                         note = n is a, c, g, or t
variation                308..309
                         note = n is a, c, g, or t
variation                311..313
                         note = n is a, c, g, or t
variation                489
                         note = n is a, c, g, or t
variation                1158
                         note = n is a, c, g, or t
variation                1284
                         note = n is a, c, g, or t
variation                1286
                         note = n is a, c, g, or t
SEQUENCE: 106
ctgggtgaga gtggcgaacg ggtgagtaat gcgtgaccga cctgccccat acaccggaat    60
agctcctgga aacgggtggt aatgccggat gctccagttg gatgcatgtc cttctgggaa   120
agattcatcg gtatgggang gggtcgcgtc ctatcagctt gatggcgggg taacggccca   180
ccatggcttc cacgggtagc cggcctgaga gggcgaccgg ccacattggg actgagntac   240
ggcccagnct cctacgggag gcagcagtgg ggaatattgc acaatgggcg caagcctgat   300
gcagcgannc nnngtgtggg atgacggcct tcgggttgta aaccgcttt gactgggac   360
aagcccttcg gggtgagtgt acctttcgaa taagcaccgg ctaactacgt gccagcagcc   420
gcggtaatac gtaaggtgca agcgttatcc ggaattattg ggcgtaaagg gctcgtaagc   480
ggttcgtcnc gtccggtgtg aaagtccatc gcttaacggt ggatccgcgc cgggtacggg   540
cgggcttgag tgcggtaggg gagactggaa ttcccggtgt aacggtggaa tgtgtagata   600
tcgggaagaa caccaatggc gaaggcaggt tctctgggcc tcactgacgc tgaggagcga   660
aagcgtgggg agcgaacagg attagatacc ctggtagtcc acgccgtaaa cggtggatgc   720
tggatgtggg gaccattcca cggtctccgt gtcggagcca acgcgttaag catcccgcct   780
ggggagtacg gccgcaaggc taaaactcaa agaaattgac gggggcccgc acaagcggcg   840
gagcatgcgg attaattcga tgcaacgcga agaaccttac ctgggcttga catgttcccg   900
acagccgtag agatacggtt tccccttcgg gcgggttcac aggtggtgca tggtcgtcgt   960
```

```
cagctcgtgt cgtgagatgt tgggttaagt cccgcaacga gcgcaaccct cgccctgtgt   1020
tgccagcacg tcgtggtggg aactcacggg ggaccgccgg ggtcaactcg gaggaaggtg   1080
gggatgacgt cagatcatca tgccccttac gtccagggct tcacgcatgc tacaatggcc   1140
ggtacaacgg gatgcganac cgcgaggtgg agcggatccc ttaaaacggg tctcagttcg   1200
gattggagtc tgcaacccga ctccatgaag gcggagtcgc tagtaatcgc ggatcagcaa   1260
cgccgcgggtg aatgcgttcc cggncnttgt acacaccgcc cgtcaagtca tgaaagtggg   1320
tagcacccga agccggtgg                                                1339

SEQ ID NO: 107         moltype = DNA  length = 1346
FEATURE                Location/Qualifiers
misc_feature           1..1346
                       note = I02
variation              911..913
                       note = n is a, c, g, or t
source                 1..1346
                       mol_type = unassigned DNA
                       organism = unidentified
variation              923
                       note = n is a, c, g, or t
SEQUENCE: 107
ttgcttggtg gtgagagtgg cgaacgggtg agtaatgcgt gaccgacctg ccccatacac   60
cggaatagct cctggaaacg ggtggtaatg ccggatgctc cgactcctcg catggggtgt   120
cgggaaagat ttcatcggta tgggatgggg tcgcgtccta tcaggtagtc ggcggggtaa   180
cggcccaccg agcctacgac gggtagccgg cctgagaggg cgaccggcca cattgggact   240
gagatacggc ccagactcct acgggaggca gcagtgggga atattgcaca atgggcgcaa   300
gcctgatgca gcgacgccgc gtgcgggatg acggccttcg ggttgtaaac gcttttgat   360
cgggagcaag ccttcgggtg agtgtaccttt cgaataagac accggctaac tacgtgccaa   420
cagccgcggt aatacgtagg gtgcaagcgt tatccggaat tattgggcgt aaagggctcg   480
taggcggttc gtcgcgtccg gtgtgaaagt ccatcgctta cggtggatc tgcgccgggt   540
acgggcgggc tggagtgcgg tagggggagac tggaattccc ggtgtaacgg tggaatgtgt   600
agatatcggg aagaacacca atggcgaagg caggtctctg ggccgttact gacgctgagg   660
agcgaaagcg tggggagcga acaggattag ataccctggt agtccacgcc gtaaacggtg   720
gatgctggat gtgggcccg ttccacgggt tcgtgtcgg agctaacgcg ttaagcatcc   780
cgcctgggga gtacggccgc aaggctaaaa ctcaaagaaa ttgacggggg cccgcacaag   840
cggcggagca tgcggattaa ttcgatgcaa cgcgaagaac cttacctggg cttgacatgt   900
tcccgacagc nnnagagata tgncctccct tcggggcggg ttcacaggtg gtgcatggtc   960
gtcgtcagct cgtgtcgtga gatgttgggt taagtcccgc aacgagcgca accctcgccc   1020
tgtgttgcca gcacgtcgtg gtgggaactc acggggggacc gccggggtca actcggagga   1080
aggtggggat gacgtcagat catcatgccc cttacgtcag ggcttcacgc atgctacaa   1140
tggccggtac aacgggatgc gacacgcgca cgtggagcgg atccctgaaa accggtctca   1200
gttcggattg gagtctgcaa cccgactcca tgaaggcgga gtcgctagta atcgcggatc   1260
agcaacgccg cggtgaatgc gttccgggc cttgtacaca ccgcccgtca gtcatgaaa   1320
gtgggtagca cccgaagccg gtggcc                                       1346

SEQ ID NO: 108         moltype = DNA  length = 1353
FEATURE                Location/Qualifiers
misc_feature           1..1353
                       note = I03
source                 1..1353
                       mol_type = unassigned DNA
                       organism = unidentified
SEQUENCE: 108
aagcttgctt ggtggtgaga gtggcgaacg ggtgagtaat gcgtgaccga cctgccccat   60
gctccggaat agctcctgga aacgggtggt aatgccggat gttccacatg atcgcatgtg   120
attgtgggaa agattctatc ggcgtgggat ggggtcgcgt cctatcagct tgttggtgag   180
gtaacggctc accaaggctt cgacgggtag ccggcctgag agggcgaccg gccacattgg   240
gactgagata cggcccagac tcctacggga ggcagcagtg ggaatattg cacaatgggc   300
gcaagcctga tgcagcgacg ccgcgtgagg gatggaggcc ttcgggttgt aaacctcttt   360
tgtttgggag caagccttcg ggtgagtgta cctttcgaat aagcgccggc taactacgtg   420
ccagcagccg cggtaatacg tagggcgcaa gcgttatccg gatttattgg gcgtaaaggg   480
ctcgtaggcg gctcgtcgcg tccggtgtga aagtccatcg cttaacgtgg atctgcgcc   540
gggtacgggc gggctggagt gcggtagggg agactgaat cccggtgta acggtggaat   600
gtgtagatat cgggaagaac accgatgcg aaggcaggtc tctgggccgt cactgacgct   660
gaggacgcgaa agcgtgggga gcgaacagga ttagataccc tggtagtcca cgccgtaaa   720
cggtggacgct ggatgtgggg cacgttccac gtgttccgtg tcggagctaa cgcgttaagc   780
gtcccgcctg gggagtacgg ccgcaaggct aaaactcaaa gaattgacg gggcccgca   840
caagcggcgg agcatgcgga ttaattcgat gcaacgcgaa gaaccttacc tgggcttgac   900
atgttcccga cgacgccaga gatggcgttt cccttcgggg cggggttcaca ggtggtgcat   960
ggtcgtcgtc agctcgtgtc gtgagatgtt gggttaagtc ccgcaacgag cgcaaccctc   1020
gccccgtgtt gccagcacgt tatggtggga actcacgggg gaccgccggg gttaactcgg   1080
aggaaggtgg ggatgacgtc agatcatcat gcccccttacg tccagggctt cacgcatgct   1140
acaatgccg gtacagcggg atgcgacatg gcgacatgga gcggatccct gaaaaccggt   1200
ctcagttcga atcggagcct gcaacccggc tccgtgaagg cggagtcgct agtaatcgcg   1260
gatcagcaac gccgcggtga atgcgttccc gggccttgta cacaccgccc gtcaagtcat   1320
gaaagtgggc agcacccgaa gccggtggcc taa                               1353

SEQ ID NO: 109         moltype = DNA  length = 1338
FEATURE                Location/Qualifiers
misc_feature           1..1338
```

```
                        note = I04
source                  1..1338
                        mol_type = unassigned DNA
                        organism = unidentified
SEQUENCE: 109
ggtggtgaga gtggcgaacg ggtgagtaat gcgtgaccga cctgccccat acaccggaat    60
agctcctgga acgggtggt aatgccggat gctccagttg atcgcatggt cttctgggaa    120
agctttcgcg gtatgggatg gggtcgcgtc ctatcagctt gacggcgggg taacggccca   180
ccgtggcttc gacgggtagc cggcctgaga gggcgaccgg ccacattggg actgagatac   240
ggcccagact cctacgggag gcagcagtgg ggaatattgc acaatgggcg caagcctgat   300
gcagcgacgc cgcgtgaggg atggaggcct cgggttgta aacctctttt atcggggagc    360
aagcgagagt gagtttaccc gttgaataag caccggctaa ctacgtgcca gcagccgcgg   420
taatacgtag ggtgcaagcg ttatccgaa ttattgggcg taagggctc gtaggcggtt     480
cgtcgcgtcc ggtgtgaaag tccatcgctt aacggtggt ccgcgccggg tacgggcggg    540
cttgagtgcg gtaggggaga ctggaattcc cggtgtaacg gtggaatgtg tagatatcgg   600
gaagaacacc aatggcgaag gcaggtctct gggccgttac tgacgctgag gagcgaaagc   660
gtggggagcg aacaggatta gataccctgg tagtccacgc cgtaaacggt ggatgctgga   720
tgtgggggccc gttccacggg ttccgtgtcg gagctaacgc gttaagcatc ccgcctgggg  780
agtacgccg caaggctaaa actcaaagaa attgacgggg gcccgcacaa cggcggagc     840
atgcggatta attcgatgca acgcgaagaa ccttacctgg gcttgacatg ttcccgacgg   900
tcgtagagat gcggcttccc ttcggggcgg gttcacaggt ggtgcatggt cgtcgtcagc   960
tcgtgtcgtg agatgttggg ttaagtcccg caacgagcgc aaccctcgcc ccgtgttgcc   1020
agcggattat gccggaact cacggggac cgccggggtt aactcggagg aaggtgggga    1080
tgacgtcaga tcatcatgcc ccttacgtcc agggcttcac gcatgctaca atggccgta   1140
caacgggatg cgacgcggcg acgcggagcg gatccctgaa aaccggtctc agttcggatc  1200
gcagtctgca actcgactgc gtgaaggcgg agtcgctagt aatcgcgaat cagcaacgtc  1260
gcggtgaatg cgttcccggg ccttgtacac accgcccgtc aagtcatgaa agtgggcagc  1320
acccgaagcc ggtggcct                                                 1338

SEQ ID NO: 110          moltype = DNA  length = 1326
FEATURE                 Location/Qualifiers
misc_feature            1..1326
                        note = I05
source                  1..1326
                        mol_type = unassigned DNA
                        organism = unidentified
SEQUENCE: 110
gataagcg agtggcgaac ggctgagtaa cacgtggaga acctgccccc tccccgggga    60
tagccgcccg aaaggacggg taataccgga taccccgggg tgccgcatgg cacccggct   120
aaagccccga cggagggga tggctccgcg gcccatcagg tagacggcgg ggtgacggcc   180
caccgtgccg acaacgggta gccgggttga gagaccgacc ggccagattg ggactgagac  240
acggcccaga ctcctacggg aggcagcagt ggggaatctt gcgcaatggg gggaaccctg  300
acgcagcgac gccgcgtgcg ggacgcagc ctttgggttg taaacgcgt tcagcaggga    360
agagtcaaga ctgtacctgc agaagaagcc ccggctaact acgtgccagc agccgcggta  420
atacgtaggg ggcgagcgtt atccggattc attgggcgta aagcgcgcgt aggcggcccg  480
gcaggccggg ggtcgaagcg gggggctcaa ccccccgaag ccccccggaac ctccgcggct 540
tgggtccggt aggggggagt ggaacacccg gtgtagcggt ggaatgcgca gatatcgggt  600
ggaacaccgg tggcgaaggc ggccctctgg gccgagaccg acgctgaggc gcgaaagctg  660
ggggagcgaa caggattaga taccctggta gtccagccg taaacgatgg acgctaggtg   720
tggggggacg atccccccgt gccgcagcca acgcattaag cgtcccgcct ggggagtacg  780
gccgcaaggc taaaactcaa aggaattgac ggggggcccg caagcaggag gagcatgtgg  840
cttaattcga agcaacgcga agaaccttac cagggcttga catatgggtg aagcggggga  900
gaccccgtgg ccgagaggag cccatacagg tggtgcatgg ctgtcgtcag ctcgtgtcgt  960
gagatgttgg gttaagtccc gcaacgagcg caaccccgc cgcgtgttgc catcgggtga   1020
tgccgggaac ccacgcggga ccgccgccgt caaggcggga gagggcggga acgacgtcaa  1080
gtcatcatgc cccttatgcc ctgggctgca cacgtgctac aatggccggt acagagggat  1140
gccaccccgc gagggggagc ggatcccgga aagccggccc cagttcggat tggggctgc   1200
aacccgcccc catgaagtcg gagttgctag taatcgcgga tcagcatgcc gcggtgaatg  1260
cgttcccggg ccttgtacac accgcccgtc acaccccgg agtcgtctgc acccgaagtc   1320
gccggc                                                              1326

SEQ ID NO: 111          moltype = DNA  length = 729
FEATURE                 Location/Qualifiers
misc_feature            1..729
                        note = I06
source                  1..729
                        mol_type = unassigned DNA
                        organism = unidentified
variation               13
                        note = n is a, c, g, or t
SEQUENCE: 111
acctgccttc ggncagaagc gagtggcgaa cggctgagta acacgtggag aacctgcccc   60
ctcccccggg atagccgccc gaaaggacgg gtaataccgg ataccccggg tgccgcatg   120
gcacccggc taaagccccg acgggagggg atggctccgc ggcccatcag gtagacggcg   180
gggtgacggc ccaccgtgcc gacaacgggt agccgggttg agagaccgac cggccagatt  240
gggactgaga cacggcccag actcctacgg gaggcagcag tggggaatct tgcgcaatgg  300
ggggaaccct gacgcagcga cgccgcgtgc gggacgagg ccttcgggtc gtaaccgct    360
ttcagcaggg aagagtcaag actgtacctg cagaagaagc cccggctaac tacgtgccag  420
cagccgcggt aatacgtagg gggcgagcgt tatccggatt cattgggcgt aaagcgcgcg  480
```

```
taggcggccc ggcaggccgg gggtcgaagc gggggggctca acccctcgaa gcccccggaa    540
cctccgcggc ttgggtccgg taggggaggg tggaacaccc ggtgtagcgg tggaatgcgc    600
agatatcggg tggaacaccg gtggcgaagg cggccctctg ggccgagacc gacgctgagg    660
cgcgaaagct gggggagcga acaggattag ataccctggt agtcccagcc gtaaacgatg    720
gacgctagg                                                            729

SEQ ID NO: 112         moltype = DNA   length = 1338
FEATURE                Location/Qualifiers
misc_feature           1..1338
                       note = I07
source                 1..1338
                       mol_type = unassigned DNA
                       organism = unidentified
SEQUENCE: 112
gtggtgagag tggcgaacgg gtgagtaatg cgtgaccgac ctgccccata caccggaata    60
gctcctggaa acgggtggta atgccggatg ctccagttga tcgcatggtc ttctgggaaa    120
gctttcgcgg tatgggatgg ggtcgcgtcc tatcagcttg acggcggggt aacggcccac    180
cgtggcttcg acgggtagcc ggcctgagag ggcgaccggc cacattggga ctgagatacg    240
gcccagactc ctacgggagg cagcagtggg gaatattgca caatgggcgc aagcctgatg    300
cagcgacgcc gcgtgaggga tggaggcctt cgggttgtaa acctcttttta tcggggagca    360
agcgagagtg agtttacccg ttgaataagc accggctaac tacgtgccag cagccgcggt    420
aatacgtagg gtgcaagcgt tatccggaat tattgggcgt aaagggctcg taggcggttc    480
gtcgcgtccg gtgtgaaagt ccatcgctta acggtggatc cgcgccgggt acgggcgggc    540
ttgagtgcgg taggggagac tggaattccc ggtgtaacgg tggaatgtgt agatatcggg    600
aagaacacca atggcgaagg caggtctctg ggccgttact gacgctgagg agcgaaagcg    660
tggggagcga acaggattag ataccctggt agtccacgcc gtaaacgttg gatgctggat    720
gtggggcccg ttccacgggt tccgtgtcgg agctaacgcg ttaagcatcc cgcctgggga    780
gtacggccgc aaggctaaaa ctcaaagaaa ttgacggggg cccgcacaag cggcggagca    840
tgcggattaa ttcgatgcaa cgcgaagaac cttacctggg cttgacatgt cccgacggt    900
cgtagagatg cggcttccct tcggggcggg ttcacaggtg gtgcatggtc gtcgtcagct    960
cgtgtcgtga gatgttgggt taagtcccgc aacgagcgca accctcgccc cgtgttgcca    1020
gcggattatg ccgggaactc acgggggacc gccggggtta actcggagga aggtggggat    1080
gacgtcagat catcatgccc cttacgtcca gggcttcacg catgctacaa tggccggtac    1140
aacgggatgc gacgcggcga cgcggagcgg atccctgaaa accggtctca gttcggatcg    1200
cagtctgcaa ctcgactgcg tgaaggcgga gtcgctagta atcgcgaatc agcaacgtcg    1260
cggtgaatgc gttcccgggc cttgtacaca ccgcccgtca agtcatgaaa gtgggcagca    1320
cccgaagccg gtggccta                                                  1338

SEQ ID NO: 113         moltype = DNA   length = 1337
FEATURE                Location/Qualifiers
misc_feature           1..1337
                       note = I08
variation              105
                       note = n is a, c, g, or t
variation              117..119
                       note = n is a, c, g, or t
source                 1..1337
                       mol_type = unassigned DNA
                       organism = unidentified
SEQUENCE: 113
ttgatggatg gcgaccggcg cacgggtgag taacacgtat ccaacctgcc gacaacactg    60
ggatagcctt tcgaaagaaa gattaatacc ggatggcata attantccgc atgggannnt    120
tattaaagaa tttcggttgt cgatggggat gcgttccatt aggcagttgg cggggtaacg    180
gcccaccaaa ccaacgatgg ataggggttc tgagaggaag gtcccccaca ttggaactga    240
gacacggtcc aaactcctac gggaggcagc agtgaggaat attggtcaat ggacgagagt    300
ctgaaccagc caagtagcgt gaaggatgac tgccctatgg gttgtaaact tcttttatac    360
gggaataaag ttagccacgt gtggcttttt gtatgtaccg tatgaataag gatcggctaa    420
ctccgtgcca gcagccgcgg taatacggag gatccgagcg ttatccggat ttattgggtt    480
taaagggagc gtaggcgggt tgttaagtca gttgtgaaag tttgcggctc aaccgtaaaa    540
ttgcagttga tactggcgac cttgagtgca acagaggtgg gcggaattcg tggtgtagcg    600
gtgaaatgct tagatatcac gaagaactcc gattgcgaag gcagcttact ggattgtaac    660
tgacgctgat gctcgaaagt gtgggtatca aacaggatta gataccctgg tagtccacac    720
agtaaacgat gaatactcgc tgttggcgat atactgtcag cggccaagcg aaagcattaa    780
gtattccacc tggggagtac gccggcaacg gtgaaactca aaggaattga cgggggcccg    840
cacaagcgga ggaacatgtg gtttaattcg atgatacgcg aggaaccttac ccgggctta    900
aattgcaact gacggaatcg gaaacggttc tttcttcgga cagttgtgaa ggtgctgcat    960
ggttgtcgtc agctcgtgcc gtgaggtgtc ggcttaagtg ccataacgag cgcaacccctt    1020
acgggtagtt accatcaggt tatgctgggg actctacccg gactgccgtc gtaagatgtg    1080
aggaaggtgg ggatgacgtc aaatcagcac gcccttacg tccggggcta cacacgtgtt    1140
acaatggggg gtacagaagg cagctacacg gcgacggtgt gctaatcccg aaagcctctc    1200
tcagttcgga ttgagtctg caacccgact ccatgaagct ggattcgcta gtaatcgcgc    1260
atcagccacg gcgcggtgaa tacgttcccg ggccttgtac acaccgcccg tcaagccatg    1320
aaagccgggg gtacctg                                                   1337

SEQ ID NO: 114         moltype = DNA   length = 1353
FEATURE                Location/Qualifiers
misc_feature           1..1353
                       note = I09
source                 1..1353
```

```
                      mol_type = unassigned DNA
                      organism = unidentified
SEQUENCE: 114
ttagcttgct aaggccgatg gcgaccggcg cacgggtgag taacgcgtat ccaacctgcc    60
ttacactctt ggacagcctt ctgaaaggga gattaataca agatgttatc atgagtaagc   120
attttcgcat gattaaaggt ttaccggtgt aagatgggga tgcgttccat tagatagtag   180
gcggggtaac ggcccaccta gtcttcgatg gatagggggt ctgagaggaa ggtcccccac   240
attggaactg agacacggtc caaactccta cgggaggcag cagtgaggaa tattggtcaa   300
tggacgagag tctgaaccag ccaagtagcg tgaaggatga aggttctatg gattgtaaac   360
ttcttttata cgggaataaa cgaatccacg cgtggatttt tgcatgtacc gtatgaataa   420
ggatcggcta actccgtgcc agcagccgcg gtaatacgga ggatccgagc gttatccgga   480
tttattgggt ttaaagggag cgtagatggg ttgttaagtc agttgtgaaa gtttgcggct   540
caaccgtaaa attgcaattg atactggcag tcttgagtac agttgaggta ggcggaattc   600
gtggtgtagc ggtgaaatgc ttagatatca cgaagaactc cgattgcgaa ggcagccttac  660
taacctgtaa ctgacattga tgctcgaaaa tgtgggtatc aaacaggatt agataccctg   720
gtagtccaca cggtaaacga tgaatactcg ctgtaggcga tataccggtct gcggccaagc   780
gaaagcatta agtattccac ctggggagta cgccggcaac ggtgaaactc aaaggaattg   840
acggggggcc gcacaagcgg aggaacatgt ggtttaattc gatgatacgc gaggaacctt   900
acccgggctt aaaattgcaac cgaatatggc ggaaacgcca tagctagcaa tagcggttgt   960
gaaggtgctg catggttgtc gtcagctcgt gccgtgaggt gtcggcttaa gtgccataac  1020
gagcgcaacc cttgccgata gttactaaca ggttatgctg aggactctgt cgggactgcc  1080
atcgtaagat gtgaggaagg tggggatgac gtcaaatcag cacggcccctt acgtccgggg  1140
ctacacacgt gttacaatgg ggggtacaga gggctgctac cacgcaagtg gatgccaatc  1200
ccaaaaacct ctctcagttc ggattgaagt ctgcaacccg acttcatgaa gctggattcg  1260
ctagtaatcg cgcatcagcc acggcgcggt gaatacgttc ccgggccttg tacacaccgc  1320
ccgtcaagcc atgggagccg ggggtacctg aag                                1353

SEQ ID NO: 115       moltype = DNA  length = 1350
FEATURE              Location/Qualifiers
misc_feature         1..1350
                     note = I10
source               1..1350
                     mol_type = unassigned DNA
                     organism = unidentified
SEQUENCE: 115
cttagcttgc taaggccgat ggcgaccggc gcacgggtga gtaacacgta tccaacctgc    60
cgtctactct tggacagcct tctgaaagga agattaatac aagatggcat catgagtccg   120
catgttcaca tgattaaagg tattccggta gacgatgggg atgcgttcca ttagatagta   180
ggcggggtaa cggcccacct agtcttcgat ggatagggtt tctgagagga aggtccccca   240
cattggaact gagacacggt ccaaactcct acgggaggca gcagtgagga atattggtca   300
atgggcgaga gcctgaacca gccaagtagc gtgaaggatg actgccctat gggttgtaaa   360
cttcttttat aaaggaataa agtcgggtat ggataccgt ttgcatgtac tttatgaata   420
aggatcggct aactccgtgc cagcagccgc ggtaatacgg aggatccgag cgttatccga   480
atttattggg tttaaaggga gcgtagatgg atgtttaagt cagttgtgaa agtttgcggc   540
tcaaccgtaa aattgcagtt gatactggat atcttgagtg cagttgaggc aggcggaatt   600
cgtggtgtag cggtgaaatg cttagatatc acgaagaact ccgattgcga aggcagcctg   660
ctaagctgca actgacattg aggctcgaaa gtgtgggtat caaacaggat tagataccct   720
ggtagtccac acggtaaacg atgaatactc gctgtttgcg atatactgca agcggccaag   780
cgaaagcgtt aagtattcca cctggggagt acgccggcaa cggtgaaact caaaggaatt   840
gacgggggcc cgcacaagcg gaggaacatg tggtttaatt cgatgatacg cgaggaacct   900
tacccgggct taaattgcag atgaattacg gtgaaagccg taagccgaca cgcatctgtg   960
aaggtgctgc atggttgtcg tcagctcgtg ccgtgaggtg tcggcttaag tgccataacg  1020
agcgcaaccc ttgttgtcag ttactaacag gttccgctga ggactctgac aagactgcca  1080
tcgtaagatg tgaggaaggt ggggatgacg tcaaatcagc acggccctta cgtccggggc  1140
tacacacgtg ttacaatggg gggtacagag ggccgctacc acgcgagtgg atgccaatcc  1200
caaaaacctc tctcagttcg gactggagtc tgcaacccga ctccacgaag ctggattcgc  1260
tagtaatcgc gcatcagcca cggcgcggt aatacgttcc cgggccttgt acacaccgcc  1320
cgtcaagcca tgggagccgg gggtacctga                                    1350

SEQ ID NO: 116       moltype = DNA  length = 1356
FEATURE              Location/Qualifiers
misc_feature         1..1356
                     note = I11
source               1..1356
                     mol_type = unassigned DNA
                     organism = unidentified
SEQUENCE: 116
tcttagcttg ctaaggctga tggcgaccgg cgcacgggtg agtaacacgt atccaacctg    60
ccgtctactc ttggccagcc ttctgaaagg aagattaatc caggatggga tcatgagttc   120
acatgtccgc atgattaaag gtattttccg gtagacgatg gggatgcgtt ccattagata   180
gtaggcgggg taacggccca cctagtcaac gatgataggg ggttctgaga ggaaggtccc   240
ccacattgga actgagacac ggtccaaact cctacgggag cagcagtga ggaatattgg   300
tcaatgggcg atggcctgaa ccagccaagt agcgtgaagg atgactgccc tatggggtgt   360
aaacttcttt tataaaggaa taaagtcggg tatggatacc cgtttgcatg tacttttatga   420
ataaggatcg gctaactccg tgccagcagc cgcggtaata cggaggatcc gagcgttatc   480
cggatttatt gggtttaaag gggagcgtaga tggatgttta gtcagttgt gaaagtttgc   540
ggctcaaccg taaaattgca gttgatactg gatgtcttga gtgcagttga ggcaggcgga   600
attcgtggtg tagcggtgaa atgcttagat atcacgaaga actccgattg cgaaggcagc   660
ctgctaagct gcaactgaca ttgaggctcg aaagtgtggg tatcaaacag gattagatac   720
```

```
cctggtagtc cacacggtaa acgatgaata ctcgctgttt gcatatacg gcaagcggcc    780
aagcgaaagc gttaagtatt ccacctgggg agtacgccgg caacggtgaa actcaaagga    840
attgacgggg gcccgcacaa gcggaggaac atgtggttta attcgatgat acgcgaggaa    900
ccttaccccgg gcttaaattg cactcgaatg atccggaaac ggttcagcta gcaatagcga   960
gtgtgaaggt gctgcatggt tgtcgtcagc tcgtgccgtg aggtgtcggc ttaagtgcca   1020
taacgagcgc aacccttgtt gtcagttact aacaggtgat gctgaggact ctgacaagac   1080
tgccatcgta agatgtgagg aaggtgggga tgacgtcaaa tcagcacggc ccttacgtcc   1140
ggggctacac acgtgttaca atgggggta cagagggccg ctaccacgcg agtggatgcc    1200
aatccctaaa acccctctca gttcggactg gagtctgcaa cccgactcca cgaagctgga   1260
ttcgctagta atcgcgcatc agccacggcg cggtgaatac gttcccgggc cttgtacaca   1320
ccgcccgtca agccatggga gccggggta cctgaa                              1356
```

| SEQ ID NO: 117 | moltype = DNA length = 1353 |
|---|---|
| FEATURE | Location/Qualifiers |
| misc_feature | 1..1353 |
| | note = I12 |
| variation | 6 |
| | note = n is a, c, g, or t |
| variation | 8 |
| | note = n is a, c, g, or t |
| source | 1..1353 |
| | mol_type = unassigned DNA |
| | organism = unidentified |

```
SEQUENCE: 117
tgtagnanta cagattgatg gcgaccggcg cacgggtgag taacgcgtat gcaacttacc    60
tatcagaggg ggatagcccg gcgaaagtcg gattaatacc ccataaaaca ggggtcccgc   120
atgggaatat ttgttaaaga ttcatcgctg atagataggc atgcgttcca ttaggcagtt   180
ggcgggggtaa cggcccacca aaccgacgat ggatagggt tctgagagga aggtcccccca   240
cattggtact gagacacgga ccaaactcct acggaggca gcagtgagga atattggtca    300
atggccgaga ggctgaacca gccaagtcgc gtgaaggaag aaggatctat ggtttgtaaa   360
cttcttttat aggggaataa agtgaggac gtgtcctttt ttgtatgtac cctatgaata    420
agcatcggct aactccgtgc cagcagccgc ggtaatacgg aggatgcgag cgttatccgg   480
atttattggg tttaaagggt gcgtaggtgg tgatttaagt cagcggtgaa agtttgtggc   540
tcaaccataa aattgccgtt gaaactgggt tacttgagtg tgtttgaggt aggcggaatg   600
cgtggtgtag cggtgaaatg catagatatc acgcagaact ccgattgcga aggcagctta   660
ctaaaccata actgacactg aagcacgaaa gcgtggggat caaacaggat tagataccct   720
ggtagtccac gcagtaaacg atgattacta ggagtttgcg atacaatgta agctctacag   780
cgaaagcgtt aagtaatcca cctggggagt acgccggcaa cggtgaaact caaaggaatt   840
gacgggggcc cgcacaagcg gaggaacatg tggtttaatt cgatgatacg cgaggaacct   900
tacccgggtt tgaacgtagt ctgaccggag tggaaacact ccttctagca atagcagatt   960
acgaggtgct gcatggttgt cgtcagctcg tgccgtgagg tgtcggctta agtgccataa  1020
cgagcgcaac ccttatcact agttactaac aggtgaagct gaggactctg gtgagactgc   1080
cagcgtaagc tgtgaggaag gtgggatga gtcaaatca ggcgccct tacatccgga      1140
gcgacacacg tgttacaatg gcatggacaa agggcagcta cctggcgaca ggatgctaat   1200
ctccaaacca tgtctcagtt cggatcgag tctgcaactc gactccgtga agctggattc    1260
gctagtaatc gcgcatcagc catggcgcgg tgaatacgtt cccgggcctt gtacacaccg   1320
cccgtcaagc catgggagcc ggggggtacct gaa                               1353
```

| SEQ ID NO: 118 | moltype = DNA length = 824 |
|---|---|
| FEATURE | Location/Qualifiers |
| misc_feature | 1..824 |
| | note = I13 |
| source | 1..824 |
| | mol_type = unassigned DNA |
| | organism = unidentified |

```
SEQUENCE: 118
ggcgaccggc gcacgggtga gtaacgcgta tgcaacttac ctatcagagg gggataaccc    60
ggcgaaagtc ggactaatac cgcatgaagc agggggcccg catggggata tttgctaaag   120
attcatcgct gatagatagg catgcgttcc attaggcagt tggcgggta acggcccaca    180
aaaccgacga tggataggg ttctgagagg aaggtccccc acattggtac tgagacacgg    240
accaaactcc tacgggaggc agcagtgagg aatattggtc aatggcgta agcctgaacc    300
agccaagtcg cgtgagggat gaaggttcta tggatcgtaa acctctttta agggaata    360
aagtgcggga cgtgtcctgt tttgtatgta ccttatgaat aaggatcggc taactccgtg   420
ccagcagccg cggtaatacg gaggatccga gcgttatccg gatttattgg tgttaaaggg   480
tgcgtaggcg gccttttaag tcagcggtga agtctgtgg ctcaaccata gaattgccgt    540
tgaaactggg ggcttgagt atgtttgagg caggcggaat gcgtggtgta gcggtgaaat    600
gcttagatat cacgcagaac cccgattgcg aaggcagcct gccaagccat gactgacgct   660
gatgcacgaa agcgtgggga tcaaacagga ttagataccc tggtagtcca cgcagtaaac   720
gatgatcact agctgtttgc gatacagtgt aagcggcaca gcgaaagcgt taagtgatcc   780
acctggggag tacgccggca acggtgaaac tcaaaggaat tgac                    824
```

| SEQ ID NO: 119 | moltype = DNA length = 1348 |
|---|---|
| FEATURE | Location/Qualifiers |
| misc_feature | 1..1348 |
| | note = I14 |
| source | 1..1348 |
| | mol_type = unassigned DNA |
| | organism = unidentified |

SEQUENCE: 119

```
gatagcaata tctatggtgg cgaccggcgc acgggtgcgt aacgcgtatg caacctacct   60
ttaacagggg gataacactg agaaattggt actaataccc cataatatca tagaaggcat  120
cttttatggt tgaaaattcc gatgttagat gatgggcatg cgttgtatta gctagttggt  180
ggggtaacgg ctcaccaagg cgacgataca taggggggact gagaggttaa ccccccacac  240
tggtactgag acacggacca gactcctacg ggaggcagca gtgaggaata ttggtcaatg  300
gacgcaagtc tgaaccagcc atgccgcgtg caggatgacg gctctatgag ttgtaaactc  360
tttttgtacg agggtaaacg cagatacgtg tatctgtctg aaagtatcgt acgaataagg  420
atcggctaac tccgtgccag cagccgcggt aatacgagg attcaagcgt tatccggatt  480
tattgggttt aaagggtgcg taggcggttt gataagttag aggtgaaatt tcggggctca  540
accctgaacg tgcctctaat actgttgagc tagagagtag ttgcggtagg cggaatgtat  600
ggtgtagcgg tgaaatgctt agagatcata cagaacaccg attgcgaagg cagcttacca  660
aactatatct gacgttgagg cacgaaagcg tggggagcaa acaggattag ataccctggt  720
agtccacgca gtaaacgatg ataactcgtt gtcggcgata cacagtcggt gactaagcga  780
aagcgataag ttatccaccct ggggagtacg ttcgcaagta tgaaactcaa aggaattgac  840
gggggcccgc acaagcggag gaacatgtgg tttaattcga tgatacgcga ggaaccttac  900
ccgggcttga aagttagcga cgattcttga aagaggattt cccttcgggg cgcgaaacta  960
ggtgctgcat ggttgtcgtc agctcgtgcc gtgaggtgtc gggttaagtc ccataacgag 1020
cgcaaccct accgttagtt gccatcaggt gaagctgcgg actctggcgg gactgccggt 1080
gtaagccgag aggaaggtgg ggatgacgtc aaatcagcac ggcccttacg tccggggcta 1140
cacacgtgtt acaatggtag gtacagaggg cagctaccca gcgatgggat gcgaatctcg 1200
aaagcctatc tcagttcgga ttggaggctg aaacccgcct ccatgaagtt ggattcgcta 1260
gtaatcgcgc atcagccatg gcgcggtgaa tacgttcccg ggccttgtac acaccgcccg 1320
tcaagccatg ggagccgggg gtgcctga                                     1348

SEQ ID NO: 120           moltype = DNA   length = 1337
FEATURE                  Location/Qualifiers
misc_feature             1..1337
                         note = I15
variation                838..839
                         note = n is a, c, g, or t
source                   1..1337
                         mol_type = unassigned DNA
                         organism = unidentified
SEQUENCE: 120
ttctttgctg gcgaccggcg cacgggtgag taacacgtat ccaacctgcc gatgactcgg   60
ggatagcctt tcgaaagaaa gattaatacc cgatggtata tctgaaaggc atctttcagc  120
tattaaagaa tttcggtcat tgatggggat gcgttccatt aggttgttgg cggggtaacg  180
gcccaccaag ccatcgatgg ataggggttc tgagaggaag gtcccccaca ttggaactga  240
gacacggtcc aaactcctac gggaggcagc agtgaggaat attggtcaat ggacgagagt  300
ctgaaccagc caagtagcgt gaaggatgac tgccctatgg gttgtaaact tcttttatac  360
gggaataaag ttgggcacgt gtgcctttt gtatgtaccg tatgaataag gatcggctaa  420
ctccgtgcca gcagccgcgg taatacgagg atccgagcg ttatccggat ttattgggtt  480
taaagggagt gtaggcggat gcttaagtca gttgtgaaa tttgcggctc aaccgtaaaa  540
ttgcagttga tactgggtgt cttgagtaca gtagaggcag gcggaattcg tggtgtagcg  600
gtgaaatgct tagatatcac gaagaactcc gattgcgaag gcagcttgct ggactgtaac  660
tgacgctgat gctcgaaagt gtgggtatca aacaggatta gataccctgg tagtccacac  720
agtaaacgat gaatactcgc tgtttgcgat atacagtaag gcccaagcg aaagcgttaa  780
gtattccacc tggggagtac gccggcaacg tgaaactcaa aggaattga cgggggcnng  840
cacaagcgga ggaacatgtg gtttaattcg atgatacgcg aggaaccttac ccgggcttaa  900
aattgcaaat gaatgttctg gaaacagatc agccgcaagg catttgtgaa ggtgctgcat  960
ggttgtcgtc agctcgtgcc gtgaggtgtc gcttaagtca ccataacgag cgcaaccctt 1020
atcgatagtt accatcaggt tatgctgggg actctgtcga gactgccgtc gtaagatgtg 1080
aggaaggtgg ggatgacgtc aaatcagcac ggcccttacg tccggggcta cacacgtgtt 1140
acaatggggg gtacagaagg cagctacacg gcgacgtgat gctaatccct aaaacctctc 1200
tcagttcgga ttggagtctg caacccgact ccatgaagct ggattcgcta gtaatcgcgc 1260
atcagccacg gcgcggtgaa tacgttcccg ggccttgtac acaccgcccg tcaagccatg 1320
aaagccgggg gtacctg                                                 1337

SEQ ID NO: 121           moltype = DNA   length = 1343
FEATURE                  Location/Qualifiers
misc_feature             1..1343
                         note = I16
source                   1..1343
                         mol_type = unassigned DNA
                         organism = unidentified
variation                5
                         note = n is a, c, g, or t
variation                7
                         note = n is a, c, g, or t
variation                110..113
                         note = n is a, c, g, or t
variation                337..338
                         note = n is a, c, g, or t
variation                1170
                         note = n is a, c, g, or t
SEQUENCE: 121
cttgnanact gaaagatggcg accggcgcac gggtgagtaa cacgtatcca acctgccgat   60
aactccggaa tagcctttcg aaagaaagat taataccgga tagcatacgn nnntcgcatg  120
atattttat taaagaattt cggttatcga tggggatgcg ttccattagt tgttggcgg   180
```

```
ggtaacggcc caccaagact acgatggata ggggttctga gaggaaggtc ccccacattg   240
gaactgagac acggtccaaa ctcctacggg aggcagcagt gaggaatatt ggtcaatggg   300
cgagagcctg aaccagccaa gtagcgtgaa ggatgannge tctatgggtc gtaaacttct   360
tttatatggg aataaagttt tccacgtgtg aattttgta tgtaccatat gaataaggat   420
cggctaactc cgtgccagca gccgcggtaa tacggaggat ccgagcgtta tccggattta   480
ttgggtttaa agggagcgta ggtggattgt taagtcagtt gtgaaagttt gcggctcaac   540
cgtaaaattg cagttgaaac tggcagtctt gagtacagta gaggtgggcg gaattcgtgg   600
tgtagcggtg aaatgcttag atatcacgaa gaactccgat tgcgaaggca gctcactaga   660
ctgtcactga cactgatgct cgaaagtgtg ggtatcaaac aggattagat accctggtag   720
tccacacagt aaacgatgaa tactcgctgt ttgcgatata cagtaagcgg ccaagcgaaa   780
gcattaagta ttccacctgg ggagtacgcc ggcaacggtg aaactcaaag gaattgacgg   840
gggcccgcac aagcggagga acatgtggtt taattcgatg atacgcgagg aaccttaccc   900
gggcttaaat tgcaacagaa tatattgaaa acagtatagc cgtaaggctg ttgtgaaggt   960
gctgcatggt tgtcgtcagc tcgtgccgtg aggtgtcggc ttaagtgcca taacgagcgc  1020
aacccttatc tttagttact aacaggtcat gctgaggact ctagagagac tgccgtcgta  1080
agatgtgagg aaggtgggga tgacgtcaaa tcagcacggc ccttacgtcc ggggctacac  1140
acgtgttaca atgggggta cagaaggcan ctacctggtg acaggatgct aatcccaaaa  1200
acctctctca gttcggatcg aagtctgcaa cccgacttcg tgaagctgga ttcgctagta  1260
atcgcgcatc agccatgcg cggtgaatac gttcccgggc cttgtacaca ccgcccgtca  1320
agccatgaaa gccgggggta cct                                         1343

SEQ ID NO: 122         moltype = DNA  length = 1335
FEATURE                Location/Qualifiers
misc_feature           1..1335
                       note = I17
source                 1..1335
                       mol_type = unassigned DNA
                       organism = unidentified
SEQUENCE: 122
gggtggcgac cggcgcacgg gtgcgtaacg cgtatgcaac ctacccataa caggggata    60
acactgagaa attggtacta atacccata acatcagaac cggcatcggt tttggttgaa   120
aactccggtg gttatggatg ggcatgcgtt gtattagctg gttggtgagg taacggctca   180
ccaaggcaac gatacatagg gggactgaga ggttaacccc ccacattggt actgagacac   240
ggaccaaact cctacgggag gcagcagtga ggaatattgg tcaatggacg caagtctgaa   300
ccagccatgc cgcgtgcagg aagacggctc tatgagttgt aaactgcttt tgtacgaggg   360
taaacgcttc tacgtgtagg agcctgaaag tatcgtacga ataaggatcg gctaactccg   420
tgccagcagc cgcggtaata cggaggatcc aagcgttatc cggatttatt gggtttaaag   480
ggtgcgtagg cggtttgata agttagaggt gaaataccgg tgcttaacac cggaactgcc   540
tctaatactg ttgaactaga gagtagttgc ggtaggcgga atgtatggtg tagcggtaa   600
atgcttagag atcatacaga acaccgattg cgaaggcagc ttaccaaact atatctgacg   660
ttgaggcacg aaagcgtggg gagcaaacag gattagatac cctggtagtc cacgcagtaa   720
acgatgataa ctcgctgtcg gcgatacaca gtcggcggct aagcgaaagc gataagttat   780
ccacctgggg agtacgttcg caagaatgaa actcaaagga attgacgggg gcccgcacaa   840
gcggaggaac atgtggttta attcgatgat acgcgaggaa ccttacccgg gcttgaaagt   900
tactgacgat tctggaaaca ggattccct tcggggcagg aaactaggtg ctgcatggtt   960
gtcgtcagct cgtgccgtga ggtgtcgggt taagtcccat aacgagcgca acccctaccg  1020
ttagttgcca tcaggtcaag ctgggcactc tggcgggact gccggtgtaa gccgagagga  1080
aggtggggat gacgtcaaat cagcacggcc cttacgtccg gggctacaca cgtgttacaa  1140
tggtaggtac agagggcagc tacccagtga tgggatgcga atctcgaaag cctatctcag  1200
ttcggatcgg aggctgaaac ccgcctccgt gaagttggat cgctagtaa tcgcgcatca  1260
gccatgcgc ggtgaatacg ttcccgggcc ttgtacacac cgcccgtcaa gccatggaag  1320
ctggggtgc ctgaa                                                    1335

SEQ ID NO: 123         moltype = DNA  length = 1309
FEATURE                Location/Qualifiers
misc_feature           1..1309
                       note = I18
source                 1..1309
                       mol_type = unassigned DNA
                       organism = unidentified
SEQUENCE: 123
cgtatgcaac ctgcccgata ccggggtata gccatggaa acgtggatta acaccccata    60
gtacttttat cctgcatggg atgtgagtta aatgttcaag gtatcggatg ggcatgcgtc   120
ctattagtta gttggcgggg taacagccca ccaagacgat gataggtagg ggttctgaga   180
ggaaggtccc ccacattgga actgagacac ggtccaaact cctacgggag gcagcagtga   240
ggaatattgg tcaatggacg taagtctgaa ccagccaagt cgcgtgaggg aagactgccc   300
tatgggttgt aaacctcttt tataaggaa gaataagttc tacgtgtaga atgatgcctg   360
taccttatga ataagcatcg gctaactccg tgccagcagc cgcggtaata cggaggatgc   420
gagcgttatc cggatttatt gggtttaaag ggtgcgtagg cggtttatta agttagtgt   480
taaatatttg agctaaactc aattgtgcca ttaatactgg taaactgag tacagacgag   540
gtaggcggaa taagttaagt agcggtgaaa tgcatagata taacttagaa ctccgatagc   600
gaaggcagct taccagactg taactgacgc tgatgcacga gagcgtgggt agcgaacagg   660
attagatacc ctggtagtcc acgccgtaaa cgatgctcac tggttctgtg cgatatattg   720
tacggatta agcgaaagta ttaagtgagc cacctgggaa gtacgatcga   780
ctcaaaggaa ttgacggggg cccgcacaag cggaggaaca tgtggtttaa ttcgatgata   840
cgcgaggaac cttacctggg tttaaatggg aaatgtcgta tttggaaaca gatattctct   900
tcggagcgtt tttcaaggtg ctgcatggtt gtcgtcagct cgtgccgtga ggtgtcgggt  960
taagtcccat aacgagcgca acccttaccg ttagttgcta gcatgtaatg atgagcactc  1020
taacgggact gccaccgtaa ggtgagagga aggcgggat gacgtcaaat cagcacggcc  1080
```

```
cttacaccca gggctacaca cgtgttacaa tggccggtac agagggccgc taccaggtga 1140
ctggatgcca atctcaaaag ccggtcgtag ttcggattgg agtctgtaac ccgactccat 1200
gaagttggat tcgctagtaa tcgcgcatca gccatggcgc ggtgaatacg ttcccgggcc 1260
ttgtacacac cgcccgtcaa gccatggaag ccggggggtgc ctgaagtcc            1309
```

```
SEQ ID NO: 124            moltype = DNA   length = 1339
FEATURE                   Location/Qualifiers
misc_feature              1..1339
                          note = I19
source                    1..1339
                          mol_type = unassigned DNA
                          organism = unidentified
variation                 10
                          note = n is a, c, g, or t
variation                 124..125
                          note = n is a, c, g, or t
variation                 183
                          note = n is a, c, g, or t
variation                 190..191
                          note = n is a, c, g, or t
variation                 911
                          note = n is a, c, g, or t
SEQUENCE: 124
agagagcttn ctttctcgag cgagtggcga acgggtgagt aacgcgtgag gaacctgcct  60
caaagagggg gacaacagtt ggaaacgact gctaataccg cataagccca cgggtcggca 120
tcgnncagag ggaaaaggag caatccgctt tgagatggcc tcgcgtccga ttagctagtt 180
ggngaggtan nggcccacca aggcgacgat cggtagccgg actgagaggt tgaacggcca 240
cattgggact gagacacggc ccagactcct acgggaggca gcagtgggga atattgcaca 300
atgggggaaa ccctgatgca gcgacgccgc gtggaggaag aaggtcttcg gattgtaaac 360
tcctgttgtt ggggaagata atgacggtac ccaacaagta agtgacggct aactacgtgc 420
cagcagccgc ggtaaaacgt aggtcacaag cgttgtccgg aattactggg tgtaaaggga 480
gcgcaggcgg gaagacaagt tggaagtgaa atctatgggc tcaacccata aactgctttc 540
aaaactgttt ttcttgagta gtgcagaggt aggcggaatt cccggtgtag cggtggaatg 600
cgtagatatc gggaggaaca ccagtggcga aggcggccta ctgggcacca actgacgctg 660
aggctcgaaa gtgtgggtag caaacaggat tagataccct ggtagtccac accgtaaacg 720
atgattacta ggtgttggag gattgacccc ttcagtgccg cagttaacac aataagtaat 780
ccacctgggg agtacgaccg caaggttgaa actcaaagga attgacgggg cccgcacaa 840
gcagtggagt atgtggttta attcgacgca acgcgaagaa ccttaccaag tcttgacatc 900
ccttgacaga natagaaata tgttttctct tcggagcaag gagacaggtg gtgcatggtt 960
gtcgtcagct cgtgtcgtga gatgttgggt taagtcccgc aacgagcgca acccttatgg 1020
tcagttacta cgcaagagga ctctggccag actgccgttg acaaaacgga ggaaggtggg 1080
gatgacgtca atcatcatgc cctttatga cttgggctac acacgtacta caatggcgtt 1140
aaacaaagag aagcaagacc gcgaggtgga gcaaaactca aaaacaagt cccagttcgt 1200
actgcaggct gcaactcgcc tgcacgaagt cggaattgct agtaatcgtg gatcagcatg 1260
ccacggtgaa tacgttcccg ggccttgtac acaccgcccg tcacaccatg agagccgggg 1320
ggacccgaag tcggtagtc                                             1339
```

```
SEQ ID NO: 125            moltype = DNA   length = 1339
FEATURE                   Location/Qualifiers
misc_feature              1..1339
                          note = I20
variation                 192
                          note = n is a, c, g, or t
variation                 205..206
                          note = n is a, c, g, or t
variation                 1337
                          note = n is a, c, g, or t
source                    1..1339
                          mol_type = unassigned DNA
                          organism = unidentified
SEQUENCE: 125
gagagagctt gctttctcga gcgagtggcg aacgggtgag taacgcgtga ggaacctgcc  60
tcaaagaggg ggacaacagt tggaaacgac tgctaataccc gcataagccc acgggtcggc 120
atcgaccaga gggaaaagga gtaatccgct ttgagatggc ctcgcgtccg attagctagt 180
tggtgaggta anggcccacc aaggnnacga tcggtagccg gactgagagg ttgaacggcc 240
acattgggac tgagacacgg cccagactcc tacgggaggc agcagtgggg aatattgcac 300
aatgggggaa accctgatgc agcgacgccg cgtggaggaa gaaggtcttc ggattgtaaa 360
ctcctgttgt tgggaagata atgacggta cccaacaagt aagtgacggc taactacgtg 420
ccagcagccg cggtaaaacg taggtcacaa gcgttgtccg gaattactgg gtgtaaaggg 480
agcgcaggcg ggaagacaag ttggaagtga aatctatggg ctcaacccat aaactgcttt 540
caaaactgtt tttcttgagt agtgcagagg taggcggaat tccggtgta gcggtggaat 600
gcgtagatat cgggaggaac accagtggcg aaggcggcct actgggcacc aactgacgct 660
gaggctcgaa agtgtgggta gcaaacagga ttagataccc tggtagtcca ccgtaaac 720
gatgattact aggtgttgga ggattgaccc cttcagtgcc gcagttaaca caataagtaa 780
tccacctggg gagtacgacc gcaaggttga aactcaaagg aattgacggg gcccgcaca 840
agcagtggag tatgtggttt aattcgacgc aacgcgaaga accttaccaa gtcttgacat 900
cccttgacag acatagaaat atgttttctc ttcggagcaa ggagacaggt ggtgcatggt 960
tgtcgtcagc tcgtgtcgtg agatgttggg ttaagtcccg caacgagcgc aacccttatg 1020
gtcagttact acgcaagagg actctggcca gactgccgtt gacaaaacgg aggaaggtgg 1080
```

```
ggatgacgtc aaatcatcat gcccttatg acttgggcta cacacgtact acaatggcgt   1140
taaacaaaga gaagcaagac cgcgaggtgg agcaaaactc agaaacaacg tcccagttcg   1200
gactgcaggc tgcaactcgc ctgcacgaag tcggaattgc tagtaatcgt ggatcagcat   1260
gccacggtga atacgttccc gggccttgta cacaccgccc gtcacaccat gagagccggg   1320
gggacccgaa gtcggtngt                                                 1339
```

```
SEQ ID NO: 126          moltype = DNA   length = 1354
FEATURE                 Location/Qualifiers
misc_feature            1..1354
                        note = I21
variation               184..187
                        note = n is a, c, g, or t
source                  1..1354
                        mol_type = unassigned DNA
                        organism = unidentified
variation               573..574
                        note = n is a, c, g, or t
variation               752..755
                        note = n is a, c, g, or t
variation               1175..1176
                        note = n is a, c, g, or t
SEQUENCE: 126
cattgagact tcggtggatt tgatctattt ctagtggcgg acgggtgagt aacgcgtggg     60
taacctgcct tatacagggg gataacagtc agaaatggct gctaataccg cataagcgca   120
cagagctgca tggctcagtg tgaaaaactc cggtggtata agatggaccc gcgttggatt   180
agcnnnntgg tggggtaacg gcccaccaag gcgacgatcc atagccggcc tgagagggtg   240
aacggccaca ttgggactga gacacgcccg agactcctac gggaggcagc agtgggaat    300
attgcacaat gggggaaacc ctgatgcagc gacgccgcgt gaaggaagaa gtatctcggt   360
atgtaaactt ctatcagcag gaagatagt gacggtacct gactaagaag ccccggctaa   420
ctacgtgcca gcagccgcgg taatacgtag ggggcaagcg ttatccggat ttactgggtg   480
taaagggagc gtagacggtg tgcaagtct gatgtgaaag catgggctc aacctgtgga   540
ctgcattgga aactgtcata cttgagtgcc ggnngggtaa gcggaattcc tagtgtagcg   600
gtgaaatgcg tagatattag gaggaacacc agtggcgaag gcggcttact ggacggtaac   660
tgacgttgag gctcgaaagc gtggggagca aacaggatta gataccctgg tagtccacgc   720
cgtaaacgat gaatactagg tgtcggggag cnnnnctctt cggtgccgtc gcaaacgcag   780
taagtattcc acctggggag tacgttcgca agaatgaaac tcaaaggaat tgacgggggac   840
ccgcacaagc ggtggagcat gtggtttaat tcgaagcaac gcgaagaacc ttaccaagtc   900
ttgacatccg cctgaccgat ccttaaccgg atctttcctt cgggacaggc gagacaggtg   960
gtgcatggtt gtcgtcagct cgtgtcgtga gatgttggtt taagtcccgc aacgagcgca  1020
accctatcc tcagtagcca gcatttaagg tgggcactct ggggagactg ccagggataa  1080
cctgagggaa ggcggggatg acgtcaaagt catcatgccc ttatgatttg gctacacac   1140
gtgctacaat ggcgtaaaca aagggaagcg agatnngag atggagcaaa tcccaaaaat  1200
aacgtcccag ttcggactgt agtctgcaac ccgactacga caagctggaa tcgctagtaa  1260
tcgcggatca gaatgccgcg gtgaatacgt tcccgggtct tgtacacacc gcccgtcaca  1320
ccatgggagt cagtaacgcc cgaagtcagt gacc                              1354
```

```
SEQ ID NO: 127          moltype = DNA   length = 1264
FEATURE                 Location/Qualifiers
misc_feature            1..1264
                        note = I22
variation               144..145
                        note = n is a, c, g, or t
source                  1..1264
                        mol_type = unassigned DNA
                        organism = unidentified
SEQUENCE: 127
ttacttggat ttcttcggaa tgacgagtat tgtgactgag cggcggacgg gtgagtaacg     60
cgtgggtaac ctgcctcata caggggggata acagttagaa atgactgcta ataccgcata   120
agaccacagc accgcatggt gcannggtaa aaactccggt ggtatgagat ggacccgcgt   180
ctgattagct ggttggtggg gtaacggcct accaaggcga cgatcagtag ccggcctgag   240
agggcgaccg gccacattgg gactgagaca cggcccaaac tcctacggga ggcagcagtg   300
gggaatattg cacaatgggg gaaaccctga tgcagcgacg ccgcgtgaag gaagaagtat   360
ttcggtatgt aaacttctat cagcagggaa gaaaatgacg gtacctgact aagaagcccc   420
ggctaactac gtgccagcag ccgcggtaat acgtaggggg caagcgttgt ccggaatttac   480
gagaggtaag cggaattcct agtgtagcgg tgaaatgcgt agatattagg aggaacacca   540
gtggcgaagg cggcttactg gacgatgact gacgttgagg ctcgaaagcg tggggagcaa   600
acaggattag ataccctggt agtccacgcc gtaaacgatg actactaggt gtcgggtggc   660
aaagccattc ggtgccgcag caaacgcaat aagtagtcca cctggggagt acgttcgcaa   720
gaatgaaact caaaggaatt gacgggggacc cgcacaagcg gtggagcatg tgggtttaatt   780
cgaagcaacg cgaagaacct tacctgtctc tgacatcccg gtgaccgctc cgtaatggga   840
gcttttcttc ggaacaccgg agacaggtgg tgcatggttg tcgtcagctc gtgtcgtgag   900
atgttgggtt aagtcccgca acgagcgcaa ccctatcttc agtagccag cggtttggcc   960
gggcactctg gagagactgc caggataac ctggaggaag gtgggatga cgtcaaatca  1020
tcatgcccct tatgagcagg gctacacacg tgctacaatg gcgtaaacaa agggaggcga  1080
actcgcgagg gtaagcaaat cccaaaaata acgtctcagt tcggattgta gtctgcaact  1140
cgactacatg aagctggaat cgctagtaat cgcgaatcag aatgtcgcgg tgaatacgtt  1200
cccgggtctt gtacacaccg cccgtcacac catgggagtc agtaacgccc gaagtcagtg  1260
accc                                                                1264
```

| SEQ ID NO: 128 | moltype = DNA   length = 1340 |
| --- | --- |
| FEATURE | Location/Qualifiers |
| misc_feature | 1..1340 |
| | note = I23 |
| source | 1..1340 |
| | mol_type = unassigned DNA |
| | organism = unidentified |

SEQUENCE: 128

```
gagaagcttg cttttctgat ctagtggcgg acgggtgagt aacacgtgag caatctgcct    60
ttcagagggg gataccgatt ggaaacgatc gttaataccg cataatataa ttgaaccgca   120
tgatttgatt atcaaagatt tatcgctgaa agatgagctc cgtctgatt agctagttgg    180
taaggtaacg gcttaccaag gcgacgatca gtagccggac tgagaggttg atcgccaca    240
ttgggactga gacacggccc agactcctac gggaggcagc agtggggaat attgcacaat   300
ggaggaaact ctgatgcagc gatgccgcgt gagggaagaa ggttttagga ttgtaaacct   360
ctgtcttcag ggacgaaaaa tgacggtacc tgaggaggaa gctccggcta actacgtgcc   420
agcagccgcg gtaatacgta gggagcgagc gttgtccgga attactgggt gtaaagggag   480
cgtaggcggg atcgcaagtc agatgtgaaa actatgggct taacccataa actgcatttg   540
aaactgtggt tcttgagtga agtagaggta agcggaattc ctagtgtagc ggtgaaatgc   600
gtagatatta ggaggaacat cagtggcgaa ggcggcttac tgggctttaa ctgacgctga   660
ggctcgaaag cgtggggagc aaacaggatt agataccctg gtagtccacg ccgtaaacga   720
tgattactag gtgtgggggg actgaccccct tccgtgccgc agcaaacgca ataagtaatc   780
caccctggga gtacgaccgc aaggttgaaa ctcaaaggaa ttgacggggg cccgcacaag   840
cagtggagta tgtggattaa ttcgaagcaa cgcgaagaac cttaccaggt cttgacatcg   900
tatgcatagc tcagagatga gtgaaatctc ttcggagaca tatagacagg tggtgcatgg   960
ttgtcgtcag ctcgtgtcgt gagatgttgg gttaagtccc gcaacgagcg caacccttac  1020
tgttagttgc tacgcaagag cactctagca ggactgccgt tgcaaaacga gaggaaggtg  1080
gggatgacgt caaatcatca tgccccttat gacctgggcc tcacacgtac tacaatggct  1140
gtcaacagag ggatgcaaag ccgcgaggtg gagcgaaccc ctaaaagcag tcttagttcg  1200
gattgtaggc tgcaacccgc ctacatgaag tcggaattgc tagtaatcgc agatcagcat  1260
gctgcggtga atacgttccc gggccttgta cacaccgccc gtcacgccat gggagtcggt  1320
aacacccgaa gcctgtagtc                                             1340
```

| SEQ ID NO: 129 | moltype = DNA   length = 1337 |
| --- | --- |
| FEATURE | Location/Qualifiers |
| misc_feature | 1..1337 |
| | note = I24 |
| variation | 53..54 |
| | note = n is a, c, g, or t |
| variation | 113..115 |
| | note = n is a, c, g, or t |
| source | 1..1337 |
| | mol_type = unassigned DNA |
| | organism = unidentified |
| variation | 123..125 |
| | note = n is a, c, g, or t |
| variation | 1155..1156 |
| | note = n is a, c, g, or t |
| variation | 1336 |
| | note = n is a, c, g, or t |

SEQUENCE: 129

```
agagagcttg ctttctcgag cgagtggcga acgggtgagt aacgcgtgag gannctgcct    60
caaagagggg gacaacagtt ggaaacgact gctaataccg cataagccca cgnnccgca   120
tgnnncagag ggaaaaggag taatccgctt tgagatggcc tcgcgtccga ttagctagtt   180
ggtgaggtaa cggcccacca aggcgacgat cggtagccgg actgagaggt tgaacggcca   240
cattgggact gagacacggc ccagactcct acgggaggca gcagtgggga atattgcaca   300
atggggggaaa ccctgatgca gcgacgccgc gtgaggaag aaggtcttcg gattgtaaac   360
tcctgttgtt ggggaagata atgacggtac caacaagga agtgacggct aactacgtgc   420
cagcagccgc ggtaaaacgt aggtcacaag cgttgtccgg aattactggg tgtaaaggga   480
gcgcaggcgg gaagacaagt tggaagtgaa atctatgggc tcaacccata aactgctttc   540
aaaactgttt tcttgagta gtgcagaggt aggcggaatt cccggtgtag cggtggaatg   600
cgtagatatc gggaggaaca ccagtggcga aggcggccta ctgggcacca actgacgctg   660
aggctcgaaa gtgtgggtag caaacaggat tagataccct ggtagtccac accgtaaacg   720
atgattacta ggtgttggag gattgaccccc ttcagtgccg cagttaacac aataagtaat   780
ccacctggga agtacgaccg caaggttgaa actcaaagga attgacgggg gcccgcacaa   840
gcagtgcagt atgtggttta attcgacgca acgcgaagaa ccttaccaag tcttgacatc   900
ccttgacaga catagaaata tgtaatctct tcggagcaag agacaggtg gtgcatggtt   960
gtcgtcagct cgtgtcgtga gatgttgggt taagtcccgc aacgagcgca accttatgg  1020
tcagttacta cgcaaggaga ctctggccag actgccgttg acaaaacgga ggaaggtggg  1080
gatgacgtca aatcatcatg cccttttatga cttgggctac acacgtacta caatggccg  1140
aaacaaagag aagcnngacc gcgaggtgga gcaaaactca gaaacaacgt cccagttcgg  1200
actgcaggct gcaactcgcc tgcacgaagt cggaattgct agtaatcgtg gatcagcatg  1260
ccacggtgaa tacgttcccg ggccttgtac acaccgcccg tcacaccatg agagccgggg  1320
ggacccgaag tcggtng                                                1337
```

| SEQ ID NO: 130 | moltype = DNA   length = 1353 |
| --- | --- |
| FEATURE | Location/Qualifiers |
| misc_feature | 1..1353 |
| | note = I25 |
| variation | 570..572 |

-continued

```
                        note = n is a, c, g, or t
source                  1..1353
                        mol_type = unassigned DNA
                        organism = unidentified
SEQUENCE: 130
gattcttcgg atgaagactt ttgtgactga gcggcggacg ggtgagtaac gcgtgggtaa    60
cctgcctcat acagggggat aacagttaga aatgactgct aataccgcat aagaccacgg   120
taccgcatgg tacagtggta aaaactccgg tggtatgaga tggacccgcg tctgattagg   180
tagttggtgg ggtaacggcc taccaagccg acgatcagta gccgacctga gagggtgacc   240
ggccacattg ggactgagac acggcccaga ctcctacggg aggcagcagt ggggaatatt   300
gcacaatgga ggaaactctg atgcagcgac gccgcgtgaa ggatgaagta tttcggtatg   360
taaacttcta tcagcaggga agaaaatgac ggtacctgac taagaagccc ggctaacta    420
cgtgccagca gccgcggtaa tacgtagggg gcaagcgtta tccggattta ctgggtgtaa   480
agggagcgta gacggcacgg caagccagat gtgaaagccc gggctcaac ccccgggactg   540
catttggaac tgctgagcta gagtgtcggn nnggcaagtg gaattcctag tgtagcggtg   600
aaatgcgtag atattaggag gaacaccagt ggcgaaggcg gcttgctgga cgatgactga   660
cgttgaggct cgaaagcgtg gggagcaaac aggattagat accctggtag tccacgccgt   720
aaacgatgac tgctaggtgt cgggtggcaa agccattcgt tgccgcagct aacgcaataa   780
gcagtccacc tggggagtac gttcgcaaga atgaaactca aaggaattga cggggacccg   840
cacaagcggt ggagcatgtg gtttaattcg aagcaacgcg aagaaccttta cctgatcttg   900
acatcccgat gaccgcttcg taatggaagc ttttcttcgg aacatcggtg acaggtggtg   960
catggttgtc gtcagctcgt gtcgtgagat gttgggttaa gtcccgcaac gagcgcaacc  1020
cctatcttca gtagccagca ggttaagctg gcactctgg agagactgcc agggataacc   1080
tggaggaagg tggggatgac gtcaaatcat catgcccctt atgaccaggg ctacacacgt  1140
gctacaatgg cgtaaacaaa gagaagcgaa ctcgcgaggg taagcaaatc tcaaaataa   1200
cgtctcagtt cggattgtag tctgcaactc gactacatga agctgaaatc gctagtaatc  1260
gcagatcaga atgctgcggt gaatacgttc ccgggtcttg tacacaccgc ccgtcacacc  1320
atgggagtca gtaacgcccg aagtcagtga ccc                                1353

SEQ ID NO: 131             moltype = DNA  length = 1361
FEATURE                    Location/Qualifiers
misc_feature               1..1361
                           note = I26
variation                  9
                           note = n is a, c, g, or t
variation                  939..940
                           note = n is a, c, g, or t
variation                  1052..1053
                           note = n is a, c, g, or t
variation                  1357
                           note = n is a, c, g, or t
source                     1..1361
                           mol_type = unassigned DNA
                           organism = unidentified
SEQUENCE: 131
cttaagtttng attcttcgga tgaagactt tgtgactgag cggcggacgg gtgagtaacg    60
cgtgggtaac ctgcctcata caggggata acagttagaa atggctgcta ataccgcata   120
agaccacagt actgcatggt acagtggtaa aaactccggt ggtatgagat ggacccgcgt   180
ctgattaggt agttggtgag gtaacggcca ccaagccga cgatcagtag ccgacctgag   240
agggtgaccg gccacattgg gactgagaca cggcccagac tcctacggga ggcagcagtg   300
gggaatattg cacaatgggc gaaagcctga tgcagcgacg ccgcgtgaag gatgaagtat   360
ttcggtatgt aaacttctat cagcagggaa gaaaatgacg gtacctgact aagaagcccc   420
ggctaactac gtgccagcag ccgcggtaat acgtaggggg caagcgttat ccggatttac   480
tgggtgtaaa gggagcgtag acggctgtgc aagtctgaag tgaaaggcat gggctcaacc   540
tgtggactgc tttggaaact gtgcagctag agtgtcggaa aggtaagtgg aattcctagt   600
gtagcggtga aatgcgtaga tattaggagg aacaccagtg gcgaaggcgg cttactggac   660
gatgactgac gttgaggctc gaaagcgtgg ggagcaaaca ggattagata ccctggtagt   720
ccacgccgta aacgatgact gctaggtgtc gggtagcaaa gctattcggt gccgcagcta   780
acgcaataag cagtccacct ggggagtacg ttcgcaagaa tgaaactcaa aggaattgac   840
ggggacccgc acaagcggtg gagcatgtgg tttaattcga agcaacgcga agaaccttac   900
ctgatcttga catcccgatg accgcttcgt aatggaagnn tttcttcgga acatcggtga   960
caggtggtgc atggttgtcg tcagctcgtg tcgtgagatg ttgggttaag tcccgcaacg  1020
agcgcaaccc ttatcttcag tagccagcat nnggatggg cactctggag agactgccag  1080
ggataacctg gaggaaggtg gggatgacgt caaatcatca tgccccttat gaccagggct  1140
acacacgtgc tacaatggcg taaacaaagg gaagcagagc gcgaggccg agcaaatctc   1200
aaaaataacg tctcagttcg gattgtagtc tgcaactcga ctacatgaag ctggaatcgc  1260
tagtaatcgc agatcagaat gctgcggtga atacgttccc gggtcttgta cacaccgccc  1320
gtcacaccat gggagtcagt aacgcccgaa gtcagtnacc c                       1361

SEQ ID NO: 132             moltype = DNA  length = 1345
FEATURE                    Location/Qualifiers
misc_feature               1..1345
                           note = I27
source                     1..1345
                           mol_type = unassigned DNA
                           organism = unidentified
SEQUENCE: 132
tttcttcgga actgaagatt tggtgattga gtggcggacg ggtgagtaac gcgtgggtaa    60
cctgccctgt acaggggat aacagtcaga atgactgct aataccgcat aagaccacag   120
```

```
caccgcatgg tgcaggggta aaaactccgg tggtacagga tggacccgcg tctgattagc    180
tggttggtga ggtaacggct caccaaggcg acgatcagta gccggcttga gagagtgaac    240
ggccacattg ggactgagac acggcccaaa ctcctacggg aggcagcagt ggggaatatt    300
gcacaatggg ggaaacctg atgcagcgac gccgcgtgag tgaagaagta tctcggtatg    360
taaagctcta tcagcaggga agaaaatgac ggtacctgac taagaagccc cggctaacta    420
cgtgccagca gccgcggtaa tacgtagggg gcaagcgtta tccggaatta ctgggtgtaa    480
agggtgcgta ggtggtatgg caagtcagaa gtgaaaaccc agggcttaac tctgggactg    540
cttttgaaac tgtcagactg gagtgcagga gaggtaagcg gaattcctag tgtagcggtg    600
aaatgcgtag atattaggag gaacatcagt ggcgaaggcg gcttactgga ctgaaactga    660
cactgaggca cgaaagcgtg gggagcaaac aggattagat accctggtag tccacgccgt    720
aaacgatgaa tactaggtgt cggggccgta gaggcttcgg tgccgcagcc aacgcagtaa    780
gtattccacc tggggagtac gttcgcaaga atgaaactca aaggaattga cggggacccg    840
cacaagcggt ggagcatgtg gtttaattcg aagcaacgcg aagaacctta cctggtcttg    900
acatccttct gaccggtcct taaccggacc tttccttcgg gacaggagag acaggtggtg    960
catggttgtc gtcagctcgt gtcgtgagat gttgggttaa gtcccgcaac gagcgcaacc   1020
cctatcttta gtagccagca tatcaggtgg gcactctaga gagactgcca gggataacct   1080
ggaggaaggt ggggacgacg tcaaatcatc atgcccctta tgaccagggc tacacacgtg   1140
ctacaatggc gtaaacagag ggaagcagcc tcgtgagag agcaaatcc caaaaataac   1200
gtctcagttc ggattgtagt ctgcaactcg actacatgaa gctggaatcg ctagtaatcg   1260
cgaatcagaa tgtcgcggtg aatacgttcc cgggtcttgt acacaccgcc cgtcacacca   1320
tgggagtcag taacgcccga agtca                                        1345

SEQ ID NO: 133          moltype = DNA   length = 400
FEATURE                 Location/Qualifiers
misc_feature            1..400
                        note = I28
variation               63..68
                        note = n is a, c, g, or t
variation               120..121
                        note = n is a, c, g, or t
source                  1..400
                        mol_type = unassigned DNA
                        organism = unidentified
SEQUENCE: 133
gcggcggacg ggtgagtaac gcgtgggtaa cctgccctgt acacacggat aacataccga    60
aannnnnnct aatacgggat aacataagaa attcgcatgt ttttcttatc aaagctccgn   120
nggtacagga tggacccgcg tctgattagc tagttggtga ggtaacggct caccaaggcg   180
acgatcagta gccgacctga gagggtgatc ggccacattg gaactgagac acggtccaaa   240
ctcctacggg aggcagcagt ggggaatatt gcacaatggg cgaaagcctg atgcagcaac   300
gccgcgtgag caatgaaggc cttcgggtcg taaagctctg tcctcaagga agataatgac   360
ggtacttgag gaggaagccc cggctaacta cgtgccagca                         400

SEQ ID NO: 134          moltype = DNA   length = 1366
FEATURE                 Location/Qualifiers
misc_feature            1..1366
                        note = I29
source                  1..1366
                        mol_type = unassigned DNA
                        organism = unidentified
SEQUENCE: 134
gggtgctcat gacggaggat tcgtccaacg gattgagtta cctagtggcg gacgggtgag    60
taacgcgtga ggaacctgcc ttggagaggg gaataacact ccgaaaggag tgctaatacc   120
gcatgatgca gttgggtcgc atggctctga ctgccaaaga tttatcgctc tgagatggcc   180
tcgcgtctga ttagctagta ggcggggtaa cggcccacct aggcgacgat cagtagccgg   240
actgagaggt tgaccggcca cattgagact gagacacgg ccagactcct acgggaggca   300
gcagtgggga atattgggca atgggcgcaa gcctgaccca gcaacgccgc gtgaaggaag   360
aaggctttcg ggttgtaaac ttctttgtc ggggacgaaa caaatgacgg tacctgacga   420
ataagccacg gctaactacg tgccagcagc cgcggtaata cgtaggtggc aagcgttatc   480
cggatttact gggtgtaaag ggcgtgtagg cgggattgca agtcagatgt gaaaactggg   540
ggctcaacct ccagcctgca tttgaaactg tagttcttga gtgctggaga ggcaatcgga   600
attccgtgtg tagcggtgaa atgcgtagat atacggagga acaccagtgg cgaaggcgga   660
ttgctggaca gtaactgacg ctgaggcgcg aaagcgtggg gagcaaacag gattagatac   720
cctggtagtc cacgccgtaa acgatggata ctaggtgtgg gggtctgac ccctccgtg    780
ccgcagttaa cacaataagt atcccacctg gggagtacga tcgcaaggtt gaaactcaaa   840
ggaattgacg ggggcccgca caagcggtgg agtatgtgg ttaattcgaa gcaacgcgaa   900
gaaccttacc agggcttgac atcccactaa cgaggcagaa atgcgttagg tgcccttcgg   960
ggaaagtgga gacaggtggt gcatggttgt cgtcagctcg tgtcgtgaga tgttgggtta  1020
agtcccgcaa cgagcgcaac ccttattgtt agttgctaca aagagcact ctagcgagac  1080
tgccgttgac aaaacggagg aaggtgggga cgacgtcaaa tcatcatgcc ccttatgtcc  1140
tgggccacac acgtactaca atggtggtaa acagagggag gcaataccgc gaggtggagc  1200
aaatccctaa aagccatccc agttcggatt gcaggctgaa accgcctgt atgaagttgg  1260
aatcgctagt aatcgcggat cagcatgccg cggtgaatac gttccggggc cttgtacaca  1320
ccgcccgtca caccatgaga gtcgggaaca cccgaagtcc gtagcc                 1366

SEQ ID NO: 135          moltype = DNA   length = 1358
FEATURE                 Location/Qualifiers
misc_feature            1..1358
                        note = I30
source                  1..1358
```

```
                        mol_type = unassigned DNA
                        organism = unidentified
SEQUENCE: 135
ttagaaagag gattcgtcca attgataagg ttacttagtg gcggacgggt gagtaacgcg    60
tgaggaacct gcctcggagt ggggaataac agaccgaaag gcctgctaat accgcatgat   120
gcagttggac cgcatggtcc tgactgccaa agatttatcg ctctgagatg gcctcgcgtc   180
tgattagctt gttggcgggg taatggccca ccaaggcgac gatcagtagc cggactgaga   240
ggttggccgg ccacattggg actgagacac ggcccagact cctacgggag gcagcagtgg   300
ggaatattgg gcaatgggcg caagcctgac ccagcaacgc cgcgtgaagg aagaaggctt   360
tcgggttgta aacttctttt ctcagggacg aacaaatgac ggtacctgag gaataagcca   420
cggctaacta cgtgccagca gccgcggtaa tacgtaggtg gcaagcgtta tccggattta   480
ctgggtgtaa agggcgtgta ggcgggaagg caagtcagat gtgaaaacta tgggctcaac   540
ccatagcctg catttgaaac tgttttcctt gagtgctgga gaggcaatcg gaattccgtg   600
tgtagcggtg aaatgcgtag atatacggag gaacaccagt ggcgaaggcg gattgctgga   660
cagtaactga cgctgaggcg cgaaagcgtg gggagcaaac aggattagat accctggtag   720
tccacgctgt aaacgatgga tactaggtgt ggggggtctg accccctccg tgccgcagtt   780
aacacaataa gtatcccacc tggggagtac gatcgcaagg ttgaaactca aaggaattga   840
cgggggcccg cacaagcggt ggagtatgtg gtttaattcg aagcaacgcg aagaaccttta  900
ccagggcttg acatcctact aacgaagcag agatgcatta ggtgcccttc ggggaaagta   960
gagacaggtg gtgcatggtt gtcgtcagct cgtgtcgtga gatgttgggt taagtcccgc  1020
aacgagcgca acccttattg ttagttgcta cgcaagagca ctctagcgag actgccgttg  1080
acaaaacgga ggaaggcggg gacgacgtca aatcatcatg ccccttatgt cctgggctac  1140
acacgtacta caatggtggt aaacagaggg aagcaagacc gcgaggtgga gcaaatccct  1200
aaaagccatc ccagttcgga ttgcaggctg aaacccgcct gtatgaagtt ggaatcgcta  1260
gtaatcgcgg atcagcatgc cgcggtgaat acgttcccgg gccttgtaca caccgcccgt  1320
cacaccatga gagtcgggaa cacccgaagt ccgtagtc                          1358

SEQ ID NO: 136         moltype = DNA   length = 1342
FEATURE                Location/Qualifiers
misc_feature           1..1342
                       note = I31
source                 1..1342
                       mol_type = unassigned DNA
                       organism = unidentified
SEQUENCE: 136
ggcgaacggg tgagtaatac ataagtaacc tggcatctac aggggggataa ctgatggaaa   60
cgtcagctaa gaccgcatag gtgtagagat cgcatgaact ctatatgaaa agtgctacgg   120
gactggtaga tgatggactt atggcgcatt agctggttgg tagggtaacg gcctaccaag   180
gcgacgatgc gtagccgacc tgagacgggtg accggccaca ctgggactga gacacgcccc   240
agactcctac gggaggcagc agtagggaat tttcggcaat gggggaaacc ctgaccgagc   300
aacgccgcgt gaaggaagaa gtaattcgtt atgtaaactt ctgtcataga ggaagaacgg   360
tggatatagg gaatgatatc caagtgacgg tactctataa gaaagccacg gctaactacg   420
tgccagcagc cgcggtaata cgtaggtggc gagcgttatc cggaattatt gggcgtaaag   480
agggagcagg cggcactaag ggtctgtggt gaaagatcga agcttaactt cggtaagcca   540
tggaaaccgt agagctagag tgtgtgagag gatcgtggaa ttccatgtgt agcggtgaaa   600
tgcgtagata tatggaggaa caccagtggc gaaggcgacg atctggcgca taactgacgc   660
tcagtcccga aagcgtgggg agcaaatagg attagatacc ctagtagtcc acgccgtaaa   720
cgatgagtac taagtgttgg gagtcaaatc tcagtgctgc agttaacgca ataagtactc   780
cgcctgagta gtacgttcgc aagaatgaaa ctcaaaggaa ttgacggggg cccgcacaag   840
cggtggagca tgtggtttaa ttcgaagcaa cgcgaagaac cttaccaggt cttgacatcg   900
atctaaaggc tccagagatg gagagatagc tatagagaag cagaggtggtg catggttgtc  960
gtcagctcgt gtcgtgagat gttgggttaa gtcccgcaac gagcgcaacc cctgttgcca  1020
gttgccagca ttaagttggg gactctggcg agactgccgg tgacaagccg gaggaaggcg  1080
gggatgacgt caaatcatca tgccccttat gacctgggct acacacgtgc tacaatggac  1140
agagcagagg gaagcgaagc cgcgaggtgg agcgaaaccc ataaaactgt tctcagttcg  1200
gactcagtc tgcaactcga ctgcacgaag atgaatcgc tagtaatcgc gaatcagcat  1260
gtcgcggtga atacgttctc gggccttgta cacaccgccc gtcacaccat gagagtcggt  1320
aacacccgaa gccggtggcc ta                                           1342

SEQ ID NO: 137         moltype = DNA   length = 1390
FEATURE                Location/Qualifiers
misc_feature           1..1390
                       note = I32
variation              921..923
                       note = n is a, c, g, or t
source                 1..1390
                       mol_type = unassigned DNA
                       organism = unidentified
variation              972
                       note = n is a, c, g, or t
variation              983
                       note = n is a, c, g, or t
variation              990..991
                       note = n is a, c, g, or t
SEQUENCE: 137
atgagaagct tgcttcttat tgattcgagt ggcaaacggg tgagtaacgc gtaagcaacc    60
tgcccttcag atggggacaa cagctggaaa cggctgctaa taccgaatac gttctttttg   120
tcgcatggca gagggaagaa agggaggctc ttcggagctt tcgctgaagg aggggcttgc   180
gtctgattag ctagttggag gggtaacggc ccaccaaggc gacgatcagt agccggtctg   240
```

```
agaggatgaa cggccacatt gggactgaga cacggcccag actcctacgg gaggcagcag    300
tggggaatct tccgcaatgg acgaaagtct gacggagcaa cgccgcgtga acgatgacgg    360
ccttcgggtt gtaaagttct gttatacggg acgaatggcg tagcggtcaa tacccgttac    420
gagtgacggt accgtaagag aaagccacgg ctaactacgt gccagcagcc gcggtaatac    480
gtaggtggca agcgttgtcc ggaattattg ggcgtaaagc gcgcgcaggc ggcgtcgtaa    540
gtcggtctta aaagtgcggg gcttaacccc gtgaggggac cgaaactgcg atgctagagt    600
atcggagagg aaagcggaat tcctagtgta cgcgtgaaat gcgtagatat taggaggaac    660
accagtggcg aaagcggctt tctgacgac aactgacgct gaggcgcgaa agccagggga     720
gcaaacggga ttagataccc cggtagtcct ggccgtaaac gatggatact aggtgtagga    780
ggtatcgacc ccttctgtgc cggagttaac gcaataagta tcccgcctgg ggagtacggc    840
cgcaaggctg aaactcaaag gaattgacgg gggcccgcac aagcggtgga gtatgtggtt    900
taattcgacg caacgcgaag nnncttacca agccttgaca ttgattgcta tggatagaga    960
tatccagttc cncttcggag ganaagaaan naggtggtgc acggctgtcg tcagctcgtg   1020
tcgtgagatg ttgggttaag tcccgcaacg agcgcaaccc ctatcttctg ttaccagcgg   1080
ttcggccggg gactcaggag agactgccgc agacaatgcg gaggaaggcg gggatgacgt   1140
caagtcatca tgcccttat ggcttgggct acacacgtac tacaatggct cttaatagag    1200
ggaagcgaag gagcgatccg gagcaaaccc caaaaacaga gtcccagttc ggattgcagg   1260
ctgcaactcg cctgcatgaa gcaggaatcg ctagtaatcg caggtcagca tactgcggtg   1320
aatacgttcc cgggccttgt acacaccgcc cgtcacacca cgaaagtcat tcacaccga    1380
agccggtgag                                                          1390

SEQ ID NO: 138         moltype = DNA   length = 1373
FEATURE                Location/Qualifiers
misc_feature           1..1373
                       note = I33
source                 1..1373
                       mol_type = unassigned DNA
                       organism = unidentified
SEQUENCE: 138
atctagtggc aaacgggtga gtaacacgta aacaacctgc cttcaggatg gggacaacag     60
acggaaacga ctgctaatac cgaatacgtt ccttaggtcg catgacttta ggaagaaagg    120
gtggcctcta cttgtaagct atcgcctgaa gaggggtttg cgtctgatta ggtagttggt    180
gaggtaacgg cccaccaagc cgacgatcag tagccggtct gagaggatga acggccacac    240
tggaactgag acacggtcca gactcctacg ggaggcagca gtggggaatc ttccgcaatg    300
ggcgaaagcc tgacggagca acgccgcgtg agtgatgacg gccttcgggt tgtaaagctc    360
tgtgatcggg gacgaacggt cagcagacga atactctgct gaagtgacgg tacccgaata    420
gcaagccacg gctaactacg tgccagcagc cgcggtaata cgtaggtggc aagcgttgtc    480
cggaattatt gggcgtaaag cgcgcgcagg cggcttctta agtccatctt aaaagtgcgg    540
ggcttaaccc cgtgatggga tggaaactga gaggctgaac tatcggagag gaaagtgaa    600
ttcctagtgt agcggtgaaa tgcgtagaga ttaggaagaa caccggtggc gaaggcgact    660
ttctggacga caactgacgc tgaggcgcga aagcgtgggg agcaaacagg attagatacc    720
ctggtagtcc acgccgtaaa cgatgaatac taggtgtagg aggtatcgac cccttctgtg    780
ccggagtcaa cacaataagt attccgcctg ggaagtacga tcgcaagatt aaaactcaaa    840
ggaattgacg gggccccgca caagcggtgg agtatgtggt ttaattcgac gcaacgcgaa    900
gaaccttacc aggtcttgac attgatcgct attccaagaa attggaagtt ctccttcggg    960
agacgagaaa acaggtggtg cacggctgtc gtcagctcgt gtcgtgagat gttgggttaa   1020
gtcccgcaac gagcgcaacc cctatcttat gttaccagcg cgttatggtg gggactcatg   1080
agagaccgcc gcggacaacg cggaggaagg tggggatgac gtcaagtcat catgcccctt   1140
atgacctggg ctacacacgt actacaatgg gtgtcaacaa agagaagcga agccgcgagg   1200
cagagcaaac ctcaaaaaca cacccccagt tcagattgca ggctgcaacc cgcctgcatg   1260
aagtaggaat cgctagtaat cgcgggtcag catacccgcgg tgaatacgtt cccgggcctt   1320
gtacacaccg cccgtcacac tatgagagtc agaaacaccc gaagccggtg agg          1373

SEQ ID NO: 139         moltype = DNA   length = 1366
FEATURE                Location/Qualifiers
misc_feature           1..1366
                       note = I34
source                 1..1366
                       mol_type = unassigned DNA
                       organism = unidentified
SEQUENCE: 139
ttcttagtgg cgaacgggtg agtaacgcgt gggcaacctg ccctccagtt ggggacaaca     60
ttccgaaagg gatgctaata ccgaatgtgc tccctcctcc gcatggagga gggaggaaag    120
atggctctg cttgcaagct atcgctggaa gatgggccgc cgtctgatta gctagttggt     180
ggggtaacgg ctcaccaagg cgatgatcag tagccggtct gagaggatga acggccacat    240
tgggactgag acacgcccca aactcctacg ggaggcagca gtggggaatc ttccgcaatg    300
gacgaaagtc tgacggagca acgccgcgtg agtgatgaag gtcttcggat tgtaaaactc    360
tgttgttagg gacgaaagca ccgtgttcga acaggtcatg gtgttgacgg tacctaacga    420
ggaagccacg gctaactacg tgccagcagc cgcggtaata cgtaggtggc aagcgttgtc    480
cggaattatt gggcgtaaag agcatgtagg cgggcttta agtctgacgt gaaaatgcgg    540
ggcttaaccc cgtatggcgt tggatactgg aagtcttgag tgcaggagag gaaagggaa    600
tcccagtgt agcggtgaaa tgcgtagata ttggaggaa caccagtggc gaaggcgcct     660
ttctggactg tgtctgacgc tgagatgcga aagccagggt agcaaacggg attagatacc    720
ccggtagtcc tggccgtaaa cgatggatac taggtgtagg agtatcgcc cccttctgtg    780
ccggagttaa cgcaataagt atcccgcctg gggactacga tcgcaagatt gaaactcaaa    840
ggaattgacg gggccccgca caagcggtgg agtatgtggt ttaattcgac gcaacgcgaa    900
gaaccttacc aaggcttgac attgagtgaa agacctagag ataggtccct ccttcgggg    960
acacgaaaac aggtggtgca tggctgtcgt cagctcgtgt cgtgagatgt tgggttaagt   1020
cccgcaacga gcgcaacccc tatcctatgt taccagcgcg taatgcgggg gactcatagg   1080
```

```
agactgccag ggataacttg gaggaaggcg gggatgacgt caagtcatca tgcccttat    1140
gtcttgggct acacacgtac tacaatggtc ggcaacaaag ggcagcgaaa ccgcgaggtg    1200
gagcaaatcc cagaaacccg accccagttc ggatcgtagg ctgcaacccg cctacgtgaa    1260
gttggaatcg ctagtaatcg caggtcagca tactgcggtg aatacgttcc cgggccttgt    1320
acacaccgcc cgtcacacca cgaaagttgg taacacccga agccgg                   1366

SEQ ID NO: 140          moltype = DNA  length = 1387
FEATURE                 Location/Qualifiers
misc_feature            1..1387
                        note = I35
variation               11
                        note = n is a, c, g, or t
variation               190
                        note = n is a, c, g, or t
source                  1..1387
                        mol_type = unassigned DNA
                        organism = unidentified
variation               399
                        note = n is a, c, g, or t
SEQUENCE: 140
cttgctcttt nttggattct agtggcaaac gggtgagtaa cacgtaaaca acctgccttc    60
aggatgggga caacagacgg aaacgactgc taataccgca taccttccaa tttccgcatg   120
gagataggaa gaaagggtgg cctctacttg taagctatcg cctgaagagg ggtttgcgtc   180
tgattagctn gttggtgagg taacggccca ccaaggcgac gatcagtagc cggtctgaga   240
ggatgaacgc ccacactgga actgagacac ggtccagact cctacgggag gcagcagtgg   300
ggaatcttcc gcaatggacg aaagtctgac ggagcaacgc cgcgtgaacg atgaaggtct   360
tcggattgta aagttctgtg atccgggacg aaggcattna ttgagaacat tgattgatgt   420
tgacggtacc ggaaaagcaa gccacggcta actacgtgcc agcagccgcg gtaatacgta   480
ggtggcaagc gttgtccgga attattgggc gtaaagcgcg cgcaggcggc cgtgcaagtc   540
catcttaaaa gcgtgggggct taaccccatg aggggatgga aactgcatgg ctggagtgtc   600
ggaggggaaa gtggaattcc tagtgtagcg gtgaaatgcg tagagattag gaagaacacc   660
ggtggcgaag cgactttct agacgacaac tgacgctgag gcgcgaaagc gtggggagca   720
aacaggatta gataccctgg tagtccacgc cgtaaacgat ggatactagg tgtaggaggt   780
atcgacccct tctgtgccgg agttaacgca ataagtatcc cgcctgggaa gtacgatcgc   840
aagattaaaa ctcaaaggaa ttgacggggg cccgcacaag cggtggagta tgtggtttaa   900
ttcgacgcaa cgcgaagaac cttaccaagc cttgacattg atcgcaatct gcagaaatgc   960
ggagttcctc ttcggaggac gagaaaacag gtggtgcacg gctgtcgtca gctcgtgtcg   1020
tgagatgttg ggttaagtcc cgcaacgagc gcaaccccta tcttctgttg ccagcacgta   1080
aaggtgggaa ctcaggagag accgccgcgg acaacgcgga ggaaggcggg gatgacgtca   1140
agtcatcatg cccttatgg cttgggctac acacgtacta caatgggtgc aaacaaagag   1200
aagcgaagtc gcgagacgga gcggacctca taaacgcact cccagttcag attgcaggct   1260
gcaacccgc tgcatgaagt aggaatcgct agtaatcgcg gtcagcata ccgcggtgaa   1320
tacgttcccg ggccttgtac acaccgcccg tcacactatg agagtcagag acacccaaag   1380
ccggtgg                                                              1387

SEQ ID NO: 141          moltype = DNA  length = 1386
FEATURE                 Location/Qualifiers
misc_feature            1..1386
                        note = I36
variation               20
                        note = n is a, c, g, or t
variation               112..113
                        note = n is a, c, g, or t
variation               115..117
                        note = n is a, c, g, or t
source                  1..1386
                        mol_type = unassigned DNA
                        organism = unidentified
variation               130
                        note = n is a, c, g, or t
variation               189
                        note = n is a, c, g, or t
variation               1200..1201
                        note = n is a, c, g, or t
SEQUENCE: 141
gagaagcttg cttccttatcn attctagtgg caaacgggtg agtaacgcgt aagcaacctg    60
cccttcagat ggggacaaca gctggaaacg gctgctaata ccgaatacgt tnntnnngcc   120
gcatgacgan atgaagaaag ggaggccttc gggcttttcgc tggaggaggg gcttgcgtct   180
gattagctng ttggaggggt aacggcccac caaggcgacg atcagtaacg ggtctgagag   240
gatgaacggc cacattggga ctgagacacg gcccagactc ctacgggagg cagcagtggg   300
gaatcttccg caatggacga aagtctgacg gagcaacgcc gcgtgaacga tgacggcctt   360
cgggttgtaa agttctgtta tatgggacga acaggacatc ggttaatacc cggtgtcttt   420
gacggtaccg taagagaaag ccacggctaa ctacgtgcca gcagccgcgg taatacgtag   480
gtgcaagcg ttgtccggaa ttattgggcg taaagggcgc gcaggcggca tcgcaagtcg   540
gtcttaaaag tgcggggctt aaccccgtga gggaccgaaa actgtgaagc tcgagtgtcg   600
gagaggaaag cggaattcct agtgtagcgg tgaaatgcgt agatattagg aggaacacca   660
gtggcgaaag cggctttctg gacgacaact gacgctgagg cgcgaaagcc aggggagcaa   720
acgggattag ataccccggt agtcctggcc gtaaacgatg gatactaggt gtaggaggta   780
tcgactcctt ctgtgccgga gttaacgcaa taagtatccc gcctgggag tacggccgca   840
```

-continued

```
aggctgaaac tcaaaggaat tgacgggggc ccgcacaagc ggtggagtat gtggtttaat    900
tcgacgcaac gcgaagaacc ttaccaagcc ttgacattga ttgctacgga aagagatttc    960
cggttcttct tcggaagaca agaaaacagg tggtgcacgg ctgtcgtcag ctcgtgtcgt   1020
gagatgttgg gttaagtccc gcaacgagcg caacccctat cttctgttgc cagcacctcg   1080
ggtggggact cagaagagac tgccgcagac aatgcgaggg aaggcgggga tgacgtcaag   1140
tcatcatgcc ccttatggct tgggctacac acgtactaca atggctctta atagagggan   1200
ncgaaggagc gatccggagc aaaccccaaa aacagagtcc cagttcggat tgcaggctgc   1260
aactcgcctg catgaagcag gaatcgctag taatcgcagg tcagcatact gcggtgaata   1320
cgttcccggg ccttgtacac accgcccgtc acaccacgaa agtcattcac acccgaagcc   1380
ggtgag                                                               1386
```

| SEQ ID NO: 142 | moltype = DNA  length = 1364 |
|---|---|
| FEATURE | Location/Qualifiers |
| misc_feature | 1..1364 |
| | note = I37 |
| source | 1..1364 |
| | mol_type = unassigned DNA |
| | organism = unidentified |
| variation | 939..940 |
| | note = n is a, c, g, or t |

SEQUENCE: 142
```
cggcagcgcg gggagcttgc tccctggcgg cgagtggcgc acgggtgagt aatacatcgg     60
aacgtgtctt ctagtggggg ataactgccc gaaagggcag ctaataccgc atgagacctg    120
aggggtgaaag cggggggatcg caagacctcg cgctggaaga gcggccgatg tccgattagc   180
tagttggtga ggtaaaggct caccaaggcg acgatcggta gctggtctga gaggacgacc    240
agccacactg ggactgagac acggcccaga ctcctacggg aggcagcagt ggggaatttt    300
ggacaatggg ggcaaccctg atccagccat gccgcgtgca ggatgaaggt cttcggattg    360
taaactgctt ttgtcaggga cgaaaaggga tgcgataaca ccgtattccg ctgacggtac    420
ctgaagaata agcaccggct aactacgtgc cagcagccgc ggtaatacgt agggtgcaag    480
cgttaatcgg aattactggg cgtaaagcgt gcgcaggcgg ttctgtaaga tagatgtgaa    540
atccccgggc tcaacctggg aattgcatat atgactgcag gacttgagtt tgtcagagga    600
gggtggaatt ccacgtgtag cagtgaaatg cgtagatatg tggaagaaca ccgatggcga    660
aggcagccct ctgggacatg actgacgctc atgcacgaaa gcgtggggag caaacaggat    720
tagataccct ggtagtccac gccctaaacg atgtctacta gttgttgggg acgatagtcc    780
ttggtaacgc agctaacgcg tgaagtagac cgcctgggga gtacggtcgc aagattaaaa    840
ctcaaaggaa ttgacgggga cccgcacaag cggtggatga tgtggattaa ttcgatgcaa    900
cgcgaaaaac cttacctagc cttgacatgc caggaaggnn tgagagatca ggccgtgccc    960
gcaagggaat ctggacacag gtgctgcatg gctgtcgtca gctcgtgtcg tgagatgttg   1020
ggttaagtcc cgcaacgagc gcaacccttg tcattagttg ctacgaaagg gcactctaat   1080
gagactgccg gtgacaaacc ggaggaaggt ggggatgacg tcaagtcctc atggccctta   1140
tggctagggc ctcacacgtc acaatggt cggaacagag ggaagcgaag ccgcgaggtg    1200
aagccaatcc cagaaaaccg atcgtagtcc ggattgcagt ctgcaactcg actgcatgaa   1260
gtcggaatcg ctagtaatcg cggatcagca tgccgcggtg aatacgttcc cgggtcttgt   1320
acacaccgcc cgtcaccacca tgggagtggg gttcaccaga agac                   1364
```

| SEQ ID NO: 143 | moltype = DNA  length = 1343 |
|---|---|
| FEATURE | Location/Qualifiers |
| misc_feature | 1..1343 |
| | note = I38 |
| source | 1..1343 |
| | mol_type = unassigned DNA |
| | organism = unidentified |

SEQUENCE: 143
```
ggaaacggat tagcggcgga cgggtgagta acacgtgggt aacctgcctc atagagggga     60
atagcctccc gaaagggaga ttaataccgc ataacattgc agtttcgcat gaaacagcaa    120
ttaaaggagc aatccgctat gagatgaccc cgcggcgcat tagctagttg gtaaggtaat    180
ggcttaccaa ggcgacgatg cgtagccgac ctgagagggt gatcggccac attgggactg    240
agacacggcc cagactccta cgggaggcag cagtggggaa tattgcacaa tgggggaaac    300
cctgatgcag caacgccgcg tgagtgatga cggtcttcgg attgtaaagc tctgtctttg    360
gggacgataa tgacggtacc caaggaggaa gccacggcta actacgtgcc agcagccgcg    420
gtaatacgta ggtggcgagc gttgtccgga tttactgggc gtaaagggag cgtaggcgga    480
tttttaagtg ggatgtgaaa tacccgggct caacctgggt gctgcattcc aaactgggaa    540
tctagagtgc aggaggggag agtggaattc ctagtgtagc ggtgaaatgc gtagagatta    600
ggaagaacac cagtggcgaa ggcgactctc tggactgtaa ctgacgctga ggctcgaaag    660
cgtggggagc aacaggatt agatacctg gtagtccacg ccgtaaacga tgaatactag    720
gtgtagggt tcaacacct ctgtgccgcc gctaacgcat taagtattcc gcctggggag    780
tacggtcgca agattaaaac tcaaaggaat tgacgggggc ccgcacaagt agcggagcat    840
gtggtttaat tcgaagcaac gcgaagaacc ttacctagac ttgacatcct ctgcattacc    900
cttaatcggg gaagttcctt cgggaacaga gtgacaggtg gtgcatggtt gtcgtcagct    960
cgtgtcgtga gatgttgggt taagtcccgc aacgagcgca accccctattg ttagttgcta   1020
ccattaagtt gagcactcta gcgagactgc ctgggttaac caggaggaag gtggggatga   1080
cgtcaaatca tcatgcccct tatgtctagg gctacacacg tgctacaatg gcaagtacag   1140
agagatgcaa taccgcgagg tggagctaaa cttcaaaact tgtctcagtt cggattgtag   1200
gctgaaactc gcctacatga agctggagtt actagtaatc gcgaatcagc atgtcgcggt   1260
gaatacgttc ccgggccttg tacacaccgc ccgtcacacc atgagagttg gcaatacccca   1320
aagttcgtga gctaacgcgt aag                                           1343
```

| SEQ ID NO: 144 | moltype = DNA  length = 1318 |
|---|---|
| FEATURE | Location/Qualifiers |

```
misc_feature            1..1318
                        note = I39
source                  1..1318
                        mol_type = unassigned DNA
                        organism = unidentified
SEQUENCE: 144
cttagtggcg acgggtgag taacgcgtga gtaacctgcc tttcagaggg gaataacatt    60
ctgaaaagaa tgctaatacc gcatgagatc gtagtatcgc atggtacagc gaccaaagga   120
gcaatccgct gaaagatgga ctcgcgtccg attagctagt tggtgagata aaggcccacc   180
aaggcgacga tcggtagccg gactgagagg ttgaacggcc acattgggac tgagacacgg   240
cccagactcc tacgggaggc agcagtgggg gatattgcac aatgggggaa accctgatgc   300
agcaacgccg cgtgaaggaa gaaggtcttc ggattgtaaa cttctgtcct cagggaagat   360
aatgacggta cctgaggagg aagctccggc taactacgtg ccagcagccg cggtaatacg   420
tagggagcaa gcgttgtccg gatttactgg gtgtaaaggg tgcgtaggcg gatctgcaag   480
tcagtagtga aatcccaggg cttaaccctg gaactgctat tgaaactgtg ggtcttgagt   540
gaggtagagg caggcggaat tcccggtgta gcggtgaaat gcgtagagat cgggaggaac   600
accagtggcg aaggcggcct gctgggcctt aactgacgct gaggcacgaa agcatgggta   660
gcaaacagga ttagataccc tggtagtcca tgccgtaaac gatgattact aggtgtgggt   720
ggtctgaccc catccgtgcc ggagttaaca caataagtaa tccacctggg gagtacggcc   780
gcaaggttga aactcaaagg aattgacggg ggcccgcaca agcagtggag tatgtggttt   840
aattcgaagc aacgcgaaga accttaccag gtcttgacat cctgctaacg aggtagagat   900
acgttaggtg cccttcgggg aaagcagaga caggtggtgc atggttgtcg tcagctccgtt  960
tcgtgagatg ttgggttaag tcccgcaacg agcgcaaccc ctgctattag ttgctacgca  1020
agagcactct aataggactg ccgttgacaa aacggaggaa ggtggggacg acgtcaaatc  1080
atcatgcccc ttatgacctg gctacacac gtactacaat ggccgtcaac agagagaagc   1140
aaagccgcga ggtggagcaa aactctaaaa acggtccgtc ttcggatcgt aggctgcaac  1200
ccgcctacgt gaagttgaa ttgctagtaa tcgcggatca tcatgccgcg gtgaatacgt   1260
tcccgggcct tgtacacacc gcccgtcaca ccatgggagc cggtaatacc cgaagtca    1318

SEQ ID NO: 145          moltype = DNA   length = 1360
FEATURE                 Location/Qualifiers
misc_feature            1..1360
                        note = I40
source                  1..1360
                        mol_type = unassigned DNA
                        organism = unidentified
SEQUENCE: 145
tcatgacaga ggattcgtcc aatggagtga gttacttagt ggcggacggg tgagtaacgc    60
gtgagtaacc tgccttggag tgggaataa caggtggaaa catctgctaa taccgcatga   120
tgcagttggg tcgcatggct ctgactgcca aagatttatc gctctgagat ggactcgcgt   180
ctgattagct ggttggcggg gtaacggcc accaaggcga cgatcagtag ccggactgag   240
aggttggccg gccacattgg gactgagaca cggcccagac tcctacggga ggcagcagtg   300
gggaatattg gcaatgggcg caagcctga cccagcaacg ccgtgaag gaagaaggct   360
ttcgggttgt aaacttcttt tctcaggac gaagcaagtg acggtacctg aggaataagc   420
cacggctaac tacgtgccag cagccgcggt aatacgtagg tggcgagcgt tatccggatt   480
tactgggtgt aaagggcgtg taggcgggac tgcaagtcag atgtgaaaac catgggctca   540
acctgctgga tgcatttgaa actgtagttc ttgagtactg gagaggcaga ggaattcct    600
agtgtagcgg tgaaatgcgt agatattagg aggaacacca gtggcgaagg cggtctgctg   660
gacagcaact gacgctgagg cgcgaaagcg tgggagcaa acaggattag ataccctggt   720
agtccacgct gtaaacgatg gatactaggt gtgggggtc tgacccctc cgtgccgcag    780
ttaacacaat aagtatccca cctggggagt acgatccgcaa ggttgaaact caaaggaatt   840
gacgggggcc cgcacaagcg gtggagtatg tggtttaatt cgaagcaacg cgaagaacct   900
taccagggct tgacatcccg gtgaccggtc tagagataca ccttcttctt cggaagcgcc   960
ggtgacaggt ggtgcatggt tgtcgtcagc tcgtgtcgtg agatgtggg ttaagtcccg    1020
caacgagcgc aaccccttatt gttagttgct acgcaagtag actctagcga gatgccgtt   1080
gacaaaacgg aggaaggtgg ggacgacgtc aaatcatcat gccccttatg tcctgggcca   1140
cacacgtact acaatggtgg tcaacagagg gaagcaagac cgcgaggtgg agcaaaccc    1200
taaaagccat cccagttcgg attgcaggct gcaactcgcc tgtatgaagt tggaatcgct   1260
agtaatcgcg gatcagcatg ccgcggtgaa tacgttcccg ggccttgtac acaccgcccg   1320
tcacaccatg agagtcggga cacccgaag tccgtagcct                          1360

SEQ ID NO: 146          moltype = DNA   length = 1370
FEATURE                 Location/Qualifiers
misc_feature            1..1370
                        note = I41
source                  1..1370
                        mol_type = unassigned DNA
                        organism = unidentified
SEQUENCE: 146
gtgctcatga cggagttttc ggacaacgga ttgggttact tagtggcgga cgggtgagta    60
acgcgtgagg aacctgcctc ggagtgggga ataacacacc gaaaggtgtg ctaataccgc   120
ataatgcagt tgggtcgcat gactctgact gccaaagatt tatcgctctg atggcctc    180
gcgtctgatt agctagttgg cggggtaacg gcccaccaag cgacgatca gtagccggac    240
tgagaggttg accggccaca ttgggactga gacacggccc agactcctac gggaggcagc   300
agtgggggaat attgggcaat gggcgcaagc ctgacccagc aacgccgcgt gaaggaagaa   360
ggctttcggg ttgtaaactt cttttgtcag gacgaaaca aatgacggta cctgacgaat   420
aagccacggc taactacgtg ccagcagccg cggtaatacg taggtggcaa gcgttatccg   480
gatttactgg gtgtaaaggg cgtgtaggcg ggactgcaag tcaggtgtga aaaccagggg   540
ctcaacctct ggcctgcatt tgaaactgta gttcttgagt gctggagagg caatcggaat   600
```

-continued

```
tccgtgtgta gcggtgaaat gcgtagatat acggaggaac accagtggcg aaggcggatt    660
gctggacagt aactgacgct gaggcgcgaa agcgtgggga gcaaacagga ttagataccc    720
tggtagtcca cgccgtaaac gatggatact aggtgtgggg ggactgaccc cctccgtgcc    780
gcagttaaca caataagtat cccacctggg gagtacgatc gcaaggttga aactcaaagg    840
aattgacggg ggcccgcaca agcggtggag tatgtggttt aattcgaagc aacgcgaaga    900
accttaccag ggcttgacat cctactaacg aagcagagat gcattaggtg cccttcgggg    960
aaagtagaga caggtggtgc atggttgtcg tcagctcgtg tcgtgagatg ttgggttaag    1020
tcccgcaacg agcgcaaccc ctattgttag ttgctacgca agagcactct agcgagactg    1080
ccgttgacaa aacggaggaa ggtggggacg acgtcaaatc atcatgcccc ttatgtcctg    1140
ggccacacac gtactacaat ggtggttaac agagggggagc aataccgcga ggtgagcaa    1200
atccctaaaa gccatcccag ttcggattgc aggctgaaac ccgcctgtat gaagttggaa    1260
tcgctagtaa tcgcggatca gcatgccgcg gtgaatacgt tcccgggcct tgtacacacc    1320
gcccgtcaca ccatgagagt cgggaacacc cgaagtccgt agcctaaccg                1370

SEQ ID NO: 147             moltype = DNA   length = 1341
FEATURE                    Location/Qualifiers
misc_feature               1..1341
                           note = I42
variation                  120..121
                           note = n is a, c, g, or t
source                     1..1341
                           mol_type = unassigned DNA
                           organism = unidentified
SEQUENCE: 147
ttgcaccttc aagttagtgg cggacgggtg agtaacgcgt gagcaacctg cctcaaagag    60
ggggataacg tctggaaacg gacgctaata ccgcatgacg tattcgatag gcatctattn    120
nataccaaag gagcaatccg ctttgagatg ggctcgcgtc tgattagctg gttggtgggg    180
taaaggccta ccaaggcgac gatcagtagc cggactgaga ggttgaacgg ccacattggg    240
actgagacac ggcccagact cctacgggag gcagcagtgg gggatattgc acaatggggg    300
aaaccctgat gcagcaacgc cgcgtgaagg aagacggttt tcggattgta aacttctgtt    360
cttagtgacg ataatgacgg tagctaagga gaaagctccg gctaactacg tgccagcagc    420
cgcggtaata cgtagggagc gagcgttgtc cggaattact gggtgtaaag ggagcgtagg    480
cgggagatca agtcagatgt gaaaactatg ggctcaaccc ataacctgca tttgaaactg    540
gttttcttga gtgaagtaga ggcaggcgga attccgagtg tagcggtgaa atgcgtagat    600
attcggagga acaccagtgg cgaaggcggc ctgctgggtc tttactgacg ctgaggctcg    660
aaagcatggg gagcaaacag gattagatac cctggtagtc catgccgtaa acgatgatta    720
ctaggtgtgg ggtggctgac ccattccgtg ccggagttaa cacaataagt aatccacctg    780
gggagtacgg ccgcaaggtt gaaactcaaa ggaattgacg ggggcccgca caagcagtgg    840
agtatgtggt ttaattcgaa gcaacgcgaa gaaccttacc aggtcttgac atccgactaa    900
cgaagtagag atacattagg tgcccttcgg ggaaagtcga gacaggtggt gcatggttgt    960
cgtcagctcg tgtcgtgaga tgttgggtta agtcccgcaa cgagcgcaac ccttgtcatt    1020
agttgctacg caagagcact ctaatgagac tgccgttgac aaaacggagg aaggtgggga    1080
cgacgtcaaa tcatcatgcc cctttatgacc tgggctacac acgtactaca atggccgtta    1140
acagagggaa gcaatactgt gaagtggagc aaaacccctaa aaacggtccc agttcagatt    1200
gcaggctgca acccgcctgc atgaagtcgg aattgctagt aatcgcggat cagcatgccg    1260
cggtgaatac gttcccgggc cttgtacaca ccgcccgtca ccatgggag gccggtaata    1320
cccgaagtcg gtagtctaac c                                              1341

SEQ ID NO: 148             moltype = DNA   length = 20
FEATURE                    Location/Qualifiers
source                     1..20
                           mol_type = other DNA
                           organism = synthetic construct
SEQUENCE: 148
gcgaccagac ctacatgcgt                                                 20

SEQ ID NO: 149             moltype = DNA   length = 19
FEATURE                    Location/Qualifiers
misc_feature               1..19
                           note = Artificially synthesized primer sequence
source                     1..19
                           mol_type = other DNA
                           organism = synthetic construct
SEQUENCE: 149
agtcgaaaga gcccgcgtc                                                  19

SEQ ID NO: 150             moltype = DNA   length = 20
FEATURE                    Location/Qualifiers
misc_feature               1..20
                           note = Artificially synthesized primer sequence
source                     1..20
                           mol_type = other DNA
                           organism = synthetic construct
SEQUENCE: 150
agcactagcg gctgtggtat                                                 20

SEQ ID NO: 151             moltype = DNA   length = 20
FEATURE                    Location/Qualifiers
misc_feature               1..20
```

```
                    note = Artificially synthesized primer sequence
source              1..20
                    mol_type = other DNA
                    organism = synthetic construct
SEQUENCE: 151
acttactcgg gcccttgatt                                                    20

SEQ ID NO: 152      moltype = DNA  length = 20
FEATURE             Location/Qualifiers
misc_feature        1..20
                    note = Artificially synthesized primer sequence
source              1..20
                    mol_type = other DNA
                    organism = synthetic construct
SEQUENCE: 152
cttcgccttc atcagcttca                                                    20

SEQ ID NO: 153      moltype = DNA  length = 20
FEATURE             Location/Qualifiers
misc_feature        1..20
                    note = Artificially synthesized primer sequence
source              1..20
                    mol_type = other DNA
                    organism = synthetic construct
SEQUENCE: 153
tcatcattaa cgcgggtcag                                                    20

SEQ ID NO: 154      moltype = DNA  length = 17
FEATURE             Location/Qualifiers
misc_feature        1..17
                    note = Artificially synthesized primer sequence
source              1..17
                    mol_type = other DNA
                    organism = synthetic construct
SEQUENCE: 154
ggtgaatacg ttcccgg                                                       17

SEQ ID NO: 155      moltype = DNA  length = 22
FEATURE             Location/Qualifiers
misc_feature        1..22
                    note = Artificially synthesized primer sequence
source              1..22
                    mol_type = other DNA
                    organism = synthetic construct
SEQUENCE: 155
tacggctacc ttgttacgac tt                                                 22

SEQ ID NO: 156      moltype = DNA  length = 20
FEATURE             Location/Qualifiers
misc_feature        1..20
                    note = Artificially synthesized primer sequence
source              1..20
                    mol_type = other DNA
                    organism = synthetic construct
SEQUENCE: 156
agrgtttgat ymtggctcag                                                    20

SEQ ID NO: 157      moltype = DNA  length = 19
FEATURE             Location/Qualifiers
misc_feature        1..19
                    note = Artificially synthesized primer sequence
source              1..19
                    mol_type = other DNA
                    organism = synthetic construct
SEQUENCE: 157
ggytaccttg ttacgactt                                                     19
```